US012807546B2

(12) United States Patent
Thompson et al.

(10) Patent No.: US 12,807,546 B2
(45) **Date of Patent: *Nov. 24, 2026**

(54) METHODS FOR PROMOTING PLANT HEALTH USING FREE ENZYMES AND MICROORGANISMS THAT OVEREXPRESS ENZYMES

(71) Applicant: Spogen Biotech Inc., St. Louis, MO (US)

(72) Inventors: Brian M. Thompson, Creve Coeur, MO (US); Jorg Augustin, Chesterfield, MO (US)

(73) Assignee: Spogen Biotech Inc., St. Louis, MO (US)

( * ) Notice: Subject to any disclaimer, the term of this patent is extended or adjusted under 35 U.S.C. 154(b) by 35 days.

This patent is subject to a terminal disclaimer.

(21) Appl. No.: 18/476,256

(22) Filed: Sep. 27, 2023

(65) Prior Publication Data

US 2024/0132417 A1 Apr. 25, 2024
US 2024/0228394 A9 Jul. 11, 2024

Related U.S. Application Data

(60) Continuation of application No. 18/302,458, filed on Apr. 18, 2023, which is a continuation of application No. 17/459,019, filed on Aug. 27, 2021, now Pat. No. 12,630,484, which is a division of application No. 15/460,468, filed on Mar. 16, 2017, now Pat. No. 11,124,460.

(60) Provisional application No. 62/309,426, filed on Mar. 16, 2016.

(51) Int. Cl.

| | |
|---|---|
| ***C05F 17/20*** | (2020.01) |
| ***A01N 63/50*** | (2020.01) |
| ***C05B 15/00*** | (2006.01) |
| ***C05C 9/00*** | (2006.01) |
| ***C05F 11/08*** | (2006.01) |
| ***C05G 3/60*** | (2020.01) |
| ***C07K 14/415*** | (2006.01) |
| ***C12N 1/20*** | (2006.01) |
| ***C12N 9/78*** | (2006.01) |
| ***C12N 15/82*** | (2006.01) |

(52) U.S. Cl.

CPC .............. *C05F 17/20* (2020.01); *A01N 63/50* (2020.01); *C05B 15/00* (2013.01); *C05C 9/00* (2013.01); *C05F 11/08* (2013.01); *C05G 3/60* (2020.02); *C07K 14/415* (2013.01); *C12N 1/20* (2013.01); *C12N 9/78* (2013.01); *C12N 15/8237* (2013.01); *C12N 15/8249* (2013.01); *C12N 15/8279* (2013.01); *C12Y 302/01* (2013.01); *C12Y 305/99007* (2013.01); *C12Y 402/0202* (2013.01); *Y02A 40/22* (2018.01); *Y02P 60/21* (2015.11)

(58) Field of Classification Search

None

See application file for complete search history.

(56) References Cited

U.S. PATENT DOCUMENTS

| | | | |
|---|---|---|---|
| 4,383,845 | A | 5/1983 | Rutherford |
| 5,017,374 | A | 5/1991 | Humphrey |
| 5,348,743 | A | 9/1994 | Ryals et al. |
| 5,631,007 | A | 5/1997 | Ryals et al. |
| 5,776,448 | A | 7/1998 | Suslow et al. |
| 5,958,104 | A | 9/1999 | Nonomura et al. |
| 6,184,440 | B1 | 2/2001 | Shoseyov et al. |
| 6,323,023 | B1 | 11/2001 | Shoseyov et al. |
| 6,333,302 | B1 | 12/2001 | Beer et al. |
| 6,346,131 | B1 | 2/2002 | Bergevin et al. |
| 6,548,743 | B1 | 4/2003 | Sheen et al. |
| 6,566,114 | B1 | 5/2003 | Kauppinen et al. |
| 6,630,340 | B2 | 10/2003 | Wilting et al. |
| 7,417,181 | B2 | 8/2008 | Wang et al. |
| 7,432,097 | B2 | 10/2008 | Short et al. |
| 7,504,120 | B2 | 3/2009 | Steer et al. |
| 7,615,681 | B2 | 11/2009 | Georges et al. |

(Continued)

FOREIGN PATENT DOCUMENTS

| | | |
|---|---|---|
| CA | 2951582 | 1/2016 |
| CN | 101056536 | 10/2007 |

(Continued)

OTHER PUBLICATIONS

Yang et al. Cloning, overexpression, and characterization of a bacterial Ca2+-dependent phospholipase D. Protein Sci. Dec. 2002; 11(12):2958-68. (Year: 2002).*

(Continued)

*Primary Examiner* — Cynthia E Collins

(74) *Attorney, Agent, or Firm* — Dentons US LLP

(57) ABSTRACT

Methods for stimulating plant growth and/or promoting plant health using free enzymes or recombinant microorganisms that overexpress enzymes are provided. Plant seeds coated with free enzymes or recombinant microorganisms that overexpress enzymes are also provided. Compositions comprising a fertilizer and an enzyme or a recombinant microorganism that overexpresses an enzyme are provided. Modified enzymes having ACC deaminase activity, recombinant microorganisms expressing the modified enzymes, plant seeds treated with the modified enzymes or recombinant microorganisms, and methods for stimulating plant growth and/or promoting plant health using the modified enzymes or recombinant microorganisms are also provided.

12 Claims, No Drawings

Specification includes a Sequence Listing.

(56) References Cited

U.S. PATENT DOCUMENTS

| | | | |
|---|---|---|---|
| 7,919,678 B2 | 4/2011 | Mironov | |
| 7,960,148 B2 | 6/2011 | Steer et al. | |
| 8,097,769 B2 | 1/2012 | Sarria-Millan et al. | |
| 8,815,571 B2 | 8/2014 | Abbas et al. | |
| 9,068,189 B2 | 6/2015 | Mishra et al. | |
| 9,068,194 B2 | 6/2015 | Unkefer et al. | |
| 9,125,419 B2 | 9/2015 | Asolkar et al. | |
| 9,132,175 B2 | 9/2015 | Stewart et al. | |
| 9,476,058 B2 | 10/2016 | Lim | |
| 9,540,633 B2 | 1/2017 | Brinch-Pedersen et al. | |
| 9,573,980 B2 | 2/2017 | Thompson et al. | |
| 9,790,134 B2 * | 10/2017 | Bobeck | C05G 3/90 |
| 9,826,743 B2 | 11/2017 | Curtis et al. | |
| 9,845,342 B2 | 12/2017 | Thompson et al. | |
| 9,850,289 B2 | 12/2017 | Thompson et al. | |
| 9,932,275 B2 | 4/2018 | Puah et al. | |
| 10,072,252 B2 | 9/2018 | Chabriere et al. | |
| 10,173,938 B2 | 1/2019 | Rosas Gajardo et al. | |
| 10,244,765 B2 | 4/2019 | Pierce et al. | |
| 10,851,027 B2 | 12/2020 | Adam | |
| 11,124,460 B2 | 9/2021 | Thompson et al. | |
| 11,134,681 B2 | 10/2021 | Thompson et al. | |
| 11,406,107 B2 | 8/2022 | Curtis et al. | |
| 11,882,829 B2 | 1/2024 | Thompson et al. | |
| 11,905,315 B2 | 2/2024 | Thompson et al. | |
| 12,031,164 B2 | 7/2024 | Thompson et al. | |
| 12,351,532 B2 | 7/2025 | Thompson et al. | |
| 12,351,533 B2 | 7/2025 | Thompson et al. | |
| 12,391,729 B2 | 8/2025 | Thompson et al. | |
| 12,630,484 B2 | 5/2026 | Thompson et al. | |
| 2003/0026797 A1 | 2/2003 | Beudeker | |
| 2003/0167506 A1 | 9/2003 | Multani et al. | |
| 2003/0228679 A1 | 12/2003 | Smith et al. | |
| 2006/0088923 A1 | 4/2006 | Jacob et al. | |
| 2008/0233175 A1 | 9/2008 | Steer et al. | |
| 2008/0299185 A1 | 12/2008 | Ortenzi et al. | |
| 2009/0099079 A1 | 4/2009 | Emalfarb et al. | |
| 2009/0100536 A1 | 4/2009 | Adams et al. | |
| 2009/0104165 A1 | 4/2009 | Lorito et al. | |
| 2010/0205690 A1 | 8/2010 | Blasing et al. | |
| 2010/0233124 A1 | 9/2010 | Stewart et al. | |
| 2011/0165635 A1 | 7/2011 | Copenhaver et al. | |
| 2011/0230343 A1 | 9/2011 | Schroers et al. | |
| 2011/0281316 A1 | 11/2011 | Stewart et al. | |
| 2011/0321197 A1 | 12/2011 | Schon et al. | |
| 2012/0227134 A1 | 9/2012 | Schon et al. | |
| 2012/0259101 A1 | 10/2012 | Tan et al. | |
| 2012/0266327 A1 | 10/2012 | Sanz Molinero et al. | |
| 2013/0116124 A1 | 5/2013 | Baroja Fernandez et al. | |
| 2013/0216653 A1 | 8/2013 | Perkins et al. | |
| 2013/0324493 A1 | 12/2013 | Ma et al. | |
| 2014/0031576 A1 | 1/2014 | Toriumi | |
| 2014/0087942 A1 | 3/2014 | Trias et al. | |
| 2014/0259225 A1 | 9/2014 | Frank et al. | |
| 2014/0274707 A1 | 9/2014 | Thompson et al. | |
| 2014/0308748 A1 | 10/2014 | Mishra et al. | |
| 2014/0342905 A1 | 11/2014 | Bullis et al. | |
| 2015/0166889 A1 | 6/2015 | Huang et al. | |
| 2015/0274605 A1 | 10/2015 | Waldron et al. | |
| 2015/0299058 A1 | 10/2015 | Lamb et al. | |
| 2015/0368627 A1 | 12/2015 | Sun et al. | |
| 2016/0015039 A1 | 1/2016 | Pierce | |
| 2016/0031948 A1 | 2/2016 | Thompson et al. | |
| 2016/0073640 A1 | 3/2016 | Curtis et al. | |
| 2016/0108096 A1 | 4/2016 | Thompson et al. | |
| 2016/0236996 A1 | 8/2016 | Chaudhry | |
| 2016/0340658 A1 | 11/2016 | Lessl et al. | |
| 2017/0135353 A1 | 5/2017 | Thompson et al. | |
| 2017/0283472 A1 | 10/2017 | Curtis et al. | |
| 2017/0290339 A1 | 10/2017 | Curtis et al. | |
| 2017/0295785 A1 | 10/2017 | Curtis et al. | |
| 2017/0295797 A1 | 10/2017 | Curtis et al. | |
| 2017/0295798 A1 | 10/2017 | Curtis et al. | |
| 2017/0318808 A1 | 11/2017 | Curtis et al. | |
| 2017/0347664 A1 | 12/2017 | Thompson et al. | |
| 2020/0216828 A1 | 7/2020 | Thompson et al. | |
| 2022/0055961 A1 | 2/2022 | Thompson et al. | |
| 2022/0135492 A1 | 5/2022 | Thompson et al. | |
| 2023/0069595 A1 | 3/2023 | Curtis et al. | |
| 2023/0134066 A1 | 5/2023 | Thompson et al. | |
| 2023/0301340 A1 | 9/2023 | Coleman et al. | |
| 2023/0322642 A1 | 10/2023 | Thompson et al. | |
| 2024/0109819 A1 | 4/2024 | Thompson et al. | |
| 2024/0132418 A1 | 4/2024 | Thompson et al. | |
| 2024/0132419 A1 | 4/2024 | Thompson et al. | |
| 2024/0199709 A1 | 6/2024 | Thompson et al. | |
| 2024/0206466 A1 | 6/2024 | Thompson et al. | |
| 2024/0324599 A1 | 10/2024 | Thompson et al. | |
| 2025/0136525 A1 | 5/2025 | Thompson et al. | |
| 2025/0223240 A1 | 7/2025 | Thompson et al. | |
| 2025/0289770 A1 | 9/2025 | Thompson et al. | |
| 2025/0296895 A1 | 9/2025 | Thompson et al. | |
| 2025/0296896 A1 | 9/2025 | Thompson et al. | |
| 2025/0388630 A1 | 12/2025 | Thompson et al. | |
| 2026/0217621 A1 | 7/2026 | Thompson et al. | |
| 2026/0217622 A1 | 7/2026 | Thompson et al. | |
| 2026/0231954 A1 | 8/2026 | Thompson et al. | |

FOREIGN PATENT DOCUMENTS

| | | | |
|---|---|---|---|
| CN | 101434498 | | 5/2009 |
| CN | 101497542 | | 8/2009 |
| CN | 101481666 | | 8/2011 |
| CN | 104481666 | | 8/2011 |
| CN | 102674960 | | 9/2012 |
| CN | 103073337 | | 5/2013 |
| CN | 103086784 | A | 5/2013 |
| CN | 103467148 | | 12/2013 |
| CN | 103708907 | | 4/2014 |
| CN | 104388448 | | 3/2015 |
| CN | 104488964 | | 4/2015 |
| CN | 104498403 | | 4/2015 |
| CN | 104761307 | | 7/2015 |
| CN | 104829287 | | 8/2015 |
| CN | 104892199 | | 9/2015 |
| CN | 104909884 | | 9/2015 |
| CN | 104909920 | | 9/2015 |
| CN | 104945037 | | 9/2015 |
| CN | 104945164 | A | 9/2015 |
| CN | 105085053 | | 11/2015 |
| CN | 105152771 | | 12/2015 |
| CN | 105237137 | | 1/2016 |
| EP | 0184288 | | 6/1986 |
| EP | 0272002 | | 6/1988 |
| EP | 0792363 | A1 | 9/1997 |
| EP | 1205545 | | 5/2002 |
| EP | 1207197 | | 5/2002 |
| EP | 1 359 134 | A1 | 5/2003 |
| EP | 0 901 527 | B1 | 8/2005 |
| EP | 1185631 | B1 | 8/2006 |
| EP | 1 590 466 | B1 | 9/2010 |
| EP | 2276835 | B1 | 1/2011 |
| EP | 2357242 | | 8/2011 |
| EP | 2 561 760 | A2 | 2/2013 |
| EP | 2690080 | A1 | 1/2014 |
| EP | 2 069 504 | B1 | 6/2015 |
| EP | 2 658 961 | B1 | 8/2015 |
| ES | 2294348 | | 4/2008 |
| JP | S5785307 | | 5/1982 |
| JP | 253870 | A | 9/2000 |
| JP | 2007191401 | | 8/2007 |
| KR | 20030015943 | | 2/2003 |
| RU | 2160778 | C1 | 12/2000 |
| RU | 2503721 | C2 | 3/2009 |
| RU | 2529949 | C2 | 11/2009 |
| RU | 2012129907 | A | 6/2011 |
| RU | 2439148 | C1 | 1/2012 |
| SU | 829080 | | 5/1981 |
| WO | 1997032973 | | 9/1997 |
| WO | 02/00232 | A2 | 1/2002 |
| WO | 03/066846 | A1 | 8/2003 |
| WO | 2005/028654 | A1 | 3/2005 |
| WO | 2006/012366 | A2 | 2/2006 |
| WO | 2007022447 | | 2/2007 |

(56) References Cited

FOREIGN PATENT DOCUMENTS

| | | |
|---|---|---|
| WO | 2007/078127 A1 | 7/2007 |
| WO | 2007086898 A2 | 8/2007 |
| WO | 2008/017483 A2 | 2/2008 |
| WO | 2008030858 | 3/2008 |
| WO | 2008100112 | 8/2008 |
| WO | 2009/037329 A2 | 3/2009 |
| WO | 2010/046221 A1 | 4/2010 |
| WO | 2011/106794 A1 | 9/2011 |
| WO | 2011158203 | 12/2011 |
| WO | 2013/102934 A1 | 7/2013 |
| WO | 2013116700 | 8/2013 |
| WO | 2014/004487 A1 | 1/2014 |
| WO | 2014/145964 A1 | 9/2014 |
| WO | 2014159628 | 10/2014 |
| WO | 2015/118516 A1 | 8/2015 |
| WO | 2016/044529 | 3/2016 |
| WO | 2016/044533 A1 | 3/2016 |
| WO | 2016/044542 A1 | 3/2016 |
| WO | 2016/044548 | 3/2016 |
| WO | 2016/044575 | 3/2016 |
| WO | 2016/044661 A1 | 3/2016 |
| WO | 2016029646 | 3/2016 |
| WO | 2019/060574 A1 | 5/2019 |
| ZA | 858430 | 6/1986 |

OTHER PUBLICATIONS

Liu et al. How to achieve high-level expression of microbial enzymes. Bioengineered, Apr. 25, 2013;4(4):212-223. (Year: 2013).*
Borrelli et al. Recombinant Lipases and Phospholipases and Their Use as Biocatalysts for Industrial Applications. Int. J. Mol. Sci. Sep. 1, 2015;16(9):20774-840. (Year: 2015).*
U.S. Appl. No. 19/230,942, filed Jun. 6, 2025, Thompson, et al.
U.S. Appl. No. 19/230,965, filed Jun. 6, 2025, Thompson, et al.
U.S. Appl. No. 17/932,994, filed Sep. 16, 2022, Thompson et al.
Ahemad, M., et al., "Mechanisms and Applications of Plant Growth Promoting Rhizobacteria: Current Perspective," Journal of King Saud University—Science, 2014, pp. 1-20, vol. 26.
Bae, C., et al., "Multiple Classes of Immune-Related Proteases Associated with the Cell Death Response in Pepper Plants," PLoS One, May 2013, pp. 1-11, vol. 8, Issue 5, e63533.
Berlemont, R., et al., "Phylogenetic Distribution of Potential Cellulases in Bacteria," Applied and Environmental Microbiology, Mar. 2013, pp. 1545-1554, vol. 79, No. 5.
Chakraborty, U., et al., "Plant Growth Promotion and Induction of Resistance in Camellia sinesis by Bacillus megaterium," Journal of Basic Microbiology, 2006, pp. 186-195, vol. 46, No. 3.
Chapman, K. D., "Phospholipase Activity During Plant Growth and Development and in Response to Environmental stress," Trends in Plant Science, Nov. 1998, pp. 419-426, vol. 3, No. 11.
Choudhart, D. K., et al., "Interactions of *Bacillus* spp. and Plants—Witih Special Reference to Induced Systemic Resistance (ISR)," Microbiological Research, 2009, pp. 493-513, vol. 164, No. 5.
Corbineau, F., et al., "Improvement of Germination of Terminalia Ivorensis Seeds," Forest Genetic Resources Information No. 21, http://www.fao.org/docrep/006/v3030e/V3030E10.htm, 7 pages.
De Freitas, J. R., et al., "Phosphate-Solubilizing Rhizobacteria Enhance the Growth and Yield but not Phosphorus Uptake of Canola (*Brassica napus* L.)," Biology and Fertility of Soils, 1997, pp. 358-364, vol. 24, Issue 4.
Dong, Y. H., et al., "Identification of Quorum-Quenching N-Acyll Homoserine Lactonases from *Bacillus* Species," Applied and Environmental Microbiology, Apr. 2002, pp. 1754-1759, vol. 68, No. 4.
Dourado, M. N., et al., "Biotechnological and Agronomic Potential of Endophytic Pink-Pigmented Methylotrophic *Methylobacterium* spp.," BioMed Research International, 2015, 19 pages, Article ID 909016, vol. 2015, Hindawi Publishing Corporation.
Dowd, P. E., et al., "The Emerging Roles of Phospholipase C in Plant Growth and Development," Lipid Signaling in Plants, Plant Cell Monographs 16, 2010, pp. 23-37.
Faria, D. C., et al., "Endophytic Bacteria Isolated From Orchid and Their Potential to Promote Plant Growth," World Journal of Microbiology and Biotechnology, Feb. 2013, pp. 217-221, vol. 29, Issue 2.
Gamalero, E., et al., "Bacterial Modulation of Plant Ethylene Levels," Plant Physiology, Sep. 2015, pp. 13-22, vol. 169.
Glick, B. R., "Modulation of Plant Ethylene Levels by the Bacterial Enzyme ACC Deaminase," FEMS Microbiology Letters, 2005, pp. 1-7, vol. 251.
Gnanaraj, M., et al., "Isolation and Gene Expression Analysis of Phospholipase C in Response to Abiotic Stresses from Vigna radiata (L.) Wilczek," Indian Journal of Experimental Biology, Jun. 2015, pp. 335-341, vol. 53.
Goldberg, L. J., et al., "A Bacterial Spore Demonstrating Rapid Larvicidal Activity Against Anopheles Sergentii, Uranotaenia Unguiculata, Culex Univitattus, Aedes Aegypti and Culex Pipiens," Mosquito News, Sep. 1977, pp. 355-358, vol. 37, No. 3.
Guerchicoff, A., et al., "Identification and Characterization of a Previously Undescribed cyt Gene in *Bacillus thuringiensis* subsp. israelensis," Applied and Environmental Microbiology, Jul. 1997, pp. 2716-2721, vol. 63, No. 7.
Gujar, P. D . . . , et al., "Effect of Phytase from Aspergillus niger on Plant Growth and Mineral Assimilation in Wheat (*Triticum aestivum* Linn.) and its Potential for Use as a Soil Amendment," Journal of the Science and Food Agriculture, 2013, pp. 2242-2247, vol. 93, No. 9.
Hafeez, F. Y., et al., "PGPR: Versatile Tool to Combat Soil Borne Pathogens and Improve Plant Health," Aspects of Applied Biology, Crop Protection in Southern Britain, 2011, pp. 241-245, vol. 106.
Han, W., et al., "The Application of Exogenous Cellulase to Improve Soil Fertility and Plant GrowthDue to Acceleration of Straw Decomposition," Bioresource Technology, 2010, pp. 3724-3731, vol. 101.
Hartati, S., et al., "Overexpression of Poplar Cellulase Accelerates Growth and Disturbs the Closing Movements of Leaves in Sengon," Plant Physiology, Jun. 2008, pp. 552-561, vol. 147.
Hong, Y., et al., "Phospholipases in Plant Response to Nitrogen and Phosphorus Availability," Phospholipases in Plant Signaling, Signaling and Communication in Plants, 2014, pp. 159-180, vol. 20, Springer, Berlin, Heidelberg.
Hontzeas, N., et al., "Changes in Gene Expression in Canola Roots Induced by ACC-Deaminase-Containing Plant-Growth-Promotoing Bacteria," Molecular Plant-Microbe Interactions, Aug. 2004, pp. 865-871, vol. 17, No. 8.
Howard, G., et al., "Effects of Cellulolytic Ruminol Bacteria and of Cell Extracts on Germination of Euonymus americanus L. Seeds," Applied and Environmental Microbiology, Jan. 1988, pp. 218-224, vol. 54, No. 1.
Idriss, E. E., et al., "Extracellular Phytase Activity of Bacillus amyloliquefaciens FZB45 Contributes to its Plant-Growth-Promoting Effect," Microbiology, 2002, pp. 2097-2109, vol. 148.
International Search Report issued for PCT/US2017/022662 dated Jun. 5, 2017, 5 pages.
Islam, M. R, et al., "Characterization of Plant Growth-Promoting Traits of Free-Living Diazotrophic Bacteria and Their Inoculation Effects on Growth and Nitrogen Uptake of Crop Plants," Journal of Microbiology and Biotechnology, Oct. 2009, pp. 1213-1222, vol. 19, No. 10.
Jackson, W. T., "Effect of Pectinase and Cellulase Preparations on the Growth and Development of Root Hairs," Physiologia Plantarum, 1959, pp. 502-510, vol. 12.
Jeong, H., et al., "Draft Genome Sequence of the Paenibacillus polymyxa Type Strain (ATCC 842T), A Plant Growth-Promoting Bacterium," Journal of Bacteriologoy, 2011, pp. 5026-5027, vol. 193, No. 18.
Kim, J. F., et al., "Genome Sequence of the Polymyxim-Producing Plant-Probiotic Rhizobacterium Paenibacillus polymyxa E681," Journal of Bacteriology, 2010, pp. 6103-6104, vol. 192, No. 22.
Kong, Z., et al., "Effects of 1-aminocyclopropane-1-carboxylate (ACC) Deaminase-Overproducing Sinorhizobium meliloti on Plant Growth and Copper Tolerance of Medicago lupulina," Plant and Soil, Jun. 2015, pp. 383-398, vol. 391, Issue 1 (Abstract only, 7 pages).

(56) References Cited

OTHER PUBLICATIONS

Leite, H. A., et al., "Bacillus subtilis and Enterobacter cloacae endophytes from healthy Theobroma cacao L. Trees can systemically colonize seedlings and promote growth," Applied Microbiology and Biotechnology, Dec. 2012, pp. 2639-2651, vol. 97, No. 6.
Li, J., et al., "An ACC Deaminase Minus Mutant of Enterobacter cloacae UW4 No Longer Promotes Root Elongation," Current Microbiology, Aug. 2000, pp. 101-105, vol. 41, No. 2.
Li, W., et al., "Cloning of the Thermostable Cellulose Gene from the Newly Isolated Bacillus subtillus and its Expression in *Excherichia coli*," Molecular Biotechnology, 2008, pp. 195-201, vol. 40, Issue 2.
Li, Z, et al., "A Colorimetric Assay of 1-aminocyclopropane-1-carboxylate (ACC) Based on Ninhydrin Reaction for Rapid Screening of Bacteria Containing ACC Deaminase," Letters in Applied Microbiology, 2011, pp. 178-185, vol. 53.
Lin, Z, et al., "Recent Advances in Ethylene Research," Journal of Experimental Botany, 2009, pp. 3311-3336, vol. 60, Issue 12.
Liu, J. L., et al., "Effects of Two Plant Growth-Promotoing Rhizobacteria Containing 1-aminocyclopropane-1-carboxylate Deaminase on Oat Growth in Petroleum-Contaminated Soil," Internaitonal Journal of Environmental Science and Technology, Dec. 2015, pp. 3887-3894, vol. 12, Issue 12 (Abstract only, 6 pages).
Liu, W. et al., "THIS1 is a Putative Lipase that Regulates Tillering, Plant Height, and Spikelet Fertility in Rice," Journal of Experimental Botany, 2013, pp. 1-14, vol. 64, No. 14.
Medie< F., et al., "Genome Analysis Highlight the Different Biological Roles of Cellulases," Nature Reviews, Microbiology, Mar. 2012, pp. 227-234, vol. 10.
Meldau, D. G., et al., "A Native Plant Growth Promoting Bacterium, *Bacillus* sp.B55, Rescues Growth Performance of an Ethylene-Insensitive Plant Genotype in Nature," Frontiers in Plant Science, Jun. 2012, pp. 1-13, vol. 3, Article 112.
Mercado, J. A., et al., "Expression of the B-1,3-Glucanase Gene bgn13.1 From Trichoderma harzianum in Strawberry Increases Tolerance to Crown Rot Diseases But Interferes with Plant Growth," Transgenic Research, 2015, 11 pages, vol. 24, No. 6.
Ngamau, C., "Endophytic bacterial associated with bananas (*Musi* spp.) in Kenya and their potential as biological fertilizers," A theses submitted in fulfillment for the degree of Doctor of Philosophy in Plant Science in the Jomo Kenyatta University of Agriculture and Technology, 2013, 191 pages.
Oh, T. K., et al., "Expression of Aspergillus nidulans phy Gene in Nicotiana benthamiana Produces Active Phytase with Broad Specificities," International Journal of Molecular Sciences, 2014, pp. 15571-15591, vol. 15, No. 9.
Penrose, D. M., et al., "Levels of ACC and Related Compounds in Exudate and Extracts of Canola Seeds Treated with ACC Deaminase-Containing Plant Growth-Promoting Bacteria," Canadian Journal of Microbiology, Apr. 2001, pp. 368-372, vol. 47, No. 4.
Phitsuwan, P., et al., "Present and Potential Applications of Cellulases in Agriculture, Biotechnology, and Bioenergy," Folia Microbiology, 2013, pp. 163-176, vol. 58.
Pilar-Izquierdo, M. D., et al., "Barley Seed Coating with Free and Immobilized Alkaline Phosphatase to Improve P Uptake and Plant Growth," Crops and Soils Research Paper, Journal of Agricultural Science, 2012, pp. 691-701, vol. 150.
Ping, R., et al., "Effect of Cellulase on Germination of Pinus tabulaeformis Seeds and Grow Seedlings," Journal of Northwest Forestry College, 2005, pp. 78-79, vol. 20, No. 1 (Abstract, 1 page).
Reetha, S., et al., "Screening of Cellulase and Pectinase by Using Pseudomonas fluorescence and Bacillus subtilis," International Letters of Natural Sciences, 2014, pp. 75-80, vol. 8, No. 2.
Saleh, S., et al., "Involvement of gacS and rpoS in Enhancement of the Plant Growth-Promoting Capabilities of Enterobacter cloacae CAL2 and UW4," Canadian Journal of Microbiology, Aug. 2001, pp. 698-705, vol. 47, No. 8.
Sales, J., et al., "Coffee (*coffee arabica* L.) Seeds Germination After Treatment With Different Concentrations and Embedding Times in Cellulase," Ciencia e Agrotecnologia [online], 2003, pp. 557-564, vol. 27, No. 3, ISSN 1413-7054, http://dx.doi.org/10,1590/S1413-70542003000300009, (Abstract only 1 page).
Shahid, M., et la., "Root Colonization and Growth Promotion of Sunflower (*Helianthus annuus* L.) by Phosphate Solubilizing *Enterobacter* sp. Fs-11," World Journal of Microbiology and Biotechnology, 2012, pp. 2749-2758, vol. 28, Issue 8.
Shani, Z., et al., "Expression of Endo-1,4-B-Gllucanase (cel1) in *Arabidopsis thaliana* is Associated with Plant Growth Xylem Development and Cell Wall Thickening," Plant Cell Reports, 2006, pp. 1067-1074, vol. 25, No. 10.
Shankar, M., et al., "Root Colonization of a Rice Growt Promoting Strain of Enterobacter cloacae," Journal of Basic Microbiology, 2011, pp. 523-530, vol. 51, No. 5.
Shao, J., et al., "Contribution of Indole-3-acetic Acid in the Plant Growth Promotion b the Rhizospheric Strain Bacillus amyloliquefaciens SQR9," Biology and Fertility of Soils, Apr. 2015, pp. 321-330, vol. 51, Issue 3.
Shen, M., et al., "Effect of Plant Growth-Promoting Rhizobacteria (PGPRs) on Plant Growth, Yield, and Quality of Tomato (*Lycopersicon esculentum* Mill.) Under Simulated Seawater Irrigation," The Journal of General and Applied Microbiology, 2012, pp. 253-262, vol. 58, No. 4.
Siddikee, Md., A., et al., "Halotolerant Bacteria with ACC Deaminase Activity Alleviate Salt Stress Effect in Canola Seed Germination," Journal of the Korean Society for Applied Biological Chemistry, Apr. 2015, pp. 237-241, vol. 58, Issue 2.
Singh, B., et al., "Microbial Phytases in Phosphorus Acquisition and Plant Growth Promotion," Physiology and Molecular Biology of Plants, Apr.-Jun. 2011, pp. 93-103, vol. 17, Issue 2.
Singh, B., et la., "Plant Growth Promotion by an Extracellular HAP-Phytase of a Thermophilic Mold Sporotrichum thermophile," Applied Biochemistry and Biotechnology, Mar. 2010, pp. 1267-1276, vol. 160, Issue 5.
Smirnova, I., et al., "The Effect of Inoculaton by Cellulolytic Bacteria Bacillus cytaseus on Wheat Productivity," Plant Growth-Promoting Rhizobacteria (PGPR) for Substainable Agriculture, Proceedings of the 2nd Asian PGPR Conference, Aug. 21-24, 2011, pp. 185-191, Beijing, P. R. China.
Stearns, J. C., et la., "Effects of Bacterial ACC Deamnase on *Brassica napus* Gene Expression," Molecular Plant-Microbe Interactions, 2012, pp. 668-676, vol. 25, No. 5.
Trivedi, P., et al., "Plant Growth Promotion Abilities and Formulation of Bacillus megaterium Strain B 388 (MTCC6521) Isolated from a Temperate Himalayan Location," Indian Journal of Microbiology, 2008, pp. 342-347, vol. 48, Issue 3.
Vendan, R. T., et al., "Diversity of Endophytic Bacteria in Ginseng and Their Potential for Plant Growth Promotion," The Journal of Microbiology, 2010, pp. 559-565, vol. 48, Issue 5.
Wang, X., et al., "PLD: Phospholipase Ds in Plant Signaling," Phospholipases in Plant Signaling, 2013, pp. 3-26.
Written Opinion issued for PCT/US2017/022662 dated Jun. 5, 2017, 6 pages.
Yadav, S., et al., "Diversityand Phylogeny of Plant Growth-Promoting Bacilli from Moderately Acidic Soil," Journal of Basic Microbiology, Feb. 2011, pp. 98-106, vol. 51, Issue 1.
Zeigler, D. R., "Bacillus Thuringiensis Bacillus Cereus," Bacillus Genetic Stock Center Catalog of Strains, 1999, Seventh Edition, vol. 2, 58 pages.
Fan, L., et al., "Antisense Suppression of Phospholipase D(alpha) Retards Abscisic Acid- and Ethylene-Promoted Senescence of Postharvest *Arabidopsis* Leaves," The Plant Cell, Dec. 1997, pp. 2183-2196, vol. 9.
Glass, M., et la., "Endo-(beta)-1,4-Glucanases Impact Plant Cell Wall Development by Influencing Cellulose Crystallizaiton," Journal of Integrative Plant Biology, Apr. 2015, pp. 396-410, vol. 57, Issue 4.
Hong, Y., et al., "Phospholipase D(alpha)3 is Involved in the Hyperormotic Response in *Arabidopsis*," The Plant Clel, Mar. 208, pp. 803-816, vol. 20.
Li, M., et al., Overexpression of Patatin-Related Phospholipase AIll(delta) Altered Plant Growth and Increased Seed Oil Content in Camelina, Plant Biotechnology Journal, 2015, pp. 766-778, vol. 13.

(56) References Cited

OTHER PUBLICATIONS

Shani, Z, et al., "Growth Enhancement of Transgenic Poplar Plants by Overexpression of *Arabidopsis thaliana* Endo-1,4-beta-Gllucanase (cel1)," Molecular Breeding, 2004, pp. 321-330, vol. 14.
Sadowski, M. I., et al., "The Sequence-Structure Relationship and Protein Function Prediction," Current Opinion in Structural Biology, 2009, pp. 357-362, vol. 19, No. 3.
Seffernick, J. L., et al., "Melamine Deaminase and Afrazine Chlorohydrolase: 98 Percent Identical but Functionally Different," Journal of Bacteriology, Apr. 2001, pp. 2405-2410, vol. 183, No. 8.
Sloma, A., et al., "Cloning and Characterization of the Gene for an Additional Extracellular Serine Protease of Bacillus subtilis," Journal of Bacteriology, Nov. 1991, pp. 6889-6895, vol. 173, No. 21.
Tang, S., et al., "Identification of Dehalobacter Reductive Dehalogenases that Catalyse Dechlorination of Chloroform, 1,1,1-Trichlorethane and 1,1-Dichlorethane," Phil.
Thallinger, B., et al., "Antimicrobial Enzymes: An Emerging Strategy to Fight Microbes and Microbial Biofilms," Biotechnology Journal, 2013, pp. 97-109, vol. 8, No. 1.
Valbuzzi, A., et al., "A Novel Member of the Subtilsin-like Protease Family from Bacillus subtilis," Microbiology, 1999, pp. 3121-3127, vol. 145, Par 11.
Bewley, J. D., "Breaking Down the Walls—A Role for Endo-beta-mannanase in Release from Seed Dormancy?," Trends in Plant Science, Dec. 1997, pp. S1360-S1365, vol. 2, No. 12.
Leviatov, S., et al., "Involvement of Endomannanase in the Control of Tomato Seed Germination Under Low Temperature Conditions," Annals of Botany, 1995, pp. 1-6, vol. 76.
Partial Supplementary European Search Report issued for EP17767505.5 dated Feb. 26, 2020, 5 pages.
Rodriguez-Gacio, M. C., et al., "Softening-up Mannan-rich Cell Walls," Journal of Experimental Botany, 2012, pp. 3975-3988, vol. 63, No. 11.
Yang, P., et al., "A Novel Beta-Mannanase with High Specific Activity from Bacillus circulans CGMCC1554: Gene Cloning, Expression and Enzymatic Characterization," Applied Biochemistry and Biotechnology, 2009, pp. 85-94, vol. 159, No. 1.
Akinrinlola, et al., "Evaluation of Bacillus Strains for Plant Growth Promotion and Predictability of Efficacy b In Vitro Physiological Traits," Intl. Journal of Microbiology, vol. 2008, Article ID 5686874, 11 pages.
Benfield, et al., "Structural Studies Examining the Substrate Specificity Profiles of PC-PLCBc Proteiins Variants" (2007), vol. 460, No. 1, pp. 41-47.
Cheng, "Purification and Characterization of a Thermostable Beta-Mannanase from Bacillus Subtilis BE-91: Potential Application in Inflammatory Diseases" BioMed Research International (2016) vol. 2016, Article ID 6380147, pp. 1-7.
UniProtKB Accession No. W7KRH1, Intracellular Serine-Protease, Apr. 16, 2014, 2 pages.
UniProtKB Accession No. A0A380XNG8, Intracellular Serine Protease, Nov. 7, 2018, 1 page.
Di Benedetto, et al., "Isolation, Screening, and Characterization of Plant-Growth-Promoting Bacteria from Durum Wheat Rhizosphere to Improve N and P Nutrient Use Efficiency," Microorganisms (2019) vol. 7, No. 541, pp. 1-18.
Dowd and Gilrow, "The Emerging Roles of Phospholipase C in Plant Growth and Development," Plant Cell Monographs (2009) vol. 16, pp. 23-27.
Dunne, C., et al., "Overproduction of an Inducible Extracellular Serine Protease Improves Biological Control of Pythium ultimum by Stenotrophomonas maltophilia Strain W81," Microbiology, (2000) vol. 146, Part 8 pp. 2069-2078.
Emi, et al., "Crystllization and Some Properties of Mannanase" Agricultural and Biological Chemistry (1972) vol. 36, No. 6, pp. 991-1001.
Geng et al., "A Novel Serine Protease, Sep1 from Bacillus Firmus DS-1 Has Nematicidal Activityand Degrades Multiple Intestinal-Associated Nematode Proteins," Scientific Reports, (2016) vol. 6, pp. 1-12.
Khan, N., et al., "Antifungal Activity of *Bacillus* Species Against Fusarium and Analysis of the Potential Mechanisms Used in Biocontrol," Frontiers in Microbiology (2018) vol. 9, Article 2363, pp. 1-12.
Li, et al., "Structure Prediction and Enzymatic Properties of Phytase PhyS," Advances in Enzyme Research (2019) vol. 7, pp. 57-65.
Quan, et al., "Purification and Properties of a Phytase from Candida Krusei WZ-001," Journal of Bioscience (2002) vol. 94, No. 5, pp. 419-425.
Quecine, et al., "Sugarcane Growth Promotion by the Endoophytic Bacterium Pantoea Agglomerans 33.1," Applied and Environmental Microbiology (2012) vol. 78, No. 21, pp. 7511-7518.
Raddadi, et al., "Screening of Plant Growth Promoting Traits of Bacillus Thuringiensis" Annals of Microbiology (2008) vol. 58, No. 1, pp. 47-52.
Van Pouderoyen, et al., "Structural Insights Into the Processivity of Endopolygalacturonase I form Aspergillus niger," FEBS Letters (2003) vol. 554, No. 3, pp. 462-466.
Yen, Y. H., et al., "An Antifungal Protease Produced byPseudomonas aeruginosa M-1001 with Shrimp and Crab Shell Powder as a Carbon Source," Enzyme and Microbial Technology (2006) vol. 39, pp. 311-317.
K. Jetiyanon, et al., "Film Coating of Seeds with Bacillus Cereus RS87 Spores for Early Plant Growth Enhancement," Canadian Journal of Microbiology (2008) vol. 54, pp. 861-867.
U.S. Appl. No. 18/680,688, filed May 31, 2024, Thompson, et al.
U.S. Appl. No. 18/615,771, filed Mar. 25, 2024, Thompson, et al.
Matos. Invitation to Pay Additional Search Fees. PCT/US24/21327, mailed May 31, 2024.
S. Shah, et al., "Isolation and Characterization of ACC Deaminase Genes From Two Different Plant Growth-Promoting Rhizobacteria" Canadian Journal of Microbiology (1998) vol. 44, pp. 833-843.
Vasil et al. Herbicide Resistant Fertile Transgenic Wheat Plants Obtained by Microprojectile Bombardment of Regenerable Embryogenic Callus Bio/Technology vol. 10, pp. 667-674 (1992).
UniProt\KB Accession Nno. C4PKL1, Purple acid phosphatase, Jul. 7, 2009.
Murashige, T. and Skoog, F. (1962) A Revised Medium for Rapid Growth and Bioassays with Tobacco Tissue Cultures, Physiologia Plantarum 15, 473-497.
Siddikee, Md. A., et al. , "Regulation of Ethylene Biosynthesis Under Salt Stress in Red Pepper (*Capsicum annum* L.) by 1-Aminocclopropane-1-Carboxylic Acid (ACC) Deaminase-Producing Halotolerant Bacteria," Journal of Plant Growth Regulation, 2012, pp. 265-272, vol. 31, Issue 2.
Brandt Steric P DS Water Soluble Fertilizer Product Description, Brandt Consolidated, Inc., Springfield, IL, May 2013.
UniProtKB Accession No. P23903, Glucan endo-1,3-beta-glucosidase A1, Nov. 1, 1991.
UniProtKB Accession No. 052864, Phosphatidyl-degrading phospholipase C, Jun. 1, 1998.
Bailey-Smith et al., The ExsA protein of Bacillus cereus is required for assembly of coat and exosporium into the spore surface, J. Bacteriol, 187(11): 3800-3806, 2005.
Boydston et al., The ExsY protein is required for complete formation of the exosporium of Bacillus anthracis, J Bacteriol, 188(21): 7440-7448, 2006.
Crane et al., Bacterial Nitric Oxide Synthases, Annual Review in Biochemistry 79:445-470, 2010.
Thompson, Amino-Terminal Sequences of the Bacillus anthracis Exosporium Proteins BclA and BclB Important for Localization and Attachment to the Spore Surface, A Thesis presented to the Faculty of the Graduate School at the University of Missouri-Columbia, 2008.
Thompson et al., Assembly of the BclB Glycoprotein into the Exosporium and Evidence for its role in the Formation of Exosporium "cap" Structure in Bacillus anthracis, Molecular Microbiology 86(5): 1073-1084, 2012.
Thompson and Stewart, Targeting of the BclA and BclB proteins to the Bacillus anthracis spore surface, Mol Microbiol, 70(2): 421-434, 2008.

(56) References Cited

OTHER PUBLICATIONS

Akinrinlola, et al., "Evaluation of Bacillus Strains for Plant Growth Promotion and Predictability of Efficacy by In Vitro Physiological Traits", Intl. Journal of Microbioloby vol. 2008 Article ID 5686874, 11 pages.
Benfield, et al., "Structural Studies Examining the Substrate Specificity Profiles of PC-PLCBc Proteins Variants" (2007) vol. 460, No. 1 pp. 41-47.
Cheng, "Purification and Characterization of a Thermostable β-Mannanase from Bacillus Subtilis BE-91: Potential Application in Inflammatory Diseases" BioMed Research International (2016) vol. 2016, Article ID 6380147, pp. 1-7.
Singh, et al. Protein Engineering Approaches in the Post-Genomic Era. Current Protein and Peptide Science, vol. 18 (1), pp. 1-11, (2017).
Zhang, et al. Propagated Perturbations from a Peripheral Mutation Show Interactions Supporting WW Domain Thermostability. Structure, vol. 26(11), pp. 1474-1485, (2018).
GenBank Accession No. P33378. Dated Jun. 11, 2014. Retrieved from <https://www.ncbi.nlm.nih.gov/protein/P33378>.
Aakre, et al. Inhibition of Bacillus cereus phospholipase C by univalent anions. The Biochemical Journal 203, 799-801, (1982).
Goldfine, et al. "Nonspecific phospholipase C of Listeria monocytogenes: activity on phospholipids in Triton X-100-mixed micelles and in biological membranes". J Bacteriol 175, 4298-4306, (1993).
Huang, et al. "Recombinant broad-range phospholipase C from Listeria monocytogenes exhibits optimal activity at acidic pH". Biochimica et Biophysica Acta (BBA)—Proteins and Proteomics 1864(6), 697-705, (2016).
Monturiol-Gross, et al. "Bacterial phospholipases C with dual activity: phosphatidylcholinesterase and sphingomyelinase". FEBS Open Bio, vol. 11(12), pp. 3262-3275, (2021).
Otnaess. "The hydrolysis of sphingomyelin by phospholipase C from Bacillus cereus". FEBS Letters 114, 202-204, (1980).
Pomerantsev, et al. "Phosphatidylcholine-specific phospholipase C and sphingomyelinase activities in bacteria of the Bacillus cereus group". Infect Immun. (2003); 71(11): 6591-606.
Tan, et al. "Cloning, overexpression, refolding, and purification of the nonspecific phospholipase C from Bacillus cereus". Protein Expr Purif 10, 365-372, (1997).
Zuckert, et al. "Modulation of enzymatic activity and biological function of Listeria monocytogenes broad-range phospholipase C by amino acid substitutions and by replacement with the Bacillus cereus ortholog". Infect Immun 66, 4823-4831, (1998).
Han, W. et al., "Short-term effects of exogenous protease application on soil fertility", European Journal of Soil Biology, 46, pp. 144-150, Feb. 2, 2010 (Feb. 2, 2010).
Molla, A. et al., "Trichoderma-Enriched Biofertilizer Enhances Production and Nutritional Quality of Tomato (*Lycopersicon esculentum* Mill.) and Minimizes NPK Fertilizer Use", Agriculatural Research, 1, pp. 265-272, Jul. 5, 2012 (May 7, 2012).
Extended European Search Report issued in EP Application No. 24152365.3, dated Oct. 11, 2024.
"Seed priming," Homegrown Goodness, dated Mar. 13, 2012, retrieved from <https://alanbishop.proboards.com/thread/6126/seed-priming>, retrieved Apr. 29, 2025.
Xu et al., Isolation and Potential of *Ochrobactrum* sp. NW-3 to Increase the Growth of Cucumber, Int. J. Argric. Pol. Res. 3(9): 341-350, 2015.
Fidanza, "Fairy Ring 101." USGA Sponsored, Green Section Record, (2009), retrieved from <https://www.usga.org/content/dam/usga/pdf/imported/course-care/090308.pdf>.
U.S. Appl. No. 18/392,771, filed Dec. 21, 2023, Thompson, et al.
U.S. Appl. No. 18/398,650, filed Dec. 28, 2023, Thompson, et al.
Simontacchi, M., et al., "Enzymatic Sources of Nitric Oxide during Seed Germination." In: Lamattina, L., Polacco, J.C. (eds) Nitric Oxide in Plant Growth, Development and Stress Physiology. Plant Cell Monographs, vol. 5. Springer, Berlin, Heidelberg. (2006).
Zheng, et al., "Exogenous nitric oxide improves seed germination in wheat against mitochondrial oxidative damage induced by high salinity", Environmental and Experimental Botany, vol. 67, Issue 1. pp. 222-227; (2009).
U.S. Appl. No. 18/461,008, filed Sep. 5, 2023, Curtis, et al.
U.S. Appl. No. 18/476,259, filed Sep. 27, 2023, Thompson, et al.
U.S. Appl. No. 18/476,264, filed Sep. 27, 2023, Thompson, et al.
U.S. Appl. No. 18/476,270, filed Sep. 27, 2023, Thompson, et al.
Giorno, et al. "Morphogenesis of the *Bacillus anthracis* Spore". Journal of Bacteriology, Feb. 2007, vol. 189 (3), p. 691-705.
Sabaratnam, et al. "Mechanism of antagonism by *Streptomyces griseocarneus* (strain Di944) against fungal 1 pathogens of greenhouse-grown tomato transplants." Canadian Journal of Plant Biology, vol. 37 (2), pp. 197-211, (2015).
Saile et al., Bacillus anthracis multiplication, persistence, and genetic exchange in the rhizosphere of grass plants, Appl. Environ. Microbiol., 72(5):3168-3174, 2006.
U.S. Appl. No. 19/223,300, filed May 30, 2025, Thompson, et al.
Vikram et al., Production of Plant Growth Promoting Substances by Phosphate Solubilizing Bacteria Isolated from Vertisols, Journal of Plant Sciences 2(3): 326-333, 2007.
Dennis, Kinetic dependence of phospholipase A2 activity on the detergent Triton-X100, Journal of Lipid Research 14(2):152-159, 1973.
De La Cruz et al., Purification and characterization of an endo-beta-1,6-glucanase from Trichoderma harzianum that is related to its mycoparasitism, J. Bacteriol. 177(7):1864-71, 1995.
Hontzeas et al., Expression and characterization of 1-aminocyclopropane-1-carboxylate deaminase from the rhizobacterium Pseudomonas putida UW4: a key enzyme in bacterial plant growth promotion, Biochimica et Biophysical Acta (FFA)-Proteins and Proteomics 1703(1):11-19, 2004.
Gelb et al., Cloning and recombinant expression of a structurally novel human secreted phospholipase A2, Journal of Biological Chemistry 275(51):39823-39826, 2000.
Gellatly et al., Purification and characterization of a potato tuber acid phosphatase having significant phosphotyrosine phosphatase activity, Plant Physiology 106(1):223-232, 1994.
Kashyap et al., Production, purification, and characterization of pectinase from a *Bacillus* sp. DT7, World Journal of Microbiology and Biotechnology 16:277-282, 2000.
Slein & Logan Jr, Partial purification and properties of two phospholipases of Bacillus cereus, J. Bacteriol. 85(2):369-81, 1963.
U.S. Appl. No. 19/091,458, filed Mar. 26, 2025, Thompson, et al.
Wang, Y. et al.; "Two distinct manganese-containing superoxide dismutase genes in Bacillus cereus: their physiological characterizations and roles in surviving in wheat rhizosphere"; FEMS Microbiology Letters; vol. 272(2), pp. 206-213; 2007.
Inaoka, T. et al., "SodA and Manganese are Essential for Resistance to Oxidative Stress in Growing and Sporulationg Cells of Bacillus subtilis"; Journal of Bacteriology, vol. 181, No. 6; pp. 1939-1943; 1999.
Rasko, et al., UniProt Accession No. Q738B1—"DUF4183 domain-containing protein"—Bacillus cereus, (strain ATCC 10987/ NRS 248), (2004). Retrieved from <https://www.uniprot.org/uniprotkb/Q738B1/entry>.
U.S. Appl. No. 19/462,015, filed Jan. 28, 2026, Thompson, et al.
U.S. Appl. No. 19/462,018, filed Jan. 28, 2026, Thompson, et al.
U.S. Appl. No. 19/253,154, filed Jun. 27, 2025, Brian Thompson, et al.
Australian Office Action regarding Australian App. No. 2025201978, dated May 7, 2026.
Thomas, P.W. et al., "The quorum-quenching lactonase from Bacillus thuringiensis is a metalloprotein," Biochemistry, 2005, vol. 44, p. 7559-7569.
European Office Action regarding European App. No. 17767505.5, mailed Aug. 8, 2025.
Misas-Villamil, J. et al., "Enzyme-inhibitor interactions at the plant-pathogen interface", Elsevier, Current Opinion in Plant Biology, 2008, pp. 380-388.

(56) References Cited

OTHER PUBLICATIONS

Adav, S. et al., "Quantitative Secretomic Analysis of Trichoderma reesei Strains Reveals Enzymatic Composition for Lignocellulosic Biomass Degradation," Molecular and Cellular Proteomics, 11(7):M111.012419, 2012.
Pozo, M. et al., "Functional analysis of tvsp1, a serine protease-encoding gene in the biocontrol agent Trichoderma virens," Fungal Genetics and Biology 41(3): 336-348, 2004.
U.S. Appl. No. 19/469,859, filed Sep. 26, 2025, Thompson, et al.
Khan et al., "Microbial Strategies for Crop Improvement", Springer-Verlag Berlin, Heidelberg, pp. 1-358, 2009.
Trouillefou et al., "Protected activity of a phytase immobilized in mesoporous silica with benefits to plant phosphorus nutrition", J Sol-Gel Sci Technol, 74, pp. 55-65, 2015.
Office Action regarding Canada App. No. 3,221,950, dated Jul. 16, 2026.
Office Action regarding Australia App. No. 2024219963, dated Aug. 4, 2026.

* cited by examiner

METHODS FOR PROMOTING PLANT HEALTH USING FREE ENZYMES AND MICROORGANISMS THAT OVEREXPRESS ENZYMES

CROSS-REFERENCE TO RELATED APPLICATIONS

This application is a continuation of co-pending U.S. patent application Ser. No. 18/302,458, filed Apr. 18, 2023, which is a continuation of Ser. No. 17/459,019, filed Aug. 27, 2021, which is a divisional of U.S. patent application Ser. No. 15/460,468, filed Mar. 16, 2017, now U.S. Pat. No. 11,124,460, issued Sep. 21, 2021, which claims the benefit of U.S. Provisional Application Ser. No. 62/309,426, filed on Mar. 16, 2016, the entirety of each of which is herein incorporated by reference.

INCORPORATION OF SEQUENCE LISTING

The sequence listing that is contained in the XML file named "LMNE115USC4_ST26", which is 183 kilobytes as measured in Microsoft Windows operating system and was created on Sep. 8, 2023, is filed electronically herewith and incorporated herein by reference.

FIELD OF THE INVENTION

Methods for stimulating plant growth and/or promoting plant health using free enzymes or recombinant microorganisms that overexpress enzymes are provided. Plant seeds treated with free enzymes or recombinant microorganisms that overexpress enzymes are also provided. Compositions comprising a fertilizer and an enzyme or a recombinant microorganism that overexpresses an enzyme are provided. Modified enzymes having ACC deaminase activity, recombinant microorganisms expressing the modified enzymes, plant seeds treated with the modified enzymes or recombinant microorganisms, and methods for stimulating plant growth and/or promoting plant health using the modified enzymes or recombinant microorganisms are also provided.

BACKGROUND OF THE INVENTION

Within the zone surrounding a plant's roots is a region called the rhizosphere. In the rhizosphere, bacteria, fungi, and other organisms compete for nutrients and for binding to the root structures of the plant. Both detrimental and beneficial bacteria and fungi can occupy the rhizosphere. The bacteria, fungi, and the root system of the plant can all be influenced by the actions of enzymes in the rhizosphere. Augmentation of soil or treatment of plants with certain of these enzymes would have beneficial effects on the overall populations of beneficial soil bacteria and fungi, create a healthier overall soil environment for plant growth, improve plant growth, and provide for the protection of plants against certain bacterial and fungal pathogens. The environment around the roots of a plant (the rhizosphere) is a unique mixture of bacteria, fungi, nutrients, and roots that has different qualities than that of native soil. The symbiotic relationship between these organisms is unique, and could be altered for the better with inclusion of exogenous proteins.

Thus, there exists a need in the art for a method for effectively delivering enzymes and other proteins to plants. Furthermore, there exists a need in the art for a enhancing the response of plants to enzymes and providing benefit to the grower.

SUMMARY OF THE INVENTION

An enzyme is provided. The enzyme comprises an amino acid sequence encoding an enzyme having 1-aminocyclopropane-1-carboxylate deaminase (ACC deaminase) activity and a signal peptide. The signal peptide results in secretion of the enzyme when the enzyme is expressed in a microorganism. Recombinant microorganisms that express the enzyme are also provided. Formulations comprising the enzyme or the recombinant microorganism and an agriculturally acceptable carrier are also provided. Plant seeds treated with the enzyme, the recombinant microorganism, or the formulation are also provided.

An enzyme having ACC deaminase activity is provided. The amino acid sequence of the enzyme comprises at least one amino acid substitution relative to the sequence of a wild-type D-cysteine desulfhydrase or ACC deaminase enzyme from a *Bacillus* genus bacterium. The amino acid substitution results in increased ACC deaminase activity as compared to the ACC deaminase as compared to ACC deaminase activity of the wild-type D-cysteine desulfhydrase or ACC deaminase enzyme under the same conditions. Recombinant microorganisms that express the enzyme are also provided. Formulations comprising the enzyme or the recombinant microorganism and an agriculturally acceptable carrier are also provided. Plant seeds treated with the enzyme, the recombinant microorganism, or the formulation are also provided.

A method for stimulating plant growth and/or promoting plant health is provided. The method comprises applying any of the enzymes having ACC deaminase activity or a formulation comprising such an enzyme and an agriculturally acceptable carrier to a plant growth medium, a plant, a plant seed, or an area surrounding a plant or a plant seed.

Another method for stimulating plant growth and/or promoting plant health is provided. The method comprises applying any of the recombinant microorganisms that express an enzyme having ACC deaminase activity or a formulation comprising such a recombinant microorganism and an agriculturally acceptable carrier to a plant growth medium, a plant, a plant seed, or an area surrounding a plant or a plant seed.

Yet another method for stimulating plant growth and/or promoting plant health is provided. The method comprises applying a free enzyme to a plant growth medium, a plant, a plant seed, or an area surrounding a plant or a plant seed. The enzyme is selected from a phospholipase, a lipase, a xylanase, a xylosidase, a lactonase, a mannanase, a pectinase, a chitosanase, a protease, an acid phosphatase, a non-cellulolytic glucanase, an ACC deaminase, and combinations of any thereof.

Another method for stimulating plant growth and/or promoting plant health is provided. The method comprises applying two or more free enzymes to a plant growth medium, a plant, a plant seed, or an area surrounding a plant or a plant seed. The enzymes are independently selected from a phospholipase, a lipase, a xylanase, a xylosidase, a lactonase, a chitosanase, a protease, a phytase, an acid phosphatase, a mannanase, a pectinase, a glucanase, and an ACC deaminase.

A further method for stimulating plant growth and/or promoting plant health is provided. The method comprises applying a free enzyme to a plant or a plant seed. The enzyme comprises a glucanase. Applying the enzyme to the plant seed comprises: (a) applying the enzyme to the plant seed at the time of planting; or (b) coating the plant seed with the enzyme.

Yet another method for stimulating plant growth and/or promoting plant health is provided. The method comprises applying a free enzyme to a plant growth medium, a plant, a plant seed, or an area surrounding a plant or a plant seed. The enzyme comprises a glucanase. The method further comprises applying an expansin protein to the plant growth medium, the plant, the plant seed, or the area surrounding a plant or a plant seed.

Another method for stimulating plant growth and/or promoting plant health is provided. The method comprises applying a free enzyme to a plant or a plant seed. The enzyme comprises a phytase.

A further method for stimulating plant growth and/or promoting plant health is provided. The method comprises applying a fertilizer and a free enzyme to a plant growth medium, an area surrounding a plant or a plant seed, or to a plant or a plant seed. The free enzyme comprises a phytase.

A further method for stimulating plant growth and/or promoting plant health is provided. The method comprises applying a recombinant microorganism to a plant growth medium, a plant, a plant seed, or an area surrounding a plant or a plant seed. The recombinant microorganism expresses an enzyme or an expansin protein, wherein expression of the enzyme or expansin protein is increased as compared to the expression level of the enzyme or expansin protein in a wild-type microorganism of the same kind under the same conditions. The enzyme is selected from a phospholipase, a lipase, a xylanase, a xylosidase, a lactonase, a chitosanase, a glucanase, a mannanase, a pectinase, a protease, a phytase, an acid phosphatase, and combinations of any thereof. The enzyme or expansin protein is expressed during vegetative growth of the recombinant microorganism.

Another method for stimulating plant growth and/or promoting plant health is provided. The method comprises applying a recombinant microorganism to a plant growth medium, a plant, a plant seed, or an area surrounding a plant or a plant seed. The recombinant microorganism expresses an enzyme or an expansin protein, wherein expression of the enzyme or expansin protein is increased as compared to the expression level of the enzyme or expansin protein in a wild-type microorganism of the same kind under the same conditions. The enzyme is selected from a phospholipase, a lipase, a xylanase, a xylosidase, a lactonase, a chitosanase, a glucanase, a protease, a mannanase, a pectinase, a phytase, an acid phosphatase, an ACC deaminase, and combinations of any thereof. The enzyme or expansin protein further comprises a signal peptide that results in secretion of the enzyme or expansin protein.

Another method for stimulating plant growth and/or promoting plant health is provided. The method comprises applying a recombinant microorganism to a plant growth medium, a plant, a plant seed, or an area surrounding a plant or a plant seed. The recombinant microorganism expresses an enzyme or an expansin protein, wherein expression of the enzyme or expansin protein is increased as compared to the expression level of the enzyme or expansin protein in a wild-type microorganism of the same kind under the same conditions. The enzyme is selected from a phospholipase, a lipase, a xylanase, a xylosidase, a lactonase, a chitosanase, a glucanase, a protease, a phytase, a mannanase, a pectinase, an acid phosphatase, and combinations of any thereof. The enzyme or expansin protein is not bound to the exosporium of a recombinant *Bacillus cereus* family member.

A further method for stimulating plant growth and/or promoting plant health is provided. The method comprises applying a recombinant microorganism to a plant growth medium, a plant, a plant seed, or an area surrounding a plant or a plant seed. The recombinant microorganism expresses an enzyme or an expansin protein, wherein expression of the enzyme or expansin protein is increased as compared to the expression level the enzyme or expansin protein in a wild-type microorganism of the same kind under the same conditions. The enzyme is selected from a phospholipase, a lipase, a xylanase, a xylosidase, a lactonase, a chitosanase, a glucanase, a protease, a phytase, a mannanase, a pectinase, an acid phosphatase, and combinations of any thereof. The enzyme or expansin protein is not part of a fusion protein.

A treated plant seed is provided. The plant seed is treated with a free enzyme. The enzyme is selected from a phospholipase, a lipase, a xylanase, a xylosidase, a mannanase, a pectinase, a lactonase, a chitosanase, a protease, a phytase, an acid phosphatase, a non-cellulolytic glucanase, an ACC deaminase, and combinations of any thereof.

Another treated plant seed is provided. The plant seed is treated with two or more free enzymes, wherein the enzymes are independently selected from a phospholipase, a lipase, a xylanase, a xylosidase, a lactonase, a chitosanase, a mannanase, a pectinase, a protease, a phytase, an acid phosphatase, a glucanase, and an ACC deaminase.

A coated plant seed is provided. The plant seed is coated with a free enzyme. The enzyme comprises a glucanase.

A treated plant seed is provided. The plant seed is treated with a free enzyme and an expansin protein. The enzyme comprises a glucanase.

A plant seed is provided. The plant seed is coated with a recombinant microorganism. The recombinant microorganism expresses an enzyme or an expansin protein, wherein expression of the enzyme or expansin protein is increased as compared to the expression level of the enzyme or expansin protein in a wild-type microorganism of the same kind under the same conditions. The enzyme is selected from a phospholipase, a lipase, a xylanase, a xylosidase, a lactonase, a chitosanase, a glucanase, a protease, a phytase, a mannanase, a pectinase, an acid phosphatase, an ACC deaminase, and combinations of any thereof. The enzyme or expansin protein is expressed during vegetative growth of the recombinant microorganism.

Another plant seed is provided. The plant seed is coated with a recombinant microorganism. The recombinant microorganism expresses an enzyme or expansin protein, wherein expression of the enzyme is increased as compared to the expression level of the enzyme or expansin protein in a wild-type microorganism of the same kind under the same conditions. The enzyme is selected from a phospholipase, a lipase, a xylanase, a xylosidase, a lactonase, a chitosanase, a glucanase, a protease, a mannanase, a pectinase, a phytase, an acid phosphatase, an ACC deaminase, and combinations of any thereof. The enzyme or expansin protein further comprises a signal peptide that results in secretion of the enzyme or expansin protein.

Yet another plant seed is provided. The plant seed is coated with a recombinant microorganism. The recombinant microorganism expresses an enzyme or an expansin protein, wherein expression of the enzyme or expansin protein is increased as compared to the expression level of the enzyme or expansin protein in a wild-type microorganism of the same kind under the same conditions. The enzyme is selected from a phospholipase, a lipase, a xylanase, a xylosidase, a lactonase, a chitosanase, a glucanase, a protease, a mannanase, a pectinase, a phytase, an acid phosphatase, an ACC deaminase, and combinations of any thereof. The enzyme or expansin protein is not bound to the exosporium of a recombinant *Bacillus cereus* family member.

Another plant seed is provided. The plant seed is coated with a recombinant microorganism. The recombinant microorganism expresses an enzyme or an expansin protein, wherein expression of the enzyme or expansin protein is increased as compared to the expression level the enzyme or expansin protein in a wild-type microorganism of the same kind under the same conditions. The enzyme is selected from a phospholipase, a lipase, a xylanase, a xylosidase, a lactonase, a chitosanase, a glucanase, a protease, a mannanase, a pectinase, a phytase, an acid phosphatase, an ACC deaminase, and combinations of any thereof. The enzyme or expansin protein is not part of a fusion protein.

A composition is provided. The composition comprises a fertilizer and an enzyme or an expansin protein. The enzyme is selected from a phospholipase, a lipase, a xylanase, a xylosidase, a lactonase, a mannanase, a pectinase, a chitosanase, a protease, an acid phosphatase, a phytase, a glucanase, an ACC deaminase, and combinations of any thereof.

Another composition is provided. The composition comprises a fertilizer and a recombinant microorganism. The recombinant microorganism expresses an enzyme or an expansin protein, wherein expression of the enzyme or expansin protein is increased as compared to the expression level of the enzyme or expansin protein in a wild-type microorganism of the same kind under the same conditions. The enzyme is selected from a phospholipase, a lipase, a xylanase, a xylosidase, a lactonase, a mannanase, a pectinase, a chitosanase, a protease, an acid phosphatase, a phytase, a glucanase, an ACC deaminase, and combinations of any thereof. The enzyme or expansin protein is expressed during vegetative growth of the recombinant microorganism.

Yet another composition is provided. The composition comprises a fertilizer and a recombinant microorganism. The recombinant microorganism expresses an enzyme or an expansin protein, wherein expression of the enzyme or expansin protein is increased as compared to the expression level of the enzyme or expansin protein in a wild-type microorganism of the same kind under the same conditions. The enzyme is selected from a phospholipase, a lipase, a xylanase, a xylosidase, a lactonase, a mannanase, a pectinase, a chitosanase, a protease, an acid phosphatase, a phytase, a glucanase, an ACC deaminase, and combinations of any thereof. The enzyme or expansin protein further comprises a signal peptide that results in secretion of the enzyme or expansin protein.

A further composition is provided. The composition comprises a fertilizer and a recombinant microorganism. The recombinant microorganism expresses an enzyme or an expansin protein, wherein expression of the enzyme or expansin protein is increased as compared to the expression level of the enzyme or expansin protein in a wild-type microorganism of the same kind under the same conditions. The enzyme is selected from a phospholipase, a lipase, a xylanase, a xylosidase, a lactonase, a mannanase, a pectinase, a chitosanase, a protease, an acid phosphatase, a phytase, a glucanase, an ACC deaminase, and combinations of any thereof. The enzyme or expansin protein is not bound to the exosporium of a recombinant *Bacillus cereus* family member.

Another composition is provided. The composition comprises a fertilizer and a recombinant microorganism. The recombinant microorganism expresses an enzyme or an expansin protein, wherein expression of the enzyme or expansin protein is increased as compared to the expression level of the enzyme or expansin protein in a wild-type microorganism of the same kind under the same conditions. The enzyme is selected from a phospholipase, a lipase, a xylanase, a xylosidase, a lactonase, a mannanase, a pectinase, a chitosanase, a protease, an acid phosphatase, a phytase, a glucanase, an ACC deaminase, and combinations of any thereof. The enzyme or expansin protein is not part of a fusion protein.

The features of the invention are further defined in the appended claims and the list of embodiments provided below in the Section entitled "EMBODIMENTS." Other objects and features will be in part apparent and in part pointed out hereinafter.

DEFINITIONS

When the articles "a," "an," "one," "the," and "said" are used herein, they mean "at least one" or "one or more" unless otherwise indicated.

The term "*Bacillus cereus* family member" as used herein refers to any *Bacillus* species that is capable of producing an exosporium. Thus, the *Bacillus cereus* family of bacteria includes the species *Bacillus anthracis, Bacillus cereus, Bacillus thuringiensis, Bacillus mycoides, Bacillus pseudomycoides, Bacillus samanii, Bacillus gaemokensis, Bacillus weihenstephensis*, and *Bacillus toyoiensis. Bacillus cereus* family members are also referred to in the art as "*Bacillus cereus* senso lato."

The terms "composition" and "formulation" are used interchangeably herein to refer to a mixture of two or more chemical or biological substances (for example, a mixture of an enzyme and an agriculturally acceptable carrier or a mixture of a recombinant microorganism and an agriculturally acceptable carrier).

The terms "comprising," "including," and "having" are intended to be inclusive and mean that there may be additional elements other than the listed elements.

The term "foliar" used herein with respect to the application of enzymes or recombinant microorganisms to plants means that the enzyme or recombinant microorganism is applied to one or more aerial portions of the plant, including stems, leaves, fruits, flowers, or other exposed aerial portions of the plant.

The term "free enzyme" as used herein refers to an enzyme preparation that is substantially free of intact cells. The term "free enzyme" includes, but is not limited to, crude cell extracts containing an enzyme, partially purified, substantially purified, or purified enzyme. Free enzymes can optionally be immobilized on a chemical matrix or support to allow for controlled release of the enzyme. Free enzyme preparations preferably do not include enzymes bound to exosporium of a *Bacillus cereus* family member. Free enzymes also preferably do not include enzymes bound to exosporium of an intact *Bacillus cereus* family member spore.

The term "fusion protein" as used herein refers to a protein having a polypeptide sequence that comprises sequences derived from two or more separate proteins. A fusion protein can be generated by joining together a nucleic acid molecule that encodes all or part of a first polypeptide with a nucleic acid molecule that encodes all or part of a second polypeptide to create a nucleic acid sequence which, when expressed, yields a single polypeptide having functional properties derived from each of the original proteins.

The term "germination rate" as used herein refers to the number of seeds that germinate during a particular time period. For example, a germination rate of 85% indicates that 85 out of 100 seeds germinate during a given time period.

The term "glucanase" as used herein refers to any enzyme that is capable of hydrolyzing a glycoside bond. The term "non-cellulolytic glucanase" as used herein refers to any glucanase whose primary enzyme activity is not directed to cellulose or cellulose subunits as a substrate. A non-cellulolytic glucanase is preferably incapable of using cellulose as a substrate.

The term "immobilizing" as used herein in reference to immobilizing an enzyme on a matrix or support refers to the binding of the enzyme to the matrix or support such that the enzyme is maintained on the matrix or support or released from the support over a controlled period of time, instead of dissipating into the environment in an uncontrolled manner.

The terms "native sequence," "native amino acid sequence," "wild-type sequence," and "wild-type amino acid sequence" are used interchangeably herein to refer to an amino acid sequence as it exists in a naturally occurring protein.

The terms "overexpress" and "overexpression" as used herein in reference to recombinant microorganisms mean that the recombinant microorganism has been modified such that the recombinant microorganism expresses a protein (e.g., an enzyme) at a level that is increased as compared to the expression level of the same protein a wild-type microorganism of the same kind under the same conditions.

A "plant growth medium" includes any material that is capable of supporting the growth of a plant.

The terms "promoting plant growth" and "stimulating plant growth" are used interchangeably herein, and refer to the ability to enhance or increase at least one of the plant's height, weight, leaf size, root size, fruit size, or stem size, and/or the ability to increase protein yield from the plant and/or to increase crop yield.

The term "promoting plant health" refers to any beneficial effect on the health of a plant, including but not limited to increased germination rate, increased synchronous germination, decreased susceptibility to a pathogen, decreased susceptibility to an environmental stress (e.g., drought, flood, heat, freezing, salt, heavy metals, low pH, high pH, or a combination of any thereof), increased crop yield, increased root nodulation, and increased nutrient uptake and/or nutrient content (e.g., increased sugar uptake or sugar content or increased protein uptake or protein content).

The term "rhizosphere" is used interchangeably with "root zone" to denote that segment of the soil that surrounds the roots of a plant and is influenced by them.

The term "partially purified" as used herein in reference to the enzymes means that a crude preparation of the enzyme (e.g., a cell lysate) has been subjected to procedures that remove at least some non-enzyme components (e.g., waste proteins, dead cell material, excess water, and/or unwanted cell debris). In a partially purified enzyme preparation, the enzyme preferably comprises at least 1% of the total protein content in the preparation, more preferably at least 3% of the total protein content in the preparation, and even more preferably greater than 5% of the total protein content in the preparation.

The term "substantially purified" as used herein in reference to the enzymes means that the enzyme preparation has been subjected to procedures that remove a substantial amount of non-enzyme components (e.g., waste proteins, dead cell material, excess water, and/or unwanted cell debris). In a substantially purified enzyme preparation, the enzyme preferably comprises greater than 30% of the total protein content in the preparation, more preferably greater than about 40% of the total protein content in the preparation, and even more preferably greater than 50% of the total protein content in the preparation.

The term "synergistically effective amount" as used herein refers an amount of a first substance (e.g., a first enzyme) that when used in combination with a second substance (e.g., a second enzyme) that produces a biological effect that is greater than the sum of the biological effects of each of the respective first and second substances when used alone.

DESCRIPTION OF THE PREFERRED EMBODIMENTS

The present invention is generally directed methods stimulating plant growth and/or promoting plant health. The methods comprise applying free enzymes, expansin proteins, or recombinant bacteria that overexpress enzymes to a plant growth medium, a plant, a plant seed, or an area surrounding a plant seed. The present invention is also directed to seeds treated or coated with free enzymes or recombinant bacteria that overexpress enzymes. The present invention is also directed to compositions comprising a fertilizer and an enzyme or recombinant bacteria that overexpress an enzyme. The use of free enzymes or recombinant bacteria that overexpress enzymes for delivering enzymes to plants allows for short bursts of enzyme activity, which in turn provides a safe, short-lived impact on the plant with limited residual materials remaining on harvestable plant material. Alternatively, in situations where a more prolonged effect is desired, the free enzymes can be immobilized on a matrix or support in order to provide controlled release of the enzymes.

I. Enzyme and Expansin Protein Sequences

For ease of reference, illustrative sequences for wild-type and modified ACC deaminase enzymes, as well as sequences for the other enzymes and the expansin proteins that can be used in connection with the methods, seeds, and compositions described herein, are provided below.

A. D-Cysteine Desulfhydrases and ACC Deaminases

For ease of reference, descriptions of illustrative D-cysteine desulfhydrase and 1-aminocyclopropane-1-carboxylate deaminase (ACC deaminase) nucleotide sequences are provided in Table 1 below, together with their SEQ ID NOs. Table 2 below provides the corresponding amino acid sequences for the nucleotide sequences listed in Table 1. As explained in greater detail hereinbelow, mutation of certain amino acids in a wild-type D-cysteine desulfhydrase or ACC deaminase enzyme can result in an enzyme having increased ACC deaminase activity as compared to the ACC deaminase activity of the wild-type enzyme under the same conditions.

In Table 1, SEQ ID NOs. 1-3 and 111 are nucleotide sequences for wild-type enzymes that exhibit both ACC deaminase and D-cysteine desulfhydrase activity, and SEQ ID NOs. 4-6 and 112 are nucleotide sequences that code for corresponding versions of these enzymes having two amino acid substitutions relative to the wild-type sequence that result in increased ACC deaminase activity. Thus, for example, SEQ ID NO: 1 provides the nucleotide sequence for a wild-type enzyme, and SEQ ID NO: 4 provides the nucleotide sequence for the same enzyme wherein the nucleotide sequence has been altered to encode an enzyme having two amino acid substitutions relative to the enzyme encoded by SEQ ID NO: 1. Similarly, SEQ ID NO: 2 provides the nucleotide sequence for a wild-type enzyme, and SEQ ID NO: 5 provides the nucleotide sequence for the same enzyme wherein the nucleotide sequence has been altered to encode an enzyme having two amino acid substitutions relative to the enzyme encoded by SEQ ID NO: 2. Likewise, SEQ ID NO: 3 is a wild-type sequence and SEQ ID NO: 6 provides the corresponding altered sequence, and SEQ ID NO 111 is a wild-type sequence and SEQ ID NO: 112 provides the corresponding altered sequence.

In Table 2, SEQ ID NOs. 7-9 and 113 are amino acid sequences for wild-type enzymes that exhibit both ACC deaminase and D-cysteine desulfhydrase activity, and SEQ ID NOs. 10-12 and 114 are amino acid sequences for the corresponding versions of these enzymes having two amino acid substitutions relative to the wild-type sequence that result in increased enzyme activity. Thus, SEQ ID NO: 7 is a wild-type sequence and SEQ ID NO: 10 provides the amino acid sequence for the same enzyme having the two amino acid substitutions relative to the wild-type sequence. SEQ ID NOs. 8 and 11, 9 and 12, and 113 and 114 are related to one another in the same manner. The substituted amino acids are shown in SEQ ID NOs. 10-12 and 114 in Table 2 in bold and underlined text.

TABLE 1

Nucleotide sequences for D-cysteine desulfhydrases and ACC deaminases

| Enzyme | SEQ ID NO. for nucleotide sequence |
|---|---|
| D-Cysteine Desulfhydrase (ACC deaminase native 1b) Wild-type, *Bacillus thuringiensis* | 1 |
| D-Cysteine Desulfhydrase (ACC deaminase native 2b) Wild-type, *Bacillus pseudomycoides* | 2 |
| D-Cysteine Desulfhydrase (ACC deaminase native 3b) Wild-type, *Bacillus thuringiensis* | 3 |
| D-Cysteine Desulfhydrase (ACC deaminase) Wild-type, *Bacillus thuringiensis* strain IS5056 | 111 |
| D-Cysteine Desulfhydrase (ACC deaminase native 1b) With mutations, *Bacillus thuringiensis* | 4 |
| D-Cysteine Desulfhydrase (ACC deaminase native 2b) With mutations, *Bacillus pseudomycoides* | 5 |
| D-Cysteine Desulfhydrase (ACC deaminase native 3b) With mutations, *Bacillus thuringiensis* | 6 |
| ACC deaminase (D-Cysteine Desulfhydrase) With mutations, *Bacillus thuringiensis* strain IS5056 | 112 |

TABLE 2

Amino acid sequences for D-cysteine desulfhydrases and ACC deaminases

| Enzyme (SEQ ID NO) | Amino acid sequence |
|---|---|
| D-Cysteine Desulfhydrase (ACC deaminase native 1b) Wild-type *Bacillus thuringiensis* (SEQ ID NO: 7) | MNLAKFPRKKYTESYTPIEKLNNFSEALGGPTIYFKRDDLLGLT AGGNKTRKLEFLVADAEAKGADTLITAGGIQSNHCRLTLAAA VKEKMKCILVLEEGLEPEEKPDFNGNYFLYHLLGAENVIVVPN GADLMEEMHKVAKEVSEKGNTPYVIPVGGSNPTGAMGYVAC AQEIMAQSFDQGIDFSTVVCVSGSAGMHAGLITGFAGTQSHIP VIGINVSRGKAEQEEKVAKLVDETSAHVGIPNFIPRDAVTCFDE YVGPGYALPTPEMVEAVQLLAKTEGILLDPVYTGKAVAGLIDL IKKGTFNKEDNILFVHSGGSPALYANTSLFA |
| D-Cysteine Desulfhydrase (ACC deaminase native 2b) Wild-type *Bacillus pseudomycoides* (SEQ ID NO: 8) | MNLAKFPRKKYTESYTPIEKLNHFSEVLGGPSIYFKRDDLLGLT AGGNKTRKLEFLVADAQAKGVDTLITAGGIQSNHCRLTLAAA VKEKMKCILVLEEGLEPEEKPDFNGNYFLYHLLGAENVIVVPN GTDLMDEMQKVAKEVTEKGHTPYVIPVGGSNPTGAMGYIAC AEEIMAQSFEQGIDFNAVVCVSGSGGMHAGLITGFYGRQTGIPI IGMNVSRGKAEQEEKVCKLVQETSAHVGIPNSIPREAVTCFDE YVGPGYALPTPEMVEAVQLLAKTEGILLDPVYTGKAVAGLIDII RKGTFKKEDNILFVHSGGSPALYANTSLFS |
| D-Cysteine Desulfhydrase (ACC deaminase native 3b) Wild-type *Bacillus thuringiensis* (SEQ ID NO: 9) | MNLAKFPRKKYTESYTPIEKLNNFSEVLGGPTIYFKRDDLLGLT AGGNKTRKLEFLVADAQAKGADTLITAGGIQSNHCRLTLAAA VKEKMKCILVLEEGLEPEEKPDFNGNYFLYHLLGAENVIVVPN GADLMEEMHKVAKEVSEKGNTPYVIPVGGSNPTGAMGYVAC AQEIMAQSFEQGIDFSSVVCVSGSGGMHAGLITGFAGTQSHIPV IGINVSRGKAEQEEKVAKLVDETSAHVGIPNFISRDAVTCFDQY VGPGYALPTQEMVEAVQLLAKTEGILLDPVYTGKAVAGLIDLI KKGTFNKEDNILFVHSGGSPALYANTSLFA |
| D-Cysteine Desulfhydrase (ACC deaminase) *Bacillus thuringiensis* strain IS5056 Wild-type (SEQ ID NO: 113) | MNLAKFPRKKYTESYTPIEKLNNFSEALGGPTIYFKRDDLLGLT AGGNKTRKLEFLVADAQEKGADTLITAGGIQSNHCRLTLAAA VKEKMKCILVLEEGLEPEEKRDFNGNYFLYHLLGAENVIVVPN GADLMEEMNKVAKEVSEKGSTPYVIPVGGSNPTGAMGYVAC AQEIMAQSFEQGIDFSSVVCVSGSGGMHAGLITGFSGTQSHIPV IGINVSRGKAEQEEKVAKLVDETSAHVGIPNFISRDAVTCFDEY VGPGYALPTPEMVEAVQLLAKTEGILLDPVYTGKAVAGLIDLI RKGKFNKEDNILFVHSGGSPALYANTSLFA |
| D-Cysteine Desulfhydrase (ACC deaminase native 1b) With mutations *Bacillus thuringiensis* (SEQ ID NO: 10) | MNLAKFPRKKYTESYTPIEKLNNFSEALGGPTIYFKRDDLLGLT AGGNKTRKLEFLVADAEAKGADTLITAGGIQSNHCRLTLAAA VKEKMKCILVLEEGLEPEEKPDFNGNYFLYHLLGAENVIVVPN GADLMEEMHKVAKEVSEKGNTPYVIPVGGSNPTGAMGYVAC AQEIMAQSFDQGIDFSTVVCVSGSAGMHAGLITGFAGTQSHIP VIGINVSRGKAEQEEKVAKLVDETSAHVGIPNFIPRDAVTCFDE YVGPGYALPTPEMVEAVQLLAKTEGILLDPVY**E**GKAVAGLIDL IKKGTFNKEDNILFVH**L**GGSPALYANTSLFA |

TABLE 2 -continued

| Amino acid sequences for D-cysteine desulfhydrases and ACC deaminases | |
|---|---|
| Enzyme (SEQ ID NO) | Amino acid sequence |
| D-Cysteine Desulfhydrase (ACC deaminase native 2b) With mutations *Bacillus pseudomycoides* (SEQ ID NO: 11) | MNLAKFPRKKYTESYTPIEKLNHFSEVLGGPSIYFKRDDLLGLT AGGNKTRKLEFLVADAQAKGVDTLITAGGIQSNHCRLTLAAA VKEKMKCILVLEEGLEPEEKPDFNGNYFLYHLLGAENVIVVPN GTDLMDEMQKVAKEVTEKGHTPYVIPVGGSNPTGAMGYIAC AEEIMAQSFEQGIDFNAVVCVSGSGGMHAGLITGFYGRQTGIPI IGMNVSRGKAEQEEKVCKLVQETSAHVGIPNSIPREAVTCFDE YVGPGYALPTPEMVEAVQLLAKTEGILLDPVY**E**GKAVAGLIDI IRKGTFKKEDNILFVH**L**GGSPALYANTSLFS |
| D-Cysteine Desulfhydrase (ACC deaminase native 3b) With mutations *Bacillus thuringiensis* (SEQ ID NO: 12) | MNLAKFPRKKYTESYTPIEKLNNFSEVLGGPTIYFKRDDLLGLT AGGNKTRKLEFLVADAQAKGADTLITAGGIQSNHCRLTLAAA VKEKMKCILVLEEGLEPEEKPDFNGNYFLYHLLGAENVIVVPN GADLMEEMHKVAKEVSEKGNTPYVIPVGGSNPTGAMGYVAC AQEIMAQSFEQGIDFSSVVCVSGSGGMHAGLITGFAGTQSHIPV IGINVSRGKAEQEEKVAKLVDETSAHVGIPNFISRDAVTCFDQY VGPGYALPTQEMVEAVQLLAKTEGILLDPVY**E**GKAVAGLIDLI KKGTFNKEDNILFVH**L**GGSPALYANTSLFA |
| ACC deaminase (D-Cysteine Desulfhydrase) *Bacillus thuringiensis* strain IS5056, with mutations) (SEQ ID NO: 114) | MNLAKFPRKKYTESYTPIEKLNNFSEALGGPTIYFKRDDLLGLT AGGNKTRKLEFLVADAQEKGADTLITAGGIQSNHCRLTLAAA VKEKMKCILVLEEGLEPEEKRDFNGNYFLYHLLGAENVIVVPN GADLMEEMNKVAKEVSEKGSTPYVIPVGGSNPTGAMGYVAC AQEIMAQSFEQGIDFSSVVCVSGSGGMHAGLITGFSGTQSHIPV IGINVSRGKAEQEEKVAKLVDETSAHVGIPNFISRDAVTCFDEY VGPGYALPTPEMVEAVQLLAKTEGILLDPVY**E**GKAVAGLIDLI RKGKFNKEDNILFVH**L**GGSPALYANTSLFA |

B. Phospholipases

For ease of reference, descriptions of illustrative phospholipase amino acid sequences are provided in Table 3 below, together with their SEQ ID NOs.

TABLE 3

| Amino acid sequences for phospholipases | |
|---|---|
| Enzyme | SEQ ID NO. for amino acid sequence |
| Phospholipase 2, *Bacillus thuringiensis* | 13 |
| Phospholipase C, *Bacillus thuringiensis* | 14 |
| Phospholipase C (Zinc dependent phospholipase C (alpha toxin)) *Bacillus thuringiensis* serovar israelensis 4Q7 | 15 |
| Phospholipase C ((nSMase) hydrolysis of sphingomyelin to ceramide and phosphorylcholine) *Bacillus thuringiensis* serovar israelensis 4Q7 | 16 |
| Phospholipase C (Zinc dependent phospholipase C (alpha toxin)), *Bacillus cereus* ATCC 10987 | 17 |
| Phospholipase C *Clostridium perfringens* str 13 (*C. welchii*) Type I | 18 |
| Phospholipase D, *Streptomyces chromofuscus* | 19 |
| Phosphatidylcholine-specific phospholipase C *Bacillus cereus* | 115 |
| Phosphatidylinositol phospholipase C *Bacillus cereus* | 116 |
| Phospholipase D (PLD) *Acidovorax avenae* | 117 |

The native amino acid sequences of the phospholipases of SEQ ID NOs. 13, 14, and 15 include the signal peptide sequence MKKKVLALAAAITLVAPLQSVAFA (SEQ ID NO: 49) at the amino-terminus of the sequence, immediately preceding the first amino acid of SEQ ID NOs. 13, 14, and 15. This signal peptide is not included in SEQ ID NOs. 13, 14, or 15. However, the signal peptide of SEQ ID NO: 49, or another signal peptide, can optionally be included at the amino-terminus of the phospholipases of any of SEQ ID NOs. 13, 14, and 15, or at the amino-terminus of any of the other enzymes or expansin proteins described herein.

The native amino acid sequence of the phospholipase of SEQ ID NO: 16 includes the signal peptide MKGKLLKGVLSLGVGLGALYSGTSAQAE (SEQ ID NO: 50) at the amino-terminus of the sequence, immediately preceding the first amino acid of SEQ ID NO: 16. This signal peptide is not included in SEQ ID NO: 16. However, the signal peptide of SEQ ID NO: 50, or another signal peptide, can optionally be included at the amino terminus of the phospholipase of SEQ ID NO: 16, or at the amino-terminus of any of the other enzymes or expansin proteins described herein.

The native amino acid sequence of the phospholipase of SEQ ID NO: 17 includes the signal peptide MKKKVLALAAAITVVAPLQSVAFA (SEQ ID NO: 51) at the amino terminus of the sequence, immediately preceding the first amino acid of SEQ ID NO: 17. This signal peptide is not included in SEQ ID NO: 17. However, the signal peptide of SEQ ID NO: 51, or another signal peptide, can optionally be included at the amino terminus of the phospholipase of SEQ ID NO: 17, or at the amino terminus of any of the other enzymes or expansin proteins described herein.

The native amino acid sequence of the phospholipase of SEQ ID NO: 18 includes the signal peptide MKRKICKALICATLATSLWAGASTKVYAW (SEQ ID NO: 52) at the amino-terminus of the sequence, immediately preceding the first amino acid of SEQ ID NO: 18. This signal peptide is not included in SEQ ID NO: 18. However, the signal peptide of SEQ ID NO: 52, or another signal peptide, can optionally be included at the amino terminus of the phospholipase of SEQ ID NO: 18, or at the amino-terminus of any of the other enzymes or expansin proteins described herein.

The native amino acid sequence of the phospholipase of SEQ ID NO: 19 includes the signal peptide MLAGPLAAALPARATTGTPAFLHGVASGD (SEQ ID NO: 53) at the amino-terminus of the sequence, immediately preceding the first amino acid of SEQ ID NO: 19. This signal peptide is not included in SEQ ID NO: 19. However, the signal peptide of SEQ ID NO: 53, or another signal peptide, can optionally be included at the amino terminus of the phospholipase of SEQ ID NO: 19, or at the amino-terminus of any of the other enzymes or expansin proteins described herein.

The native amino acid sequence of the phospholipase of SEQ ID NO: 115 includes the signal peptide MKKKVLALAAAITLVAPLQNVAFA (SEQ ID NO: 135) at the amino-terminus of the sequence, immediately preceding the first amino acid of SEQ ID NO: 115. This signal peptide is not included in SEQ ID NO: 115. However, the signal peptide of SEQ ID NO: 135, or another signal peptide, can optionally be included at the amino-terminus of the phospholipase of SEQ ID NO: 115, or at the amino-terminus of any of the other enzymes or expansin proteins described herein.

C. Lipases

For ease of reference, descriptions of illustrative lipase amino acid sequences are provided in Table 4 below, together with their SEQ ID NOs.

TABLE 4

Amino acid sequences for lipases

| Enzyme | SEQ ID NO. for amino acid sequence |
|---|---|
| Lipase 1 (4Q7 BG78_03400) *Bacillus thuringiensis* serovar israelensis 4Q7 | 20 |
| Lipase 2 (Bsub168 estA) *Bacillus subtilis* subsp. *subtilis* str. 168 | 21 |
| Lipase, *Burkholderia cepacia* | 118 |
| Lipase, *Pseudomonas fluorescens* | 119 |
| Lipase, *Burkholderia stearothermophilus* | 120 |

The native amino acid sequence of the lipase of SEQ ID NO: 21 includes the signal peptide MKFVKRRIIALVTILMLSVTSLFALQPSAKA (SEQ ID NO: 54) at the amino-terminus of the sequence, immediately preceding the first amino acid of SEQ ID NO: 21. This signal peptide is not included in SEQ ID NO: 21. However, the signal peptide of SEQ ID NO: 54, or another signal peptide, can optionally be included at the amino terminus of the lipase of SEQ ID NO: 21, or at the amino-terminus of any of the other enzymes or expansin proteins described herein.

The native amino acid sequence of the lipase of SEQ ID NO: 118 includes the signal peptide MARTMRSRVVAGAVACAMSIAPFAGTTAVMTLATTHAAMAATAP (SEQ ID NO: 137) at the amino-terminus of the sequence, immediately preceding the first amino acid of SEQ ID NO: 118. This signal peptide is not included in SEQ ID NO: 118. However, the signal peptide of SEQ ID NO: 137, or another signal peptide, can optionally be included at the amino-terminus of the lipase of SEQ ID NO: 118, or at the amino-terminus of any of the other enzymes of expansin proteins described herein.

The native amino acid sequence of the lipase of SEQ ID NO: 119 includes the signal peptide MGIFDYKNLGTEGSKTLFADAMA (SEQ ID NO: 138) at the amino-terminus of the sequence, immediately preceding the first amino acid of SEQ ID NO: 119. This signal peptide is not included in SEQ ID NO: 119. However, the signal peptide of SEQ ID NO: 138, or another signal peptide, can optionally be included at the amino-terminus of SEQ ID NO: 119, or at the amino terminus of any of the other enzymes or expansin proteins described herein.

D. Xylanases

For ease of reference, descriptions of illustrative xylanase amino acid sequences are provided in Table 5 below, together with their SEQ ID NOs.

TABLE 5

Amino acid sequences for xylanases

| Enzyme | SEQ ID NO. for amino acid sequence |
|---|---|
| β-xylanase 3 (CsacDSM8903 2408) *Caldicellulosiruptor saccharolyticus* DSM 8903 | 22 |
| β-xylanase 2 (Bsub168 xynA) *Bacillus subtilis* subsp. *subtilis* str. 168 | 23 |
| β-xylanase 1 (Bsub168 xynD) *Bacillus subtilis* subsp. *subtilis* str. 168 | 24 |
| β-xylanase 4 (Bstearo xynA) *Geobacillus stearothermophilus* (*Bacillus stearothermophilus*) | 25 |
| Xylanase, *Thermomyces lanuginosus* | 121 |
| P-Xylanase, *Neocallimastix patriciarum* | 122 |

The native amino acid sequence of the xylanase of SEQ ID NO: 22 includes the signal peptide MCENLEMLNLSLAKTYKDYFKIGAAVTA (SEQ ID NO: 55) at the amino-terminus of the sequence, immediately preceding the first amino acid of SEQ ID NO: 22. This signal peptide is not included in SEQ ID NO: 22. However, the signal peptide of SEQ ID NO: 55, or another signal peptide, can optionally be included at the amino terminus of the xylanase of SEQ ID NO: 22, or at the amino-terminus of any of the other enzymes or expansin proteins described herein.

The native amino acid sequence of the xylanase of SEQ ID NO: 23 includes the signal peptide MFKFKKNFLVGLSAALMSISLFSATASA (SEQ ID NO: 56) at the amino-terminus of the sequence, immediately preceding the first amino acid of SEQ ID NO: 23. This signal peptide is not included in SEQ ID NO: 23. However, the signal peptide of SEQ ID NO: 56, or another signal peptide, can optionally be included at the amino terminus of the xylanase of SEQ ID NO: 23, or at the amino-terminus of any of the other enzymes or expansin proteins described herein.

The native amino acid sequence of the xylanase of SEQ ID NO: 24 includes the signal peptide MRKKCSVCLWILVLLLSCLSGKSAYA (SEQ ID NO: 57) at the amino-terminus of the sequence, immediately preceding the first amino acid of SEQ ID NO: 24. This signal peptide is not included in SEQ ID NO: 24. However, the signal peptide of SEQ ID NO: 57, or another signal peptide, can optionally be included at the amino terminus of the xylanase of SEQ ID NO: 24, or at the amino-terminus of any of the other enzymes or expansin proteins described herein.

The native amino acid sequence of the xylanase of SEQ ID NO: 25 includes the signal peptide MKLKKKMLTLLLTASMSFGLFGATSSA (SEQ ID NO: 58) at the amino-terminus of the sequence, immediately preceding the first amino acid of SEQ ID NO: 25. This signal peptide is not included in SEQ ID NO: 25. However, the signal peptide of SEQ ID NO: 58, or another signal peptide, can optionally be included at the amino terminus of the xylanase of SEQ ID NO: 25, or at the amino-terminus of any of the other enzymes or expansin proteins described herein.

E. Xylosidases

For ease of reference, descriptions of illustrative xylosidase amino acid sequences are provided in Table 6 below, together with their SEQ ID NOs.

TABLE 6

| Amino acid sequences for xylosidases | |
|---|---|
| Enzyme | SEQ ID NO. for amino acid sequence |
| Xylosidase (CsacDSM8903 2404) *Caldicellulosiruptor saccharolyticus* DSM 8903 | 26 |
| Xylosidase, *Bacillus pumilus* | 123 |

F. Lactonases

For ease of reference, descriptions of illustrative lactonase amino acid sequences are provided in Table 7 below, together with their SEQ ID NOs.

TABLE 7

| Amino acid sequences for lactonases | |
|---|---|
| Enzyme | SEQ ID NO. for amino acid sequence |
| Lactonase (AiiA), *Bacillus thuringiensis* strain B184 | 27 |
| Lactonase (AiiA), *Bacillus pseudomycoides* strain B30 | 28 |

G. Chitosanases

For ease of reference, descriptions of illustrative chitosanase amino acid sequences are provided in Table 8 below, together with their SEQ ID NOs.

TABLE 8

| Amino acid sequences for chitosanases | |
|---|---|
| Enzyme | SEQ ID NO. for amino acid sequence |
| Chitosanase (Bsub168 csn) *Bacillus subtilis* subsp. *subtilis* str. 168 | 29 |
| Chitosanase, *Streptomyces* species N174 | 124 |

The native amino acid sequence of the chitosanase of SEQ ID NO: 29 includes the signal peptide MKISMQKADFWKKAAISLLVFTMFFTLMMSETVFA (SEQ ID NO: 59) at the amino-terminus of the sequence, immediately preceding the first amino acid of SEQ ID NO: 29. This signal peptide is not included in SEQ ID NO: 29. However, the signal peptide of SEQ ID NO: 59, or another signal peptide, can optionally be included at the amino terminus of the chitosanase of SEQ ID NO: 29, or at the amino-terminus of any of the other enzymes or expansin proteins described herein.

The native amino acid sequence of the chitosanase of SEQ ID NO: 124 includes the signal peptide MHSQHRTARIALAVVLTAIPASLATAGVGYASTQASTAVK (SEQ ID NO: 139) at the amino-terminus of the sequence, immediately preceding the first amino acid of SEQ ID NO: 124. This signal peptide is not included in SEQ ID NO: 124. However, the signal peptide of SEQ ID NO: 139), or another signal peptide, can optionally be included at the amino-terminus of the chitosanase of SEQ ID NO: 124, or at the amino terminus of any of the other enzymes or expansin proteins described herein.

H. Glucanases

For ease of reference, descriptions of illustrative glucanase amino acid sequences are provided in Table 9 below, together with their SEQ ID NOs.

TABLE 9

| Amino acid sequences for glucanases | |
|---|---|
| Enzyme | SEQ ID NO. for amino acid sequence |
| Endo-1,4-β-D-glucanase, *Acidothermus cellulolyticus* | 30 |
| Endoglucanase I, *Trichoderma reesei* | 31 |
| Endoglucanase II, *Trichoderma reesei* | 32 |
| Endoglucanase IV, *Trichoderma reesei* | 33 |
| Endoglucanase V, *Trichoderma reesei* | 34 |
| Endoglucanase VII, *Trichoderma reesei* | 35 |
| beta-1,4-endoglucanase, *Trichoderma reesei* | 36 |
| Cellobiohydrolase I, *Trichoderma reesei* | 37 |
| Cellobiohydrolase II, *Trichoderma reesei* | 38 |
| beta-Glucosidase I, *Trichoderma reesei* | 39 |
| beta-Glucosidase II, *Trichoderma reesei* | 40 |
| exo-1,3-β-D-Glucanase, *Aspergillus oryzae* | 41 |
| Endoglucanase B1,4 *Bacillus subtilis* subsp. *subtilis* str. 168 | 42 |
| Lichenase (Bsub 168 bglS) *Bacillus subtilis* subsp. *subtilis* str. 168 | 43 |
| Beta-(1,3) endoglucanase (BglH) *Bacillus circulans* strain IAM1165 | 44 |
| Beta-(1,3) glucosidase (GclA) *Bacillus circulans* strain WL-12 | 45 |
| Xyloglucanase, *Paenibacillus* species | 125 |
| β-1,3-D-glucanase, *Helix pomatia* | 126 |

The native amino acid sequence of the glucanase of SEQ ID NO: 42 includes the signal peptide MKRSISIFITCLLITLLTMGGMIASPASA (SEQ ID NO: 60) at the amino-terminus of the sequence, immediately preceding the first amino acid of SEQ ID NO: 42. This signal peptide is not included in SEQ ID NO: 42. However, the signal peptide of SEQ ID NO: 60, or another signal peptide, can optionally be included at the amino terminus of the glucanase of SEQ ID NO: 42, or at the amino-terminus of any of the other enzymes or expansin proteins described herein.

The native amino acid sequence of the glucanase of SEQ ID NO: 43 includes the signal peptide MPYLKRVLLLLVTGLFMSLFAVTATASA (SEQ ID NO: 61) at the amino-terminus of the sequence, immediately preceding the first amino acid of SEQ ID NO: 43. This signal peptide is not included in SEQ ID NO: 43. However, the signal peptide of SEQ ID NO: 61, or another signal peptide, can optionally be included at the amino terminus of the glucanase of SEQ ID NO: 43, or at the amino-terminus of any of the other enzymes or expansin proteins described herein.

The native amino acid sequence of the glucanase of SEQ ID NO: 44 includes the signal peptide MKRSQTSEKRYRQRVLSLFLAVVMLASIGLLPTSKVQA (SEQ ID NO: 62) at the amino-terminus of the sequence, immediately preceding the first amino acid of SEQ ID NO: 44. This signal peptide is not included in SEQ ID NO: 44. However, the signal peptide of SEQ ID NO: 62, or another signal peptide, can optionally be included at the amino terminus of the glucanase of SEQ ID NO: 44, or at the amino-terminus of any of the other enzymes or expansin proteins described herein.

The native amino acid sequence of the glucanase of SEQ ID NO: 45 includes the signal peptide MKPSHFTEKRFMKKVLGLFLVVVMLASVGVLPTSKVQA (SEQ ID NO: 63) at the amino-terminus of the sequence, immediately preceding the first amino acid of SEQ ID NO: 45. This signal peptide is not included in SEQ ID NO: 45. However, the signal peptide of SEQ ID NO: 63, or another signal peptide, can optionally be included at the amino terminus of the glucanase of SEQ ID NO: 45, or at the amino-terminus of any of the other enzymes or expansin proteins described herein.

The native amino acid sequence of the glucanase of SEQ ID NO: 125 includes the signal peptide MFKKWKKF-GISSLALVLVAAVAFTGWSAKASA (SEQ ID NO: 140) at the amino-terminus of the sequence, immediately preceding the first amino acid of SEQ ID NO: 125. This signal peptide is not included in SEQ ID NO: 125. However, the signal peptide of SEQ ID NO: 140, or another signal peptide, can optionally be included at the amino-terminus of the glucanase of SEQ ID NO: 125, or at the amino-terminus of any of the other enzymes or expansin proteins described herein.

I. Proteases

For ease of reference, descriptions of illustrative protease amino acid sequences are provided in Table 10 below, together with their SEQ ID NOs.

TABLE 10

Amino acid sequences for proteases

| Enzyme | SEQ ID NO. for amino acid sequence |
|---|---|
| Protease 1 (Bsub168 aprX) *Bacillus subtilis* subsp. *subtilis* str. 168 | 46 |
| Protease 2 (Bsub168 vpr) *Bacillus subtilis* subsp. *subtilis* str. 168 | 47 |
| Protease 3 Engyodontium album (*Tritirachium album*) | 48 |
| Protease (aminopeptidase), *Aspergillus saitoi* | 127 |

The native amino acid sequence of the protease of SEQ ID NO: 47 includes the signal peptide MKKGIIRFLLVSFVLF-FALSTGITGVQA (SEQ ID NO: 64) at the amino-terminus of the sequence, immediately preceding the first amino acid of SEQ ID NO: 47. This signal peptide is not included in SEQ ID NO: 47. However, the signal peptide of SEQ ID NO: 64, or another signal peptide, can optionally be included at the amino terminus of the protease of SEQ ID NO: 47, or at the amino-terminus of any of the other enzymes or expansin proteins described herein.

The native amino acid sequence of the protease of SEQ ID NO: 127 includes the signal peptide MVVFSKTAALVLGL-STAVSA (SEQ ID NO: 141) at the amino-terminus of the sequence, immediately preceding the first amino acid of SEQ ID NO: 127. This signal peptide is not included in SEQ ID NO: 127. However, the signal peptide of SEQ ID NO: 141, or another signal peptide, can optionally be included at the amino-terminus of the protease of SEQ ID NO: 127, or at the amino-terminus of any of the other enzymes or expansin proteins described herein.

J. Mannanases

For ease of reference, a description of an illustrative mannanase amino acid sequence is provided in Table 11 below, together with its SEQ ID NO.

TABLE 11

Amino acid sequence for a mannanase

| Enzyme | SEQ ID NO. for amino acid sequence |
|---|---|
| Mannanase, *Bacillus* sp. | 128 |

The native amino acid sequence of the mannanase of SEQ ID NO: 128 includes the signal peptide MAKLQKGTILT-VIAALMFVILGSAAPKA (SEQ ID NO: 142) at the amino-terminus of the sequence, immediately preceding the first amino acid of SEQ ID NO: 128. This signal peptide is not included in SEQ ID NO: 128. However, the signal peptide of SEQ ID NO: 142, or another signal peptide, can optionally be included at the amino-terminus of the mannanase of SEQ ID NO: 128, or at the amino-terminus of any of the other enzymes or expansin proteins described herein.

K. Pectinases

For ease of reference, a description of an illustrative pectinase amino acid sequence is provided in Table 12 below, together with its SEQ ID NO.

TABLE 12

Amino acid sequence for a pectinase

| Enzyme (SEQ ID NO) | SEQ ID NO. for amino acid sequence |
|---|---|
| Pectolyase, *Aspergillus japonicus* | 129 |

The native amino acid sequence of the pectolyase of SEQ ID NO: 129 includes the signal peptide MPSAKPLFCLAT-LAGAALAAP (SEQ ID NO: 143) at the amino-terminus of the sequence, immediately preceding the first amino acid of SEQ ID NO: 129. This signal peptide is not included in SEQ ID NO: 129. However, the signal peptide of SEQ ID NO: 143, or another signal peptide, can optionally be included at the amino-terminus of the pectolyase of SEQ ID NO: 129, or at the amino-terminus of any of the other enzymes or expansin proteins described herein.

L. Acid Phosphatases

For ease of reference, descriptions of illustrative acid phosphatase amino acid sequences are provided in Table 13 below, together with their SEQ ID NOs.

TABLE 13

Amino acid sequences for acid phosphatases

| Enzyme | SEQ ID NO. for amino acid sequence |
|---|---|
| Acid phosphatase, *Triticum aestivum* | 130 |
| Acid phosphatase, *Triticum aestivum* | 131 |

The native amino acid sequence of the acid phosphatase of SEQ ID NO: 130 includes the signal peptide MARGS-MAAVLAVLAVAALRCAPAAA (SEQ ID NO: 144) at the amino-terminus of the sequence, immediately preceding the first amino acid of SEQ ID NO: 130. This signal peptide is not included in SEQ ID NO: 130. However, the signal peptide of SEQ ID NO: 144, or another signal peptide, can optionally be included at the amino-terminus of the acid phosphatase of SEQ ID NO: 130, or at the amino-terminus of any of the other enzymes or expansin proteins described herein.

The native amino acid sequence of the acid phosphatase of SEQ ID NO: 131 includes the signal peptide MRGLGFAALSLHVLLCLANGVSSRRTSSYV (SEQ ID NO: 145) at the amino-terminus of the sequence, immediately preceding the first amino acid of SEQ ID NO: 131. This signal peptide is not included in SEQ ID NO: 131. However, the signal peptide of SEQ ID NO: 145, or another signal peptide, can optionally be included at the amino-terminus of the acid phosphatase of SEQ ID NO: 131, or at the amino-terminus of any of the other enzymes or expansin proteins described herein.

M. Phytases

For ease of reference, descriptions of illustrative phytase amino acid sequences are provided in Table 14 below, together with their SEQ ID NOs.

TABLE 14

| Amino acid sequences for phytases | |
|---|---|
| Enzyme | SEQ ID NO. for amino acid sequence |
| Phytase, *Triticum aestivum* | 132 |
| Phytase, *Triticum aestivum* | 133 |
| Phytase, *Triticum aestivum* | 134 |

The native amino acid sequence of the phytase of SEQ ID NO: 132 includes the signal peptide MWWGSLRLLLL-LAAAVAA (SEQ ID NO: 146) at the amino-terminus of the sequence, immediately preceding the first amino acid of SEQ ID NO: 132. This signal peptide is not included in SEQ ID NO: 132. However, the signal peptide of SEQ ID NO: 146, or another signal peptide, can optionally be included at the amino-terminus of the phytase of SEQ ID NO: 132, or at the amino-terminus of any of the other enzymes or expansin proteins described herein.

The native amino acid sequence of the phytase of SEQ ID NO: 133 includes the signal peptide MWWGSLRLLLL-LAAAVAA (SEQ ID NO: 146) at the amino-terminus of the sequence, immediately preceding the first amino acid of SEQ ID NO: 133. This signal peptide is not included in SEQ ID NO: 133. However, the signal peptide of SEQ ID NO: 146, or another signal peptide, can optionally be included at the amino-terminus of the phytase of SEQ ID NO: 133, or at the amino-terminus of any of the other enzymes or expansin proteins described herein.

The native amino acid sequence of the phytase of SEQ ID NO: 134 includes the signal peptide MGIWRGSLPLLL-LAA (SEQ ID NO: 147) at the amino-terminus of the sequence, immediately preceding the first amino acid of SEQ ID NO: 134. This signal peptide is not included in SEQ ID NO: 134. However, the signal peptide of SEQ ID NO: 147, or another signal peptide, can optionally be included at the amino-terminus of the phytase of SEQ ID NO: 134, or at the amino-terminus of any of the other enzymes or expansin proteins described herein.

N. Expansin Proteins

For ease of reference, an illustrative expansin amino acid sequences is provided in Table 15 below, together with its SEQ ID NOs.

TABLE 15

| Amino acid sequence for an expansin | |
|---|---|
| Expansin Protein | SEQ ID NO. for amino acid sequence |
| Expansin (Bsub168 exlX) *Bacillus subtilis* subsp. subtilis str. 168 | 74 |

The native amino acid sequence of the expansin protein of SEQ ID NO: 74 includes the signal peptide MKKIM-SAFVGMVLLTIFCFSPQASA (SEQ ID NO: 68) at the amino terminus of the sequence, immediately preceding the first amino acid of SEQ ID NO: 74. This signal peptide is not included in SEQ ID NO: 74. However, the signal peptide of SEQ ID NO: 74, or another signal peptide, can optionally be included at the amino terminus of the protease of SEQ ID NO: 74, at the amino terminus of any of the enzymes described herein, or at the amino terminus of another expansin protein.

O. Mutations that Increase Enzyme Activity

In any of the enzymes described herein, including both free enzymes and enzymes that are expressed by a recombinant microorganism, the enzyme can comprise at least one amino acid substitution relative to the sequence of a wild-type sequence of the same enzyme, and wherein the amino acid substitution results in increased activity of the enzyme as compared to the enzyme activity of the wild-type enzyme under the same conditions.

II. Modified Enzymes Having ACC Deaminase Activity

Modified 1-aminocylopropane-1-carboxylate (ACC) deaminase enzymes are provided. ACC deaminases and D-cysteine desulfhydrases (DCD) often have similar amino acid sequences and can have overlapping enzyme activities, being able to act on both 1-aminocyclopropane-1-carboxylate (ACC) and D-cysteine as substrates. Some enzymes only have one of these activities, while others are able to act both as ACC deaminases and as D-cysteine desulfhydrases. ACC deaminases cleave ACC into ammonia and alpha-ketobutyrate, while D-cysteine desulfhydrases converts D-cysteine into pyruvate, $H_2S$, and ammonia. ACC is the immediate precursor of ethylene, which can cause undesirable effects in plants if present at high levels.

Thus, an enzyme having increased ACC deaminase activity would be beneficial for use in agriculture in order to reduce ACC levels and thereby reduce ethylene levels. Application of ACC deaminase to a plant growth medium, a plant, a plant seed, or an area surrounding a plant or a plant seed can stimulate plant growth, promote plant health (e.g., by increasing nutrient uptake), and slow fruit ripening. These effects in turn lead to increased yields, early season vigor, and resistance of plants to early season stresses. ACC deaminases can also protect plants from pathogens as well as abiotic stresses.

As explained in greater detail below, mutations can be made in enzymes that exhibit D-cysteine desulfhydrase and/or ACC deaminase activity in order to increase the ACC deaminase activity of the enzyme. In addition, enzymes having ACC deaminase activity can be modified to include a signal peptide that results in secretion of the enzyme when it is expressed in a microorganism, allowing for easier production and purification of the enzyme. Such modifications (mutations and the addition of a signal peptide) can be used individually or in combination with one another. All plants make ACC and respond to ethylene, and thus such modified ACC deaminase enzymes have broad applicability.

Amino acid sequences for three wild-type enzymes are provided above in Table 2 as SEQ ID NOs. 7-9 and 113. Sequences for the corresponding versions of these wild-type enzymes that have two amino acid substitutions that result in increased ACC deaminase activity are provided above in Table 2 as SEQ ID NOs. 10-12 and 114.

Naturally occurring ACC deaminase is not a secreted protein. ACC deaminases are found in many types of microorganisms, including bacteria of the Phyla Bacteriodetes, Firmicutes, and Actinobacteria, and bacteria of the genera *Pseudomonas, Bacillus, Rhizobium, Bradyrhizobium*, as well as many others. However, the ACC deaminases found in these bacteria are intracellular, and have limited exposure to the substrate ACC from the host plants that they colonize.

A modified ACC deaminase is provided herein that comprises a signal peptide that results in secretion of the ACC deaminase from a microorganism in which it is expressed. This ACC deaminase can be expressed in a microorganism, which can then be applied to a plant growth medium, a plant, a plant seed, or an area surrounding a plant or a plant seed. The ACC deaminase is secreted by the microorganism where it comes into contact with its substrate. The secreted ACC deaminase is thus able to stimulate growth of the plant and/or promote health of the plant.

An enzyme is provided. The enzyme comprises an amino acid sequence encoding an enzyme having 1-aminocyclopropane-1-carboxylate deaminase (ACC deaminase) activity and a signal peptide that results in secretion of the enzyme when the enzyme is expressed in a microorganism.

The enzyme having ACC deaminase activity can comprise an enzyme from a *Bacillus* genus bacterium.

In addition or in the alternative, one or more amino acid substitutions can be introduced into the amino acid sequence of an ACC deaminase enzyme to increase enzyme activity.

An enzyme having ACC deaminase activity is provided. The amino acid sequence of the enzyme comprises at least one amino acid substitution relative to the sequence of a wild-type D-cysteine desulfhydrase or ACC deaminase enzyme from a *Bacillus* genus bacterium. The amino acid substitution results in increased ACC deaminase activity as compared to the ACC deaminase activity of the wild-type D-cysteine desulfhydrase or ACC deaminase enzyme under the same conditions.

The enzyme comprising the at least one amino acid substitution can further comprise a signal peptide that results in secretion of enzyme when the enzyme is expressed in a microorganism.

For any of the enzymes having ACC deaminase activity, the microorganism in which the enzyme is expressed can comprise a bacterium of the genus *Bacillus*, a bacterium of the genus *Pseudomonas*, a bacterium of the genus *Rhizobium*, a bacterium of the genus *Paenibacillus*, a bacterium of the genus *Lysinibacillus*, a bacterium of the genus *Paracoccus*, a bacterium of the genus *Mesorhizobium*, a bacterium of the genus *Bradyrhizobium*, a bacterium of the genus *Actinobacter*, a bacterium of the genus *Arthrobacter*, a bacterium of the genus *Azotobacter*, a bacterium of the genus *Azosprillium*, a pink-pigmented facultative methyltrophic bacterium, a mycorrhizal fungus, a fungus of the genus *Glomus*, a fungus of the genus *Trichoderma*, a fungus of the genus *Kluyera*, a fungus of the genus *Gliocladium*, or a combination of any thereof.

For example, the microorganism can comprise a bacterium of the genus *Bacillus*, a bacterium of the genus *Lysinibacillus*, a bacterium of the genus *Pseudomonas*, a bacterium of the genus *Paenibacillus*, or a combination of any thereof.

For any of the enzymes having ACC deaminase activity, the enzyme can comprise a *Bacillus thuringiensis* enzyme or a *Bacillus pseudomycoides* enzyme.

The enzyme can comprise an amino acid sequence having at least 70% identity to any one of SEQ ID NOs. 7-9 and 113, wherein the enzyme has ACC deaminase activity.

The enzyme can comprise an amino acid sequence having at least 75% identity to any one of SEQ ID NOs. 7-9 and 113, wherein the enzyme has ACC deaminase activity.

The enzyme can comprise an amino acid sequence having at least 80% identity to any one of SEQ ID NOs. 7-9 and 113, wherein the enzyme has ACC deaminase activity.

The enzyme can comprise an amino acid sequence having at least 85% identity to any one of SEQ ID NOs. 7-9 and 113, wherein the enzyme has ACC deaminase activity.

The enzyme can comprise an amino acid sequence having at least 90% identity to any one of SEQ ID NOs. 7-9 and 113, wherein the enzyme has ACC deaminase activity.

The enzyme can comprise an amino acid sequence having at least 95% identity to any one of SEQ ID NOs. 7-9 and 113, wherein the enzyme has ACC deaminase activity.

The enzyme can comprise an amino acid sequence having at least 98% identity to any one of SEQ ID NOs. 7-9 and 113, wherein the enzyme has ACC deaminase activity.

The enzyme can comprise an amino acid sequence having at least 99% identity to any one of SEQ ID NOs. 7-9 and 113, wherein the enzyme has ACC deaminase activity.

The enzyme can comprise two amino acid substitutions relative to the sequence of the wild-type D-cysteine desulfhydrase or ACC deaminase enzyme, wherein the amino acid substitutions result in increased ACC deaminase activity as compared to the ACC deaminase activity of the wild-type enzyme, under the same conditions.

For example, the amino acid sequence of the enzyme can comprise a substitution of the threonine residue at position 290 of SEQ ID NO: 7 with a glutamic acid residue and a substitution of the serine residue at position 317 of SEQ ID NO: 7 with a leucine residue.

The amino acid sequence of the enzyme can comprise a substitution of the threonine residue at position 290 of SEQ ID NO: 8 with a glutamic acid residue and a substitution of the serine residue at position 317 of SEQ ID NO: 8 with a leucine residue.

The amino acid sequence of the enzyme can comprise a substitution of the threonine residue at position 290 of SEQ ID NO: 9 with a glutamic acid residue and a substitution of the serine residue at position 317 of SEQ ID NO: 9 with a leucine residue.

The amino acid sequence of the enzyme can comprise a substitution of the threonine residue at position 290 of SEQ ID NO: 113 with a glutamic acid residue and a substitution of the serine residue at position 317 of SEQ ID NO: 113 with a leucine residue.

The enzyme can comprise any one of SEQ ID NOs. 10, 11, 12, or 14.

Where the enzyme having ACC deaminase activity comprises the signal peptide but does not comprise any amino acid substitutions relative to the sequence of a wild-type D-cysteine desulfhydrase or ACC deaminase enzyme, the ACC deaminase an comprise an amino acid sequence having 100% identity to any one of SEQ ID NOs. 7-9 and 113.

Signal peptides that can be used to modify the enzymes having ACC deaminase activity are described further in Section XII below.

III. Recombinant Bacteria that Express the Modified Enzymes Having ACC Deaminase Activity, and Formulations Containing the Modified Enzymes or the Recombinant Bacterial that Express the Modified Enzymes Recombinant microorganisms that express any of the enzymes described above in Section II are also provided.

In any of the recombinant microorganisms that express an enzyme described above in Section II, the expression of the enzyme is preferably increased as compared to the level of expression of the enzyme in a wild-type microorganism of the same kind under the same conditions.

Suitable microorganisms that can be used for expression of the enzymes are described below in Section XIII.

Formulations comprising an agriculturally acceptable carrier and any of the modified enzymes described above in Section II above or a recombinant microorganism that expresses any of the modified e enzymes are also provided. Suitable carriers that can be used in such formulations and further formulation components are described below in Section XVI.

IV. Methods for Stimulating Plant Growth and/or Promoting Plant Health

Methods for stimulating plant growth and/or promoting plant health are provided. As described in greater detail below, the methods comprise applying an enzyme, expansin protein, or a recombinant microorganism that expresses an enzyme or an expansin protein to a plant growth medium, a plant, a plant seed, or an area surrounding a plant or a plant seed.

Application of the enzymes or expansin proteins or the recombinant bacteria preferably results in delivery of higher levels of enzyme or expansin protein to the plant growth medium, the plant, the plant seed, or the area surrounding the plant or plant seed than the levels of the enzyme or expansin protein that would be found in nature in the plant growth medium the plant seed, or the area surrounding the plant or the plant seed.

A. Modified Enzymes Having ACC Deaminase Activity

A method for stimulating plant growth and/or promoting plant health is provided. The method comprises applying any of the enzymes having ACC deaminase activity described above in Section II to a plant growth medium, a plant, a plant seed, or an area surrounding a plant or a plant seed. Alternatively, the method can comprise applying a formulation comprising an agriculturally acceptable carrier and any of the enzymes having ACC deaminase activity described above in Section II to a plant growth medium, a plant, a plant seed, or an area surrounding a plant or a plant seed.

A further method for stimulating plant growth and/or promoting plant health is provided. The method comprises applying any of the recombinant microorganisms that express an enzyme having ACC deaminase activity described above in Section III to a plant growth medium, a plant, a plant seed, or an area surrounding a plant or a plant seed. Alternatively, the method can comprise applying a formulation comprising an agriculturally acceptable carrier and any of the recombinant microorganisms that express an enzyme having ACC deaminase activity described above in Section III to a plant growth medium, a plant, a plant seed, or an area surrounding a plant or a plant seed.

For example, the method can comprise applying any of the enzymes described in Section II above to the plant growth medium, plant, plant seed, or area surrounding the plant or the plant seed.

The method can comprise applying free enzyme to the plant growth medium, plant, plant seed, or area surrounding the plant or the plant seed.

The method can comprise applying any of the recombinant organisms described above in Section III to the plant growth medium, plant, plant seed, or area surrounding the plant or the plant seed.

The effects of any of the enzymes having ACC deaminase activity described in this section or elsewhere herein on plants can be tested, for example, by measurements of increases in root mass, increases in plant height, increases in yield, increases in nodulation, changes to leaf senescence, changes in seed germination, and delay in fruit ripening.

B. Phospholipases, Lipases, Xylanases, Xylosidases, Lactonases, Chitosanases, Glucanases Proteases, Mannanases, Pectinases, Acid Phosphatases, Phytases, ACC Deaminases, and Expansin Proteins 1. Free Enzymes As described in greater detail below, methods for stimulating plant growth and/or promoting plant health involving the use of phospholipases, lipases, xylosidases, lactonases, chitosanases, glucanases, proteases, mannanases, pectinases, acid phosphatases, phytases, ACC deaminases, and/or expansin proteins and/or recombinant bacteria expressing such enzymes or expansin proteins are provided.

A method for stimulating plant growth and/or promoting plant health is provided. The method comprises applying a free enzyme to a plant growth medium, a plant, a plant seed, or an area surrounding a plant or a plant seed. The enzyme is selected from a phospholipase, a lipase, a xylanase, a xylosidase, a lactonase, a mannanase, a pectinase, a chitosanase, a protease, an acid phosphatase, a non-cellulolytic glucanase, an ACC deaminase, and combinations of any thereof.

The enzyme is preferably selected from a phospholipase, a lipase, a xylanase, a xylosidase, a mannanase, a pectinase, a lactonase, a chitosanase, a protease, a phytase, an acid phosphatase, an ACC deaminase, and combinations of any thereof.

Another method for stimulating plant growth and/or promoting plant health is provided. The method comprises applying two or more free enzymes to a plant growth medium, a plant, a plant seed, or an area surrounding a plant or a plant seed. The enzymes are independently selected from a phospholipase, a lipase, a xylanase, a xylosidase, a lactonase, a chitosanase, a protease, a phytase, an acid phosphatase, a mannanase, a pectinase, a glucanase, and an ACC deaminase.

A further method for stimulating plant growth and/or promoting plant health is provided. The method comprises applying a free enzyme to a plant or a plant seed. The enzyme comprises a glucanase. Applying the enzyme to the plant seed comprises: (a) applying the enzyme to the plant seed at the time of planting; or (b) coating the plant seed with the enzyme.

In the method comprising applying a free enzyme to a plant or a plant seed, wherein the enzyme comprises a glucanase, the method can comprise coating the plant seed with a seed coating formulation comprising the enzyme and an agriculturally acceptable carrier.

In the method comprising applying a free enzyme to a plant or a plant seed, wherein the enzyme comprises a glucanase, the method can further comprise applying the enzyme or an expansin protein to the plant growth medium or an area surrounding a plant or a plant seed. For example, the method can comprise applying the enzyme or the expansin protein to the plant growth medium. The method can comprise applying the enzyme and the expansin protein to the plant growth medium.

Yet another method for stimulating plant growth and/or promoting plant health is provided. The method comprises applying a free enzyme to a plant growth medium, a plant, a plant seed, or an area surrounding a plant or a plant seed. The enzyme comprises a glucanase. The method further comprises applying an expansin protein to the plant growth medium, the plant, the plant seed, or the area surrounding a plant or a plant seed.

In the method comprising applying a free enzyme and an expansin protein, applying the enzyme or the expansin protein to the plant seed comprises: (a) applying the enzyme or expansin protein to the plant seed at the time of planting; or (b) coating the plant seed with the enzyme or expansin protein. For example, the method can comprise coating the plant seed with a seed coating formulation comprising an agriculturally acceptable carrier and the enzyme, the expansin protein, or both the enzyme and the expansin protein.

Another method for stimulating plant growth and/or promoting plant health is provided. The method comprises applying a free enzyme to a plant or a plant seed. The enzyme comprises a phytase.

A further method for stimulating plant growth and/or promoting plant health is provided. The method comprises applying a fertilizer and a free enzyme to a plant growth medium, an area surrounding a plant or a plant seed, or to a plant or a plant seed. The free enzyme comprises a phytase.

2. Recombinant Microorganisms

A method for stimulating plant growth and/or promoting plant health is provided. The method comprises applying a recombinant microorganism to a plant growth medium, a plant, a plant seed, or an area surrounding a plant or a plant seed. The recombinant microorganism expresses an enzyme or an expansin protein, wherein expression of the enzyme or expansin protein is increased as compared to the expression level of the enzyme or expansin protein in a wild-type microorganism of the same kind under the same conditions. The enzyme is selected from a phospholipase, a lipase, a xylanase, a xylosidase, a lactonase, a chitosanase, a glucanase, a mannanase, a pectinase, a protease, a phytase, an acid phosphatase, and combinations of any thereof. The enzyme or expansin protein is expressed during vegetative growth of the recombinant microorganism.

Another method for stimulating plant growth and/or promoting plant health is provided. The method comprises applying a recombinant microorganism to a plant growth medium, a plant, a plant seed, or an area surrounding a plant or a plant seed. The recombinant microorganism expresses an enzyme or an expansin protein, wherein expression of the enzyme or expansin protein is increased as compared to the expression level of the enzyme or expansin protein in a wild-type microorganism of the same kind under the same conditions. The enzyme is selected from a phospholipase, a lipase, a xylanase, a xylosidase, a lactonase, a chitosanase, a glucanase, a protease, a mannanase, a pectinase, a phytase, an acid phosphatase, an ACC deaminase, and combinations of any thereof. The enzyme or expansin protein further comprises a signal peptide that results in secretion of the enzyme or expansin protein.

A further method for stimulating plant growth and/or promoting plant health is provided. The method comprises applying a recombinant microorganism to a plant growth medium, a plant, a plant seed, or an area surrounding a plant or a plant seed. The recombinant microorganism expresses an enzyme or an expansin protein, wherein expression of the enzyme or expansin protein is increased as compared to the expression level of the enzyme or expansin protein in a wild-type microorganism of the same kind under the same conditions. The enzyme is selected from a phospholipase, a lipase, a xylanase, a xylosidase, a lactonase, a chitosanase, a glucanase, a protease, a phytase, a mannanase, a pectinase, an acid phosphatase, and combinations of any thereof. The enzyme or expansin protein is not bound to the exosporium of a recombinant *Bacillus cereus* family member.

Yet another method for stimulating plant growth and/or promoting plant health is provided. The method comprises applying a recombinant microorganism to a plant growth medium, a plant, a plant seed, or an area surrounding a plant or a plant seed. The recombinant microorganism expresses an enzyme or an expansin protein, wherein expression of the enzyme or expansin protein is increased as compared to the expression level the enzyme or expansin protein in a wild-type microorganism of the same kind under the same conditions. The enzyme is selected from a phospholipase, a lipase, a xylanase, a xylosidase, a lactonase, a chitosanase, a glucanase, a protease, a phytase, a mannanase, a pectinase, an acid phosphatase, and combinations of any thereof. The enzyme or expansin protein is not part of a fusion protein.

In any of the methods, the enzyme or expansin protein can be expressed during vegetative growth of the recombinant microorganism.

Where the enzyme or expansin protein is expressed during vegetative growth of the recombinant microorganism, the recombinant microorganism can be a spore-forming microorganism.

In any of the methods other than the methods where the enzyme is not part of a fusion protein, the enzyme or expansin protein can further comprise a signal peptide that results in secretion of the enzyme or expansin protein. Suitable signal peptides are described in Section XII below.

In any of the methods, the enzyme or expansin protein is suitably not bound to the exosporium of a recombinant *Bacillus cereus* family member.

In any of the methods, the enzyme or expansin protein is suitably not bound to the exosporium of an intact *Bacillus cereus* family member spore.

In any of the methods other than the methods that involve the use of a signal peptide, the enzyme or expansin protein is suitably not part of a fusion protein.

C. Routes for Delivery of Enzymes, Expansins, and/or Recombinant Microorganisms to Plants In any of the methods described herein, the method can comprise applying the enzyme or the recombinant microorganism to the plant growth medium. For example, the enzyme or recombinant microorganism can be applied in-furrow or can be included in a soil amendment. Alternatively, or in addition, the enzyme or recombinant microorganism can be impregnated onto a dry particle, a vermiculite or other matrix, a plastic polymer, a peat moss or potting mix, prior to application to the plant growth medium. The enzyme or recombinant microorganism can also be applied to the plant growth medium via a water source, a drip irrigation line, a broadcast liquid application to the soil, or a broadcast dry application to the soil.

The plant growth medium can comprise or consist essentially of a fertilizer. The mixture of the fertilizer and the enzyme or recombinant microorganism can then be applied to soil or another plant growth medium using standard fertilizer application, methods, including in-furrow fertilizer application, 2×2 fertilizer application, broadcast fertilizer application, fertilizer impregnation, drip irrigation lines, topdressing applications, and the like.

In any of the methods described herein, the method can comprise applying the enzyme, the expansin protein, or the recombinant microorganism to the plant.

In any of the methods described herein, the method can comprise applying the enzyme, the expansin protein, or the recombinant microorganism to roots of the plant.

In any of the methods described herein, the method can comprise applying the enzyme, the expansin protein, or the recombinant microorganism foliarly.

In any of the methods described herein, the method can comprise applying the enzyme, the expansin protein, or the recombinant microorganism to the plant seed.

Where the method comprises applying the enzyme, the expansin protein, or the recombinant microorganism to a plant seed, applying the enzyme, the expansin protein, or the recombinant organism to the plant seed can comprise: (a) applying the enzyme, the expansin protein, or the recombinant organism to the plant seed at the time of planting; or (b) coating the plant seed with the enzyme, the expansin protein, or the recombinant organism.

For example, the method can comprise coating the plant seed with a seed coating formulation comprising: an agriculturally acceptable carrier and the enzyme, the expansin protein, the recombinant microorganism, or a combination thereof.

V. Plant Seeds

Plant seeds treated with an enzyme, expansin protein, or a recombinant microorganism that expresses an enzyme or expansin protein are also provided.

A. Plant Seeds Treated with Modified Enzymes Having ACC Deaminase Activity

A treated plant seed is provided. The plant seed is treated with any of the enzymes having ACC deaminase activity described above in Section II. Alternatively, the plant seed is treated with a formulation comprising any of the enzymes having ACC deaminase activity described above in Section II and an agriculturally acceptable carrier.

A further plant seed is provided. The plant seed is treated with any of the recombinant microorganisms that express an enzyme having ACC deaminase activity described above in Section III. Alternatively, the plant seed is treated with a formulation comprising any of the recombinant microorganisms that express an enzyme having ACC deaminase activity described above in Section III.

B. Plant Seeds Treated with Enzymes or Recombinant Microorganisms

Plant seeds treated with enzymes, expansin proteins, or recombinant bacteria are provided.

1. Free Enzymes

A treated plant seed is provided. The plant seed is treated with a free enzyme. The enzyme is selected from a phospholipase, a lipase, a xylanase, a xylosidase, a mannanase, a pectinase, a lactonase, a chitosanase, a protease, a phytase, an acid phosphatase, a non-cellulolytic glucanase, an ACC deaminase, and combinations of any thereof.

The enzyme is preferably selected from a phospholipase, a lipase, a xylanase, a xylosidase, a mannanase, a pectinase, a lactonase, a chitosanase, a protease, a phytase, an acid phosphatase, an ACC deaminase, and combinations of any thereof.

Another treated plant seed is provided. The plant seed is treated with two or more free enzymes, wherein the enzymes are independently selected from a phospholipase, a lipase, a xylanase, a xylosidase, a lactonase, a chitosanase, a mannanase, a pectinase, a protease, a phytase, an acid phosphatase, a glucanase, and an ACC deaminase.

A treated plant seed is provided. The plant seed is treated with a free enzyme and an expansin protein. The enzyme comprises a glucanase.

A coated plant seed is provided. The plant seed is coated with a free enzyme. The enzyme comprises a glucanase.

2. Recombinant Microorganisms

A plant seed is provided. The plant seed is coated with a recombinant microorganism. The recombinant microorganism expresses an enzyme or an expansin protein, wherein expression of the enzyme or expansin protein is increased as compared to the expression level of the enzyme or expansin protein in a wild-type microorganism of the same kind under the same conditions. The enzyme is selected from a phospholipase, a lipase, a xylanase, a xylosidase, a lactonase, a chitosanase, a glucanase, a protease, a phytase, a mannanase, a pectinase, an acid phosphatase, an ACC deaminase, and combinations of any thereof. The enzyme or expansin protein is expressed during vegetative growth of the recombinant microorganism.

Another plant seed is provided. The plant seed is coated with a recombinant microorganism. The recombinant microorganism expresses an enzyme or expansin protein, wherein expression of the enzyme is increased as compared to the expression level of the enzyme or expansin protein in a wild-type microorganism of the same kind under the same conditions. The enzyme is selected from a phospholipase, a lipase, a xylanase, a xylosidase, a lactonase, a chitosanase, a glucanase, a protease, a mannanase, a pectinase, a phytase, an acid phosphatase, an ACC deaminase, and combinations of any thereof. The enzyme or expansin protein further comprises a signal peptide that results in secretion of the enzyme or expansin protein.

A further plant seed is provided. The plant seed is coated with a recombinant microorganism. The recombinant microorganism expresses an enzyme or an expansin protein, wherein expression of the enzyme or expansin protein is increased as compared to the expression level of the enzyme or expansin protein in a wild-type microorganism of the same kind under the same conditions. The enzyme is selected from a phospholipase, a lipase, a xylanase, a xylosidase, a lactonase, a chitosanase, a glucanase, a protease, a mannanase, a pectinase, a phytase, an acid phosphatase, an ACC deaminase, and combinations of any thereof. The enzyme or expansin protein is not bound to the exosporium of a recombinant *Bacillus cereus* family member.

Yet another plant seed is provided. The plant seed is coated with a recombinant microorganism. The recombinant microorganism expresses an enzyme or an expansin protein, wherein expression of the enzyme or expansin protein is increased as compared to the expression level the enzyme or expansin protein in a wild-type microorganism of the same kind under the same conditions. The enzyme is selected from a phospholipase, a lipase, a xylanase, a xylosidase, a lactonase, a chitosanase, a glucanase, a protease, a mannanase, a pectinase, a phytase, an acid phosphatase, an ACC deaminase, and combinations of any thereof. The enzyme or expansin protein is not part of a fusion protein.

In any of the seeds, the enzyme or expansin protein can be expressed during vegetative growth of the recombinant microorganism.

Where the enzyme or expansin protein is expressed during vegetative growth of the recombinant microorganism, the recombinant microorganism can be a spore-forming microorganism.

In any of the seeds other than the seeds where the enzyme is not part of a fusion protein, the enzyme or expansin protein can further comprise a signal peptide that results in secretion of the enzyme or expansin protein. Suitable signal peptides are described in Section XII below.

In any of the seeds, the enzyme or expansin protein is suitably not bound to the exosporium of a recombinant *Bacillus cereus* family member.

In any of the seeds, the enzyme or expansin protein is suitably not bound to the exosporium of an intact *Bacillus cereus* family member spore.

In any of the seeds other than the seeds that involve the use of a signal peptide, the enzyme or expansin protein is suitably not part of a fusion protein.

C. Coated Plant Seeds

For any of the plant seeds, the plant seed can be coated with the enzyme, the recombinant microorganism, the expansin protein, or a combination of any thereof.

For example, the plant seed can be coated with the enzyme and the expansin protein.

Any of the plant seeds can be coated with a seed coating formulation comprising the enzyme, the recombinant microorganism, the expansin protein, or a combination of any thereof, and an agriculturally acceptable carrier.

VI. Compositions

Compositions comprising a fertilizer and an enzyme or expansin protein, or a recombinant microorganism that overexpresses an enzyme or an expansin protein, are provided.

A. Enzymes

A composition is provided. The composition comprises a fertilizer and an enzyme or an expansin protein. The enzyme is selected from a phospholipase, a lipase, a xylanase, a xylosidase, a lactonase, a mannanase, a pectinase, a chitosanase, a protease, an acid phosphatase, a phytase, a glucanase, an ACC deaminase, and combinations of any thereof.

The enzyme preferably comprises a free enzyme.

B. Recombinant Microorganisms

A composition is provided. The composition comprises a fertilizer and a recombinant microorganism. The recombinant microorganism expresses an enzyme or an expansin protein, wherein expression of the enzyme or expansin protein is increased as compared to the expression level of the enzyme or expansin protein in a wild-type microorganism of the same kind under the same conditions. The enzyme is selected from a phospholipase, a lipase, a xylanase, a xylosidase, a lactonase, a mannanase, a pectinase, a chitosanase, a protease, an acid phosphatase, a phytase, a glucanase, an ACC deaminase, and combinations of any thereof. The enzyme or expansin protein is expressed during vegetative growth of the recombinant microorganism.

Another composition is provided. The composition comprises a fertilizer and a recombinant microorganism. The recombinant microorganism expresses an enzyme or an expansin protein, wherein expression of the enzyme or expansin protein is increased as compared to the expression level of the enzyme or expansin protein in a wild-type microorganism of the same kind under the same conditions. The enzyme is selected from a phospholipase, a lipase, a xylanase, a xylosidase, a lactonase, a mannanase, a pectinase, a chitosanase, a protease, an acid phosphatase, a phytase, a glucanase, an ACC deaminase, and combinations of any thereof. The enzyme or expansin protein further comprises a signal peptide that results in secretion of the enzyme or expansin protein.

Yet another composition is provided. The composition comprises a fertilizer and a recombinant microorganism. The recombinant microorganism expresses an enzyme or an expansin protein, wherein expression of the enzyme or expansin protein is increased as compared to the expression level of the enzyme or expansin protein in a wild-type microorganism of the same kind under the same conditions. The enzyme is selected from a phospholipase, a lipase, a xylanase, a xylosidase, a lactonase, a mannanase, a pectinase, a chitosanase, a protease, an acid phosphatase, a phytase, a glucanase, an ACC deaminase, and combinations of any thereof. The enzyme or expansin protein is not bound to the exosporium of a recombinant *Bacillus cereus* family member.

A further composition is provided. The composition comprises a fertilizer and a recombinant microorganism. The recombinant microorganism expresses an enzyme or an expansin protein, wherein expression of the enzyme or expansin protein is increased as compared to the expression level of the enzyme or expansin protein in a wild-type microorganism of the same kind under the same conditions. The enzyme is selected from a phospholipase, a lipase, a xylanase, a xylosidase, a lactonase, a mannanase, a pectinase, a chitosanase, a protease, an acid phosphatase, a phytase, a glucanase, an ACC deaminase, and combinations of any thereof. The enzyme or expansin protein is not part of a fusion protein.

In any of the compositions, the enzyme or expansin protein can be expressed during vegetative growth of the recombinant microorganism.

Where the enzyme or expansin protein is expressed during vegetative growth of the recombinant microorganism, the recombinant microorganism can be a spore-forming microorganism.

In any of the compositions other than the compositions where the enzyme is not part of a fusion protein, the enzyme or expansin protein can further comprise a signal peptide that results in secretion of the enzyme or expansin protein. Suitable signal peptides are described in Section XII below.

In any of the compositions, the enzyme or expansin protein is suitably not bound to the exosporium of a recombinant *Bacillus cereus* family member.

In any of the compositions, the enzyme or expansin protein is suitably not bound to the exosporium of an intact *Bacillus cereus* family member spore.

In any of the compositions other than the compositions that involve the use of a signal peptide, the enzyme or expansin protein is suitably not part of a fusion protein.

C. Carriers and Additional Agrochemicals

In any of the compositions, the composition can further comprise an agriculturally acceptable carrier, a further agrochemical in addition to the fertilizer, or a combination thereof. Suitable carriers and agrochemicals are described in Section XVI below.

VII. Enzymes and Expansin Proteins for Use with the Methods, Plant Seeds, or Compositions Phospholipases, lipases, xylanases, xylosidases, lactonases, chitosanases, proteases, glucanases, expansin proteins, phytases, acid phosphatases, pectinases, mannanases, and ACC deaminases that are suitable for use in connection with the methods, seeds, and compositions are described below.

A. Phospholipases

The enzyme can comprise a phospholipase.

Phospholipases can be used for any of the plant growth stimulating or plant health promoting purposes described herein, but are especially suitable for stimulating plant growth, increasing nutrient uptake, and/or increasing root development and nodulation. Increasing root nodulation enhances the ability of the plant to form symbiotic relationships with nitrogen fixing microorganisms in the soil, resulting in increased nitrogen uptake and enhanced growth rates. These effects also lead to decreased susceptibility to environmental stresses such as drought.

Phospholipases are enzymes that have specific activity on phospholipids, releasing free fatty acids from complex phospholipids. Phospholipases can be broken down into five major classes: phospholipase A, phospholipase B, phospholipase C, phospholipase D, and phospholipase E. Each of these classes acts on specific types of phospholipids.

Where the enzyme comprises a phospholipase, the phospholipase can comprise a phospholipase A, a phospholipase B, a phospholipase C, a phospholipase D, a phospholipase E, or a combination of any thereof.

For example, the phospholipase can comprise a phospholipase A, a phospholipase C, a phospholipase D, or a combination of any thereof.

When the phospholipase comprises the phospholipase A, the phospholipase A can comprise a phospholipase A1, a phospholipase A2, or a combination thereof.

The phospholipase A2 can comprise a Group IIA phospholipase A2, a Group IIC phospholipase A2, a Group IID phospholipase A2, a Group IIE phospholipase A2, a Group IIF phospholipase A2, a Group III phospholipase A2, a Group IVA phospholipase A2, a Group IVB phospholipase A2, a Group IVC phospholipase A2, a Group IVD phospholipase A2, a Group IVE phospholipase A2, a Group VIF phospholipase A2, a Group V phospholipase A2, a Group VI phospholipase A2, a Group VII phospholipase A2, a Group X phospholipase A2, a Group XIIA phospholipase A2, a Group XIIB phospholipase A2, a Group XV phospholipase A2, a Group XVI phospholipase A2, or a combination of any thereof.

When the phospholipase comprises the phospholipase B, the phospholipase B can comprise a phospholipase B1.

When the phospholipase comprises the phospholipase C, the phospholipase C can comprise a phospholipase C beta 1, a phospholipase C beta 2, a phospholipase C beta 3, a phospholipase C beta 4, a phospholipase C delta 1, a phospholipase C delta 3, a phospholipase C delta 4, a phospholipase C epsilon 1, a phospholipase C gamma 1, a phospholipase C gamma 2, a phospholipase C eta 1, a phospholipase C eta 2, a phospholipase C zeta 1, or a combination of any thereof.

When the phospholipase comprises the phospholipase D, the phospholipase D can comprise a phospholipase D1, a phospholipase D2, a phospholipase D member 3, a phospholipase D member 4, a phospholipase D member 5, a phospholipase D member 6, or a combination of any thereof.

The phospholipase can comprise a 1-alkyl-2-acetylglycerophosphocholine esterase, a phosphatidylinositol deacylase, a phosphoinositide phospholipase C, a sphingomyelin phosphodiesterase, a sphingomyelin phosphodiesterase D, an alkylglycerophosphoethanolamine phosphodiesterase, a variant-surface-glycoprotein phospholipase C, a glycosylphosphatidylinositol phospholipase D, an N-acetylphosphatidylethanolamine-hydrolysing phospholipase D, a phosphatidylinositol diacylglycerol-lyase, a glycosylphosphatidylinositol diacylglycerol-lyase, a patatin-like phospholipase domain containing protein 2 (PNPLA2), a patatin-like phospholipase domain containing protein 3 (PNPLA3), or a combination of any thereof.

The phospholipase can comprise a *Streptomyces* phospholipase (e.g., a *Streptomyces chromofuscus* phospholipase such as *Streptomyces chromofuscus* phospholipase D), a *Bacillus* phospholipase (e.g., a *Bacillus cereus* phospholipase such as *Bacillus cereus* phosphatidylcholine-specific phospholipase C or *Bacillus cereus* phosphatidylinositol-specific phospholipase C, or a *Bacillus thuringiensis* phospholipase), a *Clostridium* phospholipase (e.g., a *Clostridium perfringens* phospholipase such as *Clostridium perfringens* phospholipase C), or a combination of any thereof.

The phospholipase can comprise an amino acid sequence having at least 70% identity to any one of SEQ ID NOs. 13-19 and 115-117.

The phospholipase can comprise an amino acid sequence having at least 75% identity to any one of SEQ ID NOs. 13-19 and 115-117.

The phospholipase can comprise an amino acid sequence having at least 80% identity to any one of SEQ ID NOs. 13-19 and 115-117.

The phospholipase can comprise an amino acid sequence having at least 85% identity to any one of SEQ ID NOs. 13-19 and 115-117.

The phospholipase can comprise an amino acid sequence having at least 90% identity to any one of SEQ ID NOs. 13-19 and 115-117.

The phospholipase can comprise an amino acid sequence having at least 95% identity to any one of SEQ ID NOs. 13-19 and 115-117.

The phospholipase can comprise an amino acid sequence having at least 98% identity to any one of SEQ ID NOs. 13-19 and 115-117.

The phospholipase can comprise an amino acid sequence having at least 99% identity to any one of SEQ ID NOs. 13-19 and 115-117.

The phospholipase can comprise an amino acid sequence having 100% identity to any one of SEQ ID NOs. 13-19 and 115-117.

Where the phospholipase comprises a *Bacillus cereus* phosphatidylcholine-specific phospholipase C (e.g., SEQ ID NO: 115), the method can further comprise applying a mannanase (e.g., SEQ ID NO: 128) or a xyloglucanase (e.g., SEQ ID NO: 125) to the plant growth medium, plant, plant seed, or area surrounding the plant or the plant seed.

Where the phospholipase comprises a *Bacillus cereus* phosphatidylcholine-specific phospholipase C (e.g., SEQ ID NO: 115), the seed can be further treated with a mannanase (e.g., SEQ ID NO: 128) or a xyloglucanase (e.g., SEQ ID NO: 125).

Where the phospholipase comprises a *Bacillus cereus* phosphatidylcholine-specific phospholipase C (e.g., SEQ ID NO: 115), the composition can further comprise a mannanase (e.g., SEQ ID NO: 128) or a xyloglucanase (e.g., SEQ ID NO: 125).

The *Bacillus cereus* phosphatidylcholine-specific phospholipase C and the mannanase can be present in the method, on the seed, or in the composition in synergistically effective amounts.

The *Bacillus cereus* phosphatidylcholine-specific phospholipase C and the xyloglucanase can be present in the method, on the seed, or in the composition in synergistically effective amounts.

B. Lipases

The enzyme can comprise a lipase.

Lipases are enzymes that have specific activity to lipids, cleaving fatty acid chains off of larger lipid molecules such as triglycerides. Lipases can be used for any of the plant growth stimulating or plant health-promoting purposes described herein, but are particularly well-suited for stimulating plant growth and enhancing nutrient uptake. These effects in turn lead to increased crop yields, improved early season vigor, and decreased susceptibility of plants to early season stresses.

The lipase can comprise a carboxyl ester lipase, a diacylglycerol lipase alpha, a diacylglycerol lipase beta, a lipase A, a hepatic lipase, a hormone-sensitive lipase, a gastric lipase, an endothelial lipase, a member H lipase, a lipase family member I, a lipase family member J, a lipase family member K, a lipase family member M, a lipase family member N, a lipoprotein lipase, a monoglyceride lipase, a pancreatic lipase-related protein 2, a pancreatic lipase-related protein 3, an acylglycerol lipase, a galactolipase, a lipoprotein lipase, or a combination of any thereof.

The lipase can comprise a *Bacillus subtilis* lipase, a *Bacillus thuringiensis* lipase, a *Bacillus cereus* lipase, a *Bacillus clausii* lipase, a *Burkholderia cepacia* lipase, a *Burkholderia stearothermophilus* lipase, a *Pseudomonas* lipase, or a combination of any thereof.

The lipase can comprise an amino acid sequence having at least 70% identity with SEQ ID NO: 20, 21, and 118-120.

The lipase can comprise an amino acid sequence having at least 75% identity with SEQ ID NO: 20, 21, and 118-120.

The lipase can comprise an amino acid sequence having at least 80% identity with SEQ ID NO: 20, 21, and 118-120.

The lipase can comprise an amino acid sequence having at least 85% identity with SEQ ID NO: 20, 21, and 118-120.

The lipase can comprise an amino acid sequence having at least 90% identity with SEQ ID NO: 20, 21, and 118-120.

The lipase can comprise an amino acid sequence having at least 95% identity with SEQ ID NO: 20, 21, and 118-120.

The lipase can comprise an amino acid sequence having at least 98% identity with SEQ ID NO: 20, 21, and 118-120.

The lipase can comprise an amino acid sequence having at least 99% identity with SEQ ID NO: 20, 21, and 118-120.

The lipase can comprise an amino acid sequence having 100% identity with SEQ ID NO: 20, 21, and 118-120.

C. Xylanases

The enzyme can comprise a xylanase.

Xylanases act on the polysaccharide xylan, a common sugar found in plants and in the soil. Xylanases can be used as a seed treatment, delivered to the plant growth medium (e.g., via in furrow application or as a soil amendment), or applied as a foliar treatment onto plants to generate smaller sugar chains that can be taken up by the plant or used to feed the surrounding microbiome.

Where the enzyme comprises a xylanase, the xylanase can comprise a beta-xylanase.

For example the beta-xylanase can comprise a glucurono-arabinoxylan endo-1,4-beta-xylanase, an exo-1,4-beta-xylanase, an endo-1,4-beta-xylanase, or a combination of any thereof.

The xylanase can comprise a *Caldicellulosiruptor* xylanase (e.g., a *Caldicellulosiruptor saccharolyticus* xylanase), a *Bacillus* xylanase (e.g., a *Bacillus subtilis* or *Bacillus stearothermophilus* xylanase), a *Neocallimastix* xylanase (e.g., a *Neocallimastix patriciarum* xylanase), a *Thermomyces* xylanase (e.g., a *Thermomyces lanuginosus* xylanase), or a combination of any thereof.

The xylanase can comprise an amino acid sequence having at least 70% identity to any one of SEQ ID NOs. 22-25, 121, and 122.

The xylanase can comprise an amino acid sequence having at least 75% identity to any one of SEQ ID NOs. 22-25, 121, and 122.

The xylanase can comprise an amino acid sequence having at least 80% identity to any one of SEQ ID NOs. 22-25, 121, and 122.

The xylanase can comprise an amino acid sequence having at least 85% identity to any one of SEQ ID NOs. 22-25, 121, and 122.

The xylanase can comprise an amino acid sequence having at least 90% identity to any one of SEQ ID NOs. 22-25, 121, and 122.

The xylanase can comprise an amino acid sequence having at least 95% identity to any one of SEQ ID NOs. 22-25, 121, and 122.

The xylanase can comprise an amino acid sequence having at least 98% identity to any one of SEQ ID NOs. 22-25, 121, and 122.

The xylanase can comprise an amino acid sequence having at least 99% identity to any one of SEQ ID NOs. 22-25, 121, and 122.

The xylanase can comprise an amino acid sequence having 100% identity to any one of SEQ ID NOs. 22-25, 121, and 122.

D. Xylosidases

The enzyme can comprise a xylosidase.

Xylosidases cleave single xylose molecules off of shorter fragments of xylan, a common polysaccharide found in plants and in the soil. Xylosidases can be used as a seed treatment, delivered to the plant growth medium (e.g., via in furrow application or as a soil amendment), or applied as a foliar treatment onto plants to generate smaller sugar chains that can be taken up by the plant or used to feed the surrounding microbiome.

For example, the xylosidase can comprise a *Caldicellulosiruptor saccharolyticus* xylosidase, a *Bacillus pumilus* xylosidase, or a combination thereof.

The xylosidase can comprise an amino acid sequence having at least 70% identity to SEQ ID NO: 26 or 123.

The xylosidase can comprise an amino acid sequence having at least 75% identity to SEQ ID NO: 26 or 123.

The xylosidase can comprise an amino acid sequence having at least 80% identity to SEQ ID NO: 26 or 123.

The xylosidase can comprise an amino acid sequence having at least 85% identity to SEQ ID NO: 26 or 123.

The xylosidase can comprise an amino acid sequence having at least 90% identity to SEQ ID NO: 26 or 123.

The xylosidase can comprise an amino acid sequence having at least 95% identity to SEQ ID NO: 26 or 123.

The xylosidase can comprise an amino acid sequence having at least 98% identity to SEQ ID NO: 26 or 123.

The xylosidase can comprise an amino acid sequence having at least 99% identity to SEQ ID NO: 26 or 123.

The xylosidase can comprise an amino acid sequence having 100% identity to SEQ ID NO: 26 or 123.

E. Lactonases

The enzyme can comprise a lactonase.

Lactonases can be used for any of the plant growth stimulating or plant health promoting purposes described herein, but are especially suitable for decreasing the susceptibility of plants to pathogens. Lactonases are also described as acyl-homoserine lactonases and are metalloenzymes produced by certain species of bacteria. For example, lactonases can be found in bacteria of the Phyla Bacteriodetes, Firmicutes, Actinobacteria, and in bacteria of the genera of *Pseudomonas* and *Bacillus*, as well as others. Lactonases target and inactivate acylated homoserine lactones. Lactonases hydrolyze the ester bonds of small hormone-like molecules commonly known as homoserine lactones. In the hydrolysis of these lactone bonds, lactonase acts to prevent these homoserine lactones from binding to their transcriptionally-regulated targets and thereby interfere with quorum sensing. However, lactonase secretion from naturally occurring bacteria that colonize soil or plants is limited and inducible, and thus it would be desirable to providing higher levels of lactonase to the environment of a plant.

Free lactonases or recombinant bacteria expressing lactonases can be applied to plants (e.g., foliarly or as a seed treatment) or a plant growth medium in order to reduce the levels of lactones in the environment. Without being bound to any particular theory, it is believed that this reduction in the level of lactones can in turn lead to reduction in plant disease, as well as a secondary increase in plant growth and development.

When expressed in a recombinant microorganism, the addition of a secretion signal to the lactonase would allow the microbe to secrete the lactonase into the environment. Suitable secretion signals are described further below in Section XII.

Where the enzyme comprises a lactonase, the lactonase can comprise a 1,4-lactonase, a 2-pyrone-4,6-dicarboxylate lactonase, a 3-oxoadipate enol-lactonase, an actinomycin lactonase, a deoxylimonate A-ring-lactonase, a gluconolactonase, an L-rhamnono-1,4-lactonase, a limonin-D-ring-lactonase, a steroid-lactonase, a triacetate-lactonase, a xylono-1,4-lactonase, or a combination of any thereof.

The lactonase can comprise a *Bacillus* lactonase (e.g., a *Bacillus thuringiensis* lactonase, a *Bacillus pseudomycoides* lactonase, or a combination thereof), an *Agrobacterium* lactonase, a *Rhodococcus* lactonase, a *Streptomyces* lactonase, an *Arthrobacter* lactonase, a *Sphingomonas* lactonase, a *Pseudomonas* lactonase, a *Klebsiella* lactonase, or a combination of any thereof.

The lactonase can comprise an AiiA.

The lactonase is preferably specific for a bacterial lactone homoserine signaling molecule.

The lactonase can comprise an amino acid sequence having at least 70% identity to SEQ ID NO: 27 or 28.

The lactonase can comprise an amino acid sequence having at least 75% identity to SEQ ID NO: 27 or 28.

The lactonase can comprise an amino acid sequence having at least 80% identity to SEQ ID NO: 27 or 28.

The lactonase can comprise an amino acid sequence having at least 85% identity to SEQ ID NO: 27 or 28.

The lactonase can comprise an amino acid sequence having at least 90% identity to SEQ ID NO: 27 or 28.

The lactonase can comprise an amino acid sequence having at least 95% identity to SEQ ID NO: 27 or 28.

The lactonase can comprise an amino acid sequence having at least 98% identity to SEQ ID NO: 27 or 28.

The lactonase can comprise an amino acid sequence having at least 99% identity to SEQ ID NO: 27 or 28.

The lactonase can comprise an amino acid sequence having 100% identity to SEQ ID NO: 27 or 28.

F. Chitosanases

The enzyme can comprise a chitosanase.

Chitosanases can be used for any of the plant growth stimulating or plant health promoting purposes described herein, but are especially suitable for increasing nutrient uptake and increasing plant growth. This in turn leads to increased crop yield, improved early season vigor, and decreased susceptibility to early season stresses. Chitosanases are also useful for protecting plants from pathogens.

The chitosanase can comprise an exo-1,4-beta-D-glucosaminidase, an endo-1,4-beta-d-glucosaminidase, or a combination thereof.

The chitosanase can comprise a *Bacillus subtilis* chitosanase, a *Streptomyces* chitosanase, or a combination of any thereof.

The chitosanase can comprise an amino acid sequence having at least 70% identity to SEQ ID NO: 29 or 124.

The chitosanase can comprise an amino acid sequence having at least 75% identity to SEQ ID NO: 29 or 124.

The chitosanase can comprise an amino acid sequence having at least 80% identity to SEQ ID NO: 29 or 124.

The chitosanase can comprise an amino acid sequence having at least 85% identity to SEQ ID NO: 29 or 124.

The chitosanase can comprise an amino acid sequence having at least 90% identity to SEQ ID NO: 29 or 124.

The chitosanase can comprise an amino acid sequence having at least 95% identity to SEQ ID NO: 29 or 124.

The chitosanase can comprise an amino acid sequence having at least 98% identity to SEQ ID NO: 29 or 124.

The chitosanase can comprise an amino acid sequence having at least 99% identity to SEQ ID NO: 29 or 124.

The chitosanase can comprise an amino acid sequence having 100% identity to SEQ ID NO: 29 or 124.

G. Proteases

The enzyme can comprise a protease.

Proteases can be used for any of the plant growth stimulating or plant health promoting purposes described herein, but are particularly useful for increasing nutrient uptake and stimulating plant growth. This in turn leads to increased crop yield, improved early season vigor, and decreased susceptibility to early season stresses. Proteases are also useful for protecting plants from pathogens.

The protease can comprise a subtilisin, an acid protease, an alkaline protease, a proteinase, a peptidase, an endopeptidase, an exopeptidase, a thermolysin, a papain, a pepsin, a trypsin, a pronase, a carboxylase, a serine protease, a glutamate protease, an aspartate protease, a cysteine protease, a threonine protease, an asparagine protease, a histidine protease, a metalloprotease, or a combination of any thereof.

For example, the protease can comprise a cysteine protease, a serine protease, a threonine protease, an aspartate protease, an asparagine protease, a metalloprotease, a glutamate protease, or a combination of any thereof.

For example, the protease can comprise a metalloprotease, a serine protease, an aspartate protease, a histidine protease, or a combination of any thereof.

The protease preferably does not consist of a methionine aminopeptidase.

The protease preferably does not comprise a methionine aminopeptidase.

The protease can comprise comprises a *Bacillus* protease (e.g., a *Bacillus subtilis* protease), an *Aspergillus* protease, or a combination thereof.

The protease can comprise an amino acid sequence having at least 70% identity to any one of SEQ ID NOs. 46-48 and 127.

The protease can comprise an amino acid sequence having at least 75% identity to any one of SEQ ID NOs. 46-48 and 127.

The protease can comprise an amino acid sequence having at least 80% identity to any one of SEQ ID NOs. 46-48 and 127.

The protease can comprise an amino acid sequence having at least 85% identity to any one of SEQ ID NOs. 46-48 and 127.

The protease can comprise an amino acid sequence having at least 90% identity to any one of SEQ ID NOs. 46-48 and 127.

The protease can comprise an amino acid sequence having at least 95% identity to any one of SEQ ID NOs. 46-48 and 127.

The protease can comprise an amino acid sequence having at least 98% identity to any one of SEQ ID NOs. 46-48 and 127.

The protease can comprise an amino acid sequence having at least 99% identity to any one of SEQ ID NOs. 46-48 and 127.

The protease can comprise an amino acid sequence having at least 100% identity to any one of SEQ ID NOs. 46-48 and 127.

H. Glucanases

The enzyme can comprise a glucanase.

Glucanases can be used for any of the plant growth stimulating or plant health promoting purposes described herein, but are particularly useful for increasing nutrient uptake and stimulating plant growth. This in turn leads to increased crop yield, improved early season vigor, and decreased susceptibility to early season stresses. Glucanases can also be used for protecting plants from pathogens and for reducing susceptibility to an environmental stress in a plant.

Glucanases use water to break chemical bonds between individual glucose molecules glucans, which are long chain polysaccharides. Glucans can be broken down into two types, alpha glucan, consisting of primarily alpha chains of glucose molecules, and beta glucans, consisting of primarily beta chains of glucose molecules. Common alpha glucans include dextrans, glycogens, pullalans, and starch. Alpha glucans generally include combinations of alpha 1,4; alpha 1,6, and/or alpha 1,3 glucans and branches. Glucanases that are specific for cleaving alpha linkages are called alpha-glucanases. Beta glucanases are specific to beta linkages between glucans. Common beta glucans include cellulose, laminarin, lichenin, zymosan. Beta glucans are commonly found with b1,3; b1,4, and/or b1,6 linkages between glucose molecules. Glucanases can be either "exo" or "endo" depending on the location of the cleavage of the polysaccharide. Alpha-, beta-, exo- and endo-glucanases are all effective for stimulating plant growth.

The glucanase can comprise an endoglucanase, an exoglucanase, or a combination thereof.

The glucanase comprises an alpha-glucanase, a beta-glucanase, or a combination thereof.

Where the glucanase comprises an alpha-glucanase, the alpha-glucanase can comprise an amylase, an alpha-1,4-glucanase, an alpha-1,6-glucanase, or a combination of any thereof.

Where the glucanase comprises a beta-glucanase, the beta-glucanase can comprise an endo-beta-glucanase, an exo-beta-glucanase, or a combination thereof.

The beta-glucanase can comprise a beta-1,3-glucanase, a beta 1,3/1,4 glucanase, a beta-1,4-glucanase, a beta-1,6-glucanase, or a combination of any thereof.

For example, the beta-glucanase can comprise the beta-1,3-glucanase, the beta-1,4-glucanase, or a combination thereof.

The beta-1,3-glucanase can comprise a beta-1,3-endoglucanase.

The beta-1,4-glucanase can comprise a beta-1,4-endoglucanase.

The glucanase can comprise a cellulase, a glycoside hydrolase, a xyloglucan:xyloglucosyl transferase, a cycloheptaglucanase, an oligoxyloglucan beta-glycosidase, a cyclohexaglucanase, a xyloglucanase, a cellulose 1,4-beta-cellobiosidase, a glucan endo-1,3-beta-D-glucosidase, a cyclomaltodextrinase, a glucan 1,3-beta-glucosidase, a glucan endo-1,3-alpha-glucosidase, an endo-1,3(4)-beta-glucanase, an exo-beta-1,4-glucanase, a lichenase, a laminarinase, a glucan 1,4-beta-glucosidase, a glucan endo-1,6-beta-glucosidase, a glucan 1,3-alpha-glucosidase, an amylopectinase, a laminarinase, or a combination of any thereof.

The glucanase can comprise a non-cellulolytic glucanase.

In any of the methods, seeds, or compositions wherein the glucanase comprises a non-cellulolytic glucanase, the non-cellulolytic glucanase can comprise a xyloglucanase, a lichenase, an amylase, an amyloglucanase, amyloglucosidase, a laminarinase, a beta-1,3-glucanase, a beta-1,6-glucanase, a beta-1,3/1,4-glucanase, an alpha-1,4-glucanase, an alpha 1,6-glucanase, or a combination of any thereof.

Where the glucanase comprises a xyloglucanase, the xyloglucanase can comprise a xyloglucan-specific endo-beta-1,4-glucanase, a xyloglucan-specific exo-beta-1,4-glucanase, or a combination thereof.

The xyloglucanase can comprise a *Paenibacillus* glucanase.

Where the glucanase comprises a xyloglucanase (e.g., SEQ ID NO: 125), the method can further comprise applying a mannanase (e.g., SEQ ID NO: 128) to the plant growth medium, plant, plant seed, or area surrounding the plant or the plant seed.

Where the glucanase comprises a xyloglucanase (e.g., SEQ ID NO: 125), the seed can be further treated with a mannanase (e.g., SEQ ID NO: 128).

Where the glucanase comprises a xyloglucanase (e.g., SEQ ID NO: 125), the composition can further comprise a mannanase (e.g., SEQ ID NO: 128).

The xyloglucanase and the mannanase can be present in the method, on the seed, or in the composition in synergistically effective amounts.

The glucanase can comprise a cellulase.

The glucanase can comprise an endocellulase, an exocellulase, or a combination thereof.

The glucanase can comprise an *Acidothermus* glucanase, a *Trichoderma* glucanase, an *Aspergillus* glucanase, a *Paenibacillus* glucanase, a *Helix* glucanase, a *Bacillus* glucanase, or a combination of any thereof.

For example, the glucanase can comprise a *Bacillus circulans* glucanase, a *Bacillus subtilis* glucanase (e.g., a *Bacillus subtilis* endoglucanase or a *Bacillus subtilis* beta-glucosidase), a *Bacillus thuringiensis* glucanase (e.g., a *Bacillus thuringiensis* endoglucanase or a *Bacillus thuringiensis* beta-glucosidase), a *Bacillus cereus* glucanase (e.g., a *Bacillus cereus* endoglucanase or a *Bacillus cereus* beta-glucosidase), a *Trichoderma reesei* glucanase (e.g., a *Trichoderma reesei* exocellulase or a *Trichoderma reesi* beta-1,4-endoglucanase), a *Bacillus clausii* glucanase (e.g., a *Bacillus clausii* endoglucanase or a *Bacillus clausii* beta-glucosidase), a *Helix pomatia* glucanase (e.g., a *Helix pomatia* beta-1,3 endoglucanase), an *Acidothermus cellulolyticus* glucanase (e.g., a *Acidothermus cellulolyticus* beta-1,4 endoglucanase), or a combination of any thereof.

The glucanase can comprise an amino acid sequence having at least 70% identity to any one of SEQ ID NOs. 30-45, 125, and 126.

The glucanase can comprise an amino acid sequence having at least 75% identity to any one of SEQ ID NOs. 30-45, 125, and 126.

The glucanase can comprise an amino acid sequence having at least 80% identity to any one of SEQ ID NOs. 30-45, 125, and 126.

The glucanase can comprise an amino acid sequence having at least 85% identity to any one of SEQ ID NOs. 30-45, 125, and 126.

The glucanase can comprise an amino acid sequence having at least 90% identity to any one of SEQ ID NOs. 30-45, 125, and 126.

The glucanase can comprise an amino acid sequence having at least 95% identity to any one of SEQ ID NOs. 30-45, 125, and 126.

The glucanase can comprise an amino acid sequence having at least 98% identity to any one of SEQ ID NOs. 30-45, 125, and 126.

The glucanase can comprise an amino acid sequence having at least 99% identity to any one of SEQ ID NOs. 30-45, 125, and 126.

The glucanase can comprise an amino acid sequence having 100% identity to any one of SEQ ID NOs. 30-45, 125, and 126.

Where a glucanase is applied in a formulation, or where a seed is coated with a seed coating formulation comprising a glucanase, the formulation can suitably comprise additional agrochemicals and/or a microbial inoculant. For example, the formulation can suitably comprise a fungicide, insecticide, a nematicide, a fertilizer, a plant hormone, a bacterial inoculant, a fungal inoculant, or a combination of any thereof. Particular fungicides, insecticides, nematicides, fertilizers, plant hormones, bacterial inoculants, and fungal inoculants are described in Section XVI below.

I. Phytases

The enzyme can comprise a phytase.

Phytases act on phytic acids in soil, a source of free phosphate for plant growth. Phytases remove select phosphates off of the phytic acids, and the freed phosphates can be taken up by nearby plants.

Where the enzyme comprises a phytase, the phytase can comprise a *Triticum aestivum* phytase.

The phytase can comprise an amino acid sequence having at least 70% identity to any one of SEQ ID NOs. 132-134.

The phytase can comprise an amino acid sequence having at least 75% identity to any one of SEQ ID NOs. 132-134.

The phytase can comprise an amino acid sequence having at least 80% identity to any one of SEQ ID NOs. 132-134.

The phytase can comprise an amino acid sequence having at least 85% identity to any one of SEQ ID NOs. 132-134.

The phytase can comprise an amino acid sequence having at least 90% identity to any one of SEQ ID NOs. 132-134.

The phytase can comprise an amino acid sequence having at least 95% identity to any one of SEQ ID NOs. 132-134.

The phytase can comprise an amino acid sequence having at least 98% identity to any one of SEQ ID NOs. 132-134.

The phytase can comprise an amino acid sequence having at least 99% identity to any one of SEQ ID NOs. 132-134.

The phytase can comprise an amino acid sequence having 100% identity to any one of SEQ ID NOs. 132-134.

The phytase can comprise a mixture of phytases comprising SEQ ID NOs. 132, 133, and 134.

J. Acid Phosphatases

The enzyme can comprise an acid phosphatase.

Acid phosphatases act on insoluble and less soluble forms of phosphates in the soil, and release them from for uptake by plants.

Where the enzyme comprises an acid phosphatase, the acid phosphatase can comprise a *Triticum aestivum* acid phosphatase.

The acid phosphatase can comprise an amino acid sequence having at least 70% identity to SEQ ID NO: 130 or 131.

The acid phosphatase can comprise an amino acid sequence having at least 75% identity to SEQ ID NO: 130 or 131.

The acid phosphatase can comprise an amino acid sequence having at least 80% identity to SEQ ID NO: 130 or 131.

The acid phosphatase can comprise an amino acid sequence having at least 85% identity to SEQ ID NO: 130 or 131.

The acid phosphatase can comprise an amino acid sequence having at least 90% identity to SEQ ID NO: 130 or 131.

The acid phosphatase can comprise an amino acid sequence having at least 95% identity to SEQ ID NO: 130 or 131.

The acid phosphatase can comprise an amino acid sequence having at least 98% identity to SEQ ID NO: 130 or 131.

The acid phosphatase can comprise an amino acid sequence having at least 99% identity to SEQ ID NO: 130 or 131.

The acid phosphatase can comprise an amino acid sequence having 100% identity to SEQ ID NO: 130 or 131.

The acid phosphatase can comprise a mixture of acid phosphatases comprising SEQ ID NOs. 130 and 131.

In any of the methods described herein that involve the use of an acid phosphatase, the method can further comprise applying a second enzyme to the plant growth medium, the plant, the plant seed, or the area surrounding the plant or the plant seed.

In any of the plant seeds described herein that are treated or coated with an acid phosphatase, the seed can be further treated or coated with a second enzyme.

Any of the compositions described herein that comprise an acid phosphatase can further comprise a second enzyme.

The second enzyme can comprise a lipase, a phospholipase, a glucanase, a xylanase, a pectinase, a mannanase, a lichenase, or a combination of any thereof. The lipase, phospholipase, glucanase, xylanase, pectinase, mannanase, or lichenase, can comprise any of the lipases, phospholipases, glucanases, xylanases, pectinases, mannanases, or lichenases described herein.

K. Pectinases

The enzyme can comprise a pectinase.

Pectinases act on pectin and related polysaccharides to release small sugars. The small sugars are in turn taken up by the plant as carbon sources and can also feed the inherent microbes that surround the plant.

Where the enzyme comprises a pectinase, the pectinase can comprise a pectolyase.

For example, the pectolyase can comprise an *Aspergillus japonicus* pectolyase.

The pectolyase can comprise an amino acid sequence having at least 70% identity to SEQ ID NO: 129.

The pectolyase can comprise an amino acid sequence having at least 75% identity to SEQ ID NO: 129.

The pectolyase can comprise an amino acid sequence having at least 80% identity to SEQ ID NO: 129.

The pectolyase can comprise an amino acid sequence having at least 85% identity to SEQ ID NO: 129.

The pectolyase can comprise an amino acid sequence having at least 90% identity to SEQ ID NO: 129.

The pectolyase can comprise an amino acid sequence having at least 95% identity to SEQ ID NO: 129.

The pectolyase can comprise an amino acid sequence having at least 98% identity to SEQ ID NO: 129.

The pectolyase can comprise an amino acid sequence having at least 99% identity to SEQ ID NO: 129.

The pectolyase can comprise an amino acid sequence having 100% identity to SEQ ID NO: 129.

L. Mannanases

The enzyme can comprise a mannanase.

Mannanases act on glucomannans and related polysaccharides to release small sugars. The small sugars are in turn taken up by the plant as carbon sources and can also feed the inherent microbes that surround the plant.

Where the enzyme comprises a mannanase, the mannanase can comprise a *Bacillus* mannanase.

The mannanase can comprise an amino sequence having at least 70% identity to SEQ ID NO: 128.

The mannanase can comprise an amino sequence having at least 75% identity to SEQ ID NO: 128.

The mannanase can comprise an amino sequence having at least 80% identity to SEQ ID NO: 128.

The mannanase can comprise an amino sequence having at least 85% identity to SEQ ID NO: 128.

The mannanase can comprise an amino sequence having at least 90% identity to SEQ ID NO: 128.

The mannanase can comprise an amino sequence having at least 95% identity to SEQ ID NO: 128.

The mannanase can comprise an amino sequence having at least 98% identity to SEQ ID NO: 128.

The mannanase can comprise an amino sequence having at least 99% identity to SEQ ID NO: 128.

The mannanase can comprise an amino sequence having 100% identity to SEQ ID NO: 128.

M. ACC Deaminases

The enzyme can comprise an ACC deaminase.

The ACC deaminase can comprise any of the enzymes described above in Section II.

The ACC deaminase can comprise an amino acid sequence having at least 70% identity to any one of SEQ ID NOs. 7-12, 113, and 114.

The ACC deaminase can comprise an amino acid sequence having at least 75% identity to any one of SEQ ID NOs. 7-12, 113, and 114.

The ACC deaminase can comprise an amino acid sequence having at least 80% identity to any one of SEQ ID NOs. 7-12, 113, and 114.

The ACC deaminase can comprise an amino acid sequence having at least 85% identity to any one of SEQ ID NOs. 7-12, 113, and 114.

The ACC deaminase can comprise an amino acid sequence having at least 90% identity to any one of SEQ ID NOs. 7-12, 113, and 114.

The ACC deaminase can comprise an amino acid sequence having at least 95% identity to any one of SEQ ID NOs. 7-12, 113, and 114.

The ACC deaminase can comprise an amino acid sequence having at least 98% identity to any one of SEQ ID NOs. 7-12, 113, and 114.

The ACC deaminase can comprise an amino acid sequence having at least 99% identity to any one of SEQ ID NOs. 7-12, 113, and 114.

The ACC deaminase can comprise an amino acid sequence having 100% identity to any one of SEQ ID NOs. 7-12, 113, and 114.

N. Expansin Proteins

Expansin proteins aid plant walls in expanding during growth of the plant. Expansins are thus particularly useful in any of the methods for stimulating plant growth described herein.

The expansin protein can comprise an amino acid sequence having at least 70% identity to SEQ ID NO: 74.

The expansin protein can comprise an amino acid sequence having at least 75% identity to SEQ ID NO: 74.

The expansin protein can comprise an amino acid sequence having at least 80% identity to SEQ ID NO: 74.

The expansin protein can comprise an amino acid sequence having at least 85% identity to SEQ ID NO: 74.

The expansin protein can comprise an amino acid sequence having at least 90% identity to SEQ ID NO: 74.

The expansin protein can comprise an amino acid sequence having at least 95% identity to SEQ ID NO: 74.

The expansin protein can comprise an amino acid sequence having at least 98% identity to SEQ ID NO: 74.

The expansin protein can comprise an amino acid sequence having at least 99% identity to SEQ ID NO: 74.

The expansin protein can comprise an amino acid sequence having at least 100% identity to SEQ ID NO: 74.

VIII. Use of Fertilizers and/or Biostimulants with the Methods, Seeds, and Compositions In any of the methods described herein, the method can further comprise applying a fertilizer, a biostimulant, or a combination thereof to the plant growth medium, the plant, the plant seed, or the area surrounding the plant or the plant seed.

For any of the plant seeds described herein, the plant seed can be further treated or coated with a fertilizer, a biostimulant, or a combination thereof.

For any of the methods, seeds, or compositions described herein, the fertilizer can comprise nitrogen, phosphate (e.g., monoammonium phosphate, diammonium phosphate, orthophosphate, orthopolyphosphate, or a combination of any thereof), potassium (e.g., potassium acetate), zinc, iron, selenium, boron, copper, or a combination of any thereof.

For example, the fertilizer can comprise 12% ammoniacal nitrogen and 58% available phosphate.

Additional fertilizers that can be used are described in Section XVI below.

The biostimulant can comprise a gibberellic acid, an indole-3-butyric acid, a kinetin, an auxin, an auxin homolog or derivative, or a combination of any thereof.

In any of the methods or seeds involving the use of a fertilizer and/or a biostimulant, the enzyme suitably comprises an acid phosphatase, a phospholipase, a mannanase, a glucanase, or a combination of any thereof. The acid phosphatase, phospholipase, mannanase, or glucanase can comprise any of the acid phosphatases, phospholipases, mannanases, or glucanase described herein.

IX. Enzyme Preparations

In any of the methods, seeds, or compositions described herein involving the use of a free enzyme and/or an expansin protein, the enzyme or expansin protein can comprise a crude cell extract containing the enzyme or expansin protein, a partially purified enzyme or expansin protein, or a substantially purified enzyme or expansin protein.

In any of the methods, seeds, or compositions described herein involving the use of a free enzyme and/or an expansin protein, the enzyme or expansin protein preferably does not comprise enzyme or expansin protein bound to exosporium of a *Bacillus cereus* family member.

In any of the methods, seeds, or compositions described herein involving the use of a free enzyme and/or expansin protein, the enzyme or expansin protein is preferably not bound to the exosporium of an intact *Bacillus cereus* family member spore.

X. Immobilization of the Enzyme and/or Expansin Protein

In any of the methods, seeds, or compositions described herein comprising the use of a free enzyme and/or an expansin protein, the enzyme or expansin protein can comprise enzyme or expansin protein that is immobilized on a matrix or support.

The matrix or support can comprise charcoal, biochar, nanocarbon, agarose, an alginate, cellulose, a cellulose derivative, silica, plastic, stainless steel, glass, polystyrene, a ceramic, dolomite, a clay, diatomaceous earth, talc, a polymer, a gum, a water-dispersable material, or a combination of any thereof.

Immobilization of the enzyme or expansin protein on the matrix or support preferably results in a slower release of the enzyme or expansin protein into the environment or onto the plant or the plant seed as compared to the release rate for the same non-immobilized enzyme or expansin proteins under the same conditions.

XI. Methods for Making Free Enzyme

Free enzyme can be prepared by a number of standard biochemical and molecular biology methods which are generally known in the art. For example, a gene encoding an enzyme can be amplified from chromosomal DNA using the polymerase chain reaction (PCR), and cloned into a suitable vector (e.g., a plasmid vector). The vector suitably comprises a multiple cloning site into which the DNA molecule encoding the fusion protein can be easily inserted. The vector also suitably contains a selectable marker, such as an antibiotic resistance gene, such that bacteria transformed, transfected, or mated with the vector can be readily identified and isolated. Where the vector is a plasmid, the plasmid suitably also comprises an origin of replication. Alternatively, DNA coding for the enzyme protein can be integrated into the chromosomal DNA of the microorganism host.

The host can then be cultured and enzyme harvested from the cultures. A crude cell extract can be used or the enzyme can be partially or substantially purified using standard biochemical techniques.

Suitable hosts for large-scale production of enzymes include but are not limited to *Bacillus* species (e.g., *Bacillus subtilis, Bacillus licheniformis, Bacillus coagulans, Bacillus megaterium, Bacillus thuringiensis, Bacillus fusiformis, Bacillus cereus*, or *Bacillus mycoides*), *Escherichia coli, Aspergillus niger, Aspergillus oryzae, Streptomyces* species, *Klebsiella* species, *Mucor* species, *Rhizopus* species, *Mortierella* species, *Kluyveromyces* species, *Candida* species, *Penicillium chrysogenum, Trichoderma* species *Saccharomyces cerevisiae, Pichia pastoris, Hansenula polymorpha, Kluyveromyces lactis, Yarrowia lipolytica, Schizosaccharomyces pombe*, and *Candida utilitis.*

Enzymes can be used as collected from whole fermentation broth, or partially or substantially purified from the fermentation batch culture.

Alternatively, enzymes can be produced by screening microorganisms and selecting microorganisms that express high levels of the enzyme. This can be done by initial selection, enrichment, and/or screening in nutritional media that contains an enzyme substrate as a nutrient source for the microorganisms. Often additional selection is performed using differential nutrition media that has an indicator to demonstrate the enzyme levels and activity of the enzymes produced by the identified microorganisms. These microorganisms can be mutated and screened for isolates that product enhanced levels of these enzymes. These microorganism can be utilized in large batch and continuous fermentation methods to create and secrete ample quantities of enzymes. Optimization of the fermentation process and conditions can generally increase the output of the microorganisms.

Enzymes can also be produced at high levels using eukaryotic cell lines, many of which can be engineered to secrete high levels of enzymes, with the advantages of different levels of critical posttranslational modifications and reduction in host enzyme production issues. These can also be scalable to larger cell culture production scale vessels and enzymes purified and treated as above. Examples of suitable eukaryotic cell lines for producing enzymes include, but are not limited to: insect cells derived from insects such as *Bombyx mori, Mamestra brassicae, Spodoptera frugiperda, Trichoplusiani*, or *Drosophila melanogaster*; and vertebrate cell lines derived from a vertebrate such as a mouse, rat, hamster, human, or dog.

Other potential sources of enzymes include cell-free protein expression vectors, including those derived from animal, bacterial, fungal, and plant origins.

Transgenic organisms such as plants, rabbit, mice, chicken, or frogs can also be used for the production of recombinant enzymes. For examples, plants can be engineered to overexpress enzymes, and the enzymes can then be collected from the plant and purified or used as crude extract. Such production systems allow for low cost expression of the enzymes and provide a source of material to deliver to plants. These methods have the added advantage of being easily scaled up and with minimal effort.

In each of these production systems, the yield and quality of the desired enzymes can be improved through processes of genetic engineering and formulation. For example, genetic engineering could involve creation of high level expression cassettes and production systems, removal of protease and degradative genes from the production microorganism, optimization of the enzyme for heat stability and long term storage stability, and enhancement of the ability of the enzyme or the production microorganism to secrete mature enzyme into the media for ease of collection and use. Additionally, expression strains can be used to induce point mutations that can lead to increased ability to produce adequate or increased levels of enzymes. In some cases, the production microorganism can also be used and delivered to the plant seed, vicinity around the plant, to the plant roots, or near the plant to get the desired effect in situ on the plant.

Other sources of enzymes include extraction from animal, plant, insect, seaweed, or other biological extracts. Common sources of industrial scale enzymes created and/or purified in this manner include porcine and bovine internal tissues, such as abomasum, liver, mucosas, pancreas, as well as plant sources such as *Carica papaya*. Another example would be the purification of glucanases from barley.

Many commercial sources of enzymes come from tissues that have high levels of target enzymes that can be used as is or in purified forms for agricultural uses.

XII. Signal Peptides

Any signal peptide can be used to modify any of the enzymes described herein such that the enzyme will be secreted from a host microorganism in which it is expressed. The type of signal peptide used will depend primarily on the identity of the host microorganism, since the secretion machinery of different microorganisms will vary in their ability to recognize specific signal peptides. Illustrative signal peptide sequences are provided below in Table 16, together with the bacterial species in which the signal peptides are found in nature. The signal peptides will result in secretion of a protein to which they are linked in the genus of bacteria in which they are found as well as closely related genera. For example, a signal sequence from *Bacillus thuringiensis* will cause secretion of a protein in bacteria of the genus *Bacillus*, as well as bacteria of the genera *Paenibacillus* and *Lysinibacillus.*

For ease of reference, descriptions of amino acid sequences for illustrative signal peptides that can be added to any of the enzymes or expansin proteins described herein to cause secretion of the enzyme or expansin proteins from a microorganism in which it is expressed are provided below in Table 16. Any of the signal peptides listed in Table 16 below can be added at the amino terminus of any of the enzymes or expansin proteins described herein to cause secretion of the enzyme or expansin protein.

TABLE 16

Amino acid sequences for signal peptides

| Source Species for Signal Peptide | SEQ ID NO. for amino acid sequence |
|---|---|
| *Bacillus thuringiensis* | 49 |
| *Bacillus thuringiensis* serovar israelensis 4Q7 | 50 |
| *Bacillus cereus* ATCC 10987 | 51 |
| *Clostridium perfingens* | 52 |
| *Streptomyces chromofuscus* | 53 |
| *Bacillus subtilis* subsp. *subtilis* str. 168 | 54 |
| *Caldicellulosiruptor saccharolyticus* | 55 |
| *Bacillus subtilis* subsp. *subtilis* str. 168 | 56 |
| *Bacillus subtilis* subsp. *subtilis* str. 168 | 57 |

TABLE 16-continued

Amino acid sequences for signal peptides

| Source Species for Signal Peptide | SEQ ID NO. for amino acid sequence |
|---|---|
| *Geobacillus stearothermophilus* (*Bacillus stearothermophilus*) | 58 |
| *Bacillus subtilis* subsp. *subtilis* str. 168 | 59 |
| *Bacillus subtilis* subsp. *subtilis* str. 168 | 60 |
| *Bacillus subtilis* subsp. *subtilis* str. 168 | 61 |
| *Bacillus circulans* | 62 |
| *Bacillus circulans* | 63 |
| *Bacillus subtilis* subsp. *subtilis* str. 168 | 64 |
| *Bacillus subtilis* subsp. *subtilis* str. 168 | 65 |
| *Bacillus subtilis* subsp. *subtilis* str. 168 | 66 |
| *Bacillus subtilis* subsp. *subtilis* str. 168 | 67 |
| *Bacillus subtilis* subsp. *subtilis* str. 168 | 68 |
| *Bacillus thuringiensis* | 69 |
| *Bacillus thuringiensis* | 70 |
| *Bacillus thuringiensis* | 71 |
| *Bacillus pseudomycoides* | 72 |
| *Bacillus thuringiensis* serovar israelensis 4Q7 | 73 |
| *Bacillus cereus* | 135 |
| *Burkholderia cepacia* | 137 |
| *Pseudomonas fluorescens* | 138 |
| *Streptomyces* species N174 | 139 |
| *Paenibacillus* species | 140 |
| *Aspergillus saitoi* | 141 |
| *Bacillus* sp. | 142 |
| *Aspergillus japonicus* | 143 |
| *Triticum aestivum* | 144 |
| *Triticum aestivum* | 145 |
| *Triticum aestivum* | 146 |
| *Triticum aestivum* | 147 |

For example, the signal peptide can comprise an amino acid sequence having at least 70% identity to with any one of SEQ ID NOs. 49-73, 135 and 137-147.

For example, the signal peptide can comprise an amino acid sequence having at least 75% identity to with any one of SEQ ID NOs. 49-73, 135 and 137-147.

For example, the signal peptide can comprise an amino acid sequence having at least 80% identity to with any one of SEQ ID NOs. 49-73, 135 and 137-147.

For example, the signal peptide can comprise an amino acid sequence having at least 85% identity to with any one of SEQ ID NOs. 49-73, 135 and 137-147.

For example, the signal peptide can comprise an amino acid sequence having at least 90% identity to with any one of SEQ ID NOs. 49-73, 135 and 137-147.

For example, the signal peptide can comprise an amino acid sequence having at least 95% identity to with any one of SEQ ID NOs. 49-73, 135 and 137-147.

For example, the signal peptide can comprise an amino acid sequence having at least 98% identity to with any one of SEQ ID NOs. 49-73, 135 and 137-147.

For example, the signal peptide can comprise an amino acid sequence having at least 99% identity to with any one of SEQ ID NOs. 49-73, 135 and 137-147.

For example, the signal peptide can comprise an amino acid sequence having 100% identity to with any one of SEQ ID NOs. 49-73, 135 and 137-147.

Signal peptides suitable for use in bacteria of the genus *Bacillus*, bacteria of the genus *Paenibacillus*, or bacteria of the genus *Lysinibacillus* are provided in SEQ ID NOs. 49-51, 54, 56-73, 135, 139, 140, and 142.

Thus, for example, the signal peptide can comprise an amino acid sequence having at least 70% identity with any one of SEQ ID NOs. 49-51, 54, 56-73, 135, 139, 140, and 142.

The signal peptide can comprise an amino acid sequence having at least 75% identity with any one of SEQ ID NOs. 49-51, 54, 56-73, 135, 139, 140, and 142.

The signal peptide can comprise an amino acid sequence having at least 80% identity with any one of SEQ ID NOs. 49-51, 54, 56-73, 135, 139, 140, and 142.

The signal peptide can comprise an amino acid sequence having at least 85% identity with any one of SEQ ID NOs. 49-51, 54, 56-73, 135, 139, 140, and 142.

The signal peptide can comprise an amino acid sequence having at least 90% identity with any one of SEQ ID NOs. 49-51, 54, 56-73, 135, 139, 140, and 142.

The signal peptide can comprise an amino acid sequence having at least 95% identity with any one of SEQ ID NOs. 49-51, 54, 56-73, 135, 139, 140, and 142.

The signal peptide can comprise an amino acid sequence having at least 98% identity with any one of SEQ ID NOs. 49-51, 54, 56-73, 135, 139, 140, and 142.

The signal peptide can comprise an amino acid sequence having at least 99% identity with any one of SEQ ID NOs. 49-51, 54, 56-73, 135, 139, 140, and 142.

The signal peptide can comprise an amino acid sequence having 100% identity with any one of SEQ ID NOs. 49-51, 54, 56-73, 135, 139, 140, and 142.

Thus, for example, when the signal peptide comprises an amino acid sequence having at least 70%, at least 75%, at least 80%, at least 85%, at least 90%, at least 95%, at least 98%, at least 99%, or 100% sequence identity with any one of SEQ ID NOs. 49-51, 54, 56-73, 135, 139, 140, and 142, the microorganism in which the enzyme or expansin protein is expressed suitably comprises a bacterium of the genus *Bacillus*, a bacterium of the genus *Paenibacillus*, a bacterium of the genus *Lysinibacillus*, a bacterium of the genus *Pseudomonas*, or a combination of any thereof.

For example, the microorganism can comprise *Bacillus mycoides, Bacillus pseudomycoides, Bacillus cereus, Bacillus firmus, Bacillus thuringiensis, Bacillus megaterium, Bacillus subtilis, Bacillus aryabbattai, Bacillus amyloliquefaciens, Bacillus circulans, Bacillus flexus, Bacillus nealsonii, Bacillus pumulis, Bacillus licheniformis, Lysinibacillus macroides, Lysinibacillus sphericus, Lysinibacillus fusiformis*, or a combination of any thereof.

The microorganism preferably comprises *Bacillus thuringiensis, Bacillus cereus, Bacillus pseudomycoides, Bacillus mycoides, Lysinibacillus macroides, Lysinibacillus fusiformis, Lysinibacillus sphericus*, or a combination of any thereof.

The signal peptide is preferably present at the amino terminus of the enzyme or expansin protein.

XIII. Recombinant Microorganisms

Recombinant microorganisms, formulations and compositions containing the recombinant microorganisms, methods for using the recombinant microorganisms, and seeds treated with the recombinant microorganisms are described herein above.

In any of the recombinant microorganisms, formulations, compositions, methods, or seeds described herein, the enzyme or expansin protein can be expressed under the control of a constitutive promoter.

In any of the recombinant microorganisms, formulations, compositions, methods, or seeds described herein, the enzyme or expansin protein can be expressed under the control of an inducible promoter.

For any of the recombinant microorganisms, formulations, compositions, methods, or seeds described herein, the recombinant microorganism can comprise a bacterium of the genus *Bacillus*, a bacterium of the genus *Paenibacillus*, a bacterium of the genus *Lysinibacillus*, a fungus of the genus *Penicillium*, a bacterium of the genus *Glomus*, a bacterium of the genus *Pseudomonas*, a bacterium of the genus *Arthrobacter*, a bacterium of the genus *Paracoccus*, a bacterium of the genus *Rhizobium*, a bacterium of the genus *Bradyrhizobium*, a bacterium of the genus *Azosprillium*, a bacterium of the genus *Enterobacter*, a bacterium of the genus *Escherichia*, or a combination of any thereof.

Where the recombinant microorganism comprises a recombinant spore-forming microorganism, the recombinant spore-forming microorganism can comprise a bacterium of the genus *Bacillus*, a bacterium of the genus *Paenibacillus*, a bacterium of the genus *Lysinibacillus*, a fungus of the genus *Penicillium*, a fungus of the genus *Glomus*, or a combination of any thereof.

For any of the recombinant microorganisms, formulations, compositions, methods, or seeds described herein, the recombinant microorganism suitably comprises a bacterium of the genus *Bacillus*, a bacterium of the genus *Paenibacillus*, a bacterium of the genus *Lysinibacillus*, or a combination of any thereof.

For example, the recombinant microorganism can comprise *Bacillus mycoides, Bacillus pseudomycoides, Bacillus cereus, Bacillus thuringiensis, Bacillus megaterium, Bacillus subtilis, Bacillus aryabbattai, Bacillus amyloliquefaciens, Bacillus circulans, Bacillus flexus, Bacillus nealsonii, Bacillus pumulis, Lysinibacillus macroides, Lysinibacillus sphericus, Lysinibacillus fusiformis*, or a combination of any thereof.

The recombinant microorganism suitably comprises *Bacillus thuringiensis, Bacillus cereus, Bacillus pseudomycoides, Lysinibacillus macroides, Lysinibacillus sphericus, Lysinibacillus fusiformis*, or a combination thereof.

For any of the recombinant microorganisms, formulations, methods, or seeds described herein, the recombinant microorganism can comprise a plant-growth promoting strain of bacteria, an endophytic strain of bacteria, or a strain of bacteria that is both plant-growth promoting and endophytic.

The strain can produce an insecticidal toxin (e.g., a Cry toxin), produce a fungicidal compound (e.g., a β-1,3-glucanase, a chitosanase, a lyticase, or a combination thereof), produce a nematicidal compound (e.g., a Cry toxin), produce a bacteriocidal compound, be resistant to one or more antibiotics, comprise one or more freely replicating plasmids, bind to plant roots, colonize plant roots, form biofilms, solubilize nutrients, secrete organic acids, or combinations thereof.

For example, the strain can comprise:

(a) *Bacillus aryabhattai* CAP53 (NRRL No. B-50819),
(b) *Bacillus aryabhattai* CAP56 (NRRL No. B-50817),
(c) *Bacillus flexus* BT054 (NRRL No. B-50816),
(d) *Paracoccus kondratievae* NC35 (NRRL No. B-50820),
(e) *Bacillus mycoides* BT155 (NRRL No. B-50921),
(f) *Enterobacter cloacae* CAP12 (NRRL No. B-50822),
(g) *Bacillus nealsonii* BOBA57 (NRRL No. NRRL B-50821),
(h) *Bacillus mycoides* EE118 (NRRL No. B-50918),
(i) *Bacillus subtilis* EE148 (NRRL No. B-50927),
(j) *Alcaligenes faecalis* EE107 (NRRL No. B-50920),
(k) *Bacillus mycoides* EE141 (NRRL NO. B-50916),
(l) *Bacillus mycoides* BT46-3 (NRRL No. B-50922),
(m)*Bacillus cereus* family member EE128 (NRRL No. B-50917),
(n) *Paenibacillus massiliensis* BT23 (NRRL No. B-50923),
(o) *Bacillus cereus* family member EE349 (NRRL No. B-50928),
(p) *Bacillus subtilis* EE218 (NRRL No. B-50926),
(q) *Bacillus megaterium* EE281 (NRRL No. B-50925),
(r) *Bacillus cereus* family member EE-B00377 (NRRL B-67119);
(s) *Bacillus pseudomycoides* EE-B00366 (NRRL B-67120),
(t) *Bacillus mycoides* EE-B00363 (NRRL B-67121),
(u) *Bacillus pumilus* EE-B00143 (NRRL B-67123),
(v) *Bacillus thuringiensis* EE-B00184 (NRRL B-67122),
(w)*Bacillus mycoides* EE116 (NRRL No. B-50919),
(x) *Bacillus cereus* family member EE417 (NRRL No. B-50974),
(y) *Bacillus subtilis* EE442 (NRRL No. B-50975),
(z) *Bacillus subtilis* EE443 (NRRL No. B-50976),
(aa) *Bacillus cereus* family member EE444 (NRRL No. B-50977),
(bb) *Bacillus subtilis* EE405 (NRRL No. B-50978),
(cc) *Bacillus cereus* family member EE439 (NRRL No. B-50979),
(dd) *Bacillus megaterium* EE385 (NRRL No. B-50980),
(ee) *Bacillus cereus* family member EE387 (NRRL No. B-50981),
(ff) *Bacillus circulans* EE388 (NRRL No. B-50982),
(gg) *Bacillus thuringiensis* EE319 (NRRL No. B-50983),
(hh) *Bacillus cereus* family member EE377 (NRRL No. B-67119),
(ii) *Bacillus mycoides* EE363 (NRRL No. B-67121),
(jj) *Bacillus pseudomycoides* EE366 (NRRL No. B-67120);
(kk) *Bacillus thuringiensis* BT013A (NRRL No. B-50924);
or a combination of any thereof.

Each of these strains has been deposited with the United States Department of Agriculture (USDA) Agricultural Research Service (ARS), having the address 1815 North University Street, Peoria, Illinois 61604 U.S.A., and are identified by the NRRL deposit numbers provided in parentheses. Strains (a)-(d), (f), and (g) were deposited on Mar. 11, 2013. Strains (e), (h)-(q), (w), and (kk) were deposited on Mar. 10, 2014. Strains (x)-(ff) were deposited on Sep. 10, 2014. Strain (gg) was deposited on Sep. 17, 2014. Strains (r)-(v), (hh), (ii), and j) were deposited on Aug. 19, 2015. *Bacillus thuringiensis* BT013A is also known as *Bacillus thuringiensis* 4Q7.

The isolation and characterization of these strains is described hereinbelow in the Examples. Partial 16S ribosomal RNA sequences for each of these strains are provided in the sequence listing and summarized below in Table 17, together with their SEQ ID NOs.

TABLE 17

Partial 16S ribosomal RNA sequences

| Strain | SEQ ID NO. for partial 16S ribosomal RNA sequence |
|---|---|
| *Bacillus mycoides* EE118 | 75 |
| *Bacillus mycoides* EE141 | 76 |
| *Bacillus mycoides* BT46-3 | 77 |
| *Bacillus cereus* family member EE128 | 78 |
| *Bacillus cereus* family member EE349 | 79 |
| *Bacillus mycoides* BT155 | 80 |
| *Bacillus cereus* family member EE439 | 81 |
| *Bacillus thuringiensis* EE417 | 82 |
| *Bacillus cereus* EE444 | 83 |
| *Bacillus thuringiensis* EE319 | 84 |

TABLE 17-continued

| Partial 16S ribosomal RNA sequences | |
|---|---|
| Strain | SEQ ID NO. for partial 16S ribosomal RNA sequence |
| *Bacillus megaterium* EE385 | 85 |
| *Bacillus* sp. EE387 | 86 |
| *Bacillus circulans* EE388 | 87 |
| *Bacillus subtilis* EE405 | 88 |
| *Lysinibacillus fusiformis* EE442 | 89 |
| *Lysinibacillus sphaericus* EE443 | 90 |
| *Bacillus aryabhattai* CAP53 | 91 |
| *Bacillus aryabhattai* CAP56 | 92 |
| *Bacillus flexus* BT054 | 93 |
| *Paracoccus kondratievae* NC35 | 94 |
| *Enterobacter cloacae* CAP12 | 95 |
| *Bacillus nealsonii* BOBA57 | 96 |
| *Bacillus subtilis* EE148 | 97 |
| *Alcaligenes faecalis* EE107 | 98 |
| *Paenibacillus massiliensis* | 99 |
| *Bacillus subtilis* EE218 | 100 |
| *Bacillus megaterium* EE281 | 101 |
| *Bacillus thuringiensis* EE184 | 102 |
| *Bacillus mycoides* EE363 | 103 |
| *Bacillus pseudomycoides* EE366 | 104 |
| *Bacillus cereus* family member EE377 | 105 |
| *Bacillus pumulis* EE143 | 106 |
| *Bacillus mycoides* EE116 | 107 |
| *Bacillus thuringiensis* BT013A | 136 |

An endophytic microorganism can be used for expression of the enzymes. While many microorganism of the rhizosphere have a symbiotic relationship with the plant, only a small subset of these microorganisms are capable of being internalized into the plant and growing endophytically. Several *Bacillus cereus* family member strains and several non-*Bacillus cereus* family member bacterial strains have been isolated from corn seedlings and found to have the ability to grow endophytically in plants. Other endophytic microorganisms would also be useful including, but not limited to, bacterial endophytes from genera: *Cellulomonas, Clavibacter, Curtobacterium, Pseudomonas, Paenibacilllus, Enterobacter, Bacillus, Klebsiella, Arthrobacter, Lysinibacillus, Pantoea, Actinomyces, Streptomyces, Alcaligenes*, and *Microbacterium*. Fungal endophytes can also be used, including fungal endophytes from the genera: *Neotyphodium, Gliocadium, Acremonium lolii, Clavicipitaceae, Ascomycetes, Idriella, Xylariaceous, Ascomycotina, Deuteromycotina, Aspergillus, Phomopsis, Wardomyces, Fusarium, Dreschrella, Pestalotia, Curvularia, Humicola, Nodulisporium*, and *Penicillium*.

Many microorganisms can colonize, live next to, live on, or become endophytic to a plant. These microorganisms would provide a useful delivery mechanism of target enzymes to the plant, the seed, the vicinity of the plant, or the plant growth medium. Microorganisms selected that can colonize the roots or become endophytic can be screened, recombinantly modified to express or overexpress an enzyme, and produced commercially and applied on the seed, to the plant, or the vicinity around the plant in order to have the strain produce the target enzymes in situ (at or near the plant). These microorganisms can also be enhanced through point mutations or through genetic engineering to express higher or novel target enzymes to benefit the plants. Point mutations can be screened by mutating the host microorganism, and selecting for mutants with higher enzyme expression levels through enzyme assays, or using selective media that identifies high enzyme expressing strains. Common strains that are beneficial producers of enzymes as well as colonizers/endophytic species include: *Bacillus argri, Bacillus aizawai, Bacillus albolactis, Bacillus amyloliquefaciens, Bacillus cereus, Bacillus coagulans, Bacillus endoparasiticus, Bacillus endorhythmos, Bacillus kurstaki, Bacillus lacticola, Bacillus lactimorbus, Bacillus firmus, Bacillus lactis, Bacillus laterosporus, Bacillus lentimorbus, Bacillus licheniformis, Bacillus megaterium, Bacillus medusa, Bacillus metiens, Bacillus natto, Bacillus nigrificans, Bacillus popillae, Bacillus pumilus, Bacillus siamensis, Bacillus sphearicus, Bacillus subtilis, Bacillus thuringiensis, Bacillus unifagellatu*, other *Bacillus* species or a combination thereof plus those listed in the category of *Bacillus* Genus in Bergey's Manual of Systematic Bacteriology, First Ed. (1986), hereby incorporated in full by reference. Other potential strains could include, but are not limited to: *Cellulomonas, Clavibacter, Curtobacterium, Pseudomonas, Paenibacilllus, Enterobacter, Bacillus, Klebsiella, Arthrobacter, Lysinibacillus, Pantoea, Actinomyces, Saccharomyces, Rhizobium, Bradyrhizobium, Candida, Streptomyces, Alcaligenes, Chromatiales, Rhizobium, Bradyrhizobium, Rhodospiralles, Rhizobiales, Rhizobacteracae*, and *Microbacterium*.

For any of the methods or seeds described herein, the recombinant microorganism can comprise a mixture of two or more of any of the recombinant microorganisms described herein.

For any of the recombinant microorganisms, formulations, methods, or seeds described herein, the recombinant microorganism can be inactivated. Inactivation results in microorganisms that are unable to reproduce. Inactivation of microorganisms can be advantageous, for example because it allows for delivery of the microorganism to a plant or a plant growth medium while reducing or eliminating any detrimental effects that the live microorganism may have on a plant or on the environment. The recombinant microorganism can be inactivated by any physical or chemical means, e.g., by heat treatment, gamma irradiation, x-ray irradiation, UV-A irradiation, UV-B irradiation, or treatment with a solvent such as gluteraldehyde, formaldehyde, hydrogen peroxide, acetic acid, bleach, chloroform, or phenol, or combination of any thereof.

XIV. Methods for Making Recombinant Microorganisms

The recombinant microorganisms can be made using standard molecular biology methods known in the art. For example, a gene encoding an enzyme can be amplified by polymerase chain reaction (PCR). Where a signal sequence is used, the gene coding for the enzyme can be ligated to DNA coding for the signal sequence. The gene can then be cloned into any suitable vector, for example a plasmid vector. The vector suitably comprises a multiple cloning site into which the DNA molecule encoding the fusion protein can be easily inserted. The vector also suitably contains a selectable marker, such as an antibiotic resistance gene, such that bacteria transformed, transfected, or mated with the vector can be readily identified and isolated. Where the vector is a plasmid, the plasmid suitably also comprises an origin of replication. Alternatively, DNA coding for the enzyme or expansin protein can be integrated into the chromosomal DNA of the microorganism host.

XV. Effects on Plants

In any of the methods described herein, plants grown in the presence of the enzyme, the expansin protein, or the microorganism can exhibit increased growth as compared to plants grown in the absence of the enzyme, the expansin protein, or the microorganism, under the same conditions.

For any of the seeds described herein, plants grown from seeds treated with the free enzyme, the expansin protein, or the microorganism can exhibit increased growth as compared to plants grown from seeds not treated with the free enzyme, the expansin protein, or the microorganism, under the same conditions.

For any of the methods or seeds described herein, seeds to which the enzyme or the microorganism has been applied can exhibit increased germination rates as compared to seeds to which the enzyme or microorganism has not been applied, under the same conditions.

In any of the methods described herein, plants grown in the presence of the enzyme, the expansin protein, or the microorganism can exhibit increased nutrient uptake as compared to plants grown in the absence of the enzyme, the expansin protein, or the microorganism, under the same conditions.

For any of the seeds described herein, plants grown from seeds treated with the free enzyme, the expansin protein, or the microorganism can exhibit increased nutrient uptake as compared to plants grown from seeds not treated with the free enzyme, the expansin protein, or the microorganism, under the same conditions.

In any of the methods described herein, plants grown in the presence of the enzyme or the microorganism can exhibit decreased susceptibility to a pathogen as compared to plants grown in the absence of the enzyme or the microorganism, under the same conditions.

For any of the seeds described herein, plants grown from seeds treated with the free enzyme or the microorganism can exhibit decreased susceptibility to a pathogen as compared to plants grown from seeds not treated with the free enzyme or the microorganism, under the same conditions.

In any of the methods described herein, plants grown in the presence of the enzyme or the microorganism can exhibit decreased susceptibility to an environmental stress as compared to plants grown in the absence of the enzyme or the microorganism, under the same conditions.

For any of the seeds described herein, plants grown from seeds treated with the free enzyme or the microorganism can exhibit decreased susceptibility to an environmental stress as compared to plants grown from seeds not treated with the free enzyme or the microorganism, under the same conditions.

For example, the plants can exhibit decreased susceptibility to drought, flood, heat, freezing, salt, heavy metals, low pH, high pH, or a combination of any thereof.

In any of the methods described herein, plants grown in the presence of the enzyme, the expansin protein, or the microorganism can exhibit increased nutrient content as compared to plants grown in the absence of the enzyme, the expansin protein, or the microorganism, under the same conditions.

For any of the seeds described herein, seeds treated with the free enzyme, the expansin protein, or the microorganism or plants grown from seeds treated with the free enzyme, the expansin protein, or the microorganism can exhibit increased nutrient content as compared to seeds not treated with the free enzyme, the expansin protein, or the microorganism or plants grown from seeds not treated with the free enzyme, the expansin protein, or the microorganism, under the same conditions.

For example, the nutrient can comprise a polysaccharide, a protein, phytic acid, a phosphatate, a phospholipid, or a combination of any thereof.

In any of the methods described herein, plants grown in the presence of the enzyme or the microorganism can exhibit increased root nodulation as compared to plants grown in the absence of the enzyme or the microorganism, under the same conditions.

For any of the seeds described herein, plants grown from seeds treated with the free enzyme or the microorganism can exhibit increased root nodulation as compared to plants grown from seeds not treated with the free enzyme or the microorganism, under the same conditions.

In any of the methods described herein, plants grown in the presence of the enzyme or the microorganism can exhibit slower fruit ripening as compared to plants grown in the absence of the enzyme or the microorganism, under the same conditions.

For any of the seeds described herein, plants grown from seeds treated with the free enzyme or the microorganism can exhibit slower fruit ripening as compared to plants grown from seeds not treated with the free enzyme or the microorganism, under the same conditions.

In any of the methods described herein, plants grown in the presence of the enzyme, the expansin protein, or the microorganism can exhibit greater crop yield as compared to plants grown in the absence of the enzyme, the expansin protein, or the microorganism, under the same conditions.

For any of the seeds described herein, plants grown from seeds treated with the free enzyme, the expansin protein, or the microorganism can exhibit greater crop yield as compared to plants grown from seeds not treated with the free enzyme, the expansin protein, or the microorganism, under the same conditions.

In any of the methods described herein, plants grown in the presence of the enzyme or the microorganism can exhibit altered leaf senescence as compared to plants grown in the absence of the enzyme or the microorganism, under the same conditions.

For any of the seeds described herein, plants grown from seeds treated with the free enzyme or the microorganism can exhibit altered leaf senescence as compared to plants grown from seeds not treated with the enzyme or the microorganism, under the same conditions.

Slower leaf senescence can lead to a greater level of photosynthesis late in the season, which in turn leads to more photosynthates, more grain fill, and a larger grain and/or increased yield.

XVI. Formulations, Compositions, and Co-Application of Agrochemicals

In any of the methods described herein, the method can comprise applying the enzyme, the expansin protein, or the microorganism in a formulation comprising an agriculturally acceptable carrier.

For any of the seeds described herein, the seed can be coated with a formulation comprising the free enzyme, the expansin protein, or the recombinant microorganism and an agriculturally acceptable carrier.

Any of the compositions described herein can comprise an agriculturally acceptable carrier.

The agriculturally acceptable carrier can comprise a dispersant, a surfactant, an additive, water, a thickener, an anti-caking agent, residue breakdown product, a composting formulation, a granular application, diatomaceous earth, an oil, a coloring agent, a stabilizer, a preservative, a polymer, a coating, or a combination thereof.

The additive can comprises an oil, a gum, a resin, a clay, a polyoxyethylene glycol, a terpene, a viscid organic, a fatty acid ester, a sulfated alcohol, an alkyl sulfonate, a petroleum sulfonate, an alcohol sulfate, a sodium alkyl butane diamate, a polyester of sodium thiobutane dioate, a benzene acetonitrile derivative, a proteinaceous material (e.g., a milk product, wheat flour, soybean meal, blood, albumin, gelatin, alfalfa meal, yeast extract, or a combination of any thereof), or a combination of any thereof.

The thickener can comprise a long chain alkylsulfonate of polyethylene glycol, a polyoxyethylene oleate, or a combination of any thereof.

The surfactant can comprise a heavy petroleum oil, a heavy petroleum distillate, a polyol fatty acid ester, a polyethoxylated fatty acid ester, an aryl alkyl polyoxyethylene glycol, an alkyl amine acetate, an alkyl aryl sulfonate, a polyhydric alcohol, an alkyl phosphate, or a combination of any thereof.

The surfactant can comprise a non-ionic surfactant.

The anti-caking agent can comprise a sodium salt (e.g., a sodium salt of monomethyl naphthalene sulfonate, a sodium salt of dimethyl naphthalene sulfonate, a sodium sulfite, a sodium sulfate, or a combination of any thereof), a calcium carbonate, diatomaceous earth, or a combination of any thereof.

The agriculturally acceptable carrier can comprise vermiculite, charcoal, sugar factory carbonation press mud, rice husk, carboxymethyl cellulose, peat, perlite, fine sand, calcium carbonate, flour, alum, a starch, talc, polyvinyl pyrrolidone, or a combination of any thereof.

The formulation or composition can comprise a seed coating formulation or composition, a liquid formulation or composition for application to plants or to a plant growth medium, or a solid formulation or composition for application to plants or to a plant growth medium.

The seed coating formulation or composition can comprise an aqueous or oil-based solution for application to seeds or a powder or granular formulation for application to seeds.

The liquid formulation or composition for application to plants or to a plant growth medium can comprise a concentrated formulation or composition or a ready-to-use formulation or composition.

The solid formulation or composition for application to plants or to a plant growth medium can comprise a granular formulation or composition or a powder agent.

The formulation or composition can further comprise an agrochemical.

Alternatively or in addition, any of the methods described herein can further comprise applying an agrochemical to the plant growth medium, the plant, the plant seed, or the area surrounding the plant or the plant seed.

Any of the plant seeds described herein can be further treated or coated with an agrochemical.

The agrochemical can comprise a fertilizer, a micronutrient fertilizer material, an insecticide, a nematicide, an herbicide, a plant growth amendment, a fungicide, an insecticide, a molluscicide, an algicide, a bacterial inoculant, a fungal inoculant, a plant hormone, or a combination of any thereof.

The bacterial inoculant can comprise a plant-growth promoting strain of bacteria, an endophytic strain of bacteria, or a strain of bacteria that is both plant-growth promoting and endophytic.

The plant-growth promoting strain of bacteria can produce an insecticidal toxin (e.g., a Cry toxin), produce a fungicidal compound (e.g., a β-1,3-glucanase, a chitosanase, a lyticase, or a combination thereof), produce a nematicidal compound (e.g., a Cry toxin), produce a bacteriocidal compound, be resistant to one or more antibiotics, comprise one or more freely replicating plasmids, bind to plant roots, colonize plant roots, form biofilms, solubilize nutrients, secrete organic acids, or combinations thereof.

The plant-growth promoting strain of bacteria can comprise *Bacillus aryabhattai* CAP53 (NRRL No. B-50819), *Bacillus aryabhattai* CAP56 (NRRL No. B-50817), *Bacillus flexus* BT054 (NRRL No. B-50816), *Paracoccus kondratievae* NC35 (NRRL No. B-50820), *Bacillus mycoides* BT155 (NRRL No. B-50921), *Enterobacter cloacae* CAP12 (NRRL No. B-50822), *Bacillus nealsonii* BOBA57 (NRRL No. NRRL B-50821), *Bacillus mycoides* EE118 (NRRL No. B-50918), *Bacillus subtilis* EE148 (NRRL No. B-50927), *Alcaligenes faecalis* EE107 (NRRL No. B-50920), *Bacillus mycoides* EE141 (NRRL NO. B-50916), *Bacillus mycoides* BT46-3 (NRRL No. B-50922), *Bacillus cereus* family member EE128 (NRRL No. B-50917), *Paenibacillus massiliensis* BT23 (NRRL No. B-50923), *Bacillus cereus* family member EE349 (NRRL No. B-50928), *Bacillus subtilis* EE218 (NRRL No. B-50926), *Bacillus megaterium* EE281 (NRRL No. B-50925), *Bacillus cereus* family member EE-B00377 (NRRL B-67119); *Bacillus pseudomycoides* EE-B00366 (NRRL B-67120), *Bacillus mycoides* EE-B00363 (NRRL B-67121), *Bacillus pumilus* EE-B00143 (NRRL B-67123), or *Bacillus thuringiensis* EE-B00184 (NRRL B-67122), *Bacillus mycoides* EE116 (NRRL No. B-50919), *Bacillus cereus* family member EE417 (NRRL No. B-50974), *Bacillus subtilis* EE442 (NRRL No. B-50975), *Bacillus subtilis* EE443 (NRRL No. B-50976), *Bacillus cereus* family member EE444 (NRRL No. B-50977), *Bacillus subtilis* EE405 (NRRL No. B-50978), *Bacillus cereus* family member EE439 (NRRL No. B-50979), *Bacillus megaterium* EE385 (NRRL No. B-50980), *Bacillus cereus* family member EE387 (NRRL No. B-50981), *Bacillus circulans* EE388 (NRRL No. B-50982), *Bacillus thuringiensis* EE319 (NRRL No. B-50983), *Bacillus cereus* family member EE377 (NRRL No. B-67119), *Bacillus mycoides* EE363 (NRRL No. B-67121), *Bacillus pseudomycoides* EE366 (NRRL No. B-67120), *Bacillus thuringiensis* BT013A (NRRL No. B-50924), or a combination of any thereof.

The agrochemical can comprise a fertilizer.

The fertilizer can comprise a liquid fertilizer or a dry fertilizer.

The agrochemical can comprise a micronutrient fertilizer material, the micronutrient fertilizer material comprising boric acid, a borate, a boron frit, copper sulfate, a copper frit, a copper chelate, a sodium tetraborate decahydrate, an iron sulfate, an iron oxide, iron ammonium sulfate, an iron frit, an iron chelate, a manganese sulfate, a manganese oxide, a manganese chelate, a manganese chloride, a manganese frit, a sodium molybdate, molybdic acid, a zinc sulfate, a zinc oxide, a zinc carbonate, a zinc frit, zinc phosphate, a zinc chelate, or a combination of any thereof.

The agrochemical can comprise an insecticide, the insecticide comprising an organophosphate, a carbamate, a pyrethroid, an acaricide, an alkyl phthalate, boric acid, a borate, a fluoride, sulfur, a haloaromatic substituted urea, a hydrocarbon ester, a biologically-based insecticide, or a combination of any thereof.

The agrochemical can comprise an herbicide, the herbicide comprising a chlorophenoxy compound, a nitrophenolic compound, a nitrocresolic compound, a dipyridyl compound, an acetamide, an aliphatic acid, an anilide, a benzamide, a benzoic acid, a benzoic acid derivative, anisic acid, an anisic acid derivative, a benzonitrile, benzothiadiazinone dioxide, a thiocarbamate, a carbamate, a carbanilate, chloropyridinyl, a cyclohexenone derivative, a dinitroaminobenzene derivative, a fluorodinitrotoluidine compound, isoxazolidinone, nicotinic acid, isopropylamine, an isopropylamine derivative, oxadiazolinone, a phosphate, a phthalate, a picolinic acid compound, a triazine, a triazole, a uracil, a urea derivative, endothall, sodium chlorate, or a combination of any thereof.

The agrochemical can comprise a fungicide, the fungicide comprising a substituted benzene, a thiocarbamate, an ethylene bis dithiocarbamate, a thiophthalidamide, a copper compound, an organomercury compound, an organotin compound, a cadmium compound, anilazine, benomyl, cyclohexamide, dodine, etridiazole, iprodione, metlaxyl, thiamimefon, triforine, or a combination of any thereof.

The agrochemical can comprise a fungal inoculant, the fungal inoculant comprising a fungal inoculant of the family Glomeraceae, a fungal inoculant of the family Claroidoglomeraceae, a fungal inoculant of the family Gigasporaceae, a fungal inoculant of the family Acaulosporaceae, a fungal inoculant of the family Sacculosporaceae, a fungal inoculant of the family Entrophosporaceae, a fungal inoculant of the family Pacidsporaceae, a fungal inoculant of the family Diversisporaceae, a fungal inoculant of the family Paraglomeraceae, a fungal inoculant of the family Archaeosporaceae, a fungal inoculant of the family Geosiphonaceae, a fungal inoculant of the family Ambisporaceae, a fungal inoculant of the family Scutellosporaceae, a fungal inoculant of the family Dentiscultataceae, a fungal inoculant of the family Racocetraceae, a fungal inoculant of the phylum Basidiomycota, a fungal inoculant of the phylum Ascomycota, a fungal inoculant of the phylum Zygomycota, or a combination of any thereof.

The agrochemical can comprise a bacterial inoculant, the bacterial inoculant comprising a bacterial inoculant of the genus *Rhizobium*, a bacterial inoculant of the genus *Bradyrhizobium*, a bacterial inoculant of the genus *Mesorhizobium*, a bacterial inoculant of the genus *Azorhizobium*, a bacterial inoculant of the genus *Allorhizobium*, a bacterial inoculant of the genus *Sinorhizobium*, a bacterial inoculant of the genus *Kluyvera*, a bacterial inoculant of the genus *Azotobacter*, a bacterial inoculant of the genus *Pseudomonas*, a bacterial inoculant of the genus *Azospirillium*, a bacterial inoculant of the genus *Bacillus*, a bacterial inoculant of the genus *Streptomyces*, a bacterial inoculant of the genus *Paenibacillus*, a bacterial inoculant of the genus *Paracoccus*, a bacterial inoculant of the genus *Enterobacter*, a bacterial inoculant of the genus *Alcaligenes*, a bacterial inoculant of the genus *Mycobacterium*, a bacterial inoculant of the genus *Trichoderma*, a bacterial inoculant of the genus *Gliocladium*, a bacterial inoculant of the genus *Glomus*, a bacterial inoculant of the genus *Klebsiella*, or a combination of any thereof.

The agrochemical can comprise an effective amount of a rhizobacteria. The rhizobacteria can comprise *Bradyrhizobium* genus bacteria (e.g., *Bradyrhizobium japonicum*), *Rhizobium* genus bacteria (e.g., *Rhizobium phaseoli, Rhizobium leguminosarum*, or a combination thereof), or a combination thereof.

The agrochemical can comprise a fungicide, the fungicide comprises aldimorph, ampropylfos, ampropylfos potassium, andoprim, anilazine, azaconazole, azoxystrobin, benalaxyl, benodanil, benomyl, benzamacril, benzamacryl-isobutyl, bialaphos, binapacryl, biphenyl, bitertanol, blasticidin-S, boscalid, bromuconazole, bupirimate, buthiobate, calcium polysulphide, capsimycin, captafol, captan, carbendazim, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram, debacarb, dichlorophen, diclobutrazole, diclofluanid, diclomezine, dicloran, diethofencarb, dimethirimol, dimethomorph, dimoxystrobin, diniconazole, diniconazole-M, dinocap, diphenylamine, dipyrithione, ditalimfos, dithianon, dodemorph, dodine, drazoxolon, edifenphos, epoxiconazole, etaconazole, ethirimol, etridiazole, famoxadon, fenapanil, fenarimol, fenbuconazole, fenfuram, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulfamide, flutolanil, flutriafol, folpet, fosetyl-aluminium, fosetyl-sodium, fthalide, fuberidazole, furalaxyl, furametpyr, furcarbonil, furconazole, furconazole-cis, furmecyclox, guazatine, hexachlorobenzene, hexaconazole, hymexazole, imazalil, imibenconazole, iminoctadine, iminoctadine albesilate, iminoctadine triacetate, iodocarb, iprobenfos (IBP), iprodione, irumamycin, isoprothiolane, isovaledione, kasugamycin, kresoxim-methyl, copper preparations, such as: copper hydroxide, copper naphthenate, copper oxychloride, copper sulphate, copper oxide, oxine-copper and Bordeaux mixture, mancopper, mancozeb, maneb, meferimzone, mepanipyrim, mepronil, metconazole, methasulfocarb, methfuroxam, metiram, metomeclam, metsulfovax, mildiomycin, myclobutanil, myclozolin, nickel dimethyldithiocarbamate, nitrothal-isopropyl, nuarimol, ofurace, oxadixyl, oxamocarb, oxolinic acid, oxycarboxim, oxyfenthiin, paclobutrazole, pefurazoate, penconazole, pencycuron, phosdiphen, pimaricin, piperalin, polyoxin, polyoxorim, probenazole, prochloraz, procymidone, propamocarb, propanosine-sodium, propiconazole, propineb, prothiocinazole, pyrazophos, pyrifenox, pyrimethanil, pyroquilon, pyroxyfur, quinconazole, quintozene (PCNB), sulphur and sulphur preparations, tebuconazole, tecloftalam, tecnazene, tetcyclasis, tetraconazole, thiabendazole, thicyofen, thifluzamide, thiophanate-methyl, tioxymid, tolclofos-methyl, tolylfluanid, triadimefon, triadimenol, triazbutil, triazoxide, trichlamide, tricyclazole, tridemorph, trifloxystrobin, triflumizole, triforine, uniconazole, validamycin A, vinclozolin, viniconazole, zarilamide, zineb, ziram and also Dagger G, OK-8705, OK-8801, a-(1,1-dimethylethyl)-(3-(2-phenoxyethyl)-1H-1,2,4-triazole-1-ethanol, a-(2,4-dichlorophenyl)-[3-fluoro-3-propyl-1H-1,2,4-triazole-1-ethanol, a-(2,4-dichlorophenyl)-[3-methoxy-a-methyl-1H-1,2,4-triazole-1-ethanol, a-(5-methyl-1,3-dioxan-5-yl)-[3-[[4-(trifluoromethyl)-phenyl]-methylene]-1H-1,2,4-triazole-1-ethanol, (5RS,6RS)-6-hydroxy-2,2,7,7-tetramethyl-5-(1H-1,2,4-triazol-1-yl)-3-octanone, (E)-a-(methoxyimino)-N-methyl-2-phenoxy-phenylacetamide, 1-isopropyl{2-methyl-1-[[[1-(4-methylphenyl)-ethyl]-amino]-carbonyl]-propyl}carbamate, 1-(2,4-dichlorophenyl)-2-(1H-1,2,4-triazol-1-yl)-ethanone-O-(phenyl methyl)-oxime, 1-(2-methyl-1-naphthalenyl)-1H-pyrrole-2,5-dione, 1-(3,5-dichlorophenyl)-3-(2-propenyl)-2,5-pyrrolidindione, 1-[(diiodomethyl)-sulphonyl]-4-methyl-benzene, 1-[[2-(2,4-dichlorophenyl)-1,3-dioxolan-2-yl]-methyl]-1H-imidazole, 1-[[2-(4-chlorophenyl)-3-phenyloxiranyl]-methyl]-1H-1,2,4-triazole, 1-[1-[2-[(2,4-dichlorophenyl)-methoxy]-phenyl]-ethenyl]-1H-imidazole, 1-methyl-5-nonyl-2-(phenylmethyl)-3-pyrrolidinole, 2',6'-dibromo-2-methyl-4'-trifluoromethoxy-4'-trifluoro-methyl-1,3-thiazole-carboxanilide, 2,2-dichloro-N-[1-(4-chlorophenyl)-ethyl]-1-ethyl-3-methyl-cyclopropanecarboxamide, 2,6-dichloro-5-(methylthio)-4-pyrimidinyl-thiocyanate, 2,6-dichloro-N-(4-trifluoromethylbenzyl)-benzamide, 2,6-dichloro-N-[[4-(trifluoromethyl)-phenyl]-methyl]-benzamide, 2-(2,3,3-triiodo-2-propenyl)-2H-tetrazole, 2-[(1-methylethyl)-sulphonyl]-5-(trichloromethyl)-1,3,4-thiadiazole, 2-[[6-deoxy-4-O-(4-O-methyl-(3-D-glycopyranosyl)-a-D-glucopyranos yl]-amino]-4-methoxy-1H-pyrrolo[2,3-d] pyrimidine-5-carbonitrile, 2-aminobutane, 2-bromo-2-(bromomethyl)-pentanedinitrile, 2-chloro-N-(2,3-dihydro-1,1,3-trimethyl-1H-inden-4-yl)-3-pyridinecarboxamide, 2-chloro-N-(2,6-dimethylphenyl)-N-(isothiocyanatomethyl)-acetamide, 2-phenylphenol (OPP), 3,4-dichloro-1-[4-(difluoromethoxy)-phenyl]-pyrrole-2,5-dione, 3,5-dichloro-N-[cyano[(1-methyl-2-propynyl)-oxy]-methyl]-benzamide, 3-(1,1-dimethylpropyl-1-oxo-1H-indene-2-carbonitrile, 3-[2-(4-chlorophenyl)-5-ethoxy-3-isoxazolidinyl]-pyridine, 4-chloro-2-cyano-N,N-dimethyl-5-(4-methylphenyl)-1H-imidazole-1-sulphonamide, 4-methyl-tetrazolo[1,5-a]quinazolin-5(4H)-one, 8-(1,1-dimethylethyl)-N-ethyl-N-propyl-1,4-dioxaspiro[4,5]decane-2-methanamine, 8-hydroxyquinoline sulphate, 9H-xanthene-2-[(phenylamino)-carbonyl]-9-carboxylic hydrazide, bis-(1-methylethyl)-3-methyl-4-[(3-methylbenzoyl)-oxy]-2,5-thiophenedicarboxylate, cis-1-(4-chlorophenyl)-2-(1H-1,2,4-triazol-1-yl)-cycloheptanol, cis-4-[3-[4-(1,1-dimethylpropyl)-phenyl-2-methylpropyl]-2,6-dimethyl-morpholine hydrochloride, ethyl [(4-chlorophenyl)-azo]-cyanoacetate, potassium bicarbonate, methanetetrathiol-sodium salt, methyl 1-(2,3-dihydro-2,2-dimethyl-inden-1-yl)-1H-imidazole-5-carboxylate, methyl N-(2,6-dimethylphenyl)-N-(5-isoxazolylcarbonyl)-DL-alaninate, methyl N-(chloroacetyl)-N-(2,6-dimethylphenyl)-DL-alaninate, N-(2,3-dichloro-4-hydroxyphenyl)-1-methyl-cyclohexanecarboxamide, N-(2,6-dimethyl phenyl)-2-methoxy-N-(tetra hydro-2-oxo-3-furanyl)-acetamide, N-(2,6-dimethyl phenyl)-2-methoxy-N-(tetrahydro-2-oxo-3-thienyl)-acetamide, N-(2-chloro-4-nitrophenyl)-4-methyl-3-nitro-benzenesulphonamide, N-(4-cyclohexylphenyl)-1,4,5,6-tetrahydro-2-pyrimidinamine, N-(4-hexylphenyl)-1,4,5,6-tetrahydro-2-pyrimidinamine, N-(5-chloro-2-methylphenyl)-2-methoxy-N-(2-oxo-3-oxazolidinyl)-acetamide, N-(6-methoxy)-3-pyridinyl)-cyclopropanecarboxamide, N-[2,2,2-trichloro-1-[(chloroacetyl)-amino]-ethyl]-benzamide, N-[3-chloro-4,5-bis(2-propinyloxy)-phenyl]-N'-methoxy-methanimidamide, N-formyl-N-hydroxy-DL-alanine-sodium salt, 0,0-diethyl [2-(dipropylamino)-2-oxoethyl]-ethylphosphoramidothioate, O-methyl S-phenyl phenylpropylphosphoramidothioate, S-methyl 1,2,3-benzothiadiazole-7-carbothioate, and spiro [2H]-1-benzopyrane-2,1'(3'H)-isobenzofuran]-3'-one, N-trichloromethyl)thio-4-cyclohexane-1,2-dicarboximide, tetramethylthioperoxydicarbonic diamide, methyl N-(2,6-dimethylphenyl)-N-(methoxyacetyl)-DL-alaninate, 4-(2,2-difluoro-1,3-benzodioxol-4-yl)-1-H-pyrrol-3-carbonitril, or a combination of any thereof.

The agrochemical can comprise a bacterial inoculant of the genus *Bacillus*, the bacterial inoculant of the genus *Bacillus* comprising *Bacillus* argri, *Bacillus aizawai, Bacillus* albolactis, *Bacillus amyloliquefaciens, Bacillus cereus, Bacillus coagulans, Bacillus endoparasiticus, Bacillus endorhythmos, Bacillus kurstaki, Bacillus lacticola, Bacillus lactimorbus, Bacillus lactis, Bacillus laterosporus, Bacillus lentimorbus, Bacillus licheniformis, Bacillus megaterium, Bacillus medusa, Bacillus metiens, Bacillus natto, Bacillus nigrificans, Bacillus popillae, Bacillus pumilus, Bacillus siamensis, Bacillus sphearicus, Bacillus* spp., *Bacillus subtilis, Bacillus thuringiensis, Bacillus unifagellatu*, or a combination of any thereof.

The agrochemical can comprise an herbicide, the herbicide comprising 2,4-D, 2,4-DB, acetochlor, acifluorfen, alachlor, ametryn, atrazine, aminopyralid, benefin, bensulfuron, bensulide, bentazon, bromacil, bromoxynil, butylate, carfentrazone, chlorimuron, chlorsulfuron, clethodim, clomazone, clopyralid, cloransulam, cycloate, DCPA, desmedipham, dicamba, dichlobenil, diclofop, diclosulam, diflufenzopyr, dimethenamid, diquat, diuron, DSMA, endothall, EPTC, ethalfluralin, ethofumesate, fenoxaprop, fluazifop-P, flucarbazone, flufenacet, flumetsulam, flumiclorac, flumioxazin, fluometuron, fluroxypyr, fomesafen, foramsulfuron, glufosinate, glyphosate, halosulfuron, hexazinone, imazamethabenz, imazamox, imazapic, imazaquin, imazethapyr, isoxaben, isoxaflutole, lactofen, linuron, MCPA, MCPB, mesotrione, metolachlor-s, metribuzin, metsulfuron, molinate, MSMA, napropamide, naptalam, nicosulfuron, norflurazon, oryzalin, oxadiazon, oxyfluorfen, paraquat, pelargonic acid, pendimethalin, phenmedipham, picloram, primisulfuron, prodiamine, prometryn, pronamide, propanil, prosulfuron, pyrazon, pyrithiobac, quinclorac, quizalofop, rimsulfuron, sethoxydim, siduron, simazine, sulfentrazone, sulfometuron, sulfosulfuron, tebuthiuron, terbacil, thiazopyr, thifensulfuron, thiobencarb, tralkoxydim, triallate, triasulfuron, tribenuron, triclopyr, trifluralin, triflusulfuron, or a combination of any thereof.

The agrochemical can comprise a fertilizer, the fertilizer comprising ammonium sulfate, ammonium nitrate, ammonium sulfate nitrate, ammonium chloride, ammonium bisulfate, ammonium polysulfide, ammonium thiosulfate, aqueous ammonia, anhydrous ammonia, ammonium polyphosphate, aluminum sulfate, calcium nitrate, calcium ammonium nitrate, calcium sulfate, calcined magnesite, calcitic limestone, calcium oxide, calcium nitrate, dolomitic limestone, hydrated lime, calcium carbonate, diammonium phosphate, monoammonium phosphate, magnesium nitrate, magnesium sulfate, potassium nitrate, potassium chloride, potassium magnesium sulfate, potassium sulfate, sodium nitrates, magnesian limestone, magnesia, urea, urea-formaldehydes, urea ammonium nitrate, sulfur-coated urea, polymer-coated urea, isobutylidene diurea, $K_2SO_4$-$2MgSO_4$, kainite, sylvinite, kieserite, Epsom salts, elemental sulfur, marl, ground oyster shells, fish meal, oil cakes, fish manure, blood meal, rock phosphate, super phosphates, slag, bone meal, wood ash, manure, bat guano, peat moss, compost, green sand, cottonseed meal, feather meal, crab meal, fish emulsion, humic acid, or a combination of any thereof.

The agrochemical can comprise a plant hormone, the plant hormone comprising a gibberellin, an auxin, a kinetin, or a combination of any thereof.

Enzymes can be formulated in many ways. Common goals for formulation enzyme products include enhancing shelf life, preserving the product from microorganisms, and enhancing enzyme activity. Enzyme products can be lyophilized to extend the shelf life of most enzymes by freeze drying, spray drying, or otherwise removing the liquid aspect of the enzyme product. Liquid and lyophilized products are often bulked out with additives, such as buffers, stabilizers, antimicrobial agents, and volume additives. Enzymes can often be encapsulated or granulated to make the final product safer and easier to use. Granulated products can have enhanced shelf life and have little enzyme activity exposed to the outside surface of the granules. Enzymes may also be attached to organic or inorganic platforms, such as plastic beads, dolomite, clays, charcoals, biochar, nanoparticles, alginates, silica beads help bind them and keep them in an easy to use form. Often, enzymes are immobilized on matrices to allow for longer activity and shelf life of the enzyme products. Common matrices include carbon, nanocarbons, agarose, alginates, cellulose and cellulosic material, silica, plastic, stainless steel, glass, polystyrene, and ceramics.

Many formulations of the enzymes can be used to prolong enzymatic activity or shelf life of the products. These include but are not limited to preservatives, biocides, stabilizers, color enhancers, odor reduction, surfactants, detergents, buffers, cofactors, ions, and other modification to the formulation to enhance the performance of the enzymes.

XVII. Plant Growth Media

In any of the methods described herein involving the use of a plant growth medium, the plant growth medium can comprise soil, water, an aqueous solution, sand, gravel, a polysaccharide, mulch, compost, peat moss, straw, logs, clay, soybean meal, yeast extract, or a combination thereof.

The plant growth medium can comprise or consist essentially of a fertilizer.

Furthermore, the plant growth medium can be supplemented with a substrate for an enzyme.

The substrate can comprise tryptophan, an adenosine monophosphate, an adenosine diphosphate, an adenosine triphosphate (e.g., adenosine-3-triphosphate), a polyphosphate, a protein meal, a trimetaphosphate, a cellulose, a methylcellulose, a chitin, a chitosan, a cellulose derivative, a phosphate, a fat, a wax, a phospholipid, a phytic acid, or a combination of any thereof.

XVIII. Plants

In any of the above methods relating to plants, the plant can be a dicotyledon, a monocotyledon, or a gymnosperm.

Likewise, for any of the seeds described herein the seed can be a seed of a dicotyledon, a monocotyledon, or a gymnosperm.

For example, where the plant is a dicotyledon or the seed is a seed of a dicotyledon, the dicotyledon can be selected from the group consisting of bean, pea, tomato, pepper, squash, alfalfa, almond, aniseseed, apple, apricot, arracha, artichoke, avocado, bambara groundnut, beet, bergamot, black pepper, black wattle, blackberry, blueberry, bitter orange, bok-choi, Brazil nut, breadfruit, broccoli, broad bean, Brussels sprouts, buckwheat, cabbage, camelina, Chinese cabbage, cacao, cantaloupe, caraway seeds, cardoon, carob, carrot, cashew nuts, cassava, castor bean, cauliflower, celeriac, celery, cherry, chestnut, chickpea, chicory, chili pepper, chrysanthemum, cinnamon, citron, clementine, clove, clover, coffee, cola nut, colza, corn, cotton, cottonseed, cowpea, crambe, cranberry, cress, cucumber, currant, custard apple, drumstick tree, earth pea, eggplant, endive, fennel, fenugreek, fig, filbert, flax, geranium, gooseberry, gourd, grape, grapefruit, guava, hemp, hempseed, henna, hop, horse bean, horseradish, indigo, jasmine, Jerusalem artichoke, jute, kale, kapok, kenaf, kohlrabi, kumquat, lavender, lemon, lentil, lespedeza, lettuce, lime, liquorice, litchi, loquat, lupine, macadamia nut, mace, mandarin, mangel, mango, medlar, melon, mint, mulberry, mustard, nectarine, niger seed, nutmeg, okra, olive, opium, orange, papaya, parsnip, pea, peach, peanut, pear, pecan nut, persimmon, pigeon pea, pistachio nut, plantain, plum, pomegranate, pomelo, poppy seed, potato, sweet potato, prune, pumpkin, quebracho, quince, trees of the genus Cinchona, quinoa, radish, ramie, rapeseed, raspberry, rhea, rhubarb, rose, rubber, rutabaga, safflower, sainfoin, salsify, sapodilla, Satsuma, scorzonera, sesame, shea tree, soybean, spinach, squash, strawberry, sugar beet, sugarcane, sunflower, swede, sweet pepper, tangerine, tea, teff, tobacco, tomato, trefoil, tung tree, turnip, urena, vetch, walnut, watermelon, yerba mate, wintercress, shepherd's purse, garden cress, peppercress, watercress, pennycress, star anise, laurel, bay laurel, cassia, jamun, dill, tamarind, peppermint, oregano, rosemary, sage, soursop, pennywort, calophyllum, balsam pear, kukui nut, Tahitian chestnut, basil, huckleberry, hibiscus, passionfruit, star apple, sassafras, cactus, St. John's wort, loosestrife, hawthorn, cilantro, curry plant, kiwi, thyme, zucchini, ulluco, jicama, waterleaf, spiny monkey orange, yellow mombin, starfruit, amaranth, wasabi, Japanese pepper, yellow plum, mashua, Chinese toon, New Zealand spinach, bower spinach, ugu, tansy, chickweed, jocote, Malay apple, paracress, sowthistle, Chinese potato, horse parsley, hedge mustard, campion, agate, cassod tree, thistle, burnet, star gooseberry, saltwort, glasswort, sorrel, silver lace fern, collard greens, primrose, cowslip, purslane, knotgrass, terebinth, tree lettuce, wild betel, West African pepper, yerba santa, tarragon, parsley, chervil, land cress, burnet saxifrage, honeyherb, butterbur, shiso, water pepper, perilla, bitter bean, oca, kampong, Chinese celery, lemon basil, Thai basil, water mimosa, cicely, cabbage-tree, moringa, mauka, ostrich fern, rice paddy herb, yellow sawah lettuce, lovage, pepper grass, maca, bottle gourd, hyacinth bean, water spinach, catsear, fishwort, Okinawan spinach, lotus sweetjuice, gallant soldier, culantro, arugula, cardoon, caigua, mitsuba, chipilin, samphire, mampat, ebolo, ivy gourd, cabbage thistle, sea kale, chaya, huauzontle, Ethiopian mustard, magenta spreen, good king henry, epazole, lamb's quarters, centella plumed cockscomb, caper, rapini, napa cabbage, mizuna, Chinese savoy, kai-lan, mustard greens, Malabar spinach, chard, marshmallow, climbing wattle, China jute, paprika, annatto seed, spearmint, savory, marjoram, cumin, chamomile, lemon balm, allspice, bilberry, cherimoya, cloudberry, damson, pitaya, durian, elderberry, feijoa, jackfruit, jambul, jujube, physalis, purple mangosteen, rambutan, redcurrant, blackcurrant, salal berry, satsuma, ugli fruit, azuki bean, black bean, black-eyed pea, borlotti bean, common bean, green bean, kidney bean, lima bean, mung bean, navy bean, pinto bean, runner bean, mangetout, snap pea, broccoflower, calabrese, nettle, bell pepper, raddichio, daikon, white radish, skirret, tat soi, broccolini, black radish, burdock root, fava bean, broccoli raab, lablab, lupin, sterculia, velvet beans, winged beans, yam beans, mulga, ironweed, umbrella bush, tjuntjula, wakalpulka, witchetty bush, wiry wattle, chia, beech nut, candlenut, colocynth, mamoncillo, Maya nut, mongongo, ogbono nut, paradise nut, and cempedak.

Where the plant is a monocotyledon or the seed is a seed of a monocotyledon, the monocotyledon can be selected from the group consisting of corn, wheat, oat, rice, barley, millet, banana, onion, garlic, asparagus, ryegrass, millet, fonio, raishan, nipa grass, turmeric, saffron, galangal, chive, cardamom, date palm, pineapple, shallot, leek, scallion, water chestnut, ramp, Job's tears, bamboo, ragi, spotless watermeal, arrowleaf elephant ear, Tahitian spinach, abaca, areca, bajra, betel nut, broom millet, broom sorghum, citronella, coconut, cocoyam, maize, dasheen, durra, durum wheat, edo, fique, formio, ginger, orchard grass, esparto grass, Sudan grass, guinea corn, Manila hemp, henequen, hybrid maize, jowar, lemon grass, maguey, bulrush millet, finger millet, foxtail millet, Japanese millet, proso millet, New Zealand flax, oats, oil palm, palm palmyra, sago palm, redtop, sisal, sorghum, spelt wheat, sweet corn, sweet sorghum, taro, teff, timothy grass, triticale, vanilla, wheat, and yam.

Where the plant is a gymnosperm or the seed is a seed of a gymnosperm, the gymnosperm can be from a family selected from the group consisting of Araucariaceae, Boweniaceae, Cephalotaxaceae, Cupressaceae, Cycadaceae, Ephedraceae, Ginkgoaceae, Gnetaceae, Pinaceae, Podocarpaceae, Taxaceae, Taxodiaceae, Welwitschiaceae, and Zamiaceae.

The plants and plant seeds described herein may include transgenic plants or plant seeds, such as transgenic cereals (wheat, rice), maize, soybean, potato, cotton, tobacco, oilseed rape and fruit plants (fruit of apples, pears, citrus fruits and grapes. Preferred transgenic plants include corn, soybeans, potatoes, cotton, tobacco and oilseed rape.

Suitable transgenic plants and seeds can be characterized by the plant's formation of toxins, especially from the *Bacillus thuringiensis* genetic material (e.g., by gene CryIA (a), CryIA (b), CryIA (c), CryIIA, CryIIIA, CryIIIB2, Cry9c, Cry2Ab, Cry3Bb, CryIF or a combination thereof). The formation of toxins in plants increases the plant's resistance to insects, arachnids, nematodes and slugs and snails (hereinafter referred to as "Bt plants"). Bt plants, for example, are commercially available under the tradename YIELD CARD® (for example maize, cotton, soybeans), KnockOut® (for example maize), StarLink® (for example maize), Bollgard® (cotton), Nucotn® (cotton) and NewLeaf® (potato) maize varieties, cotton varieties, soybean varieties and potato varieties. Herbicide tolerance plants include plants under the trade names Roundup Ready® (a glyphosate tolerance, such as corn, cotton, soybeans). Clearfield® (for example maize), Liberty Link® (tolerance with glufosinate, for example oilseed rape), IMI® (with imidazolinone tolerance) and STS® (tolerance to a sulfonylurea, such as maize).

Plant seeds as described herein can be genetically modified (e.g., any seed that results in a genetically modified plant or plant part that expresses herbicide tolerance, tolerance to environmental factors such as water stress, drought, viruses, and nitrogen production, or resistance to bacterial, fungi or insect toxins). Suitable genetically modified seeds include those of cole crops, vegetables, fruits, trees, fiber crops, oil crops, tuber crops, coffee, flowers, legume, cereals, as well as other plants of the monocotyledonous and dicotyledonous species. Preferably, the genetically modified seeds include peanut, tobacco, grasses, wheat, barley, rye, sorghum, rice, rapeseed, sugarbeet, sunflower, tomato, pepper, bean, lettuce, potato, and carrot. Most preferably, the genetically modified seeds include cotton, soybean, and corn (sweet, field, seed, or popcorn).

Particularly useful transgenic plants which may be treated according to the invention are plants containing transformation events, or a combination of transformation events, that are listed for example in the databases from various national or regional regulatory agencies (see for example http://gmoinfo.jrc.it/gmp_browse.aspx and http://www.agbios.com/dbase.php). Having described the invention in detail, it will be apparent that modifications and variations are possible without departing from the scope of the invention defined in the appended claims.

EXAMPLES

The following non-limiting examples are provided to further illustrate the present invention.

Example 1: Free Endoglucanase on Corn, Greenhouse

*Acidothermus cellulolyticus* β-1,4 endoglucanase (SEQ ID NO: 30; commercially available from Sigma-Aldrich, St. Louis MO, as product E2164) was diluted in citrate enzyme dilution buffer to concentrations of 12.5 through 1600 mU/mL. The U (units or international units) of endoglucanase activity was determined by the amount of enzyme that is required to breakdown 1 μMol/min/mL of substrate at ideal temperature and conditions. For each treatment group, 18 seeds of commercial hybrid BECK'S 6626RR corn, which contains a glyphosate tolerance trait, without seed treatment, were placed in 50 mL conical tubes. Each conical tube was vortexed, and 18 μL of enzyme solution was added to each tube for a final enzyme concentration of 0, 12.5 μU, 25 μU, 50 μU, 100 μU, 200 μU, 400 μU, 800 μU, or 1600 μU per seed of endoglucanase. The conical tubes were vortexed again for 20 seconds to gain an even coating on each seed. Seeds were allowed to dry for 5 minutes and then planted into 39.7 $cm^3$ pots containing commercial top soil at a depth of 2.54 cm, with 2 seeds per pot. After planting, 50 mL of room temperature water was added to each pot to allow for germination. The pots were kept in an artificial light plant growth room with a 13/11 hour light/day cycle, and at 21 °C day/15 °C night temperature range. Plants were watered as needed, and randomized on a 3 day cycle to avoid any cool spots within the room. At the end of 14 days, the height of the corn plants for each treatment was measured, and normalized to the height of the control plants that were seed coated with only water.

This experiment was repeated three times, and the values averaged across the experiments. As can be seen in Table 18, the major effect of endoglucanase as a seed treatment on BECK'S 6626RR (a corn hybrid with glyphosate resistance) is in the range of 100-1600 μU/seed of enzyme activity. At these values, there is a noticeable and reproducible effect on corn growth. Values below 50 μU per seed had a much lower effect on the corn growth rate for this hybrid. These enzyme treatments work well as a standalone treatment on crops.

TABLE 18

Height effects of β-1,4 endoglucanase treatment as a seed treatment

| Seed Treatment | Enzyme Activity/Seed | Height (Normalized to Control) |
|---|---|---|
| Water (Control) | 0 | 100% |
| *Acidothermus* β-1,4 Endoglucanase | 12.5 μU | 102.8% |
| *Acidothermus* β-1,4 Endoglucanase | 25 μU | 101.6% |
| *Acidothermus* β-1,4 Endoglucanase | 50 μU | 98.6% |
| Acidothermus β-1,4 Endoglucanase | 100 μU | 101.8% |
| *Acidothermus* β-1,4 Endoglucanase | 200 μU | 105% |
| *Acidothermus* β-1,4 Endoglucanase | 400 μU | 107.8% |
| *Acidothermus* β-1,4 Endoglucanase | 800 μU | 108.1% |
| *Acidothermus* β-1,4 Endoglucanase | 1600 μU | 101.2% |

Example 2: Free Endoglucanase on Corn, Greenhouse

*Acidothermus cellulolyticus* β-1,4 endoglucanase (SEQ ID NO: 30; commercially available from Sigma-Aldrich, St. Louis, MO, as product E2164) was diluted in citrate enzyme dilution buffer to concentrations of 50 through 1200 mU/mL. The U of endoglucanase activity was determined by as the amount of enzyme that is required to breakdown 1 μMol/min/mL of substrate at ideal temperature and conditions. Eighteen seeds of a commercial hybrid BECK'S 5140HR corn, which contains HERCULEX corn borer (an insect protection trait) and a glyphosate tolerance trait, without seed treatment were placed in 50 mL conical tubes. Each conical tube was vortexed and 18 μL of enzyme solution was added to each tube for a final enzyme concentration of 0, 50 μU, 100 μU, 200 μU, 400 μU, 600 μU, 800 μU, or 1200 μU per seed of endoglucanase. The conical tubes were vortexed again for 20 seconds to gain an even coating on each seed. Seeds were allowed to dry for 5 minutes and then planted into 39.7 $cm^3$ pots containing commercial top soil at a depth of 2.54 cm, with 2 seeds per pot. After planting, 50 mL of room temperature water was added to each pot to allow for germination. The pots were kept in an artificial light plant growth room with a 13/11 hour light/day cycle, and at 21 °C day/15 °C night temperature range. Plants were watered as needed, and randomized on a 3 day cycle to avoid any cool spots within the room. At the end of 14 days, the height of the corn plants for each treatment was measured, and normalized to the height of the control plants that were seed coated with only water. Each trial was replicated 3 times.

As can be seen in Table 19, the major effect of endoglucanase as a seed treatment on BECK'S 5140HR is in the range of 600-1200 μU/seed of enzyme activity. At these values, there is a noticeable and reproducible effect on corn growth. Values below 400 μU per seed had a lower effect on the corn growth rate on this hybrid. These enzyme treatments work well as a standalone treatment on crops.

TABLE 19

Height effects of β-1,4 endoglucanase treatment as a seed treatment

| Seed Treatment | Enzyme Activity/Seed | Height (Normalized to Control) |
|---|---|---|
| Water (Control) | 0 | 100% |
| *Acidothermus* β-1,4 Endoglucanase | 50μ | 100.5% |
| *Acidothermus* β-1,4 Endoglucanase | 100 μU | 97.34% |
| *Acidothermus* β-1,4 Endoglucanase | 200 μU | 94.69% |
| *Acidothermus* β-1,4 Endoglucanase | 400 μU | 98.5% |
| *Acidothermus* β-1,4 Endoglucanase | 600 μU | 102.3% |
| *Acidothermus* β-1,4 Endoglucanase | 800 μU | 103.8% |
| *Acidothermus* β-1,4 Endoglucanase | 1200 μU | 103.2% |

Example 3: Glucanases and Phospholipases on Corn, Field

*Acidothermus cellulolyticus* β-1,4 endoglucanase (SEQ ID NO: 30; commercially available from Sigma-Aldrich, St. Louis, MO, as product E2164), *Helix pomatia* β-1,3-D-glucanase (SEQ ID NO: 126; commercially available from Sigma-Aldrich, St. Louis, MO, as product 67138), *Trichoderma reesi* β-1,4 endoglucanase "cellulase" (SEQ ID NO: 36; commercially available from Worthington Biochemical Corp., Lakewood, NJ, as product ATCC26921), and *Aspergillus oryzae* exo-β-1,3-glucanase (SEQ ID NO 41; commercially available from Megazyme, Chicago, IL, as product E-EXG5AO) were diluted in citrate enzyme dilution buffer to concentrations of 600 mU/mL (for the *Acidothermus* β-1,4-endoglucanase and the *Trichoderma* β-1,4-endoglucanase) or 252 mU/mL (for the *Helix* β-1,3-D-glucanase) of activity. This grouping contained several cellulase (cellulolytic glucanase) and non-cellulolytic glucanase activities, including β-1,4-endoglucanase and β-1,3-D-glucanase activities, respectively. The U of enzyme activity was determined by as the amount of enzymes that is required to breakdown 1 μMol/min/mL of substrate at ideal temperature and conditions. *Bacillus cereus* phosphatidylinositol-specific phospholipase C (SEQ ID NO: 116; commercially available from Sigma-Aldrich, St. Louis, MO, as product P5524), *Bacillus cereus* phosphatidylcholine-specific phospholipase C (SEQ ID NO: 115; commercially available from Sigma-Aldrich, St. Louis, MO as product P6621), *Clostridium perfringens* phospholipase C (SEQ ID NO: 18; commercially available from Sigma-Aldrich, St. Louis, MO, as product P7633), and *Streptomyces chromofuscus* phospholipase D (SEQ ID NO: 19; commercially available from Sigma-Aldrich, St. Louis, MO, as product P0065) were diluted in citrate enzyme dilution buffer to a final concentration of 2.5 U/mL (for the *Bacillus* phosphatidylcholine Phospholipase C, the *Clostridium* Phospholipase C, and the *Streptomyces* Phospholipase D) or 100 U/mL (for the *Bacillus* phosphatidylinositol Phospholipase C). Each of these phospholipases have different specific activities to phospholipids and to different cleavage sites for phospholipids. Seeds of commercial hybrid BECK'S 6175YE corn, which contains HERCULEX (rootworm and corn borer protection traits), MON810 (comprising a corn borer resistance trait), a glufosinate resistance trait, and a glyphosate tolerance trait were used, without seed treatment. Seeds were placed into a batch treater at 400 seeds for each treatment. 400 μL of solution was added to each batch for a final enzyme concentration of 600 μU/seed for the *Acidothermus* β-1,4-endoglucanase and the *Trichoderma* β-1,4-endoglucanase, 252 μU/seed for the *Helix* β-1,3-D-glucanase, 100 mU/seed for the phosphatidylinositol-specific phospholipase C, or 2.5 mU/seed for the *Bacillus* phosphatidylcholine-specific Phospholipase C and the phospholipase C and D coated seeds. Each batch was allowed to mix for 20 seconds to gain an even coating on each seed. Additionally, these seeds were coated with commercial packages of prothioconazole, penflufen, metalaxyl, and clothianidin (EVERGOL Energy/PONCHO Seed Treatment, commercially available from Bayer CropScience) ("Base"). Each trial was replicated 3 times. Seeds were allowed to dry for 3 weeks, and then planted into native soil in 9.14 m rows at 10.16 cm apart, at a depth of 3.81 cm. The plants were measured for height at 2 weeks post-planting, and normalized to the height of the control plants that were seed coated with only water with Base. Results are shown in Table 16 below.

TABLE 20

Height effects of glucanases and phospholipase treatments as a seed treatment

| Seed Treatment | Enzyme Activity/Seed | Height (Normalized to Control) |
|---|---|---|
| Water + Base | 0 | 100% |
| *Acidothermus* β-1,4 Endoglucanase + Base | 600 μU | 117.6% |
| *Helix* β-1,3-D-glucanase + Base | 252 μU | 101.5% |
| *Trichoderma* β-1,4 Endoglucanase + Base | 600 μU | 114.0% |
| *Bacillus phosphatidylinositol* Phospholipase C + Base | 100 mU | 95.9% |
| *Bacillus phosphatidylcholine* Phospholipase C + Base | 2.5 mU | 100.7% |
| *Clostridium Phospholipase* C + Base | 2.5 mU | 109.2% |
| *Streptomyces Phospholipase* D + Base | 2.5 mU | 121.3% |

β-1,3-exoglucanase (*Aspergillus oryzae*; SEQ ID NO 41; commercially available from Megazyme, Chicago, IL, as product E-EXG5AO), phosphatidylinositol-specific phospholipase C (*Bacillus cereus*; SEQ ID NO: 116; commercially available from Sigma-Aldrich, St. Louis, MO as product P6621), phosphatidylcholine-specific phospholipase C (*Bacillus cereus*; SED ID NO: 115; commercially available from Sigma-Aldrich, St. Louis, MO, as product P5542), and phospholipase D (*Streptomyces chromofuscus*; SEQ ID NO: 19; commercially available from Sigma-Aldrich as product P8023) were diluted in water to 182 mU/mL (for β-1,3-exoglucanase), 100 U/mL (for the phosphatidylinositol-specific phospholipase C) or 2.5 U/mL (for the phosphatidylcholine-specific phospholipase C and the phospholipase D). The enzymes were applied as seed treatments to corn (BECK'S 5828 YH) which contains HERCULEX traits (a rootworm protection trait and corn borer resistance trait), a glufosinate resistance trait, and a glyphosate resistance trait), using the same methods described above, planted, and allowed to grow to harvest. The seed treatments were made on top of a base seed treatment containing prothioconazole, penflufen, metalaxyl, and clothianidin ("Base") and treated as described in the above section of this Example. The yield of treated crops (quantified as bushels/acre (Bu/Ac) or metric tonnes per hectare (MT/ha)) was compared to and normalized to crops grown from water treated seeds. Each treatment was independently performed at least 4 times. Corn seed treatments using these free enzymes resulted in increased corn yield compared to control corn plants that received no seed treatment. β-1,3-exoglucanase increased crop yield by approximately 4%, phosphatidylinositol-specific phospholipase C increased crop yield by approximately 3% and phospholipase D increased crop yield by approximately 2%. Average weight per ear also increased for corn plants grown from seeds treated with these three free enzymes. Results are shown in Table 21 below.

TABLE 21

Glucanases and phospholipases applied as a seed treatment to increase yield in corn

| Seed Treatment (5828 AM) | Enzyme Activity/Seed | Average Ear count per ear row | Average Weight per ear (lbs) [kg] | Absolute Change in bushels/acre (Bu/Ac) over control (+/−) [MT/ha] | Yield (Normalized to Control) |
|---|---|---|---|---|---|
| Water + Base | 0 μU/seed | 93 | 0.2694 [0.1222 kg] | 0.00 | 100% |
| β-1,3-Exoglucanase (*Aspergillus oryzae*) + Base | 182 μU/seed | 94 | 0.2769 [0.1256 kg] | +5.49 [0.34 MT/ha] | 104% |
| Phosphatidylinositol Phospholipase C (*Bacillus cereus*) + Base | 100 mU/seed | 94 | 0.2764 [0.1254 kg] | +4.02 [0.25 MT/ha] | 103% |
| Phosphatidylcholine Phospholipase C (*Bacillus cereus*) + Base | 2.5 mU/seed | 98 | 0.2477 [0.1124 kg] | −4.71 [−0.30 MT/ha] | 97% |
| Phospholipase D (*Streptomyces chromofuscus*) + Base | 2.5 mU/seed | 92 | 0.2943 [0.1335 kg] | +3.3 [0.21 MT/ha] | 102% |

Out of the phospholipases and glucanases that were tested in this trial, the β-1,3-exoglucanase, and the *Bacillus cereus* phosphatidylinositol-specific phospholipase C and *Streptomyces* phospholipase D had the best plant responses. These enzyme treatments worked on multiple hybrids and trait packages.

Example 4: Glucanases on Corn, Field

*Acidothermus cellulolyticus* β-1,4 endoglucanase (SEQ ID NO: 30; commercially available from Sigma-Aldrich, St. Louis, MO, as product E2164) was diluted in citrate enzyme dilution buffer to concentrations of 200 mU/ml and 450 mU/mL of activity. The U of endoglucanase activity was determined by as the amount of enzymes that is required to breakdown 1 μMol/min/mL of substrate at ideal temperature and conditions. 150 seeds of commercial hybrid BECK'S 6175YE, which contains, HERCULEX (rootworm and corn borer protection traits), MON810 (a corn borer resistance trait), a glufosinate resistance trait, and a glyphosate tolerance trait, without seed treatment was placed into 50 mL conical tubes at 50 seeds each. 50 μL of enzyme was added to each of the tubes with 250 μL of slurry containing prothioconazole, penflufen, metalaxyl, and clothianidin (EVERGOL Energy/PONCHO Seed Treatment) ("Base"). This led to a final enzyme concentration of 200 μU/seed and 450 μU/seed. The tubes were vortexed for 20 seconds to gain an even coating on each seed. Seeds were allowed to dry for 3 weeks, and then planted into native soil in 9.14 m rows at 10.16 cm apart, at a depth of 3.81 cm. The plants were measured for height at 2 weeks post-planting, and results were normalized to the height of the control plants that were seed coated with only water with Base (prothioconazole, penflufen, metalaxyl, and clothianidin) treatment.

The trials were repeated three times, and the values averaged across the experiments. The data in Table 22 below show that the growth rate of the corn for both concentrations of β-1,4-endoglucanase was increased at 2 weeks post-planting. At these concentrations, there is a noticeable and reproducible effect on corn growth. These enzyme treatments work well as a package on top of Base treatment on crops and on multiple hybrids and trait packages.

TABLE 22

Height effects of endoglucanase treatment as a seed treatment

| Seed Treatment | Enzyme Activity/Seed | Height (Normalized to Control) |
|---|---|---|
| Water (Control) + Base | 0 | 100% |
| *Acidothermus* β-1,4 Endoglucanase + Base | 200 μU | 115.5% |
| *Acidothermus* β-1,4 Endoglucanase + Base | 450 μU | 114.3% |

Example 5: Phospholipases on Corn, Greenhouse, High Range

*Bacillus cereus* phosphatidylcholine-specific phospholipase C (SEQ ID NO: 115; commercially available from Sigma-Aldrich, St. Louis, MO, as product P6621), *Clostridium perfringens* phospholipase C (SEQ ID NO: 18;

commercially available from Sigma-Aldrich, St. Louis, MO, as product P7633), and *Streptomyces chromofuscus* phospholipase D (SEQ ID NO: 19; commercially available from Sigma-Aldrich, St. Louis, MO, as product P0065) were diluted in 100 mM tris buffer, pH 7.0 to concentrations between of 100 U/ml to 450 U/mL. For each treatment group, 18 seeds of commercial hybrid BECK'S 6626RR corn, which contains a glyphosate tolerance trait, without seed treatment were placed in 50 mL conical tubes. Each conical tube was vortexed, and 18 μL of enzyme solution was added to each tube for a final enzyme concentration of 100 mU/mL, 200 mU/mL, or 450 mU/mL per seed of phospholipase, and vortexed again for 20 seconds to gain an even coating on each seed. Seeds were allowed to dry for 5 minutes, and the seeds were then planted into 42.24 $in^3$ (692.19 $cm^3$) pots of commercial top soil at a depth of 2.54 cm, with 2 seeds per pot. After planting, 50 mL of room temperature water was added to each pot to allow for germination. The pots were kept in an artificial light plant growth room with a 13/11 hour light/day cycle, and at 21 °C day/15 °C night temperature range. Plants were watered as needed, and rotated on a 3 day cycle to avoid any cool spots within the room. At the end of 14 days, the height of the corn plants for each treatment was measured, and normalized to the height of the control plants that were seed coated with only water. Experiments were done in triplicate.

Predominantly, it can be seen, in Table 23, that the effect of phospholipases C and D enzymes is best at values at or below 100 mU/seed. At these values, there is a noticeable and reproducible effect on corn growth. Values at or above 200 mU/seed are detrimental to corn growth. This held true for both phospholipase C and D enzymes.

TABLE 23

Height effects of phospholipases treatment as a seed treatment

| Seed Treatment | Enzyme activity/Seed | Height (Normalized to Control) |
|---|---|---|
| Water (Control) | 0 | 100% |
| Phospholipase C, *B. cereus* | 100 mU | 102.4% |
| Phospholipase C, *B. cereus* | 200 mU | 94.5% |
| Phospholipase C, *B. cereus* | 450 mU | 99.7% |
| Phospholipase C, *C. perfringens* | 200 mU | 97.4% |
| Phospholipase D, *Streptomyces* | 100 mU | 108.1% |
| Phospholipase D, *Streptomyces* | 250 mU | 98.4% |

Example 6: 2015 Soy Yield, Endoglucanases and Phospholipases

*Acidothermus cellulolyticus* β-1,4 endoglucanase (SEQ ID NO: 30; commercially available from Sigma-Aldrich, St. Louis, MO, as product E2164), *Helix pomatia* β-1,3-D-glucanase (SEQ ID NO: 126; commercially available from Sigma-Aldrich, St. Louis, MO, as product 67138), and *Trichoderma reesi* β-1,4 endoglucanase "cellulase" (SEQ ID NO: 36; commercially available from, Worthington Biochemical Corp., Lakewood, NJ) were diluted in water to concentrations of 600 mU/ml activity for the two β-1,4 endoglucanases and 252 mU/ml for the β-1,3-D-glucanase. This grouping contained several cellulolytic and non-cellulolytic glucanase activities, including both β-1,4-endoglucanase and β-1,3-D-glucanase activities. *Bacillus cereus* phosphatidylcholine-specific phospholipase C (SEQ ID NO: 115; commercially available from Sigma-Aldrich, St. Louis, MO, as product P6621), *Clostridium perfringens* phospholipase C (SEQ ID NO: 18; commercially available from Sigma-Aldrich, St. Louis, MO, as product P7633), and *Bacillus cereus* phosphatidylinositol-specific phospholipase C (SEQ ID NO: 116; commercially available from Sigma-Aldrich, St. Louis, MO, as product P5524) were diluted in water to a final concentration of 2.5 U/ml (for the *Bacillus* phosphatidylcholine-specific phospholipase C and the *Clostridium* Phospholipase C) or 100 U/ml (for the *Bacillus* phosphatidylinositol-specific phospholipase C). Each of these phospholipases has different specific activities to phospholipids and to different cleavage sites for phospholipids. 720 seeds of commercial hybrid BECK'S 294NR soybeans, which contain a nematode resistance trait (SCN-SB) and a glyphosate resistance trait (ROUNDUP READY 1), with the metalaxyl and clothianidin Base seed treatment package ("Base") were placed into paint cans and coated with commercial seed treatment (Base). Each batch was mixed, and 720 μL of solution was added to each batch to obtain the final enzyme concentrations listed in Table 24 below. Seeds were allowed to dry for 3 weeks, and then planted into native soil in 9.14 m rows at 6.35 cm apart, at a depth of 3.81 cm. The plants were harvested and yield measured at harvest. Each treatment was replicated 4 times and planted 4 times in the field. Results are shown below in Table 24 as a percentage of weight over the control (Base) treatment.

TABLE 24

Yield Increases as a Percentage of Control

| Seed Treatment | Enzyme Activity/Seed | Yield (Normalized to Control) |
|---|---|---|
| Water + Base | 0 | 100% |
| *Acidothermus* β-1,4 Endoglucanase + Base | 600 μU | 123% |
| *Helix* β-1,3-D-glucanase + Base | 252 μU | 123% |
| *Trichoderma* β-1,4 Endoglucanase + Base | 600 μU | 123% |
| *Bacillus* phosphatidylinositol Phospholipase C + Base | 100 mU | 115% |
| *Bacillus* phosphatidylcholine Phospholipase C + Base | 2.5 mU | 145% |
| *Clostridium* Phospholipase C + Base | 2.5 mU | 92% |

As can be seen in Table 24, all three glucanases lead to a noticeable increase in yield in the soybean plants, as well as the PC-PLC and PI-PLC from *Bacillus cereus.*

Example 7: 2015 Corn Yield, Endoglucanase

*Acidothermus cellulolyticus* β-1,4 endoglucanase (SEQ ID NO: 30 commercially available from Sigma-Aldrich, St. Louis, MO, as product E2164) was diluted in citrate enzyme dilution buffer to concentrations of 250 and 600 mU/ml of activity. Seeds of commercial hybrid BECK'S 5828YH corn with a prothioconazole, penflufen, metalaxyl, and clothianidin (EVERGOL Energy/PONCHO) Base seed treatment package ("Base") were placed into seed treater at 250 seeds each. Each batch was mixed, and 250 μL of solution was added to each tube for a final enzyme concentration of 200 or 600 μU/seed for the endoglucanases coated seeds. Each batch was mixed again for 20 seconds to gain an even coating on each seed. Seeds were allowed to dry for 3 weeks, and then planted into native soil in 9.14 m rows at 6.35 cm apart, at a depth of 3.81 cm. The plants were harvested and yield measured at harvest. Each treatment was replicate 4 times. Results are shown below in Table 25 as a harvest weight as a percentage over control treatment harvest weigh (normalized).

TABLE 25

| Yield Increases as a Percentage of Control | | |
|---|---|---|
| Seed Treatment | Enzyme Activity/Seed | Yield (Normalized to Control) |
| Water + Base | 0 | 100% |
| *Acidothermus* β-1,4 Endoglucanase + Base | 200 μU | 104.8% |
| *Acidothermus* β-1,4 Endoglucanase + Base | 600 μU | 102.4% |

As can be seen in Table 25, both rates of *Acidothermus* β-1,4 endoglucanase lead to an increase in the yield of the corn.

Example 8: Isolation and Identification of Plant-Growth Promoting Bacterial Strains Soil samples from rhizospheres of the healthiest and most resistant potato (*Solanum tuberosum*), yellow summer squash (*Cucurbita pepo*), tomato (*Solanum lycopersicum*), and pole bean (*Phaseolus coccineus*) plants were collected, diluted in sterile water, and spread onto nutrient agar plates. Bacterial isolates that demonstrated high growth rates and were able to be passaged and propagated were selected for further study. The selected strains were grown in minimal media ($KH_2PO_4$ 3 g, $Na_2HPO_4$ 6 g, $NH_4Cl$ 1 g, NaCl 0.50 g, $MgSO_4$ $7H_2O$ 0.15 g, $CaCl_2$ $2H_2O$ 0.013 g, and glucose 1 g, per L dry weight). Overnight cultures (30 °C) of selected strains were spun down, media decanted off, and resuspended in an equal amount of distilled water. Ten butterhead lettuce seeds per treatment were planted at a depth of 1 cm in loam top soil (Columbia, MO) that was sieved to remove large debris. Seeds were inoculated at planting in 4 cm pots with 0.5 μl of resuspended bacteria in water mixed into 10 ml of $H_2O$. Ten ml of $H_2O$ was sufficient to deliver the bacteria into the 3 $in^3$ (49.16 $cm^3$) of soil as well as saturate the soil for proper germination of seeds. Plants were grown at temperatures between 65-75 °F. (18-24 °C) with 11 hours of light/day, and 5 ml of watering every 3 days. After one week, plant heights and leaf diameters, as well as overall health of the plants were collected. Initial screening of rhizosphere isolates resulted in obtaining greater than 200 distinct species of bacteria and fungi from the rhizosphere of the four plants. Some of the bacterial species are described in Table 26. Identified strains are indicated by their proper bacterial identifications. Other strains are indicated by their unknown identification number. Inoculants giving results near control (+/−2%) were not included in the table.

TABLE 26

| Bacterial Inoculant | Avg. Height (cm) | Comparison | SEM |
|---|---|---|---|
| Uninoculated | 1.8 | Control | .07 |
| *Paracoccus kondratiavae* NC35 | 2 | 111.1% | .05 |
| *B. aryabhattai* CAP53 | 3.65 | 202.8% | .45 |
| *B. flexus* BT054 | 2.45 | 136.1% | .11 |
| *Bacillus mycoides* strain BT155 | 2.17 | 120.4% | .21 |
| *B. aryabhattai* CAP56 | 2.1 | 116.7% | .20 |
| *B. nealsonii* BOBA57 | 2.8 | 155.6% | .03 |
| *E. cloacae* CAP12 | 2.4 | 133.3% | .41 |
| Unknown 8 | 1.77 | 77.8% | .65 |
| Unknown 122 | 1.9 | 105.6% | .11 |
| Unknown 15 | 1.4 | 77.8% | .41 |
| Unknown 39 | 1.8 | 100.0% | .20 |
| Unknown 401 | 2 | 111.1% | .21 |
| Unknown 402 | 1.53 | 85.2% | .27 |
| Unknown 41 | 1.45 | 80.6% | .31 |
| Unknown 42 | 1.4 | 77.8% | .15 |
| Unknown 44 | 2.2 | 133.3% | .08 |
| Unknown 51 | 1.83 | 102.9% | .21 |

Bacterial strains that produced the greatest effect on the overall plant health and plant height in the initial lettuce trial were subjected to further identification. Bacterial strains were grown overnight in Luria Bertani broth at 37 °C, and overnight cultures were spun down in a centrifuge. Media was decanted and the remaining bacterial pellet was subjected to chromosomal DNA isolation using the Qiagen Bacterial Chromosomal DNA Isolation kit. Chromosomal DNA was subjected to PCR amplification of the 16S rRNA coding regions using the primers E338F 5'-ACT CCT ACG GGA GGC AGC AGT-3' (SEQ ID NO: 108), E1099R A 5'-GGG TTG CGC TCG TTG C-3' (SEQ ID NO: 109), and E1099R B 5'-GGG TTG CGC TCG TTA C-3' (SEQ ID NO: 110). PCR amplicons were purified using a Promega PCR purification kit, and the resultant amplicons were diluted and sent to the University of Missouri DNA Core for DNA sequencing. DNA sequences were compared to the NCBI BLAST database of bacterial isolates, and genus and species were identified by direct comparison to known strains. Top identified species are indicated in Table 26. In many cases, 16S rRNA DNA sequences were only able to delineate the genus of the selected bacterial strain. In cases where a direct identification was not forthcoming, additional biochemistry analyses, using methods standard in the field, were performed to differentiate strains at the species and strain levels, and are listed in Table 27.

TABLE 27

| Test | *E. cloacae* CAP12 | *P. kondratiavae* NC35 | *B. aryabhattai* CAP53 | *B. flexus* BT054 | *B. mycoides* BT155 | *B. aryabhattai* CAP56 | *B. nealsonii* BOBA57 |
|---|---|---|---|---|---|---|---|
| Urease | − | − | − | − | − | − | + |
| Catalase | + | + | + | + | + | + | + |
| Oxidase | − | + | + | + | − | − | − |
| Nitrate | + | + | − | + | + | − | + |
| Growth, 5% NaCl | + | − | + | + | − | + | + |
| Growth, 7.5% NaCl | − | − | + | + | − | + | − |
| Growth, 42° C. | + | + | + | + | + | + | + |
| Growth, 50° C. | − | − | + | + | − | + | − |
| Growth, pH 5 | + | − | + | + | − | + | − |
| Growth, pH 9 | + | + | + | + | + | + | + |
| Acid, Cellobiose | + | − | + | + | + | + | − |
| Acid, Lactose | + | − | + | + | + | − | + |
| Acid, Starch | − | − | − | + | − | + | − |

Example 9: Isolation and Identification of Additional Plant-Growth Promoting Bacterial Strains Soil samples from agricultural fields near Gas, Kansas were collected, diluted in sterile water, and spread onto nutrient agar plates. Bacterial isolates that demonstrated high growth rates and were able to be passaged and propagated were selected for further study. The selected strains were grown in minimal media ($KH_2PO_4$ 3 g, $Na_2HPO_4$ 6 g, $NH_4Cl$ 1 g, NaCl 0.50 g, $MgSO_4$ $7H_2O$ 0.15 g, $CaCl_2$ $2H_2O$ 0.013 g, and glucose 1 g, per L dry weight). Overnight cultures (30 °C) of selected strains were spun down, media decanted off, and resuspended in an equal amount of distilled water. Corn seeds were coated with commercial seed polymer mixed with water alone (1.6 µl per seed total) or commercial seed polymer containing selected bacterial strains (1.6 µl per seed total). Coated seeds were planted in 3 inch (7.62 cm) diameter pots at a depth of 1 inch (2.54 cm) in loam top soil (Columbia, MO) that was sieved to remove large debris. Plants were grown at temperatures between 18-24 °C. (65-75 °F) with 11 hours of light/day, and 50 ml of watering at planting and every 3 days. After two weeks, plant heights and leaf diameters, as well as overall health of the plants were collected. For germination assays and determining 3 day root length, seeds were coated as indicated above and evenly dispersed at 10 seeds per paper towel. The paper towels were wetted with 10 ml of water, rolled up, placed in a small plastic bag and incubated at 30 °C or placed on a germination heat mat at 27-30 °C. (80-85 °F.). Root measurements were recorded after 3 days. Initial screening of rhizosphere isolates resulted in obtaining greater than 100 distinct species of bacteria and fungi from the rhizosphere. Some of the bacterial species are described in Table 28. Identified strains are indicated by their proper bacterial identifications.

TABLE 28

| Bacterial Inoculant | Avg. Height (2 weeks), normalized to polymer control (%) | Avg. Root Length (3 days), normalized to polymer control (%) |
|---|---|---|
| Polymer control | 100 | 100 |
| *B. mycoides* EE118 | 111.1 | 189.1 |
| *B. subtilis* EE148 | 99.4 | 172.8 |
| *Alcaligenes faecalis* EE107 | 111.5 | 129.2 |
| *B. mycoides* EE141 | 109.2 | 143.5 |
| *B. mycoides* BT46-3 | 105.6 | 141.3 |
| *B. cereus* family member EE128 | 105.6 | — |
| *B. thuringiensis* BT013A | 101.8 | 103.8 |
| *Paenibacillus massiliensis* BT23 | 104.2 | 139.4 |
| *B. cereus* family member EE349 | 105.2 | — |
| *B. subtilis* EE218 | 106.6 | — |
| *B. megaterium* EE281 | 107.8 | — |

Bacterial strains that produced the greatest effect on plant health are described in Table 28. Bacterial strains were grown overnight in Luria Bertani broth at 37 °C, and overnight cultures were spun down in a centrifuge. Media was decanted and the remaining bacterial pellet was subjected to chromosomal DNA isolation using the Qiagen Bacterial Chromosomal DNA Isolation kit. Chromosomal DNA was subjected to PCR amplification of the 16S rRNA coding regions using the primers E338F 5'-ACT CCT ACG GGA GGC AGC AGT-3' (SEQ ID NO: 108), E1099R A 5'-GGG TTG CGC TCG TTG C-3' (SEQ ID NO: 109), and E1099R B 5'-GGG TTG CGC TCG TTA C-3' (SEQ ID NO: 110). PCR amplicons were purified using a Promega PCR purification kit, and the resultant amplicons were diluted and sent to the University of Missouri DNA Core for DNA sequencing. DNA sequences were compared to the NCBI BLAST database of bacterial isolates, and genus and species were identified by direct comparison to known strains. Top identified species are indicated in Table 28. In many cases, 16S rRNA DNA sequences were only able to delineate the genus of the selected bacterial strain. In cases where a direct identification was not forthcoming, additional biochemistry analyses, using methods standard in the field, were performed to differentiate strains at the species and strain levels, and the differentiated strains are listed in Table 29.

TABLE 29

| Test | *B. thuringiensis* BT013A | *B. cereus* family member EE349 | *B. subtilis* EE148 | *B. subtilis* EE218 | *B. megaterium* EE281 | *Paenibacillus massiliensis* BT23 |
|---|---|---|---|---|---|---|
| Motility | + | + | + | + | + | + |
| Rhizoid Colony | – | – | – | – | – | + |
| Catalase | + | + | + | + | + | + |
| Oxidase | + | – | – | – | – | – |
| Nitrate | + | + | wk | – | – | – |
| Growth, 5% NaCl | + | wk | – | + | + | – |
| Growth, 7.5% NaCl | wk | – | – | + | + | – |
| Growth, 42° C. | – | + | + | + | + | + |
| Growth, 50° C. | – | – | – | – | – | – |
| Growth, pH 5 | wk | – | + | + | + | – |
| Growth, pH 9 | + | + | – | + | + | – |
| Acid, Cellobiose | – | – | wk | + | – | + |
| Acid, Lactose | – | + | + | + | + | – |
| Acid, Starch | – | + | – | + | + | – |

TABLE 29-continued

| Test | *B. mycoides* BT46-3 | *Alcaligenes faecalis* EE107 | *B. mycoides* EE118 | *B. cereus* family member EE128 | *B. mycoides* EE141 |
|---|---|---|---|---|---|
| Motility | − | + | − | − | − |
| Rhizoid Colony | + | − | + | − | + |
| Catalase | + | + | + | + | + |
| Oxidase | − | + | − | − | − |
| Nitrate | + | + | + | + | + |
| Growth, 5% NaCl | + | + | − | + | − |
| Growth, 7.5% NaCl | − | − | − | − | − |
| Growth, 42° C. | + | + | − | + | − |
| Growth, 50° C. | − | − | − | − | − |
| Growth, pH 5 | wk | + | − | + | − |
| Growth, pH 9 | wk | + | + | + | − |
| Acid, Cellobiose | + | wk | + | − | wk |
| Acid, Lactose | + | + | − | + | wk |
| Acid, Starch | + | wk | + | + | − |

wk = weak growth or low growth

Example 10: Testing of Plant-Growth Promoting Bacterial Strains on Alfalfa

The selected strains were grown in minimal media ($KH_2PO_4$ 3 g, $Na_2HPO_4$ 6 g, $NH_4Cl$ 1 g, NaCl 0.50 g, $MgSO_4$ $7H_2O$ 0.15 g, $CaCl_2$ $2H_2O$ 0.013 g, and glucose 1 g, per L dry weight). Overnight cultures (30 °C) of selected strains were spun down, media decanted off, and bacteria resuspended in an equal amount of distilled water. Ten ZEBA-coated alfalfa seeds were planted for each treatment at a depth of 0.6 cm in loam top soil (Columbia, MO) that was sieved to remove large debris. ZEBA is a superabsorbent cornstarch based polymer used as a moisture-retention seed coating. Seeds were inoculated at planting with 0.5 μl of resuspended bacteria in water mixed into 10 ml of $H_2O$. Ten ml of $H_2O$ was sufficient to deliver the bacteria into the 3 $in^3$ (49.16 $cm^3$) of soil as well as saturate the soil for proper germination of seeds. Plants were grown at temperatures between 65-75 °F. (18-24 °C) with 11 hours of light/day, and 5 ml of watering every 3 days. Alfalfa was allowed to grow for 1 week to analyze emergence and initial outgrowth of plants under described conditions. Identified strains indicated by their proper bacterial identifications and final height data are listed in Table 30.

TABLE 30

| Bacterial Inoculant | Avg. Height (cm) | Comparison | SEM |
|---|---|---|---|
| Uninoculated | 4.82 | — | .008 |
| *B. aryabhattai* CAP56 | 4.85 | 101.20% | .016 |
| *B. nealsonii* BOBA57 | 4.86 | 101.70% | .021 |
| *E. cloacae* CAP12 | 5.6 | 116.23% | .020 |

Example 11: Testing of Plant-Growth Promoting Bacterial Strains on Cucumbers

The selected strains were grown in minimal media ($KH_2PO_4$ 3 g, $Na_2HPO_4$ 6 g, $NH_4Cl$ 1 g, NaCl 0.50 g, $MgSO_4$ $7H_2O$ 0.15 g, $CaCl_2$ $2H_2O$ 0.013 g, and glucose 1 g, per L dry weight). Overnight cultures (30 °C) of selected strains were spun down, media decanted off, and resuspended in equal amount of distilled water. Ten cucumber seeds were planted for each treatment at a depth of 1 cm in loam top soil (Columbia, MO) that was sieved to remove large debris. Seeds were inoculated at planting with 0.5 μl of resuspended bacteria in water mixed into 10 ml of $H_2O$. Ten ml of $H_2O$ was sufficient to deliver the bacteria into the 3 $in^3$ (49.16 $cm^3$) of soil as well as saturate the soil for proper germination of seeds. Plants were grown at temperatures between 65-75 °F. (18-24 °C) with 11 hours of light/day, and 5 ml of watering every 3 days. Cucumbers were allowed to grow for 2 weeks to analyze emergence and initial outgrowth of plants under described conditions. Identified strains indicated by their proper bacterial identifications and final height data are listed in Table 31.

TABLE 31

| Bacterial Inoculant | Avg. Height (cm) | Comparison | SEM |
|---|---|---|---|
| Uninoculated | 11.23 | — | .067 |
| *B. aryabhattai* CAP53 | 11.5 | 102.00% | .023 |
| *B. aryabhattai* CAP56 | 11.35 | 101.20% | .035 |
| *B. nealsonii* BOBA57 | 11.33 | 101.10% | .014 |

Example 12: Testing of Plant-Growth Promoting Bacterial Strains on Yellow Squash The selected strains were grown in minimal media ($KH_2PO_4$ 3 g, $Na_2HPO_4$ 6 g, $NH_4Cl$ 1 g, NaCl 0.50 g, $MgSO_4$ $7H_2O$ 0.15 g, $CaCl_2$ $2H_2O$ 0.013 g, and glucose 1 g, per L dry weight). Overnight cultures (30 °C) of selected strains were spun down, media decanted off, and resuspended in an equal amount of distilled water. Ten yellow squash seeds were planted for each treatment at a depth of 1 cm in loam top soil (Columbia, MO) that was sieved to remove large debris. Seeds were inoculated at planting with 0.5 μl of resuspended bacteria in water mixed into 10 ml of $H_2O$. Ten ml of $H_2O$ was sufficient to deliver the bacteria into the 3 $in^3$ (49.16 $cm^3$) of soil as well as saturate the soil for proper germination of seeds. Plants were grown at temperatures between 65-75 °F. (18-24 °C) with 11 hours of light/day, and 5 ml of watering every 3 days. Squash was allowed to grow for 2 weeks to analyze emergence and initial outgrowth of plants under described conditions. Identified strains indicated by their proper bacterial identifications, final height data, and final leaf diameter (by span of the two leaves) data are listed in Table 32.

TABLE 32

| Bacterial Inoculant | Avg. Height (cm) | Comparison | SEM | Leaf Diameter (cm) | Comparison |
|---|---|---|---|---|---|
| Uninoculated | 10.16 | — | .028 | 5.08 | — |
| *B. aryabhattai* CAP53 | 11.75 | 115.60% | .055 | 7.25 | 142.60% |
| *B. flexus* BT054 | 11.88 | 116.90% | .017 | 6.36 | 125.20% |
| *Bacillus mycoides* BT155 | 11.92 | 117.20% | .051 | 6.33 | 124.60% |
| *B. aryabhattai* CAP56 | 11.95 | 117.60% | .027 | 6.33 | 124.60% |
| *B. nealsonii* BOBA57 | 11.89 | 117.00% | .118 | 6.42 | 126.40% |
| *E. cloacae* CAP12 | 11.42 | 112.30% | .039 | 6.83 | 134.40% |

Example 13: Testing of Plant-Growth Promoting Bacterial Strains on Ryegrass

The selected strains were grown in minimal media ($KH_2PO_4$ 3 g, $Na_2HPO_4$ 6 g, $NH_4Cl$ 1 g, NaCl 0.50 g, $MgSO_4$ $7H_2O$ 0.15 g, $CaCl_2$ $2H_2O$ 0.013 g, and glucose 1 g, per L dry weight). Overnight cultures (30 °C) of selected strains were spun down, media decanted off, and resuspended in an equal amount of distilled water. Thirty ryegrass seeds were planted for each treatment at a depth of 0.3 cm in loam top soil (Columbia, MO) that was sieved to remove large debris. Seeds were inoculated at planting with 0.5 μl of resuspended bacteria in water mixed into 10 ml of $H_2O$. Ten ml of $H_2O$ was sufficient to deliver the bacteria into the 3 $in^3$ (49.16 $cm^3$) of soil as well as saturate the soil for proper germination of seeds. Plants were grown at temperatures between 65-75 °F. (18-24 °C) with 11 hours of light/day, and 5 ml of watering every 3 days. Ryegrass was allowed to grow for 1.5 weeks to analyze emergence and initial outgrowth of plants under described conditions. Identified strains indicated by their proper bacterial identifications and height data are listed in Table 33.

TABLE 33

| Bacterial Inoculant | Avg. Height (cm) | Comparison | SEM |
|---|---|---|---|
| Uninoculated | 1.61 | — | .023 |
| *B. aryabhattai* CAP53 | 2.01 | 124.70% | .012 |
| *B. flexus* BT054 | 2.21 | 137.30% | .034 |
| *Bacillus mycoides* BT155 | 2.29 | 142.20% | .049 |
| *B. aryabhattai* CAP56 | 2.19 | 136.00% | .009 |
| *B. nealsonii* BOBA57 | 2.29 | 142.40% | .045 |
| *E. cloacae* CAP12 | 1.98 | 122.50% | .015 |

Example 14: Testing of Plant-Growth Promoting Bacterial Strains on Corn

The selected strains were grown in minimal media ($KH_2PO_4$ 3 g, $Na_2HPO_4$ 6 g, $NH_4Cl$ 1 g, NaCl 0.50 g, $MgSO_4$ $7H_2O$ 0.15 g, $CaCl_2$ $2H_2O$ 0.013 g, and glucose 1 g, per L dry weight). Overnight cultures (30 °C) of selected strains were spun down, media decanted off, and resuspended in an equal amount of distilled water. Ten corn seeds were planted for each treatment at a depth of 2.5 cm in loam top soil (Columbia, MO) that was sieved to remove large debris. Seeds were inoculated at planting with 0.5 μl of resuspended bacteria in water mixed into 10 ml of $H_2O$. Ten ml of $H_2O$ was sufficient to deliver the bacteria into the 3 $in^3$ (49.16 $cm^3$) of soil as well as saturate the soil for proper germination of seeds. Plants were grown at temperatures between 65-75 °F. (18-24 °C) with 11 hours of light/day, and 5 ml of watering every 3 days. Corn was allowed to grow for 2 weeks to analyze emergence and initial outgrowth of plants under described conditions. Identified strains indicated by their proper bacterial identifications and final height data are listed in Table 34.

TABLE 34

| Bacterial Inoculant | Avg. Height (cm) | Comparison | SEM |
|---|---|---|---|
| Uninoculated | 8.9 | — | .039 |
| *B. aryabhattai* CAP53 | 11.01 | 123.60% | .081 |
| *B. flexus* BT054 | 9.96 | 112.00% | .095 |
| *Bacillus mycoides* strain BT155 | 9.6 | 107.90% | .041 |
| *B. aryabhattai* CAP56 | 9.54 | 107.10% | .088 |
| *B. nealsonii* BOBA57 | 9.23 | 103.70% | .077 |

Example 15: Testing of Plant-Growth Promoting Bacterial Strains on Soybeans

The selected strains were grown in minimal media ($KH_2PO_4$ 3 g, $Na_2HPO_4$ 6 g, $NH_4Cl$ 1 g, NaCl 0.50 g, $MgSO_4$ $7H_2O$ 0.15 g, $CaCl_2$ $2H_2O$ 0.013 g, and glucose 1 g, per L dry weight, or for *Bradyrhizobium* or *Rhizobium* on yeast mannitol media). Overnight cultures (30 °C) of selected strains were spun down, media decanted off, and resuspended in equal amount of distilled water. Ten soybean seeds were planted for each treatment at a depth of 2.5 cm in loam top soil (Columbia, MO) that was sieved to remove large debris. Seeds were inoculated at planting with 0.5 μl of resuspended bacteria in water mixed into 10 ml of $H_2O$. When testing two bacterial strains, 0.5 μl of each resuspended bacteria was mixed into 10 ml of $H_2O$. Ten ml of $H_2O$ was sufficient to deliver the bacteria into the 3 $in^3$ (49.16 $cm^3$) of soil as well as saturate the soil for proper germination of seeds. Plants were grown at temperatures between 65-75 °F. (18-24 °C) with 11 hours of light/day, and 5 ml of watering every 3 days. Soybeans were allowed to grow for 2 weeks to analyze emergence and initial outgrowth of plants under described conditions. Identified strains indicated by their proper bacterial identifications and final height data are listed in Table 35. Co-inoculation of bacteria strains in the present invention with members of the *Bradyrhizobium* sp, or *Rhizobium* sp. lead to an increase in plant growth compared to either inoculant alone.

TABLE 35

| Bacterial Inoculant | Avg. Height (cm) | Comparison | SEM |
|---|---|---|---|
| Uninoculated | 13.94 | — | .089 |
| *B. aryabhattai* CAP53 | 16.32 | 117.1% | .146 |
| *B. flexus* BT054 | 17.85 | 128.0% | .177 |
| *Bacillus mycoides* strain BT155 | 18.93 | 135.8% | .117 |
| *B. aryabhattai* CAP56 | 17.23 | 123.6% | .133 |
| *B. aryabhattai* CAP53 | 16.32 | 117.1% | .077 |
| *B. aryabhattai* CAP53 and *Bradyrhizobium* sp. | 16.72 | 119.9% | .182 |
| *B. aryabhattai* CAP53 and *Rhizobium* sp. | 17.32 | 124.2% | .086 |
| *Bradyrhizobium* sp. | 14.25 | 102.2% | |
| *Rhizobium* sp. | 14.75 | 105.8% | |

Example 16: *Bacillus cereus* Family Members with Plant Growth Promoting Attributes

*Bacillus mycoides* strain BT155, *Bacillus mycoides* strain EE118, *Bacillus mycoides* strain EE141, *Bacillus mycoides* strain BT46-3, *Bacillus cereus* family member strain EE349, *Bacillus thuringiensis* strain BT013A, and *Bacillus megaterium* strain EE281 were grown in Luria Bertani broth at 37 °C and overnight cultures were spun down, media decanted off, and resuspended in equal amount of distilled water. Twenty corn seeds were planted for each treatment at a depth of 2.5 cm in loam top soil (Columbia, MO) that was sieved to remove large debris. Seeds were inoculated at planting with 0.5 μl of resuspended bacteria in water mixed into 50 ml of $H_2O$. Fifty ml of $H_2O$ was sufficient to deliver the bacteria into the 29 $in^3$ (475.22 $cm^3$) of soil as well as saturate the soil for proper germination of seeds. Plants were grown at temperatures between 65-72 °F with 13 hours of light/day, and 5 ml of watering every 3 days. Seedlings were allowed to grow for 2 weeks to analyze emergence and initial outgrowth of plants under described conditions. Identified strains indicated by their proper bacterial identifications and final height data are listed in Table 36.

TABLE 36

| Bacterial Inoculant | Avg. Height, cm, Corn | Percentage | SEM, |
|---|---|---|---|
| $H_2O$ Control | 11.41 | 100% | .123 |
| *B. mycoides* EE118 | 12.43 | 108.9% | .207 |
| *B. mycoides* EE141 | 12.84 | 112.5% | .231 |
| *B. mycoides* BT46-3 | 11.81 | 103.5% | .089 |
| *Bacillus thuringiensis* BT013A | 12.05 | 105.6% | .148 |
| *Bacillus cereus* family member EE128 | 13.12 | 114.9% | .159 |
| *Bacillus mycoides* BT155 | 12.85 | 112.6% | .163 |
| *Bacillus megaterium* EE281 | 11.99 | 105.1% | .098 |

All plant-growth promoting bacteria tested had a beneficial effect on corn height at two weeks under the described conditions. The *Bacillus cereus* family member EE128 strain had the greatest effect in this trial, giving a greater than at 14% boost in corn height.

Example 17: Isolation, Identification, and Characterization of Endophytic *Bacillus cereus* Family Bacterial Strains

*Bacillus cereus* family member 349, discussed above in the immediately preceding example, was found to have the ability to grow endophytically. Several other *Bacillus cereus* family members that have the ability to grow endophytically were also identified: *Bacillus cereus* family member EE439, *Bacillus thuringiensis* EE417, *Bacillus cereus* EE444, *Bacillus thuringiensis* EE319, *Bacillus thuringiensis* EE-B00184, *Bacillus mycoides* EE-B00363, *Bacillus pseudomycoides* EE-B00366, and *Bacillus cereus* family member EE-B00377.

To obtain these additional *Bacillus cereus* family members, commercial hybrid corn seed was planted in potting soil and allowed to grow. The corn seeds were coated with a fungicide and a biological inoculant. Plants were grown under artificial light for 14 hours a day and plant growth over a 14 day period was determined. Plants were watered every three days over the course of the experiment. After 14 days, the plants were extracted from the soil and washed to remove excess debris. The plants were then inverted, exposed to 5% bleach for ten minutes, washed in water, exposed to hydrogen peroxide (10%) for ten minutes, washed again in water, and the stalks split with a sterile razor blade. The split halves of the stalks were placed face down onto nutrient agar plates for two hours. After two hours, the stalks were removed, and the agar plates incubated at 30 °C for 48 hours. After 48 hours, the plates were examined for colony morphology, and *Bacillus cereus* family member colonies found internal to the plant were toothpicked onto nutrient agar. These were then were grown overnight at 30 °C in brain heart infusion broth, and spun down at 10,000×g for 5 minutes. The supernatant was removed, and the pellet frozen overnight at −20 °C. Chromosomal DNA was then extracted from each clone, and the identity of each colony verified by PCR using 16S rRNA primers and amplicons were sent for DNA sequencing and identification. The 16S rRNA sequences for these strains are provided above in Table 17.

Example 18: Isolation, Identification, and Characterization of Additional Endophytic Bacterial Strains (Non-*Bacillus cereus* Family Members)

The endophytic bacterial strains *Bacillus megaterium* EE385, *Bacillus* sp. EE387, *Bacillus circulans* EE388, *Bacillus subtilis* EE405, *Lysinibacillus fusiformis* EE442, *Lysinibacillus* spp. EE443, and *Bacillus pumilus* EE-B00143 were isolated from corn seedlings. Two week old corn seedlings were first sterilized. The plants were extracted them from the soil and washed to remove excess debris. The plants were then inverted, exposed to 5% bleach for ten minutes, washed in water, exposed to hydrogen peroxide (10%) for ten minutes, and washed again in water. The stalks were then split with a sterile razor blade. The split halves of the stalks were placed face down onto nutrient agar plates for two hours. After two hours, the plant stems were removed from the plates, and the plates were then incubated at 30 °C for 48 hours. Bacilli colonies that were endophytic were selected for further analysis. These strains were grown up in brain heart infusion broth overnight at 30 °C, and the cultures subjected to extraction of DNA using a Qiagen Chromosomal DNA Kit. The DNA was PCR amplified to obtain the 16S rRNA gene, which was sent for DNA sequencing. The resultant sequences were BLAST searched using the NCBI databases to establish the identity of the Bacilli species. The 16S rRNA sequences are provided above in Table 17.

Example 19: Free ACC Deaminase on Corn, Greenhouse 1-aminocyclopropane-1-carboxylate deaminase (ACC deaminase) was applied in a foliar application as a spray to corn plants. Two amino acids of D-cysteine desulfhydrase of *Bacillus thuringiensis* strain IS5056 (SEQ ID NO: 113) were mutated, resulting in a modest increase in ACC deaminase (1-aminocyclopropane-1-carboxylate) activity. In addition to its D-cysteine desulfhydrase activity, the native D-cysteine desulfhydrase from *Bacillus thuringiensis* strain IS5056 has ample inherent ACC deaminase activity. However, for purposes of the present Example and Example 20 below, the native D-cysteine desulfhydrase from *Bacillus thuringiensis* strain IS5056 (SEQ ID NO: 113) will be referred to as a "D-cysteine desulfhydrase." Since the mutated version of the enzyme (SEQ ID NO: 114) has increased ACC deaminase activity, for purposes of the present examples, the mutated enzyme will be referred to as an "ACC deaminase." The sequences with the mutations are provided as SEQ ID NO: 112 (nucleic acid) and SEQ ID NO: 114 (protein). In Table 2, the two amino acid substitutions shown are in bold and underlined text. The threonine at position 290 of SEQ ID NO: 113 was substituted with a glutamic acid residue and serine residue at position 317 of SEQ ID NO: 113 was substituted with a leucine residue using PCR mutagenesis techniques standard in the art. The genes encoding the D-cysteine deaminase (SEQ ID NO: 111) and ACC deaminase (SEQ ID NO: 112) were then cloned into the Gram positive pBC vector (a miniaturized version of the naturally occurring plasmid pBC16) under the control of a BclA sporulation promoter. The vectors were then transformed into *Bacillus thuringiensis*. After sporulation in minimal media, which releases cellular content, including the enzymes, all cells were removed through filtration and the remaining active enzyme fractions were applied to plants. ACC deaminase activity was quantified using a standard dinitrophenol hydrazine assay (Li et al., A colorimetric assay of 1-aminocyclopropane-1-carboxylate (ACC) based on ninhydrin reaction for rapid screening of bacteria containing ACC deaminase, LETT APPL. MICROBIOL. 53(2):178-85 (2011).

The wild-type enzyme (SEQ ID NO: 113) and the enzyme with the two point mutations (SEQ ID NO: 114) were provided as free enzymes using foliar delivery to 2-week-old corn (BECK'S 5828 YH, V2 to V3 stage of development) and 4-week old soybean plants (BECK'S 297NR, V2 to V3 stage of development). BECK's 5828 YH corn contains HERCULEX (rootworm resistance and corn borer resistance traits), a glufosinate resistance trait, and a glyphosate resistance trait. BECK'S 297NR soy contains a nematode resistance trait (SCN-SB) and a glyphosate resistance trait.

Sixteen replicate plants per trial were individually treated using foliar applications of the D-cysteine desulfhydrase and the ACC deaminase enzymes and compared to a surfactant-alone control (Control). Activities of the foliar applied D-cysteine desulfhydrase (SEQ ID NO: 113) and the ACC deaminase (SEQ ID NO: 114) enzymes were standardized to the same protein content and applied using consistent use rates as foliar spray containing 0.1% non-ionic surfactant (NIS) (ALLIGARE SURFACE, Alligare LLC), which was used for delivery of the enzymes to corn and soy plants at a rate of 10 ml/plant. Activity of ACC deaminase activity is described herein as 1 mU equals 1 nmol product/mg protein/hour at 30 °C. The initial activity of the D-cysteine desulfhydrase for this assay is 500 mU/ml, and the activity of the ACC deaminase is 2,124 mU/ml. After dilution in to 10 ml/plant, the delivery of the enzyme is at 2.5% volume with a final concentration of 12.5 mU/ml final activity per plant for D-cysteine desulfhydrase and 53.1 mU/ml for ACC deaminase. The ALLIGARE SURFACE surfactant contains a blend of alkylpolyoxethylene, glycol derivatives, humectant, and formulation aids.

Two weeks after the foliar application, roots were harvested from the corn or soybean plants, rinsed with water, gently blotted dry to remove any excess water and the fresh root weight (grams) was determined. The fresh root weight for each treatment was normalized to control plants treated only with the vehicle containing only minimal media and the 0.1% non-ionic surfactant. Results are shown in Tables 37 and 38 below.

As is shown in Table 37, foliar application of ACC deaminase in corn resulted in a significant (approximately 12%) increase in fresh root mass as compared to plants treated with non-ionic surfactant treatment alone (*p value=0.015). By contrast, average fresh root mass from corn plants that received the D-cysteine desulfhydrase was comparable to that of the control plants that received the surfactant only treatment.

In soybean plants (Table 38) treated with the D-cysteine desulfhydrase, there was a slight trend towards an increase in root mass 2 weeks after foliar application. By contrast, ACC deaminase-treated soybean plants exhibited an average of a 12% increase in root mass over the control.

This study, looking at both the monocot corn and the dicot soybean, demonstrates that foliar application of ACC deaminase (and to a lesser extent, D-cysteine desulfhydrase) can directly lead to increases in root mass of the foliar-treated plants over the control treatments.

TABLE 37

Average root mass for corn plants treated with a foliar application of ACC deaminase compared to control plants

| Corn Treatment | Average Root Mass (grams fresh weight) | Standard deviation | Percent (%) Change in Root Mass Normalized to Control |
|---|---|---|---|
| Control | 2.7 | 0.36 | — |
| D-cysteine desulfhydrase (wild-type) (SEQ ID NO: 113) | 2.54 | 0.43 | 94.1% |
| ACC deaminase (with mutations) (SEQ ID NO: 114) | 3.02* | 0.33 | 111.9% |

TABLE 38

Average root mass for soybean plants treated with a foliar application of ACC deaminase compared to control plants

| Soybean Treatment | Average Root Mass (grams fresh weight) | Standard deviation | Percent (%) Change in Root Mass Normalized to Control |
|---|---|---|---|
| Control | 4.03 | 0.86 | — |
| D-cysteine desulfhydrase (wild-type) (SEQ ID NO: 113) | 4.06 | 0.78 | 100.7% |
| ACC deaminase (with mutations) (SEQ ID NO: 114) | 4.50 | 1.11 | 111.7% |

The ACC deaminase (SEQ ID NO: 114) was also applied as an in-furrow (soil-applied) treatment on rice to the area surrounding hybrid rice seed, which also resulted in increased plant growth. ACC deaminase (SEQ ID NO: 114) was were created and purified as described above, at the above initial concentrations, and delivered at a rate of 8 fl oz/Ac (584.2 ml/hectare) of enzyme for every 2.5 gallons of water/Ac (23.4 liters/hectare). 6.25 mU/ml final activity was created after dilution in water for the D-cysteine desulfhydrase, and 52.1 mU/ml final activity for ACC deaminase. Product was applied directly on top of the seed at a rate of 1 ml per seed, and allowed to dry in the soil before the seed was covered with loose soil. Results are shown in Table 39 below. An average increased height for 2 trials (36 plants each) of approximately 131%, normalized to the control, was observed for the in-furrow treatment using the rice hybrid. This study demonstrates that exogenous in-furrow application of free enzyme ACC deaminase enzyme directly impacts plant growth and vigor by increasing plant height.

TABLE 39

ACC deaminase provided growth promoting properties to rice when applied as an in-furrow treatment

| Treatment | Average Percent (%) Change Plant Height (cm) Normalized to Control, Trial 1 | Average Percent (%) Change Plant Height (cm) Normalized to Control, Trial 2 | Average Percent (%) Change Plant Height (cm) Normalized to Control, Trial 1 & 2 |
|---|---|---|---|
| ACC deaminase (with mutations) (SEQ ID NO: 114) *Bacillus thuringiensis* | 151.7% | 110.0% | 130.9% |

Example 20: ACC Deaminase Free Enzyme Delays Fruit Ripening 1-aminocyclopropane-1-carboxylate deaminase (ACC deaminase) degrades 1-aminocyclopropane-1-carboxylate (ACC), the natural precursor to ethylene ($C_2H_4$), which stimulates and regulates fruit ripening. Ethylene acts at trace levels throughout the life of a plant by stimulating or regulating the ripening of fruit, the opening of flowers, and the abscission or shredding of fruits and leaves. Ethylene is an important natural plant hormone, used in agriculture to force the ripening of fruits (Lin et al., Recent advances in ethylene research, JOURNAL OF EXPERIMENTAL BOTANY 60: 3311-3336 (2009)). Ethylene-induced ripening is characterized by an accelerated color shift (accumulation of pigments) and is accompanied by a softening of both the outer skin or peel and the flesh area internal to the outer fruit layer. To determine whether application of free ACC deaminase or D-cysteine sulfhydrase to fruit can delay fruit ripening, both enzymes were applied to unripened mango fruits.

ACC deaminase and D-cysteine sulfhydrase were characterized and had the activities described in Example 19 above. The ACC deaminase sequence having two amino acid mutations described above in Example 19 (SEQ ID NO: 114) and the native the D-cysteine desulfhydrase enzyme (SEQ ID NO: 113) were expressed and provided as free enzymes using the methods described above in Example 19. As noted above in Example 19, the native D-cysteine desulfhydrase enzyme (SEQ ID NO: 113) has both D-cysteine desulfhydrase and ACC deaminase activity.

Unripened mango fruits (commercially available variety, Keitt) were treated with the ACC deaminase or D-cysteine desulfhydrase enzymes and compared to mango fruits that were treated with a water (control) or a filtrate-alone control without enzymes (expression strain without any expressed enzyme). Four fruits were used per treatment group. The outer layer(s) of the mango fruit was completely wetted using 1 mL of the free enzymes (equal to a final protein concentration of 10 μg/mL in filtrate). The estimated ACC deaminase enzyme activity for application to fruit at application for D-cysteine desulfhydrase for this assay was 500 mU/ml, and the activity of the ACC deaminase was 2,124 mU/ml. The two control treatments (filtrate or water alone) were also applied to mango fruits using 1 mL volumes. The mango fruits were then placed in sealed plastic bags overnight. The next day, excess liquid was removed with a paper towel and fruit was blotted dry. Dried mango fruits were then placed in a sealed brown bag (separate bags used for different treatments) to enhance the ripening response for a period of 4 days. The ripening response was scored for softening and color change on a scale of 1-5 with 1 being the least ripened (firm, green or no color change/shift) and 5 being the most ripened (softened, color shift from green to yellow/pink in coloration) with varying degrees of ripening in between these low and high scores (2-4). The ripening responses for both softening and color shift were then combined to result in a "total ripening response" on a scale of 1-10, which was used to judge the effectiveness of the treatment.

Data are provided in Table 40 below and represent average scores for the fruits in each treatment group. Both ACC deaminase and D-cysteine desulfhydrase applied as free enzyme treatments to mango fruit resulted in delayed ripening as compared to the water or filtrate alone control treatments after 4 days. Free enzyme treatments of ACC deaminase or D-cysteine desulfhydrase resulted in similar effects in the overall ripening response based on softening and color change when applied to mango. These results demonstrate that both types of enzymes may be used as fruit wash/drench treatments to delay fruit ripening and may be useful for application to other economically important fruits to prevent accelerated ripening or fruit losses from other stresses.

TABLE 40

ACC deaminase and D-cysteine desulfhydrase free enzymes resulted in delayed ripening in mango fruits

| Treatment | Softening | Color Shift | Total Ripening |
|---|---|---|---|
| Water (Control) | 2 | 3 | 5 |
| Filtrate (Control) | 3 | 4 | 7 |
| ACC deaminase | 2 | 2 | 4 |
| D-cysteine desulfhydrase | 2 | 2 | 4 |

Example 21: Glucanases and Phospholipases on Soybean Seed, Field

β-1,4-endoglucanase (*Acidothermus*; SEQ ID NO: 30), β-1,3-D-glucanase (*Helix pomatia*; SEQ ID NO: 126), phosphatidylinositol-specific phospholipase C (*Bacillus cereus*; SEQ ID NO:116), and phosphatidylcholine-specific phospholipase C (*Bacillus cereus*; SEQ ID NO: 115) were applied as free enzymes to soybean seed (BECK'S 294 NR). Free enzymes were diluted in water to the concentrations (μU/seed or mU/seed) listed in Table 41 below. The unit (U) of the endoglucanase or phospholipase enzyme activity was determined by the amount of enzyme that is required to breakdown 1 μmol/min/mL of substrate (1 U=1 μmol substrate/min) at ideal temperature and conditions. Each seed received the amount of enzyme solution required for the final activity for the treatments (1 μL/seed) and was mixed with seed treatments metalaxyl and clothianidin. Seed was dried completely and then planted in the field to approximate standard practices for planting depth and row spacing (1.5 to 2 inches (3.8 cm to 5 cm) deep to ensure normal root development and on average 150,000 plants per acre (370, 658 plants per hectare) with row widths of 30 inches (76.2 cm) and seed spacing of approximately 7 to 8 seeds per foot (26 seeds per meter)). Fertilizer was applied as recommended by soil tests. Herbicides were applied for weed control and supplemented with cultivation when necessary.

Three replicate trials consisting of 600 seeds each were conducted. Soybean yield was measured at approximately six months after sowing and is reported in Table 41 below as the absolute change in bushels/acre (Bu/Ac) or metric tonnes/hectare (MT/ha) over control (water only) and as a percentage of yield normalized to the control. Applications of endoglucanases or phospholipases (β-1,4-endoglucanase (*Acidothermus*), β-1,3-D-glucanase (*Helix pomatia*), phosphatidylinositol-specific phospholipase C (*Bacillus cereus*), and phosphatidylcholine-specific phospholipase C (*Bacillus cereus*)) as seed treatments all resulted in increased yield compared to the control (water-treated) seed. Of the enzymes tested, phosphatidylcholine-specific phospholipase C (*Bacillus cereus*) provided the greatest increase in yield over the control, resulting in a more than 8 Bu/Ac (more than 0.5 MT/ha) increase or a 145% yield gain over the non-treated control seed (See Table 41).

TABLE 41

Glucanases and phospholipases applied as a seed treatment to increase yield in soybean

| Seed Treatment | Enzyme Activity/Seed | Absolute change in bushels/acre (Bu/Ac) [MT/ha] over control (+/−) | Yield (Normalized to Control) |
|---|---|---|---|
| Water Control | 0 μU/seed | 0.00 | 100.00% |
| β-1,4-Endoglucanase (*Acidothermus*) | 600 μU/seed | +1.44 [+0.10 MT/ha] | 123% |
| β-1,3-D-glucanase (*Helix pomatia*) | 600 μU/seed | +5.22 [0.35 MT/ha] | 123% |
| Phosphatidylinositol Phospholipase C (*Bacillus cereus*) | 100 mU/seed | +3.25 [0.22 MT/ha] | 115% |
| Phosphatidylcholine Phospholipase C (*Bacillus cereus*) | 2.5 mU/seed | +8.11 [0.55 MT/ha] | 145% |

Example 22: Free Phospholipases on Corn Seed, Greenhouse

Phosphatidylcholine-specific phospholipase C (PLC) from *Bacillus cereus* (SEQ ID NO: 115) was diluted in water to concentrations of 20 mU/seed to 800 mU/seed activity (as listed in Table 42 below). The unit of PLC enzyme activity was determined by the amount of enzyme that is required to breakdown 1 μmol/min/mL of substrate (1 U=1 μmol substrate/min) at ideal temperature and conditions.

Two replicate trials consisting of eighteen seeds each of a commercial hybrid (BECK'S 5828 YH corn were placed in 50 mL conical tubes. Each conical tube was vortexed and 18 μL of enzyme solution was added to each tube to achieve a final enzyme concentration of 20, 50, 100, 200, 400, 600, or 800 mU activity of PLC applied per seed. The conical tubes were vortexed again for 20 seconds to gain an even coating on each seed. Seeds were dried for 5 minutes and then planted into 39.7 $cm^3$ pots containing top soil at a depth of 2.54 cm, with 2 seeds per pot. After planting, 50 mL of room temperature water was added to each pot to allow for germination. The pots were kept in an artificial lighted growth room receiving a light level of approximately 300 $\mu mol\ m^{-2}\ s^{-1}$ for a 13/11 light/day cycle and a 21 °C day/15 °C night temperature range.

Plant height was averaged over 2 replicated trials using 18 plants per trial per treatment group. The difference in plant height after seed treatment using the PLC enzyme was normalized to the control plants that received only a water treatment. Changes in plant height are represented in Table 42 as a percentage of the average plant height normalized to the control and reported with the standard deviations (STDEV) for the 2 trials. As can be seen in Table 42, PLC enzyme activities of 50 mU/seed to 600 mU/seed resulted in significant increases in height (cm) of corn plants when compared and normalized to the water (non-enzyme) treated control plants.

TABLE 42

Phospholipase C (PLC) applied as a seed treatment to corn to promote growth

| Seed Treatment | Percent Plant height (Normalized to Control) Trial 1 | Percent Plant height (Normalized to Control) Trial 2 | Percent Plant height (Normalized to Control) Average (STDEV) |
|---|---|---|---|
| Control | 100.0% | 100.0% | 100% (2.07) |
| PLC 20 mU/seed | 98.9% | 96.6% | 97.8% (1.70) |
| PLC 50 mU/seed | 113.7% | 106.2% | 110% (1.83) |
| PLC 100 mU/seed | 116.0% | 100.5% | 108.3% (1.59) |
| PLC 200 mU/seed | 112.1% | 112.5% | 112.3% (1.83) |
| PLC 400 mU/seed | 106.2% | 108.3% | 107.3% (1.60) |
| PLC 600 mU/seed | 98.6% | 106.7% | 103.7% (1.80) |
| PLC 800 mU/seed | 99.7 | 89.4 | 94.6% (1.71) |

In a second experiment, titrations of Phospholipase D required to achieve optimal growth were determined. Phospholipase D (PLD) from *Acidovorax avenae* (SEQ ID NO: 117) was diluted in water to concentrations of 20 mU/seed to 800 mU/seed. The unit of PLD enzyme activity was determined by the amount of enzyme that is required to breakdown 1 μmol/min/mL of substrate (1 U=1 μmol substrate/min) at ideal temperature and conditions. Two replicate trials were conducted using 18 plants per trial per enzyme activity level. For each treatment group in both trials, 18 seeds of a commercial corn hybrid (BECK'S 5828 YH) were placed in 50 mL conical tubes. Each conical tube was vortexed and 18 μL of enzyme solution was added to each tube to achieve a final enzyme concentration of 20, 50, 100, 200, 400, 600, or 800 mU per seed of PLD. The titrations of PLD ranging from 20 mU/seed to 800 mU/seed were applied to the corn seed using 1 μl volumes to determine the optimal PLD seed treatment to promote growth. The conical tubes were vortexed again for 20 seconds to gain an even coating on each seed. Seeds were dried for 5 minutes and then plated into 39.7 $cm^3$ pots containing top soil at a depth of 2.54 cm, with 2 seeds per pot. After planting, 50 mL of room temperature water was added to each pot to allow for germination. The pots were kept in an artificial lighted growth room receiving a light level of approximately 300 $\mu mol\ m^{-2}\ s^{-1}$ for a 13/11 light/day cycle and a 21 °C day/15 °C night temperature range.

Plant height (in cm) was averaged over 2 replicated trials using 18 plants per trial per treatment. The height of plants generated from PLD treated seeds was normalized to control and represented as a percentage of the average plant height normalized to non-enzyme treated (water) control plants and is reported in Table 43 below with the standard deviations (STDEV) for the 2 trials.

As can be seen in Table 43, phospholipase D applied to corn seed had a positive effect on plant growth at every enzyme activity level tested. In each instance, plants treated with PLD as a seed had an increased height compared to control plants.

TABLE 43

Phospholipase D (PLD) applied as a seed treatment to corn to promote growth

| Seed Treatment | Percent Plant height (Normalized to Control) Trial 1 | Percent Plant height (Normalized to Control) Trial 2 | Percent Plant height (Normalized to Control) Average (STDEV) |
|---|---|---|---|
| Control | 100.0% | 100.0% | 100% (1.40) |
| PLD 20 mU/seed | 97.5% | 110.6% | 104.1% (1.18) |
| PLD 50 mU/seed | 101.7% | 104.4% | 103.1% (0.92) |
| PLD 100 mU/seed | 99.6% | 103.0% | 101.3% (1.05) |
| PLD 200 mU/seed | 101.5% | 104.1% | 102.8% (1.03) |
| PLD 400 mU/seed | 99.6.2% | 106.2% | 102.9% (1.14) |
| PLD 600 mU/seed | 103.1% | 98.0% | 100.6% (1.16) |
| PLD 800 mU/seed | 101.5% | 102.0% | 101.8% (0.89) |

Example 23: Free Phospholipases and Xyloglucanases on Corn and Soybean, Foliar, Greenhouse Free xyloglucanase (SEQ ID NO: 125; *Paenibacillus* sp.) and phospholipase D (SEQ ID NO: 117*; Acidovorax avenae*) were applied as foliar treatments using the enzyme concentrations as described in Table 44 (below) to 2 week old hybrid corn (BECK'S 5828 YH) with 0.1% non-ionic surfactant (ALLIGARE SURFACE) using a spray bottle and delivering 10 ml/plant. The average plant height was normalized to the control plants that received a foliar application of water plus surfactant alone. Both the xyloglucanase and phospholipase D treatments applied as a foliar spray to corn plants resulted in increased plant height compared to the control plants (Table 44). Xyloglucanase applied at a foliar use rate providing 600 μU/ml and phospholipase D applied at a foliar use rate providing 200 μU/ml to corn plants exhibited the greatest increases in plant growth resulting in increases of 106.5% and 111.1%, respectively, over the control plants.

TABLE 44

Foliar treatment of corn using xyloglucanase and phospholipase D as free enzymes to promote growth in corn plants

| Foliar Treatment | Enzyme Activity Applied | Average Percent (%) Change in Plant Height as Normalized to Control |
|---|---|---|
| Water + Surfactant (control) | — | 100% |
| Xyloglucanase (*Paenibacillus* sp.) + Surfactant | 600 μU/ml | 106.5% |
| Xyloglucanase (*Paenibacillus* sp.) + Surfactant | 3000 μU/ml | 103.1% |
| Phospholipase D (*Acidovorax*) + Surfactant | 200 μU/ml | 111.1% |
| Phospholipase D (*Acidovorax*) + Surfactant | 1000 μU/ml | 107.3% |

In another experiment, phospholipase D (PLD) from *Acidovorax* was applied as a seed treatment to soybean seed (BECK'S 297NR) using 1 μL volumes equivalent to 600 mU/seed and 800 mU/seed final activities provided per each seed (these activities were selected for testing in soy based on the titrations described above in Example 22 for corn). The PLD activities of 600 mU/seed and 800 mU/seed were applied as a seed treatment to soybean seed and resulted in positive impacts on plant growth rate.

Treated seeds were planted in and allowed to grow in a greenhouse. When plants had reached the V2 to V3 stage of development, their total biomass, root biomass, and nodulation counts were measured. The V2 to V3 stage is the earliest stage of development for nodule formation. Nodule initiation begins in soybean seedlings as soon as root hairs are present on primary or branch roots. Nitrogen fixation begins about 2 to 3 weeks after initial rhizobial infection. Soybean plants had fully formed first trifoliate leaves at the V1 to V2 stage and were measured in the peak estimated for nitrogen fixation. Effective nodulation of soybean roots result in higher yields and higher quality seed production, protein, and oil per acre.

Two independent experiments were run (18 replicate plants per trial per treatment group). Data from PLD-treated plants were normalized to control plants grown from water-treated control seeds.

PLD applied as a seed treatment using 800 mU per soybean seed resulted in significant increases in both total biomass and root biomass as compared to the plants grown from water-treated control seeds that did not receive the PLD free enzyme (Table 45).

PLD treatment also increased nodulation counts on plant roots. Both of the seed treatments, with either 600 mU or 800 mU of PLD activity, resulted in nodulation increases compared to untreated controls, with the 800 mU treatment almost doubling the number of nodules on the roots of soybean plants.

TABLE 45

Biomass effects of phospholipase D treatment as a soybean seed treatment

| Seed Treatment | Enzyme Activity/ Seed | Total Biomass (Normalized to control) | Root Biomass (Normalized to Control) | Nodulation (Normalized to Control) |
|---|---|---|---|---|
| Phospholipase D *Acidovorax* | 600 mU/seed | 101.7% | 99.0% | 121.4% |
| Phospholipase D *Acidovorax* | 800 mU/seed | 115.7% | 125.2% | 201.9% |

Example 24: Free Enzymes on Corn, Field

Free xyloglucanase, xylanase, chitosanase, lichenase, xylosidase, protease, and lipase enzymes were diluted in water to the activity levels listed in Table 46 below. Hybrid corn (BECK'S 5828 YH) seeds were treated with 1 μL free enzyme solution per seed to achieve the activities per seed (1 U=1 mol substrate/min) as shown in Table 46 below. Seeds were dried completely and planted in 4 replicate 24' (7.3 m) rows per treatment with seed spacing of 1.72 seeds/foot/row (5.64 seeds/meter/row). Field seedbeds at each location were prepared using conventional or conservation tillage methods for corn plantings. Herbicides were applied for weed control and supplemented with cultivation when necessary. Each trial was repeated 4 times. Seed treatment was applied to all treatments, which included prothioconazole, penflufen, metalaxyl, and clothianidin.

After harvest, the absolute change in bushels per acre (Bu/Ac) or metric tonnes per hectare was measured for each free enzyme treatment and normalized to the yield of the non-treated control (water) plants (Table 46, below). Control corn seed averaged 162 Bu/Ac (10.17 MT/ha). Seed treatments with lichenase, protease, or lipase resulted in the greatest increases in corn yield over the control plants. Treatment with lichenase showed the greatest yield increases compared to control plants with an average increase of 22 Bu/Ac (1.39 MT/ha), which equates to a 114% increase when normalized to corn control plants.

TABLE 46

Yield increase using free enzymes applied on corn

| Seed Treatment: Corn | Enzyme Activity/Seed | Absolute Change in bushels/acre (Bu/Ac) [MT/ha] over control (+/−) | Yield (Normalized to Control) |
|---|---|---|---|
| Water | 0 μU/seed | — | 100.00% |
| Xyloglucanase (*Paenibacillus* sp.) SEQ ID NO: 125 | 600 μU/seed | +1.09 [+0.07 MT/ha] | 100.67% |
| β-xylanase (*Bacillus stearothermophilus*) SEQ ID NO: 25 | 500 μU/seed | −6.84 [−0.43 MT/ha] | 95.78% |
| Chitosanase (*Streptomyces* species N174) SEQ ID NO: 124_ | 150 μU/seed | +7.57 [+0.48 MT/ha] | 104.67% |
| Lichenase (*Bacillus subtillis*) SEQ ID NO: 43 | 600 μU/seed | +22.17 [+1.39 MT/ha] | 113.67% |
| Protease A (*Aspergillus saitoi*) SEQ ID NO: 127 | 360 μU/seed | +14.64 [+0.92 MT/ha] | 109.02% |
| Lipase (*Burkholderia cepacia*) SEQ ID NO: 118 | 20 μU/seed | +9.50 [+0.60 MT/ha] | 105.85% |

In a second experiment, free enzymes (endoglucanase, exoglucanase, chitosanase, protease, and phytase) were applied via foliar application to corn (BECK'S Hybrid 5140 HR) at 4 locations across the Midwest at the V5-V8 stage of development, which has the HERCULEX rootworm trait and glyphosate resistance traits. To allow for even coating of plant leaves, all enzyme treatments and the control were additionally treated with a non-ionic surfactant (ALLIGARE SURFACE) provided at a final concentration of 0.1%. Absolute change in bushels/acre (Bu/Ac) (and equivalent values in MT/ha) is reported over the control plants and also reported in yield as normalized to the control plants ("water/surfactant control") (Table 47). Results from the foliar treatments using free enzymes are reported as the absolute yield Bu/Ac (or MT/ha) and the absolute change in yield for the adjusted yields (Bu/Ac or MT/ha) normalized to the control plants comparison across the 4 replications (Table 47). There were positive yield increases in the enzyme-treated as compared to the control (plants treated with water and surfactant only) plants. Phytase applied as a foliar treatment resulted in the greatest overall increase in yield (~24 Bu/Ac (~1.51 MT/ha) absolute yield change over control).

TABLE 47

Yield increase using free enzymes applied as a foliar treatment on corn

| Treatment | Absolute Yield Bu/Ac [MT/ha] | Absolute Yield Change (Bu/Ac) [MT/ha] Normalized to Control |
|---|---|---|
| Water/Surfactant Control | 177.42 [11.14 MT/ha] | — |
| β-1,4-endoglucanase (*Acidothermus*) SEQ ID NO: 30 | 190.35 [11.95 MT/ha] | 12.93 [0.81 MT/ha] |
| β-1,3-exoglucanase (*Aspergillis oryzae*) SEQ ID NO: 41 | 186.36 [11.70 MT/ha] | 8.94 [0.56 MT/ha] |
| Chitosanase (*Streptomyces* species N174) SEQ ID NO: 124 | 204.77 [12.85 MT/ha] | 27.34 [1.72 MT/ha] |
| Protease A (*Aspergillus saitoi*) SEQ ID NO: 127 | 189.35 [11.89 MT/ha] | 12.29 [0.77 MT/ha] |
| Phytase (*Triticum aestivum*) SEQ ID NOs: 132, 133, 134 | 201.08 [12.62 MT/ha] | 23.66 [1.49 MT/ha] |

Example 25: Lipases on Corn Seed, Greenhouse

An experiment was conducted to determine if lipases applied as a seed treatment to corn also promoted plant growth. Lipase (*Pseudomonas fluorescens*; SEQ ID NO: 119) was diluted in water to concentrations which provided an activity of 3000 μU and 6000 μU lipase per seed. Lipase was applied using 3000 μU/seed and 6000 μU/seed of activity to corn seed (BECK'S Corn Variety 5828 YH) using 1 μL of enzyme per seed to achieve the activities as reported per seed. Seeds were dried for 5 minutes and then planted in 39.7 $cm^3$ pots containing top soil at a depth of 2.54 cm, with 2 seeds per pot. After planting, 50 mL of room temperature water was added to each pot to allow for germination. The pots were kept in an artificial lighted growth room receiving a light level of approximately 300 $\mu mol\ m^{-2}\ s^{-1}$ for a 13/11 light/day cycle and a 21 °C day/15 °C night temperature range. At the end of 2 weeks, when the plants had all reached the V2 to V3 stage of development, the height of the corn plants treated with lipase were measured and normalized to the height of the control plants that were seed treated with water only.

The experiment was replicated twice with 18 plants per treatment group (and 3 replicates per treatment group) and the values averaged across experiments and are reported in Table 48 together with standard deviations (STDEV). Lipase applied as a free enzyme using 3000 μU and 6000 μU of activity per seed resulted in an average increase in plant height of approximately 106% and 103% respectively.

TABLE 48

| Height effects of lipase treatment as a corn seed treatment | | | |
|---|---|---|---|
| Seed Treatment | Percent Plant height (Normalized to Control) Trial 1 | Percent Plant height (Normalized to Control) Trial 2 | Percent Plant height (Normalized to Control) Average (STDEV) |
| Control (water) | 100.0% | 100.0% | 100% (1.80) |
| Lipase (*Pseudomonas*) 3000 μU/seed | 107.6% | 103.6% | 105.6% (1.67) |
| Lipase (*Pseudomonas*) 6000 μU/seed | 103.0% | 101.8% | 102.4% (1.54) |

Example 26: Lipase or Phospholipase on Corn, Greenhouse In-Furrow

Lipase (*Burkholderia cepacia*) applied as an in-furrow treatment was used to determine if application of lipase as a free enzyme to the area surrounding a corn seed would result in early stage positive growth benefits to a corn plant. Lipase enzyme (*Burkholderia cepacia*, SEQ ID NO:118) was diluted in water to the activity levels listed in Table 49 below. Corn seeds (BECK'S 6626 RR) were planted into 39.7 $cm^3$ pots containing top soil at a depth of 2.54 cm, with 2 seeds per pot. After planting but prior to covering the seed, 1 μL volumes of lipase enzyme with activities ranging from 2 μU to 200 μU were applied per in-furrow area surrounding a seed. A subset of seeds were treated instead with β-1,4-endoglucanase (*Acidothermus cellulolyticus*; SEQ ID NO: 30) applied at an activity of 1000 μU in furrow to the area surrounding the seed. The pots were kept in an artificial lighted growth room receiving a light level of approximately 300 μmol $m^{-2}$ $s^{-1}$ for a 13/11 light/day cycle and a 21 °C day/15 °C night temperature range. After approximately two weeks, when the plants had reached the V2 to V3 stage of development, their height was measured and normalized to control plants that received only water. Plants treated with lipase were further compared to those receiving β-1,4-endoglucanase (*Acidothermus*).

The experiment was repeated for a total of two trials (18 plants per trial per treatment group). The average plant height for the treatments across both trials, normalized to control is reported with standard deviations (STDEV) (Table 49). Lipase applied using 20 μU per seed as an in-furrow treatment to corn resulted in the greatest increase in plant height compared to the other lipase activities applied as in-furrow treatments. The β-1,4-endoglucanase applied as a free enzyme treatment in-furrow also resulted in positive changes in plant height and had growth promoting effects reported on corn plants. Lipase applied at 20 μU per area (per ml of volume in water) surrounding a seed was comparable to the in-furrow treated seed that received the β-1,4-endoglucanase.

TABLE 49

| Titration of lipase and effect of β-1,4-Endoglucanase as applied as an in-furrow treatment to the area surrounding a corn seed to promote growth | |
|---|---|
| Seed Treatment | Percent Plant height (Normalized to Control) Average (STDEV) |
| Control (Water) | 100% (1.15) |
| Lipase 2 μU/seed area | 100.5% (1.05) |
| Lipase 5 μU/seed area | 98.9% (1.35) |

TABLE 49-continued

| Titration of lipase and effect of β-1,4-Endoglucanase as applied as an in-furrow treatment to the area surrounding a corn seed to promote growth | |
|---|---|
| Seed Treatment | Percent Plant height (Normalized to Control) Average (STDEV) |
| Lipase 10 μU/seed area | 100.4% (1.15) |
| Lipase 20 μU/seed area | 103.9% (1.36) |
| Lipase 50 μU/seed area | 100.1% (0.97) |
| Lipase 200 μU/seed area | 101.0% (1.14) |
| β-1,4-Endoglucanase 1000 μU/seed area | 103.8% (1.25) |

In a second experiment, phosphatidylcholine-specific phospholipase C from *Bacillus cereus* (SEQ ID NO: 115) was applied with a fertilizer (SF) containing 12% ammoniacal nitrogen and 58% available phosphate (derived from monoammonium phosphate) using direct in-furrow methods as described above to corn seed (BECK'S 5828 YH). The enzyme was applied at an application rate of 8 Fl oz/Ac (584.2 ml/hectare) or approximately 1200 mU to the area surrounding a seed. This treatment resulted in an average increase in plant height averaged over 3 replicated trials of 105% as normalized to the control which used water and the fertilizer treatment alone. Results are shown in Table 50 below.

TABLE 50

| Plant height using an in-furrow treatment using free enzyme phospholipase C for corn | |
|---|---|
| Treatment | Average percent change in plant height as normalized to the control |
| Water Control + SF | 100% |
| Phospholipase CF (*Bacillus cereus*) + SF | 105% |

Example 27: Acid Phosphatase on Squash and Corn, in Furrow

The effects of acid phosphatase (alone or in combination with lipase, (3-xylanase, pectoylase, mannanase, lichenase, or xylanase) on plant growth was tested. Free enzymes comprising acid phosphatase (*Triticum aestivum*, a mixture of two different isoforms with the sequences provided herein by SEQ ID NOs. 130 and 131, commercially available from Sigma-Aldrich, St. Louis MO, as product number P3627), alone or in combination with lipase (*Pseudomonas fluorescens*, SEQ ID NO: 119), β-xylanase (*Neocallimastix patriciarum*, SEQ ID NO: 122), pectolyase (*Aspergillus*, SEQ ID NO: 129), mannanase (*Bacillus* sp., SEQ ID NO: 128), lichenase (*Bacillus subtilis*, SEQ ID NO: 43) or xylanase (*Thermomyces lanuginosus*, SEQ ID NO: 121) were applied at the activity levels listed in Table 51 using direct in-furrow applications to the area surrounding squash seeds using the same methods as described above in Example 26 (Ambassador hybrid squash, commercially available from Park Seed as product 05298). The enzyme treatments were provided to squash seeds containing a seed treatment (Thiram) and provided together with fertilizer (SF) containing 12% ammoniacal nitrogen and 58% available phosphate. The in-furrow enzyme and fertilizer alone treatments were applied using the application use rates listed as units of activity per ml of volume in Table 51 below, and delivered at 1 ml per seed to the soil around the seed. Plant height was determined for 2 trials with 18 plants measured per each trial per treatment. Data are reported in Table 51, below and provide the percent change in plant height for squash seeds receiving the in-furrow free enzyme treatment compared to the control seed (fertilizer alone control). The acid phosphatase free enzyme treatment alone exhibited on average a 49.6% increase in plant height as compared to the control plants. Squash seed that received the free enzyme in-furrow treatment comprising acid phosphatase combined with enzymes lipase, β-xylanase, pectolyase, mannanase, lichenase or xylanase had increased plant height compared to the water and fertilizer treated squash. In-furrow treatment using the acid phosphatase enzyme alone resulted in the greatest average percent increase in overall growth as represented by the increase in plant height compared to combining acid phosphatase with other enzymes (lipase, β-xylanase, pectolyase, mannanase, lichenase, or xylanase).

TABLE 51

Change in plant height with an in-furrow treatment for squash applied using an application of acid phosphatase and free enzymes

| In-Furrow Treatment (seed area = 1 ml/seed) | Enzyme Activity | Average: Percent Change in Plant Height compared to Control Squash (water & SF alone) |
|---|---|---|
| Fertilizer (SF)/seed area | — | — |
| Acid Phosphatase (AP) *Triticum* + SF | 35 μU (AP)/seed area | +49.6% |
| Acid Phosphatase (AP) *Triticum* + Lipase (LP) *Pseudomonas* + SF | 35 μU (AP) + 10 mU (LP)/seed area | +28.1% |
| Acid Phosphatase (AP) *Triticum* + β-Xylanase (XL) *Neocallimastix* + SF | 35 μU (AP) + 1500 mU (XL)/seed area | +17.0% |
| Acid Phosphatase (AP) *Triticum* + Pectolyase (PL) *Aspergillus* + SF | 35 μU (AP) + 30 mU (XL)/seed area | +21.9% |
| Acid Phosphatase (AP) *Triticum* + Mannanase (MN) *Bacillus* + SF | 35 μU (AP) + 300 mU (MN)/seed area | +18.3% |
| Acid Phosphatase (AP) *Triticum* + Lichenase (LN) *Bacillus* + SF | 35 μU (AP) + 600 mU (LN)/seed area | +14.1% |
| Acid Phosphatase (AP) *Triticum* + Xylanase (XL) *Thermomyces* + SF | 35 μU (AP) + 1500 mU (XL)/seed area | +40% |

In another experiment, free enzymes comprising acid phosphatase (*Triticum aestivum*, a mixture of two isoforms with the sequences provided herein by SEQ ID NOs. 130 and 131), phosphatidylcholine-specific phospholipase C (*Bacillus cereus*; SEQ ID NO: 115), or β-1,4-endoglucanase (*Acidothermus cellulolyticus*; SEQ ID NO: 30) were applied using direct in-furrow treatment to the area surrounding hybrid corn seed (BECK'S 5828 YH) at the rates listed in Table 52 below. The in-furrow treatments were provided together with a hormone biostimulant (CYTOPLEX, commercially available from Miller Chemical & Fertilizer, LLC) that contains a sea plant extract, kinetin, gibberellic acid and indole-3-butyric acid at 2 fl oz/Ac (146.2 ml/hectare). Plant height was determined for 2 trials with 18 plants measured in each trial per treatment group. The data, in Table 52 below, are reported as the percent change in plant height for corn seeds receiving the in-furrow treatment using the free enzymes compared to the control seeds (hormone biostimulant alone). The acid phosphatase free enzyme treatment exhibited on average a 16% and 8% increase in plant height as compared to the control plants for the 300 mU/ml and 600 mU/ml use rates, respectively, applied in-furrow per seed area. Plant height in corn grown from in-furrow treated seed with phospholipase C and β-1,4-endoglucanase also resulted in increases in plant height over the seed treated with the hormone biostimulant alone. The 300 mU/ml use rate applied for each of the free enzymes: acid phosphatase, phospholipase C and β-1,4-endoglucanase resulted in approximately 2-fold increases in plant height over the 600 mU/ml use rate applied in-furrow per seed area. Each of the three enzymes combined with the hormone biostimulant treatments had increased plant height over the hormone biostimulant alone controls.

TABLE 52

Changes in plant height using an in-furrow treatment for corn applied using an application of acid phosphatase, phospholipase C and β-1,4-endoglucanase in combination with a biostimulant

| In-Furrow Treatment | Use rate (seed area = 1 ml volume per seed) | Average: Percent Change in Plant Height compared to Control Corn with no enzyme application |
|---|---|---|
| Acid Phosphatase (*Triticum aestivum*) + Biostimulant | 300 mU/seed area | +16% |
| Acid Phosphatase (*Triticum aestivum*) + Biostimulant | 600 mU/seed area | +8% |
| Phospholipase C (*Bacillus cereus*) + Biostimulant | 300 mU/seed area | +17% |
| Phospholipase C (*Bacillus* cereus) + Biostimulant | 600 mU/seed area | +9.5% |
| β-1,4-Endoglucanase (*Acidothermus*) + Biostimulant | 300 mU/seed area | +16% |
| β-1,4-Endoglucanase (*Acidothermus*) + Biostimulant | 600 mU/seed area | +7% |

Free enzymes comprising acid phosphatase (*Triticum aestivum*, a mixture of two different isoforms with the sequences provided herein by SEQ ID NOs. 130 and 131) or phosphatidylcholine-specific phospholipase C (*Bacillus cereus*; SEQ ID NO: 115) were applied using direct in-furrow applications to the area surrounding hybrid corn seed (BECK'S 5828 YH). In-furrow treatment with the enzymes was combined with a hormone biostimulant (CYTOPLEX, commercially available from Miller Chemical & Fertilizer, LLC) treatment containing a sea plant extract, kinetin, gibberellic acid and indole-3-butyric acid. The in-furrow enzyme treatments were applied using application use rates of 2, 4 and 8 Fl. oz per seed area (59.14, 118.29, and 236.59 ml per seed area). Plant height was determined for 2 trials with 18 plants measured per each trial. The data are reported in Table 53 below as the percent change in plant height for corn seeds receiving the in-furrow treatment using the acid phosphatase or phospholipase C enzymes compared to the control seeds (biostimulant alone). The acid phosphatase free enzyme treatment increased plant height as compared to the control plants for the use rates of 2, 4 and 8 Fl. oz (59.14, 118.29, and 236.59 ml) applied per seed area (approximately 150 mU/ml, 300 mU/ml and 600 mU/ml per seed area), with 4 Fl. oz (118.29 ml) resulting in an increase of 8.3% over the control plants for the 300 mU/ml use rate. In furrow treatment of corn grown with phospholipase C resulted in increased plant height compared to corn grown using the biostimulant alone control when applied using 2 and 4 Fl. oz (59.14 and 118.29 ml) use rate per seed area (approximately equal to 150 and 300 mU per seed area, respectively). The 4 Fl. oz (118.29 ml) use rate was preferable for plant growth, resulting in an 11.4% increase in plant height over the biostimulant alone control. The biostimulant only control resulted in corn plants with slower growth rates as compared to treatment with water only.

TABLE 53

Changes in plant height using an in-furrow treatment for corn applied using an application of acid phosphatase or phospholipase C, combined with a biostimulant

| In-Furrow Treatment | Use rate (seed area = 1 ml volume per seed) | Average: Percent Change in Plant Height as over Control Corn (water & BS alone) |
|---|---|---|
| Water Control | — | — |
| Biostimulant (BS) | 2 Fl. oz/seed area (59.14 ml/seed area) | −4.9% |
| Acid Phosphatase (*Triticum aestivum*) + Biostimulant | 2 Fl. oz/seed area (59.14 ml/seed area) | +2.3% |
| Acid Phosphatase (*Triticum aestivum*) + Biostimulant | 4 Fl. oz/seed area (118.29 ml/seed area) | +8.3% |
| Acid Phosphatase (*Triticum aestivum*) + Biostimulant | 8 Fl. oz/seed area (236.59 ml/seed area) | +5.5% |
| Phospholipase C (*Bacillus cereus*) + Biostimulant | 2 Fl. oz/seed area (59.14 ml/seed area) | +5.5% |
| Phospholipase C (*Bacillus cereus*) + Biostimulant | 4 Fl. oz/seed area (118.29 ml/seed area) | +11.4% |
| Phospholipase C (*Bacillus cereus*) + Biostimulant | 8 Fl. oz/seed area (236.59 ml/seed area) | −0.1% |

Example 28: Protease or Xylosidase on Corn, in Furrow

Protease A (*Aspergillus saitoi*; SEQ ID NO: 127) and xylosidase (*Bacillus pumilus*; SEQ ID NO: 123) were applied to corn as an in-furrow free enzyme treatments, and effects on plant height and growth were examined. For both the protease A and xylosidase enzymes, similar methods were used as described above in Example 26 for the lipase in-furrow treatments with corn. In-furrow treatments (1 ml per seed) were applied to the area surrounding the corn seed (BECK'S 5828 YH) after planting of the corn but before covering the seed with loose soil. In-furrow treatments using protease A and xylosidase were delivered in 1 μL volumes equivalent to 428 μU/seed area of activity for protease and 714 μU/seed area (per ml) of activity for xylosidase. Both Protease A and xylosidase resulted in increased plant height when normalized to control plants (water only treatment). Results are shown in Table 54 below.

TABLE 54

Plant height using an in-furrow treatment for corn treated with protease A or xylosidase

| Treatment | Enzyme Activity/ml | Percent change in plant height (Normalized to Control) Average |
|---|---|---|
| Protease A (*Aspergillus saitoi*) | 714 μU | 108.4% |
| Xylosidase (*Bacillus pumilus*) | 428 μU | 112.3% |

Xylanases (*Thermomyces lanuginosus; Neocallimastix patriciarum*) applied as a seed treatment to both corn and soybean seed at activities of 600 μU/seed resulted in increased height in plants as compared to the control plants. Xylanase (*Thermomyces lanuginosus*) treatment applied to corn seed resulted in, on average, a 9% increase in plant height for corn and an average 12% increase for soybean. β-xylanase (*Neocallimastix patriciarum*) treatment applied to corn seed resulted in on average a 4% increase in plant height for corn. Xylosidase (*Bacillus pumilus*) applied as a seed treatment to corn and soybean seed at 714 μU/seed resulted in an approximate 9-11% increase for both corn and soybean plants compared to the control plants. Positive impact on plant height for the xylanase and xylosidase treatments applied as free enzyme treatments to corn and soybean seed was comparable or better than β-1,4-endoglucanase (*Acidothermus*) for both the corn and soybean plants. After two weeks, plant height was measured and normalized to plants that received only fertilizer treatment.

TABLE 55

Corn and soybean treated with endo-1,4-β-xylanase, endoglucanase, and xylosidase as seed treatments

| Seed Treatment | Corn: Average Percent change in Plant height (Normalized to Control) (STDEV) | Soybean: Average Percent change in plant height (Normalized to Control) (STDEV) |
|---|---|---|
| Water Control | 100% | 100% |
| Xylanase (*Thermomyces lanuginosus*) | 108.8% (1.39) | 112.0% (1.31) |
| β-xylanase (*Neocallimastix patriciarum*) | 104.3% (1.42) | 100.3% (0.37) |
| Xylosidase (*Bacillus pumilus*) | 108.7% (1.18) | 111.1% (1.32) |
| β-1,4-Endoglucanase (*Acidothennus*) | 109.6% (1.46) | 104.0% (1.39) |

Example 29: Xylanase or Xylosidase on Corn and Soybean Seed, Greenhouse

Free enzymes were applied as seed treatments to corn and soybean. Xylanases derived from *Thermomyces lanuginosus* (SEQ ID NO: 121) or *Neocallimastix patriciarum* (SEQ ID NO: 122) and xylosidase derived from *Bacillus pumilus* (SEQ ID NO: 123) were applied to corn (BECK'S 5828 NR) and soybean (BECK'S 297 NR) seeds in conical tubes using 2 μL volumes equivalent to activities of 600 μU per seed for the xylanases (*Thermomyces lanuginosus; Neocallimastix patriciarum*) and 714 μU per seed for the xylosidase (*Bacillus pumilus*). Two separate sets of corn and soybean seeds were treated with β-1,4-endoglucanase (*Acidothermus cellulolyticus*; SEQ ID NO: 30) at 1000 μU activity/seed. Seeds were allowed to dry after coating and planted in commercial topsoil as described above in Example 1. At the end of 14 days, the average percent change in plant height compared to water controls was determined for two replicated trials for corn and one trial for soybean with 12 plants per trial. Changes in average plant height (cm) were compared to the control plants as well as corn and soybean plants grown from seeds treated with β-1,4-endoglucanase (*Acidothermus*) which resulted in an increase in plant growth when applied as a seed treatment to both corn and soybean. Average percent change in plant height as normalized to water control treatments are reported in Table 55 below with the standard deviation from mean average (STDEV) for the 2 trials conducted in corn and soybean.

Example 30: Free Enzymes and Titration of Activities for Seed Treatment and In-Furrow Treatment on Corn and Soybean Lichenase (*Bacillus subtilis*, commercially available from Megazyme as product E-LICHN; SEQ ID NO: 43), xyloglucanase (*Paenibacillus* species, commercially available from Megazyme, as product E-XEGP; SEQ ID NO: 125), β-xylanase (*Bacillus stearothermophilus*, commercially available from Megazyme as product E-XYNBS; SEQ ID NO: 25), mannanase (*Bacillus* species, commercially available from Megazyme as product E-BMABS; SEQ ID NO: 128), lipase (*Burkholderia stearothermophilus*, commercially available from Sigma-Aldrich, as product 534641; SEQ ID NO: 120), pectolyase (*Aspergillus japonicus*, commercially available from Sigma-Aldrich, as product P3026; SEQ ID NO: 129) and β-1,4-endoglucanase (*Acidothermus cellulolyticus*, commercially available from Sigma-Aldrich, as product E2164; SEQ ID NO: 30) were each diluted in water to achieve the activity levels as listed below in Table 56. Aliquots (1 L) of these preparations were used to treat seeds in the experiments described below in this example and in Example 31.

TABLE 56

Titrations of enzymes used to determine the optimal enzyme activities as a seed treatment to corn and soybean seeds to promote growth in plants

| Enzyme | Organism derived from | Titration Use Rate (μU Activity) |
|---|---|---|
| Water Control | — | 0 μU |
| Lichenase | *Bacillus subtilis* | 400 μU |
| Lichenase | *Bacillus subtilis* | 500 μU |
| Lichenase | *Bacillus subtilis* | 600 μU |
| Lichenase | *Bacillus subtilis* | 700 μU |
| Lichenase | *Bacillus subtilis* | 800 μU |
| Lichenase | *Bacillus subtilis* | 900 μU |
| Xyloglucanase | *Paenibacillus* species | 500 μU |
| Xyloglucanase | *Paenibacillus* species | 600 μU |
| Xyloglucanase | *Paenibacillus* species | 1500 μU |
| Xyloglucanase | *Paenibacillus* species | 3000 μU |
| Xyloglucanase | *Paenibacillus* species | 4000 μU |
| β-Xylanase | *Bacillus stearothermophilus* | 50 μU |
| β-Xylanase | *Bacillus stearothermophilus* | 300 μU |
| β-Xylanase | *Bacillus stearothermophilus* | 500 μU |
| β-Xylanase | *Bacillus stearothermophilus* | 1500 μU |
| β-Xylanase | *Bacillus stearothermophilus* | 3000 μU |
| β-Xylanase | *Bacillus stearothermophilus* | 5000 μU |
| Mannanase | *Bacillus* species | 60 μU |
| Mannanase | *Bacillus* species | 300 μU |
| Mannanase | *Bacillus* species | 600 μU |
| Mannanase | *Bacillus* species | 1200 μU |
| Mannanase | *Bacillus* species | 3000 μU |
| Mannanase | *Bacillus* species | 6000 μU |
| Lipase | *Burkholderia stearothermophilus* | 2 μU |
| Lipase | *Burkholderia stearothermophilus* | 5 μU |
| Lipase | *Burkholderia stearothermophilus* | 10 μU |
| Lipase | *Burkholderia stearothermophilus* | 20 μU |
| Lipase | *Burkholderia stearothermophilus* | 50 μU |
| Lipase | *Burkholderia stearothermophilus* | 200 μU |
| Pectolyase | *Aspergillus japonicus* | 60 μU |
| Pectolyase | *Aspergillus japonicus* | 300 μU |
| Pectolyase | *Aspergillus japonicus* | 600 μU |
| Pectolyase | *Aspergillus japonicus* | 1200 μU |
| Pectolyase | *Aspergillus japonicus* | 3000 μU |
| Pectolyase | *Aspergillus japonicus* | 6000 μU |
| β-1,4-endoglucanase | *Acidothermus cellulolyticus* | 1000 μU |

Titrations of the six free enzymes (lichenase, xyloglucanase, xylanase, mannanase, lipase, and pectolyase) were tested to determine optimal activities that promote growth when used as a seed treatment on corn (BECK'S 5828 YH) and soybean (BECK'S 297 NR). Titration activities that were determined to be optimal for use as a seed treatment for the six enzymes are listed in Table 57 below (listed as free enzyme activity per seed). Experiments were conducted under the same environmental conditions in a controlled growth environment as described in Example 29. Percent changes in average plant height were determined for the six enzymes used as a seed treatment applied to corn or soybean seed (Table 57, below). Average plant height for each of the six enzymes was normalized to that of plants grown from seed that received a water control treatment and recorded as a percent change (Table 57). Additionally, the free enzymes treatments applied to corn seed included and were compared to treatment with β-1,4-endoglucanase free enzyme because this enzyme had previously been shown to promote growth when applied as a seed treatment on corn plants (see Examples 1-4, 7, 26, and 29, above).

All six free enzymes (lichenase, xyloglucanase, β-xylanase, mannanase, lipase, and pectolyase), when used as a seed treatment at their optimized activity levels on corn and soybean, increased plant height as compared to control plants grown from non-enzyme-treated seeds. Results are shown in Table 57 below. β-1,4-endoglucanase free enzyme applied to corn seed resulted in an increase in plant height for corn as normalized to the control plants. When both corn and soybean plant varieties were considered, mannanase resulted in the largest increases in plant height as normalized to the control plants (107% increase in corn and 110% increase in soybean).

TABLE 57

Height effects of free enzymes applied as a seed treatment to corn and soybean plants

| Seed Treatment: Corn | Percent change in average corn plant height (Normalized to Control) |
|---|---|
| Water Control | 100% |
| Lichenase 600 μU | 102% |
| Xyloglucanase 600 μU | 101% |
| β-xylanase 5000 μU | 100% |
| Mannanase 300 μU | 107% |
| Lipase 20 μU | 100% |
| Pectolyase 3000 μU | 107% |
| β-1,4-Endoglucanase 1000 μU | 102% |
| **Seed Treatment: Soybean** | **Percent change in average soybean plant height (Normalized to Control)** |
| Water Control | 100% |
| Lichenase 400 μU | 103% |
| Xyloglucanase 600 μU | 113.2% |
| β-xylanase 5000 μU | 105.5% |
| Mannanase 6000 μU | 110.1% |
| Lipase 200 μU | 105.4% |
| Pectolyase 300 μU | 105.8% |

Titrations of four of the same enzymes (lichenase, xyloglucanase, mannanase, and pectolyase, listed in Table 56 above) were performed to determine optimal activities for use as an in-furrow treatment on corn (BECK'S 5828 YH) for promoting plant growth. Each enzyme titration was optimized for growth potential (Table 58) and was directly applied to the area surrounding a seed using 1 ml of water per seed just prior to the completion of planting and covering the seed with soil. Two weeks after planting, plant height was measured and normalized to the height of plants that received no enzyme treatment but instead received only a water control. This experiment was repeated in three trials with 18 plants per trial and measurements were averaged across trials to generate a percent change in average corn plant height (compared to control). Data are reported in Table 58 for the four free enzymes: lichenase, xyloglucanase, mannanase, and pectolyase. Free enzymes lichenase, xyloglucanase, and pectoylase all increased corn as height compared to the water-only control when applied as in-furrow treatments to the area surrounding corn seeds.

TABLE 58

Height effects of free enzymes applied as an in-furrow treatment surrounding corn seeds

| In Furrow: Corn | Percent change in average corn plant height (Normalized to Control) |
|---|---|
| Water Control | 100% |
| Lichenase 900 μU/seed area | 101% |
| Xyloglucanase 500 μU/seed area | 104% |
| Mannanase 6000 μU/seed area | 98% |
| Pectolyase 300 μU/seed area | 103% |

Titrations of the same six free enzymes (lichenase, xyloglucanase, xylanase, mannanase, lipase, and pectolyase, listed above in Table 56) were performed to determine optimal activities for application as seed treatments on soybean (BECK'S 297 NR). The activities (μU/seed) are reported for each enzyme in Table 59 below. Three trials with 18 plants per trial were conducted and measured for changes in total biomass, shoot biomass, root biomass and nodulation. Experiments were conducted under the same environmental conditions in a controlled growth environment as described in Example 6 above. In some experiments, an additional group of seeds was treated with β-1,4-endoglucanase (1000 μU/seed). Changes in total biomass, shoot biomass, root biomass and nodulation are reported in Table 59 below as percent (%) changes as normalized to soybean seed that did not receive a treatment with free enzyme (water-treated control).

TABLE 59

Free enzymes applied as a seed treatment for promoting growth in soybean plants

| Seed Treatment: Optimized Enzyme Activity | |
|---|---|
| | Total Biomass (Normalized to Control) |
| Lichenase 800 μU | 112% |
| Xyloglucanase 3000 μU | 103% |
| P-xylanase 3000 μU | 104% |
| Mannanase 3000 μU | 116% |
| Lipase 2 μU | 111% |
| Pectolyase 6000 μU | 104% |
| β-1,4-Endoglucanase 1000 μU | 106% |
| | Shoot Biomass (Normalized to Control) |
| Lichenase 400 μU | 117% |
| Xyloglucanase 1500 μU | 98% |
| β-xylanase 5000 μU | 101% |
| Mannanase 3000 μU | 121% |
| Lipase 2 μU | 117% |
| Pectolyase 300 μU | 111% |
| β-1,4-Endoglucanase 1000 μU | 109% |
| | Root Biomass (Normalized to Control) |
| Lichenase 800 μU | 123% |
| Xyloglucanase 1500 μU | 137% |
| β-xylanase 3000 μU | 107% |
| Mannanase 600 μU | 121% |
| Lipase 2 μU | 98% |
| Pectolyase 1200 μU | 102% |
| β-1,4-Endoglucanase 1000 μU | 127% |
| | Nodulation (Normalized to Control) |
| Lichenase 700 μU | 469% |
| Xyloglucanase 3000 μU | 123% |
| β-xylanase 300 μU | 121% |
| Lipase 50 μU | 114% |

Example 31: Free Enzymes Used as a Seed Treatment to Increase Yield of Zucchini The lichenase, xyloglucanase, xylanase, lipase free enzymes described above in Example 30 and β-1,4-endoglucanase (*Acidothermus cellulolyticus*, SEQ ID NO: 30) were applied as seed treatments at an optimal rate as determined by a titration series and applied to zucchini seeds (Spineless Beauty, commercially available from Park Seed) using 1 μL volumes of the enzymes with the activities as reported in U/seed (Table 60). Total yield of the free enzyme-treated seed with lichenase, xyloglucanase, xylanase, lipase and β-1,4-endoglucanase is reported in Table 60 as the total weight of zucchini fruit harvested, normalized to the control, and is averaged for two harvests completed in the month of August (Columbia, Missouri). Free enzyme treatments applied to zucchini seed using lichenase (700 μU/seed), xylanase (3000 μU/seed), and lipase (50 μU/seed) all showed positive yield increases compared to control treatment. The increases in total harvestable yield for zucchini plants using the free enzyme seed treatments for lichenase, xylanase and lipase showed similar total yield advantages as β-1,4-Endoglucanase (1000 μU/seed).

TABLE 60

Table: Zucchini yield after treatment of zucchini seeds with free enzymes

| Treatment | Total Yield as a percentage of Control |
|---|---|
| Lichenase 700 μU | 113% |
| Xyloglucanase 3000 μU | 89% |
| β-xylanase 300 μU | 118% |
| Lipase 50 μU | 130% |
| β-1,4-Endoglucanase 1000 μU | 132% |

Example 32: Synergy of Multiple Enzymes on Corn, in Furrow

Mannanase (*Bacillus* sp.; SEQ ID NO: 128), xyloglucanase (*Paenibacillus* sp., SEQ ID NO: 125), phosphatidylcholine-specific phospholipase C (*Bacillus cereus*, SEQ ID NO: 115) and xylosidase (*Bacillus pumilus*; SEQ ID NO: 123) were applied to corn (BECK'S 5828 YH) as in-furrow free enzyme treatments, and effects on plant height and growth were examined. Enzyme treatments, including combinations of enzymes, are described in Table 61. For all the free enzymes, similar methods were used as described above in Example 26 for the lipase in-furrow treatments with corn. Briefly, in-furrow treatments were applied to the area surrounding the corn seed after planting of the corn but before covering the seed with loose soil. Each treatment was applied in a volume of 1 ml per seed, which included both the enzyme(s) and a fertilizer containing orthopolyphosphate and potassium acetate. In-furrow treatments using each enzyme were delivered at rates of 300 mU/seed area of activity for mannanase and phosphatidylcholine-specific phospholipase C, 500 mU/seed area for xyloglucanase, and 714 mU/seed area (per ml) of activity for xylosidase. The enzymes were delivered to seeds in volumes of 1 ml per seed area, containing both the enzyme(s) and the fertilizer. 54 seeds were used per treatment, divided among 3 replicates of 18 plants each. After about two weeks, plant heights were measured and normalized to control plants treated with only fertilizer.

Results are shown in Table 61 below. Mannanase or xyloglucanase alone did not result in significant height increases. Both phospholipase C and xylosidase applied alone led to an increase in plant height. Surprisingly, combinations of phospholipase C and either mannanase or xyloglucanase led to synergistic increases in plant height as compared to either treatment alone. The combination of mannanase and xyloglucanase was also more efficacious than either enzyme alone.

TABLE 61

Plant height using an in-furrow treatment for corn treated with free mannanase, xyloglucanase, xylosidase, phospholipase C, or combinations thereof

| Treatment | Enzyme Activity/ml | Average percent change in plant height (Normalized to Control) |
|---|---|---|
| Fertilizer, 8 fl oz/Ac (584.622 ml/ hectare) | N/A | 100% |
| Fertilizer + Xylosidase (*Bacillus*) | 714 mU/seed area | 105.1% |
| Fertilizer + Mannanase (*Bacillus*) | 300 mU/seed area | 100.4% |
| Fertilizer + Xyloglucanase (*Paenibacillus*) | 500 mU/seed area | 93.9% |
| Fertilizer + Phospholipase C (*Bacillus*) | 300 mU/seed area | 108.8% |
| Fertilizer + Phospholipase C (PLC) + Xyloglucanase | 300 mU/seed area (PLC) + 500 mU/seed area (xyloglucanase) | 110.9% |
| Fertilizer + Phospholipase C + Mannanase | 300 mU/seed area (PLC) + 300 mU/seed area (mannanase) | 110.6% |
| Fertilizer + Xyloglucanase + Mannanase | 500 mU/seed area (xyloglucanase) + 300 mU/seed area (mannanase) | 101.1% |

Example 33: Additive Effects of Multiple Enzymes on Squash, in Furrow

Mannanase (*Bacillus* sp.; SEQ ID NO: 128), lichenase (*Bacillus subtilis*, SEQ ID NO: 43), acid phosphatase (*Triticum aestivum*, a mixture of two different isoforms with the sequences provided herein by SEQ ID NOs. 130 and 131), pectolyase (*Aspergillus japonicus*, SEQ ID NO:129), β-xylanase (*Neocallismastix patriciarum*, SEQ ID NO: 122), and β-xylanase (*Bacillus stearothermophilius*, SEQ ID NO: 25) were applied to Ambassador hybrid squash (commercially available from Park Seed as product 05298) as in-furrow free enzyme treatments, and effects on plant height and growth were examined. For all the free enzymes, similar methods were used as described above in Example 26 for the lipase in-furrow treatments with corn. Briefly, in-furrow treatments were applied to the area surrounding the squash seed after planting of the squash but before covering the seed with loose soil. Each treatment was applied in a volume of 1 ml per seed, which included both the enzyme(s) and a fertilizer containing monoammonium phosphate). In-furrow treatments using each enzyme were delivered at rates of 300 mU/seed area of activity for mannanase, 600 mU/seed area for lichenase, 30 mU/seed area for pectolyase, 35 μU/seed area for acid phosphatase, and 1500 mU/seed area for both β-xylanases. The enzymes were delivered to seeds in volumes of 1 ml per seed area, containing both the enzyme(s) and the fertilizer. After two weeks, plant height was measured and normalized to plants that received only fertilizer treatment Results are shown in Table 62 below. Acid phosphatase alone resulted in increased height over the fertilizer alone control, and this effect was slightly better when lichenase was applied together with the acid phosphatase. A large increase was seen when the fertilizer/acid phosphatase combination was further augmented with the pectolyase, the mannanase, or either of the xylanases. These non-cellulolytic carbohydrate hydrolases add significant plant height in combination with acid phosphatase as a soil delivered mechanism.

TABLE 62

Plant height using an in-furrow treatment for squash treated with free mannanase, xylanase, acid phosphatase, pectolyase, lichenase, or combinations thereof

| Treatment | Enzyme Activity/ml | Average percent change in plant height (Normalized to Control) |
|---|---|---|
| Fertilizer, 8 fl oz/Ac (584.622 ml/ hectare) | N/A | 100% |
| Fertilizer + acid phosphatase (ACP) | 35 μU/seed area | 103.4% |
| Fertilizer + acid phosphatase + pectolyase | 35 μU/seed area (ACP) + 30 mU/seed area (pectolyase) | 113.6% |
| Fertilizer + acid phosphatase + mannanase | 35 μU/seed area (ACP) + 300 mU/seed area (mannanase) | 114.5% |
| Fertilizer + acid phosphatase + lichenase | 35 μU/seed area (ACP) + 600 mU/seed area (lichenase) | 103.7% |
| Fertilizer + acid phosphatase + β-xylanase (*Neocallismastix patriciarum*) | 35 μU/seed area (ACP) + 1500 mU/seed area (xylanase) | 110.5% |
| Fertilizer + acid phosphatase + β-xylanase (*Bacillus stearothermophilus*) | 35 μU/seed area (ACP) + 1500 mU/seed area (xylanase) | 115.1% |

In view of the above, it will be seen that the several objects of the invention are achieved and other advantageous results attained.

As various changes could be made in the above enzymes, recombinant organisms, methods, and seeds, without departing from the scope of the invention, it is intended that all matter contained in the above description shall be interpreted as illustrative and not in a limiting sense.

What is claimed is:

1. A composition comprising a recombinant *Bacillus thuringiensis* bacterium, wherein:

the recombinant *Bacillus thuringiensis* bacterium expresses an enzyme, wherein expression of the enzyme is increased as compared to the expression level of the enzyme in a wild-type microorganism of the same kind under the same conditions;

the enzyme is a phospholipase C comprising an amino acid sequence having at least 90% sequence identity to the amino acid sequence of any one of SEQ ID NOs: 14, 115, and 116; and the enzyme is not bound to the exosporium of the recombinant *Bacillus thuringiensis* bacterium; and a fertilizer, a polymer, a surfactant, an agrochemical, talc, or a plant growth medium.

2. The composition of claim 1, wherein the phospholipase comprises an amino acid sequence having at least 95% identity to any one of SEQ ID NO. 14.

3. A plant seed treated with the composition of claim 1.

4. The plant seed of claim 3, wherein the plant seed is coated with the composition.

5. The composition of claim 1, wherein the composition further comprises an agriculturally acceptable carrier or a biostimulant.

6. The composition of claim 5, wherein the agriculturally acceptable carrier comprises vermiculite, charcoal, sugar factory carbonation press mud, rice husk, carboxymethyl cellulose, peat, perlite, fine sand, calcium carbonate, flour, alum, a starch, talc, polyvinyl pyrrolidone, or a combination of any thereof.

7. The composition of claim 1, wherein the fertilizer comprises a micronutrient fertilizer material, the micronutrient fertilizer material comprising boric acid, a borate, a boron frit, copper sulfate, a copper frit, a copper chelate, a sodium tetraborate decahydrate, an iron sulfate, an iron oxide, iron ammonium sulfate, an iron frit, an iron chelate, a manganese sulfate, a manganese oxide, a manganese chelate, a manganese chloride, a manganese frit, a sodium molybdate, molybdic acid, a zinc sulfate, a zinc oxide, a zinc carbonate, a zinc frit, zinc phosphate, a zinc chelate, or a combination of any thereof.

8. The composition of claim 5, wherein the agriculturally acceptable carrier comprises a dispersant, a surfactant, an additive, water, a thickener, an anti-caking agent, residue breakdown product, a composting formulation, a granular application, diatomaceous earth, an oil, a coloring agent, a stabilizer, a preservative, a polymer, a coating, or a combination of any thereof.

9. The composition of claim 8, wherein:

the additive comprises an oil, a gum, a resin, a clay, a polyoxyethylene glycol, a terpene, a viscid organic, a fatty acid ester, a sulfated alcohol, an alkyl sulfonate, a petroleum sulfonate, an alcohol sulfate, a sodium alkyl butane diamate, a polyester of sodium thiobutane dioate, a benzene acetonitrile derivative, a proteinaceous material, or a combination of any thereof;

the additive comprises a milk product, wheat flour, soybean meal, blood, albumin, gelatin, alfalfa meal, yeast extract, or a combination of any thereof;

the anti-caking agent comprises a sodium salt, a calcium carbonate, diatomaceous earth, or a combination of any thereof the anti-caking agent comprises a sodium salt, and the sodium salt comprises a sodium salt of monomethyl naphthalene sulfonate, a sodium salt of dimethyl naphthalene sulfonate, a sodium sulfite, a sodium sulfate, or a combination of any thereof; or the thickener comprises a long chain alkyl sulfonate of polyethylene glycol, a polyoxyethylene oleate, or a combination of any thereof.

10. The composition of claim 1, wherein the surfactant comprises a heavy petroleum oil, a heavy petroleum distillate, a polyol fatty acid ester, a polyethoxylated fatty acid ester, an aryl alkyl polyoxyethylene glycol, an alkyl amine acetate, an alkyl aryl sulfonate, a polyhydric alcohol, an alkyl phosphate, or a combination of any thereof.

11. The composition of claim 1, wherein the agrochemical comprises an insecticide, a nematicide, an herbicide, a plant growth amendment, a fungicide, an insecticide, a molluscicide, an algicide, a bacterial inoculant, a fungal inoculant, a plant hormone, or a combination of any thereof.

12. The composition of claim 1, wherein the plant growth medium comprises soil, water, an aqueous solution, sand, gravel, a polysaccharide, mulch, compost, peat moss, straw, logs, clay, soybean meal, yeast extract, or a combination thereof.

* * * * *

SEQUENCE LISTING

```
Sequence total quantity: 147
SEQ ID NO: 1            moltype = DNA  length = 996
FEATURE                 Location/Qualifiers
source                  1..996
                        mol_type = genomic DNA
                        organism = Bacillus thuringiensis
SEQUENCE: 1
atgaatttag ctaaattccc gagaaaaaaa tatacagaat catatacacc aattgaaaag  60
ttaaacaact tttctgaagc acttggtggg ccgactattt attttaaacg agatgattta  120
cttggtttaa cagctggtgg taataagacg agaaagttag agtttctagt tgcggatgca  180
gaggcaaaag gtgcagatac gttaattaca gctggtggta ttcagtcaaa ccattgccgt  240
ctaacactgg cagctgcggt aaaagaaaaa atgaaatgta tccttgtatt agaagaaggg  300
cttgaaccag aagagaagcc agactttaac ggaaactatt tcttatatca tttactaggt  360
gctgaaaatg taattgttgt accaaacggg gcagatctta tggaagagat gcataaagta  420
gcgaaagaag ttagtgaaaa aggtaataca ccatatgtca taccagttgg tggatcaaat  480
cctactggtg caatgggata cgttgcttgt gcgcaagaaa ttatggcaca atcatttgac  540
caaggaattg atttcagtac agtcgtttgc gtaagcggta gcgctggtat gcacgctggt  600
ttaattactg gttttgctgg aacacaaagc cacattcctg taattggaat caacgtaagt  660
agaggaaaag ctgagcaaga agagaaagta gcaaaacttg tagatgaaac ttcagcacac  720
gttggtattc caaactttat cccgcgtgac gctgttacgt gctttgatga atatgtaggg  780
ccaggatatg cgttaccaac gccggaaatg gtagaggcag ttcagttact tgcgaaaaca  840
gaaggtattt tacttgatcc agtgtataca ggtaaagcgg tagcgggatt aatcgactta  900
attaaaaaag gtacatttaa taaagaagac aacattttat tcgtacattc aggtggttca  960
ccagctttat atgcgaatac ttctttattt gcgtaa                            996

SEQ ID NO: 2            moltype = DNA  length = 996
FEATURE                 Location/Qualifiers
source                  1..996
                        mol_type = genomic DNA
                        organism = Bacillus pseudomycoides
SEQUENCE: 2
atgaatttag cgaagtttcc tagaaagaaa tacacagaat catatacgcc aatcgaaaaa  60
ttaaatcact tttctgaagt cctaggagga ccttctattt actttaaacg agatgattta  120
cttggtttaa cagctggcgg aaataaaaca agaaaattag aattccttgt ggcggatgca  180
caggcgaaag gtgtagatac gttaattact gctggtggta ttcagtcaaa tcattgccga  240
ttaacattag cggctgcggt aaaagagaaa atgaaatgca ttcttgtatt agaagaagga  300
cttgaaccag aagaaaaacc agactttaat gggaattact tcttatatca tttattaggt  360
gctgaaaatg taatcgttgt gccaaacgga actgacctta tggatgagat gcaaaaagtg  420
gccaaagaag taactgaaaa agggcataca ccatacgtca ttccagttgg aggatccaat  480
cctaccggtg caatgggata tattgcatgt gcagaggaaa ttatggctca atcgtttgag  540
caagggatag atttcaatgc ggttgtttgt gtaagtggta gcggtggcat gcatgctggt  600
ttgattactg gattttatgg aagacaaaca gggatcccga taatcggaat gaatgtgagc  660
cgcggaaaag ctgaacaaga agaaaaagta tgtaagcttg tgcaagaaac ttcagcgcat  720
gttggtattc caaacagtat tccgcgtgag gctgtgacat gttttgatga atacgttggg  780
ccaggatacg ctttaccaac acctgaaatg gtagaagctg ttcaactttt agcaaaaaca  840
gaaggaattt tactggatcc agtatataca gggaaagcag tagctggact gatcgacata  900
attcgaaaag gtacatttaa gaaagaagat aacatcctat ttgtacattc aggtggttct  960
ccggcgttat atgcgaatac atcactattt tcctaa                            996

SEQ ID NO: 3            moltype = DNA  length = 996
FEATURE                 Location/Qualifiers
source                  1..996
                        mol_type = genomic DNA
                        organism = Bacillus thuringiensis
SEQUENCE: 3
atgaatttag ctaaattccc gagaaaaaaa tatacagagt catatacacc aattgaaaaa  60
ttaaacaatt tttctgaagt acttggtggg ccgactattt attttaaacg agatgattta  120
cttggtttaa cagctggtgg taataagacg agaaagttag agtttctagt tgcggatgca  180
caggcaaaag gtgcagatac gttaattaca gctggtggta ttcagtcaaa ccattgccgt  240
ctaacactgg cagctgcggt aaaagaaaaa atgaaatgta tccttgtatt agaagaaggg  300
cttgaaccag aagagaagcc agactttaac ggaaactatt tcttatatca cttattaggt  360
gctgaaaatg tcattgttgt accaaacgga gcagacctga tggaagaaat gcataaagta  420
gcaaaagaag taagtgaaaa agggaataca ccatatgtaa ttccagttgg tggatcaaac  480
cctacgggcg ctatgggata cgttgcttgt gcgcaagaaa ttatggcgca atcatttgag  540
caaggaattg atttcagttc agttgtttgt gtaagtggta gcggcggtat gcatgctggt  600
ttaattactg gttttgctgg aacacaaagc cacattcctg taattggaat caacgtaagt  660
agaggaaaag ctgagcaaga agagaaagta gcaaaacttg tagatgaaac ttcagcacac  720
gttggtattc caaactttat ctcgcgcgac gctgttacgt gctttgatca atatgtagga  780
ccaggctatg cgttaccaac gcaggaaatg gtagaggcag ttcagttact tgcgaaaaca  840
gaaggtattt tacttgatcc agtgtataca ggtaaagcgg tagcgggatt aatcgactta  900
attaaaaaag ggacatttaa taaagaagac aacattttat tcgtacattc aggtggttca  960
```

```
ccagctttat atgcgaatac ttctttattt gcgtaa                        996

SEQ ID NO: 4            moltype = DNA  length = 996
FEATURE                 Location/Qualifiers
source                  1..996
                        mol_type = other DNA
                        organism = Bacillus thuringiensis
SEQUENCE: 4
atgaatttag ctaaattccc gagaaaaaaa tatacagaat catatacacc aattgaaaag  60
ttaaacaact tttctgaagc acttggtggg ccgactattt attttaaacg agatgattta  120
cttggtttaa cagctggtgg taataagacg agaaagttag agtttctagt tgcggatgca  180
gaggcaaaag gtgcagatac gttaattaca gctggtggta ttcagtcaaa ccattgccgt  240
ctaacactgg cagctgcggt aaaagaaaaa atgaaatgta tccttgtatt agaagaaggg  300
cttgaaccag aagagaagcc agactttaac ggaaactatt tcttatatca tttactaggt  360
gctgaaaatg taattgttgt accaaacggg gcagatctta tggaagagat gcataaagta  420
gcgaaagaag ttagtgaaaa aggtaataca ccatatgtca taccagttgg tggatcaaat  480
cctactggtg caatgggata cgttgcttgt gcgcaagaaa ttatggcaca atcatttgac  540
caaggaattg atttcagtac agtcgtttgc gtaagcggta gcgctggtat gcacgctggt  600
ttaattactg gttttgctgg aacacaaagc cacattcctg taattggaat caacgtaagt  660
agaggaaaag ctgagcaaga agagaaagta gcaaaacttg tagatgaaac ttcagcacac  720
gttggtattc caaactttat cccgcgtgac gctgttacgt gctttgatga atatgtaggg  780
ccaggatatg cgttaccaac gccggaaatg gtagaggcag ttcagttact tgcgaaaaca  840
gaaggtattt tacttgatcc agtgtatgaa ggtaaagcgg tagcgggatt aatcgactta  900
attaaaaaag gtacatttaa taaagaagac aacattttat tcgtacattt aggtggttca  960
ccagctttat atgcgaatac ttctttattt gcgtaa                        996

SEQ ID NO: 5            moltype = DNA  length = 996
FEATURE                 Location/Qualifiers
source                  1..996
                        mol_type = other DNA
                        organism = Bacillus pseudomycoides
SEQUENCE: 5
atgaatttag cgaagtttcc tagaaagaaa tacacagaat catatacgcc aatcgaaaaa  60
ttaaatcact tttctgaagt cctaggagga ccttctattt actttaaacg agatgattta  120
cttggtttaa cagctggcgg aaataaaaca agaaaattag aattccttgt ggcggatgca  180
caggcgaaag gtgtagatac gttaattact gctggtggta ttcagtcaaa tcattgccga  240
ttaacattag cggctgcggt aaaagagaaa atgaaatgca ttcttgtatt agaagaagga  300
cttgaaccag aagaaaaacc agactttaat gggaattact tcttatatca tttattaggt  360
gctgaaaatg taatcgttgt gccaaacgga actgacctta tggatgagat gcaaaaagtg  420
gccaaagaag taactgaaaa agggcataca ccatacgtca ttccagttgg aggatccaat  480
cctaccggtg caatgggata tattgcatgt gcagaggaaa ttatggctca atcgtttgag  540
caagggatag atttcaatgc ggttgtttgt gtaagtggta gcggtggcat gcatgctggt  600
ttgattactg gattttatgg aagacaaaca gggatcccga taatcggaat gaatgtgagc  660
cgcggaaaag ctgaacaaga agaaaaagta tgtaagcttg tgcaagaaac ttcagcgcat  720
gttggtattc caaacagtat tccgcgtgag gctgtgacat gttttgatga atacgttggg  780
ccaggatacg ctttaccaac acctgaaatg gtagaagctg ttcaactttt agcaaaaaca  840
gaaggaattt tactggatcc agtatatgaa gggaaagcag tagctggact gatcgacata  900
attcgaaaag gtacatttaa gaaagaagat aacatcctat ttgtacattt aggtggttct  960
ccggcgttat atgcgaatac atcactattt tcctaa                        996

SEQ ID NO: 6            moltype = DNA  length = 996
FEATURE                 Location/Qualifiers
source                  1..996
                        mol_type = other DNA
                        organism = Bacillus thuringiensis
SEQUENCE: 6
atgaatttag ctaaattccc gagaaaaaaa tatacagagt catatacacc aattgaaaaa  60
ttaaacaatt tttctgaagt acttggtggg ccgactattt attttaaacg agatgattta  120
cttggtttaa cagctggtgg taataagacg agaaagttag agtttctagt tgcggatgca  180
caggcaaaag gtgcagatac gttaattaca gctggtggta ttcagtcaaa ccattgccgt  240
ctaacactgg cagctgcggt aaaagaaaaa atgaaatgta tccttgtatt agaagaaggg  300
cttgaaccag aagagaagcc agactttaac ggaaactatt tcttatatca cttattaggt  360
gctgaaaatg tcattgttgt accaaacgga gcagacctga tggaagaaat gcataaagta  420
gcaaaagaag taagtgaaaa agggaataca ccatatgtaa ttccagttgg tggatcaaac  480
cctacgggcg ctatgggata cgttgcttgt gcgcaagaaa ttatggcgca atcatttgag  540
caaggaattg atttcagttc agttgtttgt gtaagtggta gcggcggtat gcatgctggt  600
ttaattactg gttttgctgg aacacaaagc cacattcctg taattggaat caacgtaagt  660
agaggaaaag ctgagcaaga agagaaagta gcaaaacttg tagatgaaac ttcagcacac  720
gttggtattc caaactttat ctcgcgcgac gctgttacgt gctttgatca atatgtagga  780
ccaggctatg cgttaccaac gcaggaaatg gtagaggcag ttcagttact tgcgaaaaca  840
gaaggtattt tacttgatcc agtgtatgaa ggtaaagcgg tagcgggatt aatcgactta  900
attaaaaaag ggacatttaa taaagaagac aacattttat tcgtacattt aggtggttca  960
ccagctttat atgcgaatac ttctttattt gcgtaa                        996

SEQ ID NO: 7            moltype = AA  length = 331
FEATURE                 Location/Qualifiers
source                  1..331
                        mol_type = protein
                        organism = Bacillus thuringiensis
```

```
SEQUENCE: 7
MNLAKFPRKK YTESYTPIEK LNNFSEALGG PTIYFKRDDL LGLTAGGNKT RKLEFLVADA  60
EAKGADTLIT AGGIQSNHCR LTLAAAVKEK MKCILVLEEG LEPEEKPDFN GNYFLYHLLG  120
AENVIVVPNG ADLMEEMHKV AKEVSEKGNT PYVIPVGGSN PTGAMGYVAC AQEIMAQSFD  180
QGIDFSTVVC VSGSAGMHAG LITGFAGTQS HIPVIGINVS RGKAEQEEKV AKLVDETSAH  240
VGIPNFIPRD AVTCFDEYVG PGYALPTPEM VEAVQLLAKT EGILLDPVYT GKAVAGLIDL  300
IKKGTFNKED NILFVHSGGS PALYANTSLF A                                 331

SEQ ID NO: 8           moltype = AA  length = 331
FEATURE                Location/Qualifiers
source                 1..331
                       mol_type = protein
                       organism = Bacillus pseudomycoides
SEQUENCE: 8
MNLAKFPRKK YTESYTPIEK LNHFSEVLGG PSIYFKRDDL LGLTAGGNKT RKLEFLVADA  60
QAKGVDTLIT AGGIQSNHCR LTLAAAVKEK MKCILVLEEG LEPEEKPDFN GNYFLYHLLG  120
AENVIVVPNG TDLMDEMQKV AKEVTEKGHT PYVIPVGGSN PTGAMGYIAC AEEIMAQSFE  180
QGIDFNAVVC VSGSGGMHAG LITGFYGRQT GIPIIGMNVS RGKAEQEEKV CKLVQETSAH  240
VGIPNSIPRE AVTCFDEYVG PGYALPTPEM VEAVQLLAKT EGILLDPVYT GKAVAGLIDI  300
IRKGTFKKED NILFVHSGGS PALYANTSLF S                                 331

SEQ ID NO: 9           moltype = AA  length = 331
FEATURE                Location/Qualifiers
source                 1..331
                       mol_type = protein
                       organism = Bacillus thuringiensis
SEQUENCE: 9
MNLAKFPRKK YTESYTPIEK LNNFSEVLGG PTIYFKRDDL LGLTAGGNKT RKLEFLVADA  60
QAKGADTLIT AGGIQSNHCR LTLAAAVKEK MKCILVLEEG LEPEEKPDFN GNYFLYHLLG  120
AENVIVVPNG ADLMEEMHKV AKEVSEKGNT PYVIPVGGSN PTGAMGYVAC AQEIMAQSFE  180
QGIDFSSVVC VSGSGGMHAG LITGFAGTQS HIPVIGINVS RGKAEQEEKV AKLVDETSAH  240
VGIPNFISRD AVTCFDQYVG PGYALPTQEM VEAVQLLAKT EGILLDPVYT GKAVAGLIDL  300
IKKGTFNKED NILFVHSGGS PALYANTSLF A                                 331

SEQ ID NO: 10          moltype = AA  length = 331
FEATURE                Location/Qualifiers
source                 1..331
                       mol_type = protein
                       organism = Bacillus thuringiensis
SEQUENCE: 10
MNLAKFPRKK YTESYTPIEK LNNFSEALGG PTIYFKRDDL LGLTAGGNKT RKLEFLVADA  60
EAKGADTLIT AGGIQSNHCR LTLAAAVKEK MKCILVLEEG LEPEEKPDFN GNYFLYHLLG  120
AENVIVVPNG ADLMEEMHKV AKEVSEKGNT PYVIPVGGSN PTGAMGYVAC AQEIMAQSFD  180
QGIDFSTVVC VSGSAGMHAG LITGFAGTQS HIPVIGINVS RGKAEQEEKV AKLVDETSAH  240
VGIPNFIPRD AVTCFDEYVG PGYALPTPEM VEAVQLLAKT EGILLDPVYE GKAVAGLIDL  300
IKKGTFNKED NILFVHLGGS PALYANTSLF A                                 331

SEQ ID NO: 11          moltype = AA  length = 331
FEATURE                Location/Qualifiers
source                 1..331
                       mol_type = protein
                       organism = Bacillus pseudomycoides
SEQUENCE: 11
MNLAKFPRKK YTESYTPIEK LNHFSEVLGG PSIYFKRDDL LGLTAGGNKT RKLEFLVADA  60
QAKGVDTLIT AGGIQSNHCR LTLAAAVKEK MKCILVLEEG LEPEEKPDFN GNYFLYHLLG  120
AENVIVVPNG TDLMDEMQKV AKEVTEKGHT PYVIPVGGSN PTGAMGYIAC AEEIMAQSFE  180
QGIDFNAVVC VSGSGGMHAG LITGFYGRQT GIPIIGMNVS RGKAEQEEKV CKLVQETSAH  240
VGIPNSIPRE AVTCFDEYVG PGYALPTPEM VEAVQLLAKT EGILLDPVYE GKAVAGLIDI  300
IRKGTFKKED NILFVHLGGS PALYANTSLF S                                 331

SEQ ID NO: 12          moltype = AA  length = 331
FEATURE                Location/Qualifiers
source                 1..331
                       mol_type = protein
                       organism = Bacillus thuringiensis
SEQUENCE: 12
MNLAKFPRKK YTESYTPIEK LNNFSEVLGG PTIYFKRDDL LGLTAGGNKT RKLEFLVADA  60
QAKGADTLIT AGGIQSNHCR LTLAAAVKEK MKCILVLEEG LEPEEKPDFN GNYFLYHLLG  120
AENVIVVPNG ADLMEEMHKV AKEVSEKGNT PYVIPVGGSN PTGAMGYVAC AQEIMAQSFE  180
QGIDFSSVVC VSGSGGMHAG LITGFAGTQS HIPVIGINVS RGKAEQEEKV AKLVDETSAH  240
VGIPNFISRD AVTCFDQYVG PGYALPTQEM VEAVQLLAKT EGILLDPVYE GKAVAGLIDL  300
IKKGTFNKED NILFVHLGGS PALYANTSLF A                                 331

SEQ ID NO: 13          moltype = AA  length = 259
FEATURE                Location/Qualifiers
source                 1..259
                       mol_type = protein
                       organism = Bacillus thuringiensis
SEQUENCE: 13
```

```
HENDGGQRFG VIPRWSAEDK HKEGVNSHLW IVNRAIDIMS RNTTLVKQDR VALLNEWRTE  60
LENGIYAADY ENPYYDNSTF ASHFYDPDNG KTYIPYAKQA KETGAKYFKL AGESYKNKDM  120
QQAFFYLGLS LHYLGDVNQP MHAANFTNLS YPQGFHSKYE NFVDTIKDNY KVTDGNGYWN  180
WKGTNPEDWI HGAAVVAKQD YAGIVNDNTK DWFVRAAVSQ EYADKWRAEV TPMTGKRLMD  240
AQRVTAGYIQ LWFDTYGDR                                              259

SEQ ID NO: 14          moltype = AA  length = 259
FEATURE                Location/Qualifiers
source                 1..259
                       mol_type = protein
                       organism = Bacillus thuringiensis
SEQUENCE: 14
HENDGGQRFG VIPRWSAEDK HKEGVNSHLW IVNRAIDIMS RNTTLVKQDR VALLNEWRTE  60
LENGIYAADY ENPYYDNSTF ASHFYDPDNG KTYIPYAKQA KETGAKYFKL AGESYKNKDM  120
QQAFFYLGLS LHYLGDVNQP MHAANFTNLS YPQGFHSKYE NFVDTIKDNY KVTDGNGYWN  180
WKGTNPEDWI HGAAVVAKQD YAGIVNDNTK DWFVRAAVSQ EYADKWRAEV TPMTGKRLMD  240
AQRVTAGYIQ LWFDTYGDR                                              259

SEQ ID NO: 15          moltype = AA  length = 259
FEATURE                Location/Qualifiers
source                 1..259
                       mol_type = protein
                       organism = Bacillus thuringiensis
SEQUENCE: 15
HENDGGQRFG VIPRWSAEDK HKEGVNSHLW IVNRAIDIMS RNTTLVKQDR VALLNEWRTE  60
LENGIYAADY ENPYYDNSTF ASHFYDPDNG KTYIPYAKQA KETGAKYFKL AGESYKNKDM  120
KQAFFYLGLS LHYLGDVNQP MHAANFTNLS YPQGFHSKYE NFVDTIKDNY KVTDGNGYWN  180
WKGTNPEDWI HGAAVVAKQD YAGIVNDNTK DWFVRAAVSQ EYADKWRAEV TPMTGKRLMD  240
AQRVTAGYIQ LWFDTYGNR                                              259

SEQ ID NO: 16          moltype = AA  length = 305
FEATURE                Location/Qualifiers
source                 1..305
                       mol_type = protein
                       organism = Bacillus thuringiensis
SEQUENCE: 16
ASTNQNDTLK VMTHNVYMLS TNLYPNWGQT ERADLIGAAD YIKNQDVVIL NEVFDNSASD  60
RLLGNLKKEY PNQTAVLGRS SGSEWDKKLG NYSSSTPEDG GVAIVSKWPI AEKIQYVFAK  120
GCGPDNLSNK GFVYTKIKKN DRFIHVIGTH LQAEDSMCGK TSPASVRTNQ LKEIQDFIKN  180
KNIPNNEYVL IGGDMNVNKI NAENKNDSEY TSMFKTLNAS VPSYTGHTAT WDATTNSIAK  240
YNFPDSPAEY LDYIIASKDH ANPSYIENKV LQPKSPQWTV TSWFQKYTYN DYSDHYPVEA  300
TISMK                                                             305

SEQ ID NO: 17          moltype = AA  length = 259
FEATURE                Location/Qualifiers
source                 1..259
                       mol_type = protein
                       organism = Bacillus cereus
SEQUENCE: 17
HENDGGSKIK IVHRWSAEDK HKEGVNSHLW IVNRAIDIMS RNTTLVKQDR VAQLNEWRTE  60
LENGIYAADY ENPYYDNSTF ASHFYDPDNG KTYIPFAKQA KETGAKYFKL AGESYKNKDM  120
KQAFFYLGLS LHYLGDVNQP MHAANFTNLS YPQGFHSKYE NFVDTIKDNY KVTDGNGYWN  180
WKGTNPEEWI HGAAVVAKQD YSGIVNDNTK DWFVKAAVSQ EYADKWRAEV TPMTGKRLMD  240
AQRVTAGYIQ LWFDTYGDR                                              259

SEQ ID NO: 18          moltype = AA  length = 369
FEATURE                Location/Qualifiers
source                 1..369
                       mol_type = protein
                       organism = Clostridium perfringens
SEQUENCE: 18
DGKIDGTGTH AMIVTQGVSI LENDLSKNEP ESVRKNLEIL KENMHELQLG STYPDYDKNA  60
YDLYQDHFWD PDTDNNFSKD NSWYLAYSIP DTGESQIRKF SALARYEWQR GNYKQATFYL  120
GEAMHYFGDI DTPYHPANVT AVDSAGHVKF ETFAEERKEQ YKINTAGCKT NEDFYADILK  180
NKDFNAWSKE YARGFAKTGK SIYYSHASMS HSWDDWDYAA KVTLANSQKG TAGYIYRFLH  240
DVSEGNDPSV GKNVKELVAY ISTSGEKDAG TDDYMYFGIK TKDGKTQEWE MDNPGNDFMT  300
GSKDTYTFKL KDENLKIDDI QNMWIRKRKY TAFPDAYKPE NIKIIANGKV VVDKDINEWI  360
SGNSTYNIK                                                         369

SEQ ID NO: 19          moltype = AA  length = 495
FEATURE                Location/Qualifiers
source                 1..495
                       mol_type = protein
                       organism = Streptomyces chromofuscus
SEQUENCE: 19
PLPDGVLLWT RVTPTADATP GSGLGPDTEV GWTVATDKAF TNVVAKGSTT ATAASDHTVK  60
ADIRGLAPAT DHWFRFSAGG TDSPAGRART APAADAAVAG LRFGVVSCAN WEAGYFAAYR  120
HLAARGDLDA WLHLGDYIYE YGAGEYGTRG TSVRSHAPAH EILTLADYRV RHGRYKTDPD  180
LQALHAAAPV VAIWDDHEIA NDTWSGGAEN HTEGVEGAWA ARQAAAKQAY FEWMPVRPAI  240
```

```
AGTTYRRLRF GKLADLSLLD LRSFRAQQVS LGDGDVDDPD RTLTGRAQLD WLKAGLKSSD  300
TTWRLVGNSV MIAPFAIGSL SAELLKPLAK LLGLPQEGLA VNTDQWDGYT DDRRELLAHL  360
RSNAIRNTVF LTGDIHMAWA NDVPVNAGTY PLSASAATEF VVTSVTSDNL DDLVKVPEGT  420
VSALASPVIR AANRHVHWVD TDRHGYGVLD ITAERAQMDY YVLSDRTQAG ATASWSRSYR  480
TRSGTQRVER TYDPE                                                   495

SEQ ID NO: 20          moltype = AA  length = 240
FEATURE                Location/Qualifiers
source                 1..240
                       mol_type = protein
                       organism = Bacillus thuringiensis
SEQUENCE: 20
MRTPLSFDKD TAILLASCCE LTYEQYKQNG IFEIPDGFQY VQGFQGKAIQ TTEWFGFILE  60
SEDTIIVAFR GTQTDPDWII DSLVNQKPYP YALNGGNVHN GFLSIYESCR DSIMDMLVSL  120
PAHKKLLATG HSLGGALATL HILDARINTA FAQYGLYSFA SPKVGDIAFR NYYKLQVASS  180
FRFVNLFDVV PLLPPRNINF NDHDWEYAHV HHNMTFTKNT KSITNNHSIT TYKTCLTSHF  240

SEQ ID NO: 21          moltype = AA  length = 181
FEATURE                Location/Qualifiers
source                 1..181
                       mol_type = protein
                       organism = Bacillus subtilis
SEQUENCE: 21
AEHNPVVMVH GIGGASFNFA GIKSYLVSQG WSRDKLYAVD FWDKTGTNYN NGPVLSRFVQ  60
KVLDETGAKK VDIVAHSMGG ANTLYYIKNL DGGNKVANVV TLGGANRLTT GKALPGTDPN  120
QKILYTSIYS SADMIVMNYL SRLDGARNVQ IHGVGHIGLL YSSQVNSLIK EGLNGGGQNT  180
N                                                                  181

SEQ ID NO: 22          moltype = AA  length = 309
FEATURE                Location/Qualifiers
source                 1..309
                       mol_type = protein
                       organism = Caldicellulosiruptor saccharolyticus
SEQUENCE: 22
KDLEGVHRDI LLKHFNSLTP ENAMKFENIH PEEQRYNFEE VARIKEFAIK NDMKLRGHTF  60
VWHNQTPGWV FLDKNGEEAS KELVIERLRE HIKTLCERYK DVVYAWDVVN EAVEDKTEKL  120
LRESNWRKII GDDYIKIAFE IAREYAGDAK LFYNDYNNEM PYKLEKTYKV LKELLERGTP  180
IDGIGIQAHW NIWDKNLVSN LKKAIEVYAS LGLEIHITEL DISVFEFEDK RTDLFEPTPE  240
MLELQAKVYE DVFAVFREYK DVITSVTLWG ISDRHTWKDN FPVKGRKDWP LLFDVNGKPK  300
EALYRILRF                                                          309

SEQ ID NO: 23          moltype = AA  length = 185
FEATURE                Location/Qualifiers
source                 1..185
                       mol_type = protein
                       organism = Bacillus subtilis
SEQUENCE: 23
ASTDYWQNWT DGGGIVNAVN GSGGNYSVNW SNTGNFVVGK GWTTGSPFRT INYNAGVWAP  60
NGNGYLTLYG WTRSPLIEYY VVDSWGTYRP TGTYKGTVKS DGGTYDIYTT TRYNAPSIDG  120
DRTTFTQYWS VRQSKRPTGS NATITFSNHV NAWKSHGMNL GSNWAYQVMA TEGYQSSGSS  180
NVTVW                                                              185

SEQ ID NO: 24          moltype = AA  length = 487
FEATURE                Location/Qualifiers
source                 1..487
                       mol_type = protein
                       organism = Bacillus subtilis
SEQUENCE: 24
ATSTTIAKHI GNSNPLIDHH LGADPVALTY NGRVYIYMSS DDYEYNSNGT IKDNSFANLN  60
RVFVISSADM VNWTDHGAIP VAGANGANGG RGIAKWAGAS WAPSIAVKKI NGKDKFFLYF  120
ANSGGGIGVL TADSPIGPWT DPIGKPLVTP STPGMSGVVW LFDPAVFVDD DGTGYLYAGG  180
GVPGVSNPTQ GQWANPKTAR VIKLGPDMTS VVGSASTIDA PFMFEDSGLH KYNGTYYYSY  240
CINFGGTHPA DKPPGEIGYM TSSSPMGPFT YRGHFLKNPG AFFGGGGNNH HAVFNFKNEW  300
YVVYHAQTVS SALFGAGKGY RSPHINKLVH NADGSIQEVA ANYAGVTQIS NLNPYNRVEA  360
ETFAWNGRIL TEKSTAPGGP VNNQHVTSIQ NGDWIAVGNA DFGAGGARSF KANVASTLGG  420
KIEVRLDSAD GKLVGTLNVP STGGAQTWRE IETAVSGATG VHKVFFVFTG TGTGNLFNFD  480
YWQFTQR                                                            487

SEQ ID NO: 25          moltype = AA  length = 183
FEATURE                Location/Qualifiers
source                 1..183
                       mol_type = protein
                       organism = Bacillus stearothermophilus
SEQUENCE: 25
ATDYWQYWTD GGGMVNAVNG PGGNYSVTWQ NTGNFVVGKG WTVGSPNRVI NYNAGIWEPS  60
GNGYLTLYGW TRNALIEYYV VDSWGTYRPT GNYKGTVNSD GGTYDIYTTM RYNAPSIDGT  120
QTFQQFWSVR QSKRPTGSNV SITFSNHVNA WRSKGMNLGS SWAYQVLATE GYQSSGRSNV  180
TVW                                                                183
```

```
SEQ ID NO: 26          moltype = AA  length = 488
FEATURE                Location/Qualifiers
source                 1..488
                       mol_type = protein
                       organism = Caldicellulosiruptor saccharolyticus
SEQUENCE: 26
MERRKIMKIT INYGKRLGKI NKFWAKCVGS CHATTALRED WRKQLKKCRD ELGFEYIRFH  60
GWLNDDMSVC FRNDDGLLSF SFFNIDSIID FLLEIGMKPF IELSFMPEAL ASGTKTVFHY  120
KGNITPPKSY EEWGQLIEEL ARHLISRYGK NEVREWFFEV WNEPNLKDFF WAGTMEEYFK  180
LYKYAAFAIK KVDSELRVGG PATAIDAWIP ELKDFCTKNG VPIDFISTHQ YPTDLAFSTS  240
SNMEEAMAKA KRGELAERVK KALEEAYPLP VYYTEWNNSP SPRDPYHDIP YDAAFIVKTI  300
IDIIDLPLGC YSYWTFTDIF EECGQSSLPF HGGFGLLNIH GIPKPSYRAF QILDKLNGER  360
IEIEFEDKSP TIDCIAVQNE REIILVISNH NVPLSPIDTE NIKVVLKGIE NCREVFVERI  420
DEYNANPKRV WLEMGSPAYL NREQIEELIK ASELKKEKVS WGIVNNNEIT FDLSVLPHSV  480
VAVTIKNG                                                          488

SEQ ID NO: 27          moltype = AA  length = 250
FEATURE                Location/Qualifiers
source                 1..250
                       mol_type = protein
                       organism = Bacillus thuringiensis
SEQUENCE: 27
MTVKKLYFIP AGRCMLDHSS VNSTLTPGNL LNLPVWCYLL ETEEGPILVD TGMPEIAVNN  60
EGLFNGTFVE GQILPKMTEE DRIITILKRA GYEPDDLLYI ISSHLHFDHA GGNGAFSNTP  120
IIIQRAEYEA AQYREEYLKE CILPHLNYKI IEGDYEVVPG VRLLYTPGHS PGHQSLLIET  180
EKSGPILLTI DASYTKENFE DEVPFAGFDS ELALSSIKRL KEVVAKEKPI IFFGHDIEQE  240
KGCKVFPEYI                                                        250

SEQ ID NO: 28          moltype = AA  length = 250
FEATURE                Location/Qualifiers
source                 1..250
                       mol_type = protein
                       organism = Bacillus pseudomycoides
SEQUENCE: 28
MTVKKLYFLP AGRCMLDHSS INSTLTPGKL LDLPVWCYLL ETTEGPILID TGMPESAVDN  60
ENLFKGTFVE GQIFPKMKPD DSIVNILKRV GYAPEDLLCV ISSHFHFDHA GGNGSFSHTP  120
IIVQRTEYDA ALHREEYLKE CILPDLNYQI IEGDYEVMPG VQLLYTPGHS PGHQSIFVET  180
EKSGPVLLTI DAAYTQENFE QGVPFAGFNS EMASQSINRL KEIVLDEKPI IFFGHDMEQE  240
KRCKTFPEFL                                                        250

SEQ ID NO: 29          moltype = AA  length = 242
FEATURE                Location/Qualifiers
source                 1..242
                       mol_type = protein
                       organism = Bacillus subtilis
SEQUENCE: 29
AGLNKDQKRR AEQLTSIFEN GTTEIQYGYV ERLDDGRGYT CGRAGFTTAT GDALEVVEVY  60
TKAVPNNKLK KYLPELRRLA KEESDDTSNL KGFASAWKSL ANDKEFRAAQ DKVNDHLYYQ  120
PAMKRSDNAG LKTALARAVM YDTVIQHGDG DDPDSFYALI KRTNKKAGGS PKDGIDEKKW  180
LNKFLDVRYD DLMNPANHDT RDEWRESVAR VDVLRSIAKE NNYNLNGPIH VRSNEYGNFV  240
IK                                                                242

SEQ ID NO: 30          moltype = AA  length = 469
FEATURE                Location/Qualifiers
source                 1..469
                       mol_type = protein
                       organism = Acidothermus cellulolyticus
SEQUENCE: 30
MGTYPIRSVS GGVALAACAV LTMTTAAAAT PIHDASSPHT IPPHARLYTP PPDKGAIKQI  60
TDLLKARDVR DARLIAEMIS TPQAVWFTGG TPDQVRRDVH RVVTKAAAHH AIPVLVAYNI  120
PFRDCSQYSA GGAVDTAAYE AWIDGFAAGI GDKRAIVLLE PDSLGIIPYN TDINGNAEWC  180
KPDLSGTGLT PDEANQARYD QLNYAVDALE AHRNVSVYLD GTHSGWLGVG DIAQRLVRAG  240
VQRAQGFFVN VSNYQTTERQ IKYGTWISEC IAFANDPEEG GWRLGHYSWC ASQYYPANPN  300
DFSTWVQTDQ WYASNLGTAV PTTHFVIDTS RNGRGPNDMT AYAAAPYNQP ASVISALQGG  360
SWCNPPGRGL GLRPTVNTGV PLLDAYLWVK IPGESDGQCD AAGGARAWDY SAYTEPGWPT  420
DPSQQALFDP LWGLYDPPAG QWFPQQALQL AQLAVPPLQP QWPVPPVHH         469

SEQ ID NO: 31          moltype = AA  length = 459
FEATURE                Location/Qualifiers
source                 1..459
                       mol_type = protein
                       organism = Trichoderma reesei
SEQUENCE: 31
MAPSVTLPLT TAILAIARLV AAQQPGTSTP EVHPKLTTYK CTKSGGCVAQ DTSVVLDWNY  60
RWMHDANYNS CTVNGGVNTT LCPDEATCGK NCFIEGVDYA ASGVTTSGSS LTMNQYMPSS  120
SGGYSSVSPR LYLLDSDGEY VMLKLNGQEL SFDVDLSALP CGENGSLYLS QMDENGGANQ  180
YNTAGANYGS GYCDAQCPVQ TWRNGTLNTS HQGFCCNEMD ILEGNSRANA LTPHSCTATA  240
CDSAGCGFNP YGSGYKSYYG PGDTVDTSKT FTIITQFNTD NGSPSGNLVS ITRKYQQNGV  300
DIPSAQPGGD TISSCPSASA YGGLATMGKA LSSGMVLVFS IWNDNSQYMN WLDSGNAGPC  360
```

```
SSTEGNPSNI LANNPNTHVV FSNIRWGDIG STTNSTAPPP PPASSTTFST TRRSSTTSSS  420
PSCTQTHWGQ CGGIGYSGCK TCTSGTTCQY SNDYYSQCL                         459

SEQ ID NO: 32          moltype = AA  length = 418
FEATURE                Location/Qualifiers
source                 1..418
                       mol_type = protein
                       organism = Trichoderma reesei
SEQUENCE: 32
MNKSVAPLLL AASILYGGAV AQQTVWGQCG GIGWSGPTNC APGSACSTLN PYYAQCIPGA  60
TTITTSTRPP SGPTTTTRAT STSSSTPPTS SGVRFAGVNI AGFDFGCTTD GTCVTSKVYP  120
PLKNFTGSNN YPDGIGQMQH FVNEDGMTIF RLPVGWQYLV NNNLGGNLDS TSISKYDQLV  180
QGCLSLGAYC IVDIHNYARW NGGIIGQGGP TNAQFTSLWS QLASKYASQS RVWFGIMNEP  240
HDVNINTWAA TVQEVVTAIR NAGATSQFIS LPGNDWQSAG AFISDGSAAA LSQVTNPDGS  300
TTNLIFDVHK YLDSDNSGTH AECTTNNIDG AFSPLATWLR QNNRQAILTE TGGGNVQSCI  360
QDMCQQIQYL NQNSDVYLGY VGWGAGSFDS TYVLTETPTS SGNSWTDTSL VSSCLARK    418

SEQ ID NO: 33          moltype = AA  length = 344
FEATURE                Location/Qualifiers
source                 1..344
                       mol_type = protein
                       organism = Trichoderma reesei
SEQUENCE: 33
MIQKLSNLLV TALAVATGVV GHGHINDIVI NGVWYQAYDP TTFPYESNPP IVVGWTAADL  60
DNGFVSPDAY QNPDIICHKN ATNAKGHASV KAGDTILFQW VPVPWPHPGP IVDYLANCNG  120
DCETVDKTTL EFFKIDGVGL LSGGDPGTWA SDVLISNNNT WVVKIPDNLA PGNYVLRHEI  180
IALHSAGQAN GAQNYPQCFN IAVSGSGSLQ PSGVLGTDLY HATDPGVLIN IYTSPLNYII  240
PGPTVVSGLP TSVAQGSSAA TATASATVPG GGSGPTSRTT TTARTTQASS RPSSTPPATT  300
SAPAGGPTQT LYGQCGGSGY SGPTRCAPPA TCSTLNPYYA QCLN                   344

SEQ ID NO: 34          moltype = AA  length = 242
FEATURE                Location/Qualifiers
source                 1..242
                       mol_type = protein
                       organism = Trichoderma reesei
SEQUENCE: 34
MKATLVLGSL IVGAVSAYKA TTTRYYDGQE GACGCGSSSG AFPWQLGIGN GVYTAAGSQA  60
LFDTAGASWC GAGCGKCYQL TSTGQAPCSS CGTGGAAGQS IIVMVTNLCP NNGNAQWCPV  120
VGGTNQYGYS YHFDIMAQNE IFGDNVVVDF EPIACPGQAA SDWGTCLCVG QQETDPTPVL  180
GNDTGSTPPG SSPPATSSSP PSGGGQQTLY GQCGGAGWTG PTTCQAPGTC KVQNQWYSQC  240
LP                                                                 242

SEQ ID NO: 35          moltype = AA  length = 249
FEATURE                Location/Qualifiers
source                 1..249
                       mol_type = protein
                       organism = Trichoderma reesei
SEQUENCE: 35
MKSCAILAAL GCLAGSVLGH GQVQNFTING QYNQGFILDY YYQKQNTGHF PNVAGWYAED  60
LDLGFISPDQ YTTPDIVCHK NAAPGAISAT AAAGSNIVFQ WGPGVWPHPY GPIVTYVVEC  120
SGSCTTVNKN NLRWVKIQEA GINYNTQVWA QQDLINQGNK WTVKIPSSLR PGNYVFRHEL  180
LAAHGASSAN GMQNYPQCVN IAVTGSGTKA LPAGTPATQL YKPTDPGILF NPYTTITSYT  240
IPGPALWQG                                                          249

SEQ ID NO: 36          moltype = AA  length = 234
FEATURE                Location/Qualifiers
source                 1..234
                       mol_type = protein
                       organism = Trichoderma reesei
SEQUENCE: 36
MKFLQVLPAL IPAALAQTSC DQWATFTGNG YTVSNNLWGA SAGSGFGCVT AVSLSGGASW  60
HADWQWSGGQ NNVKSYQNSQ IAIPQKRTVN SISSMPTTAS WSYSGSNIRA NVAYDLFTAA  120
NPNHVTYSGD YELMIWLGKY GDIGPIGSSQ GTVNVGGQSW TLYYGYNGAM QVYSFVAQTN  180
TTNYSGDVKN FFNYLRDNKG YNAAGQYVLS YQFGTEPFTG SGTLNVASWT ASIN        234

SEQ ID NO: 37          moltype = AA  length = 513
FEATURE                Location/Qualifiers
source                 1..513
                       mol_type = protein
                       organism = Trichoderma reesei
SEQUENCE: 37
MYRKLAVISA FLATARAQSA CTLQSETHPP LTWQKCSSGG TCTQQTGSVV IDANWRWTHA  60
TNSSTNCYDG NTWSSTLCPD NETCAKNCCL DGAAYASTYG VTTSGNSLSI GFVTQSAQKN  120
VGARLYLMAS DTTYQEFTLL GNEFSFDVDV SQLPCGLNGA LYFVSMDADG GVSKYPTNTA  180
GAKYGTGYCD SQCPRDLKFI NGQANVEGWE PSSNNANTGI GGHGSCCSEM DIWEANSISE  240
ALTPHPCTTV GQEICEGDGC GGTYSDNRYG GTCDPDGCDW NPYRLGNTSF YGPGSSFTLD  300
TTKKLTVVTQ FETSGAINRY YVQNGVTFQQ PNAELGSYSG NELNDDYCTA EEAEFGGSSF  360
SDKGGLTQFK KATSGGMVLV MSLWDDYYAN MLWLDSTYPT NETSSTPGAV RGSCSTSSGV  420
PAQVESQSPN AKVTFSNIKF GPIGSTGNPS GGNPPGGNRG TTTTRRPATT TGSSPGPTQS  480
```

```
HYGQCGGIGY SGPTVCASGT TCQVLNPYYS QCL                          513

SEQ ID NO: 38          moltype = AA  length = 471
FEATURE                Location/Qualifiers
source                 1..471
                       mol_type = protein
                       organism = Trichoderma reesei
SEQUENCE: 38
MIVGILTTLA TLATLAASVP LEERQACSSV WGQCGGQNWS GPTCCASGST CVYSNDYYSQ  60
CLPGAASSSS STRAASTTSR VSPTTSRSSS ATPPPGSTTT RVPPVGSGTA TYSGNPFVGV  120
TPWANAYYAS EVSSLAIPSL TGAMATAAAA VAKVPSFMWL DTLDKTPLME QTLADIRTAN  180
KNGGNYAGQF VVYDLPDRDC AALASNGEYS IADGGVAKYK NYIDTIRQIV VEYSDIRTLL  240
VIEPDSLANL VTNLGTPKCA NAQSAYLECI NYAVTQLNLP NVAMYLDAGH AGWLGWPANQ  300
DPAAQLFANV YKNASSPRAL RGLATNVANY NGWNITSPPS YTQGNAVYNE KLYIHAIGPL  360
LANHGWSNAF FITDQGRSGK QPTGQQQWGD WCNVIGTGFG IRPSANTGDS LLDSFVWVKP  420
GGECDGTSDS SAPRFDSHCA LPDALQPAPQ AGAWFQAYFV QLLTNANPSF L          471

SEQ ID NO: 39          moltype = AA  length = 744
FEATURE                Location/Qualifiers
source                 1..744
                       mol_type = protein
                       organism = Trichoderma reesei
SEQUENCE: 39
MRYRTAAALA LATGPFARAD SHSTSGASAE AVVPPAGTPW GTAYDKAKAA LAKLNLQDKV  60
GIVSGVGWNG GPCVGNTSPA SKISYPSLCL QDGPLGVRYS TGSTAFTPGV QAASTWDVNL  120
IRERGQFIGE EVKASGIHVI LGPVAGPLGK TPQGGRNWEG FGVDPYLTGI AMGQTINGIQ  180
SVGVQATAKH YILNEQELNR ETISSNPDDR TLHELYTWPF ADAVQANVAS VMCSYNKVNT  240
TWACEDQYTL QTVLKDQLGF PGYVMTDWNA QHTTVQSANS GLDMSMPGTD FNGNNRLWGP  300
ALTNAVNSNQ VPTSRVDDMV TRILAAWYLT GQDQAGYPSF NISRNVQGNH KTNVRAIARD  360
GIVLLKNDAN ILPLKKPASI AVVGSAAIIG NHARNSPSCN DKGCDDGALG MGWGSGAVNY  420
PYFVAPYDAI NTRASSQGTQ VTLSNTDNTS SGASAARGKD VAIVFITADS GEGYITVEGN  480
AGDRNNLDPW HNGNALVQAV AGANSNVIVV VHSVGAIILE QILALPQVKA VVWAGLPSQE  540
SGNALVDVLW GDVSPSGKLV YTIAKSPNDY NTRIVSGGSD SFSEGLFIDY KHFDDANITP  600
RYEFGYGLSY TKFNYSRLSV LSTAKSGPAT GAVVPGGPSD LFQNVATVTV DIANSGQVTG  660
AEVAQLYITY PSSAPRTPPK QLRGFAKLNL TPGQSGTATF NIRRRDLSYW DTASQKWVVP  720
SGSFGISVGA SSRDIRLTST LSVA                                    744

SEQ ID NO: 40          moltype = AA  length = 466
FEATURE                Location/Qualifiers
source                 1..466
                       mol_type = protein
                       organism = Trichoderma reesei
SEQUENCE: 40
MLPKDFQWGF ATAAYQIEGA VDQDGRGPSI WDTFCAQPGK IADGSSGVTA CDSYNRTAED  60
IALLKSLGAK SYRFSISWSR IIPEGGRGDA VNQAGIDHYV KFVDDLLDAG ITPFITLFHW  120
DLPEGLHQRY GGLLNRTEFP LDFENYARVM FRALPKVRNW ITFNEPLCSA IPGYGSGTFA  180
PGRQSTSEPW TVGHNILVAH GRAVKAYRDD FKPASGDGQI GIVLNGDFTY PWDAADPADK  240
EAAERRLEFF TAWFADPIYL GDYPASMRKQ LGDRLPTFTP EERALVHGSN DFYGMNHYTS  300
NYIRHRSSPA SADDTVGNVD VLFTNKQGNC IGPETQSPWL RPCAAGFRDF LVWISKRYGY  360
PPIYVTENGT SIKGESDLPK EKILEDDFRV KYYNEYIRAM VTAVELDGVN VKGYFAWSLM  420
DNFEWADGYV TRFGVTYVDY ENGQKRFPKK SAKSLKPLFD ELIAAA             466

SEQ ID NO: 41          moltype = AA  length = 405
FEATURE                Location/Qualifiers
source                 1..405
                       mol_type = protein
                       organism = Aspergillus oryzae
SEQUENCE: 41
MLPLLLCIVP YCWSSRLDPR ASSFDYNGEK VRGVNLGGWL VLEPWITPSI FDAAGAEAVD  60
EWSLTKILGK EEAEARLSAH WKSFVSAGDF QRMADAGLNH VRIPIGYWAL GPLEGDPYVD  120
GQLEYLDKAV EWAGAAGLKV LIDLHGAPGS QNGFDNSGRR GAIQWQQGDT VEQTLDAFDL  180
LAERYLGSDT VAAIEAINEP NIPGGVDQGK LQEYYGSVYG IVNKYNAGTS VVYGDGFLPV  240
ESWNGFKTEG SKVVMDTHHY HMFDNGLIAM DIDSHIDAVC QFAHQHLEAS DKPVIVGEWT  300
GAVTDCAKYL NGKGNGARYD GSYAADKAIG DCSSLATGFV SKLSDEERSD MRRFIEAQLD  360
AFELKSGWVF WTWKTEGAPG WDMSDLLEAG VFPTSPDDRE FPKQC              405

SEQ ID NO: 42          moltype = AA  length = 470
FEATURE                Location/Qualifiers
source                 1..470
                       mol_type = protein
                       organism = Bacillus subtilis
SEQUENCE: 42
AGTKTPVAKN GQLSIKGTQL VNRDGKAVQL KGISSHGLQW YGEYVNKDSL KWLRDDWGIT  60
VFRAAMYTAD GGYIDNPSVK NKVKEAVEAA KELGIYVIID WHILNDGNPN QNKEKAKEFF  120
KEMSSLYGNT PNVIYEIANE PNGDVNWKRD IKPYAEEVIS VIRKNDPDNI IIVGTGTWSQ  180
DVNDAADDQL KDANVMYALH FYAGTHGQFL RDKANYALSK GAPIFVTEWG TSDASGNGGV  240
FLDQSREWLK YLDSKTISWV NWNLSDKQES SSALKPGASK TGGWRLSDLS ASGTFVRENI  300
LGTKDSTKDI PETPSKDKPT QENGISVQYR AGDGSMNSNQ IRPQLQIKNN GNTTVDLKDV  360
TARYWYKAKN KGQNFDCDYA QIGCGNVTHK FVTLHKPKQG ADTYLELGFK NGTLAPGAST  420
```

```
GNIQLRLHND DWSNYAQSGD YSFFKSNTFK TTKKITLYDQ GKLIWGTEPN          470

SEQ ID NO: 43          moltype = AA  length = 214
FEATURE                Location/Qualifiers
source                 1..214
                       mol_type = protein
                       organism = Bacillus subtilis
SEQUENCE: 43
QTGGSFFDPF NGYNSGFWQK ADGYSNGNMF NCTWRANNVS MTSLGEMRLA LTSPAYNKFD  60
CGENRSVQTY GYGLYEVRMK PAKNTGIVSS FFTYTGPTDG TPWDEIDIEF LGKDTTKVQF  120
NYYTNGAGNH EKIVDLGFDA ANAYHTYAFD WQPNSIKWYV DGQLKHTATN QIPTTPGKIM  180
MNLWNGTGVD EWLGSYNGVN PLYAHYDWVR YTKK                          214

SEQ ID NO: 44          moltype = AA  length = 839
FEATURE                Location/Qualifiers
source                 1..839
                       mol_type = protein
                       organism = Bacillus circulans
SEQUENCE: 44
AETAGTTITS MSYFSTADGP IITKSGVGQA SYGFVMPIFN GGSATWNDVA QDLGVKVKVN  60
GSWVDIDSVS SFVYNQNWGH WNDGGFTGYW FTLSATTEIQ LYSKANEVTL EYSLVFQNIN  120
KTTITAMTPT QGPQITAGFT GGAGFTYPIF NHDPAITYAA VADDLKVYVK PVNSSQWIDI  180
DNNAASGWIY DQNFGQFTDG GGGYWFNVTE SINVKLESKT SSTNIVYTIS FNEPVRNSYV  240
LTPYEGTTFT ADASGAIGIP LPKIDGGAPI GTELGNFVYQ ININGQWVDL DNSSQSGFVY  300
SANGYNNMSA ANQWGYWADH IYGLWFQPIQ VDMQIRIGYP LNGQAGGSVG SNFVNYTLIG  360
NPDAPRPDVN DQEDIPIGTP NDSAIEGMNL IWQDEFNGTA LDQSKWNYET GYYLNDDPNT  420
WGWGNSELQH YTDRAQNVFV QDGKLNIKAL NEPKSFPQDP SRYAQYSSGK INTKDHFSLK  480
YGRVDFRAKL PTGNGIWPAL WMLPQDNVYG TWASSGEIDV MEAKGRLPGS TSGAVHFGGQ  540
WPTNRYLSGE YHFPEGQTFA NDYHVYSVVW EEDNIKWYVD GKFFFKVTRD QWYSAAAPNN  600
PNAPFDQPFY LIMNLAIGGT FDGGRTPDPS DIPATMQVDY VRVYKEGEGG GQNPGNVPVT  660
GVTVNPTTAQ VEVGQSVQLN ASVAPSNATN KQVTWSVSGS SIASVSPNGL VTGLAQGTTT  720
VTATTADGNK AASATITVAP APSTVIVIGD EVKGLKKIGD DLLFYVNGAT FADLHYKVNN  780
GGQLNVAMAP TGNGNYTYPV HNLKHGDTVE YFFTYNPGQG ALDTPWQTYV HGVTQGTPE   839

SEQ ID NO: 45          moltype = AA  length = 644
FEATURE                Location/Qualifiers
source                 1..644
                       mol_type = protein
                       organism = Bacillus circulans
SEQUENCE: 45
AGTTVTSMEY FSPADGPVIS KSGVGKASYG FVMPKFNGGS ATWNDVYSDV GVNVKVGNNW  60
VDIDQAGGYI YNQNWGHWSD GGFNGYWFTL SATTEIQLYS KANGVKLEYQ LVFQNINKTT  120
ITAMNPTQGP QITASFTGGA GFTYPTFNND SAVTYEAVAD DLKVYVKPVN SSSWIDIDNN  180
AASGWIYDHN FGQFTDGGGG YWFNVTESIN VKLESKTSSA NLVYTITFNE PTRNSYVITP  240
YEGTTFTADA NGSIGIPLPK IDGGAPIAKE LGNFVYQINI NGQWVDLSNS SQSKFAYSAN  300
GYNNMSDANQ WGYWADYIYG LWFQPIQENM QIRIGYPLNG QAGGNIGNNF VNYTFIGNPN  360
APRPDVSDQE DISIGTPTDP AIAGMNLIWQ DEFNGTTLDT SKWNYETGYY LNNDPATWGW  420
GNAELQHYTN STQNVYVQDG KLNIKAMNDS KSFPQDPNRY AQYSSGKINT KDKLSLKYGR  480
VDFRAKLPTG DGVWPALWML PKDSVYGTWA ASGEIDVMEA RGRLPGSVSG TIHFGGQWPV  540
NQSSGGDYHF PEGQTFANDY HVYSVVWEED NIKWYVDGKF FYKVTNQQWY STAAPNNPNA  600
PFDEPFYLIM NLAVGGNFDG GRTPNASDIP ATMQVDYVRV YKEQ                644

SEQ ID NO: 46          moltype = AA  length = 442
FEATURE                Location/Qualifiers
source                 1..442
                       mol_type = protein
                       organism = Bacillus subtilis
SEQUENCE: 46
MFGYSMVQMV RANAHKLDWP LRETVLQLYK PFKWTPCFLH KFFETKLQNR KKMSVIIEFE  60
EGCHETGFQM AGEVLQKEKR SKLKSRFNKI NCCSAEVTPS ALHSLLSECS NIRKVYLNRE  120
VKALLDTATE ASHAKEVVRN GQTLTGKGVT VAVVDTGIYP HPDLEGRIIG FADMVNQKTE  180
PYDDNGHGTH CAGDVASSGA SSSGQYRGPA PEANLIGVKV LNKQGSGTLA DIIEGVEWCI  240
QYNEDNPDEP IDIMSMSLGG DALRYDHEQE DPLVRAVEEA WSAGIVVCVA AGNSGPDSQT  300
IASPGVSEKV ITVGALDDNN TASSDDDTVA SFSSRGPTVY GKEKPDILAP GVNIISLRSP  360
NSYIDKLQKS SRVGSQYFTM SGTSMATPIC AGIAALILQQ NPDLTPDEVK ELLKNGTDKW  420
KDEDPNIYGA GAVNAENSVP GQ                                        442

SEQ ID NO: 47          moltype = AA  length = 778
FEATURE                Location/Qualifiers
source                 1..778
                       mol_type = protein
                       organism = Bacillus subtilis
SEQUENCE: 47
APASSKTSAD LEKAEVFGDI DMTTSKKTTV IVELKEKSLA EAKEAGESQS KSKLKTARTK  60
AKNKAIKAVK NGKVNREYEQ VFSGFSMKLP ANEIPKLLAV KDVKAVYPNV TYKTDNMKDK  120
DVTISEDAVS PQMDDSAPYI GANDAWDLGY TGKGIKVAII DTGVEYNHPD LKKNFGQYKG  180
YDFVDNDYDP KETPTGDPRG EATDHGTHVA GTVAANGTIK GVAPDATLLA YRVLGPGGSG  240
TTENVIAGVE RAVQDGADVM NLSLGNSLNN PDWATSTALD WAMSEGVVAV TSNGNSGPNG  300
WTVGSPGTSR EAISVGATQL PLNEYAVTFG SYSSAKVMGY NKEDDVKALN NKEVELVEAG  360
```

```
IGEAKDFEGK DLTGKVAVVK RGSIAFVDKA DNAKKAGAIG MVVYNNLSGE IEANVPGMSV  420
PTIKLSLEDG EKLVSALKAG ETKTTFKLTV SKALGEQVAD FSSRGPVMDT WMIKPDISAP  480
GVNIVSTIPT HDPDHPYGYG SKQGTSMASP HIAGAVAVIK QAKPKWSVEQ IKAAIMNTAV  540
TLKDSDGEVY PHNAQGAGSA RIMNAIKADS LVSPGSYSYG TFLKENGNET KNETFTIENQ  600
SSIRKSYTLE YSFNGSGIST SGTSRVVIPA HQTGKATAKV KVNTKKTKAG TYEGTVIVRE  660
GGKTVAKVPT LLIVKEPDYP RVTSVSVSEG SVQGTYQIET YLPAGAEELA FLVYDSNLDF  720
AGQAGIYKNQ DKGYQYFDWD GTINGGTKLP AGEYYLLAYA ANKGKSSQVL TEEPFTVE    778

SEQ ID NO: 48          moltype = AA  length = 373
FEATURE                Location/Qualifiers
source                 1..373
                       mol_type = protein
                       organism = Engyodontium album
SEQUENCE: 48
MMAPAVEQRS EAAPLIEARG EMVANKYIVK FKEGSALSAL DAAMEKISGK PDHVYKNVFS  60
GFAATLDENM VRVLRAHPDV EYIEQDAVVT INAAQTNAPW GLARISSTSP GTSTYYYDES  120
AGQGSCVYVI DTGIEASHPE FEGRAQMVKT YYYSSRDGNG HGTHCAGTVG SRTYGVAKKT  180
QLFGVKVLDD NGSGQYSTII AGMDFVASDK NNRNCPKGVV ASLSLGGGYS SSVNSAAARL  240
QSSGVMVAVA AGNNNADARN YSPASEPSVC TVGASDRYDR RSSFSNYGSV LDIFGPGTSI  300
LSTWIGGSTR SISGTSMATP HVAGLAAYLM TLGKTTAASA CRYIADTANK GDLSNIPFGT  360
VNLLAYNNYQ AVD                                                    373

SEQ ID NO: 49          moltype = AA  length = 24
FEATURE                Location/Qualifiers
source                 1..24
                       mol_type = protein
                       organism = Bacillus thuringiensis
SEQUENCE: 49
MKKKVLALAA AITLVAPLQS VAFA                                       24

SEQ ID NO: 50          moltype = AA  length = 28
FEATURE                Location/Qualifiers
source                 1..28
                       mol_type = protein
                       organism = Bacillus thuringiensis
SEQUENCE: 50
MKGKLLKGVL SLGVGLGALY SGTSAQAE                                   28

SEQ ID NO: 51          moltype = AA  length = 24
FEATURE                Location/Qualifiers
source                 1..24
                       mol_type = protein
                       organism = Bacillus cereus
SEQUENCE: 51
MKKKVLALAA AITVVAPLQS VAFA                                       24

SEQ ID NO: 52          moltype = AA  length = 29
FEATURE                Location/Qualifiers
source                 1..29
                       mol_type = protein
                       organism = Clostridium perfringens
SEQUENCE: 52
MKRKICKALI CATLATSLWA GASTKVYAW                                  29

SEQ ID NO: 53          moltype = AA  length = 29
FEATURE                Location/Qualifiers
source                 1..29
                       mol_type = protein
                       organism = Streptomyces chromofuscus
SEQUENCE: 53
MLAGPLAAAL PARATTGTPA FLHGVASGD                                  29

SEQ ID NO: 54          moltype = AA  length = 31
FEATURE                Location/Qualifiers
source                 1..31
                       mol_type = protein
                       organism = Bacillus subtilis
SEQUENCE: 54
MKFVKRRIIA LVTILMLSVT SLFALQPSAK A                               31

SEQ ID NO: 55          moltype = AA  length = 28
FEATURE                Location/Qualifiers
source                 1..28
                       mol_type = protein
                       organism = Caldicellulosiruptor saccharolyticus
SEQUENCE: 55
MCENLEMLNL SLAKTYKDYF KIGAAVTA                                   28

SEQ ID NO: 56          moltype = AA  length = 28
```

```
FEATURE                Location/Qualifiers
source                 1..28
                       mol_type = protein
                       organism = Bacillus subtilis
SEQUENCE: 56
MFKFKKNFLV GLSAALMSIS LFSATASA                                     28

SEQ ID NO: 57          moltype = AA  length = 26
FEATURE                Location/Qualifiers
source                 1..26
                       mol_type = protein
                       organism = Bacillus subtilis
SEQUENCE: 57
MRKKCSVCLW ILVLLLSCLS GKSAYA                                       26

SEQ ID NO: 58          moltype = AA  length = 27
FEATURE                Location/Qualifiers
source                 1..27
                       mol_type = protein
                       organism = Bacillus stearothermophilus
SEQUENCE: 58
MKLKKKMLTL LLTASMSFGL FGATSSA                                      27

SEQ ID NO: 59          moltype = AA  length = 35
FEATURE                Location/Qualifiers
source                 1..35
                       mol_type = protein
                       organism = Bacillus subtilis
SEQUENCE: 59
MKISMQKADF WKKAAISLLV FTMFFTLMMS ETVFA                             35

SEQ ID NO: 60          moltype = AA  length = 29
FEATURE                Location/Qualifiers
source                 1..29
                       mol_type = protein
                       organism = Bacillus subtilis
SEQUENCE: 60
MKRSISIFIT CLLITLLTMG GMIASPASA                                    29

SEQ ID NO: 61          moltype = AA  length = 28
FEATURE                Location/Qualifiers
source                 1..28
                       mol_type = protein
                       organism = Bacillus subtilis
SEQUENCE: 61
MPYLKRVLLL LVTGLFMSLF AVTATASA                                     28

SEQ ID NO: 62          moltype = AA  length = 38
FEATURE                Location/Qualifiers
source                 1..38
                       mol_type = protein
                       organism = Bacillus circulans
SEQUENCE: 62
MKRSQTSEKR YRQRVLSLFL AVVMLASIGL LPTSKVQA                          38

SEQ ID NO: 63          moltype = AA  length = 38
FEATURE                Location/Qualifiers
source                 1..38
                       mol_type = protein
                       organism = Bacillus circulans
SEQUENCE: 63
MKPSHFTEKR FMKKVLGLFL VVVMLASVGV LPTSKVQA                          38

SEQ ID NO: 64          moltype = AA  length = 28
FEATURE                Location/Qualifiers
source                 1..28
                       mol_type = protein
                       organism = Bacillus subtilis
SEQUENCE: 64
MKKGIIRFLL VSFVLFFALS TGITGVQA                                     28

SEQ ID NO: 65          moltype = AA  length = 32
FEATURE                Location/Qualifiers
source                 1..32
                       mol_type = protein
                       organism = Bacillus subtilis
SEQUENCE: 65
MKKFPKKLLP IAVLSSIAFS SLASGSVPEA SA                                32
```

```
SEQ ID NO: 66          moltype = AA  length = 41
FEATURE                Location/Qualifiers
source                 1..41
                       mol_type = protein
                       organism = Bacillus subtilis
SEQUENCE: 66
MKKMSLFQNM KSKLLPIAAV SVLTAGIFAG AELQQTEKAS A                        41

SEQ ID NO: 67          moltype = AA  length = 26
FEATURE                Location/Qualifiers
source                 1..26
                       mol_type = protein
                       organism = Bacillus subtilis
SEQUENCE: 67
MKVPKTMLLS TAAGLLLSLT ATSVSA                                         26

SEQ ID NO: 68          moltype = AA  length = 25
FEATURE                Location/Qualifiers
source                 1..25
                       mol_type = protein
                       organism = Bacillus subtilis
SEQUENCE: 68
MKKIMSAFVG MVLLTIFCFS PQASA                                          25

SEQ ID NO: 69          moltype = AA  length = 46
FEATURE                Location/Qualifiers
source                 1..46
                       mol_type = protein
                       organism = Bacillus thuringiensis
SEQUENCE: 69
MPLNISFILK GEMAMRSQKF TLLLLSLLLF LPLFLTNFIT PNLALA                   46

SEQ ID NO: 70          moltype = AA  length = 27
FEATURE                Location/Qualifiers
source                 1..27
                       mol_type = protein
                       organism = Bacillus thuringiensis
SEQUENCE: 70
MLNKFKFFCC ILVMFLLLPL SPFQTQA                                        27

SEQ ID NO: 71          moltype = AA  length = 43
FEATURE                Location/Qualifiers
source                 1..43
                       mol_type = protein
                       organism = Bacillus thuringiensis
SEQUENCE: 71
MNKIIHLDNF LYRSVNMLNK FKFFCCILVM FLLLPLSPFQ TQA                      43

SEQ ID NO: 72          moltype = AA  length = 23
FEATURE                Location/Qualifiers
source                 1..23
                       mol_type = protein
                       organism = Bacillus pseudomycoides
SEQUENCE: 72
MEYKPLIMGY LHTWSKGFIG GYE                                            23

SEQ ID NO: 73          moltype = AA  length = 25
FEATURE                Location/Qualifiers
source                 1..25
                       mol_type = protein
                       organism = Bacillus thuringiensis
SEQUENCE: 73
MKKKVLALAA AITLVAPLQS VAFAH                                          25

SEQ ID NO: 74          moltype = AA  length = 207
FEATURE                Location/Qualifiers
source                 1..207
                       mol_type = protein
                       organism = Bacillus subtilis
SEQUENCE: 74
AYDDLHEGYA TYTGSGYSGG AFLLDPIPSD MEITAINPAD LNYGGVKAAL AGSYLEVEGP  60
KGKTTVYVTD LYPEGARGAL DLSPNAFRKI GNMKDGKINI KWRVVKAPIT GNFTYRIKEG  120
SSRWWAAIQV RNHKYPVMKM EYEKDGKWIN MEKMDYNHFV STNLGTGSLK VRMTDIRGKV  180
VKDTIPKLPE SGTSKAYTVP GHVQFPE                                        207

SEQ ID NO: 75          moltype = DNA  length = 711
FEATURE                Location/Qualifiers
source                 1..711
                       mol_type = genomic DNA
```

```
                         organism = Bacillus mycoides
SEQUENCE: 75
ggagcacgcc gcgtgagtgn ngaaggcttt cgggtcgtaa aactctgttg ttagggaaga  60
acaagtgcta gttgaataag ctggcacctt gacggtacct aaccagaaag ccacggctaa  120
ctacgtgcca gcagccgcgg taatacgtag gtggcaagcg ttatccggaa ttattgggcg  180
taaagcgcgc gcaggtggtt tcttaagtct gatgtgaaag cccacggctc aaccgtggag  240
ggtcattgga aactgggaga cttgagtgca gaagaggaaa gtggaattcc atgtgtagcg  300
gtgaaatgcg tagagatatg gaggaacacc agtggcgaag gcgactttct ggtctgtaac  360
tgacactgag gcgcgaaagc gtggggagca aacaggatta gataccctgg tagtccacgc  420
cgtaaacgat gagtgctaag tgttagaggg tttccgccct ttagtgctga agttaacgca  480
ttaagcactc cgcctgggga gtacggccgc aaggctgaaa ctcaaaggaa ttgacggggg  540
cccgcacaag cggtggagca tgtggtttaa ttcgaagcaa cgcgaagaac cttaccaggt  600
cttgacatcc tctgaaaact ctagagatag agcttctcct tcgggagcag agtgacaggt  660
ggtgcatggt tgtcgtcagc tcgtgtcgtg agatgttggg ttaagtcccg c           711

SEQ ID NO: 76            moltype = DNA  length = 719
FEATURE                  Location/Qualifiers
source                   1..719
                         mol_type = genomic DNA
                         organism = Bacillus mycoides
SEQUENCE: 76
aaagtctgac ggagcacgcc gcgtgagtga tgaaggcttt cgggtcgtaa aactctgttg  60
ttagggaaga acaagtgcta gttgaataag ctggcacctt gacggtacct aaccagaaag  120
ccacggctaa ctacgtgcca gcagccgcgg taatacgtag gtggcaagcg ttatccggaa  180
ttattgggcg taaagcgcgc gcaggtggtt tcttaagtct gatgtgaaag cccacggctc  240
aaccgtggag ggtcattgga aactgggaga cttgagtgca gaagaggaaa gtggaattcc  300
atgtgtagcg gtgaaatgcg tagagatatg gaggaacacc agtggcgaag gcgactttct  360
ggtctgtaac tgacactgag gcgcgaaagc gtggggagca aacaggatta gataccctgg  420
tagtccacgc cgtaaacgat gagtgctaag tgttagaggg tttccgccct ttagtgctga  480
agttaacgca ttaagcactc cgcctgggga gtacggccgc aaggctgaaa ctcaaaggaa  540
ttgacggggg cccgcacaag cggtggagca tgtggtttaa ttcgaagcaa cgcgaagaac  600
cttaccaggt cttgacatcc tctgaaaacn ctagagatan nncttctcct tcgggagcag  660
agtgacaggt ggtgcatggt tgtcgtcagc tcgtgtcgtg agatgttggg ttaagtccc   719

SEQ ID NO: 77            moltype = DNA  length = 709
FEATURE                  Location/Qualifiers
source                   1..709
                         mol_type = genomic DNA
                         organism = Bacillus mycoides
SEQUENCE: 77
ggagcacgcc gcgtgagtga tgaaggcttt cgggtcgtaa aactctgttg ttagggaaga  60
acaagtgcta gttgaataag ctggcacctt gacggtacct aaccagaaag ccacggctaa  120
ctacgtgcca gcagccgcgg taatacgtag gtggcaagcg ttatccggaa ttattgggcg  180
taaagcgcgc gcaggtggtt tcttaagtct gatgtgaaag cccacggctc aaccgtggag  240
ggtcattgga aactgggaga cttgagtgca gaagaggaaa gtggaattcc atgtgtagcg  300
gtgaaatgcg tagagatatg gaggaacacc agtggcgaag gcgactttct ggtctgtaac  360
tgacactgag gcgcgaaagc gtggggagca aacaggatta gataccctgg tagtccacgc  420
cgtaaacgat gagtgctaag tgttagaggg tttccgccct ttagtgctga agttaacgca  480
ttaagcactc cgcctgggga gtacggccgc aaggctgaaa ctcaaaggaa ttgacggggg  540
cccgcacaag cggtggagca tgtggtttaa ttcgaagcaa cgcgaagaac cttaccaggt  600
cttgacatcc tctgacaacc ctagagatag ggcttcccct tcgggggcag agtgacaggt  660
ggtgcatggt tgtcgtcagc tcgtgtcgtg agatgttggg ttaagtccc             709

SEQ ID NO: 78            moltype = DNA  length = 713
FEATURE                  Location/Qualifiers
source                   1..713
                         mol_type = genomic DNA
                         organism = Bacillus cereus
SEQUENCE: 78
gganccaacgc cgcgtgagtg angaaggctt tcgggtcgta aaactctgtt gttagggaag  60
aacaagtgct agttgaataa gctggcacct tgacggtacc taaccagaaa gccacggcta  120
actacgtgcc agcagccgcg gtaatacgta ggtggcaagc gttatccgga attattgggc  180
gtaaagcgcg cgcaggtggt ttcttaagtc tgatgtgaaa gcccacggct caaccgtgga  240
gggtcattgg aaactgggag acttgagtgc agaagaggaa agtggaattc catgtgtagc  300
ggtgaaatgc gtagagatat ggaggaacac cagtggcgaa ggcgactttc tggtctgtaa  360
ctgacactga ggcgcgaaag cgtggggagc aaacaggatt agataccctg gtagtccacg  420
ccgtaaacga tgagtgctaa gtgttagagg gtttccgccc tttagtgctg aagttaacgc  480
attaagcact ccgcctgggg agtacggccg caaggctgaa actcaaagga attgacgggg  540
gcccgcacaa gcggtggagc atgtggttta attcgaagca acgcgaagaa ccttaccagg  600
tcttgacatc ctctgaaaac tctagagata gagcttctcc ttcgggagca gagtgacagg  660
tggtgcatgg ttgtcgtcag ctcgtgtcgt gagatgntgg gttaagtccc gca         713

SEQ ID NO: 79            moltype = DNA  length = 686
FEATURE                  Location/Qualifiers
source                   1..686
                         mol_type = genomic DNA
                         organism = Bacillus cereus
SEQUENCE: 79
aaggctttcg ggtcgtaaaa ctctgttgtt agggaagaac aagtgctagt tgaataagct  60
```

```
ggcaccttga cggtacctaa ccagaaagcc acggctaact acgtgccagc agccgcggta  120
atacgtaggt ggcaagcgtt atccggaatt attgggcgta aagcgcgcgc aggtggtttc  180
ttaagtctga tgtgaaagcc cacggctcaa ccgtggaggg tcattggaaa ctgggagact  240
tgagtgcaga agaggaaagt ggaattccat gtgtagcggt gaaatgcgta gagatatgga  300
ggaacaccag tggcgaaggc gactttctgg tctgtaactg acactgaggc gcgaaagcgt  360
ggggagcaaa caggattaga taccctggta gtccacgccg taaacgatga gtgctaagtg  420
ttagagggtt tccgcccttt agtgctgaag ttaacgcatt aagcactccg cctggggagt  480
acggccgcaa ggctgaaact caaaggaatt gacgggggcc cgcacaagcg gtggagcatg  540
tggtttaatt cgaagcaacg cgaagaacct taccaggtct tgacatcctc tgaaaaccct  600
agagataggg cttctccttc gggagcagag tgacaggtgg tgcatggttg tcgtcagctc  660
gtgtcgtgag atgttgggtt aagtcc                                      686

SEQ ID NO: 80          moltype = DNA  length = 717
FEATURE                Location/Qualifiers
source                 1..717
                       mol_type = genomic DNA
                       organism = Bacillus mycoides
SEQUENCE: 80
gtctgangga ncacgccgcg tgagtgatga aggctttcgg gtcgtaaaac tctgttgtta  60
gggaagaaca agtgctagtt gaataagctg gcaccttgac ggtacctaac cagaaagcca  120
cggctaacta cgtgccagca gccgcggtaa tacgtaggtg gcaagcgtta tccggaatta  180
ttgggcgtaa agcgcgcgca ggtggtttct taagtctgat gtgaaagccc acggctcaac  240
cgtggagggt cattggaaac tgggagactt gagtgcagaa gaggaaagtg gaattccatg  300
tgtagcggtg aaatgcgtag agatatggag gaacaccagt ggcgaaggcg actttctggt  360
ctgtaactga cactgaggcg cgaaagcgtg gggagcaaac aggattagat accctggtag  420
tccacgccgt aaacgatgag tgctaagtgt tagagggttt ccgcccttta gtgctgaagt  480
taacgcatta agcactccgc ctggggagta cggccgcaag gctgaaactc aaaggaattg  540
acgggggccc gcacaagcgg tggagcatgt ggtttaattc gaagcaacgc gaagaacctt  600
accaggtctt gacatcctct gacaacccta gagatagggc ttccccttcg gggcagagt   660
gacaggtggt gcatggttgt cgtcagctcg tgtcgtgaga tgttgggtta agtcccg     717

SEQ ID NO: 81          moltype = DNA  length = 720
FEATURE                Location/Qualifiers
source                 1..720
                       mol_type = genomic DNA
                       organism = Bacillus cereus
SEQUENCE: 81
tntgacggan cacgccgcgt gagtgatgaa ggctttcggg tcgtaaaact ctgttgttag  60
ggaagaacaa gtgctagttg aataagctgg caccttgacg gtacctaacc agaaagccac  120
ggctaactac gtgccagcag ccgcggtaat acgtaggtgg caagcgttat ccggaattat  180
tgggcgtaaa gcgcgcgcag gtggtttctt aagtctgatg tgaaagccca cggctcaacc  240
gtggagggtc attggaaact gggagacttg agtgcagaag aggaaagtgg aattccatgt  300
gtagcggtga aatgcgtaga gatatggagg aacaccagtg gcgaaggcga ctttctggtc  360
tgtaactgac actgaggcgc gaaagcgtgg ggagcaaaca ggattagata ccctggtagt  420
ccacgccgta aacgatgagt gctaagtgtt agagggtttc cgccctttag tgctgaagtt  480
aacgcattaa gcactccgcc tggggagtac ggccgcaagg ctgaaactca aaggaattga  540
cgggggcccg cacaagcggt ggagcatgtg gtttaattcg aagcaacgcg aagaacctta  600
ccaggtcttg acatcctctg aaaaccctag agatagggct tctccttcgg gagcagagtg  660
acaggtggtg catggttgtc gtcagctcgt gtcgtgagat gttgggttaa gtcccgcaac  720

SEQ ID NO: 82          moltype = DNA  length = 616
FEATURE                Location/Qualifiers
source                 1..616
                       mol_type = genomic DNA
                       organism = Bacillus thuringiensis
SEQUENCE: 82
ctttcnggnc gnaaaactct gttgttangg aanaacaant gctanttgaa taagctggcg  60
ccttgacggt acctaaccnn aaagccncgg ctaactacgt gccancagcc gcggtaatac  120
gtnngtggca agcgttatcc ggaattattg ggcgtaaagc gcgcgcaggt ggtttcttaa  180
ntctgatgtg annncccacg gctcnnccgt ggagggtcat tggaaactgg ganacttgag  240
tgcagaagag gaaagtggaa ttccatgtgt ancggtgaaa tgcgtanaga tatggangaa  300
cnccagtggc gaangcgact ttctggtctg taactgacac tgaggcgcga aagcgtgggg  360
agcaaacang attanatacc ctggnnntcc acgccgtana cnatgagtgc taagtgttan  420
agggtttccn ccctttagtg ctgaagttaa cgcattannc actccncctg gggagtacgg  480
ccgcaaggct gaaactcana ggaattgacn ggngcccnca cnngcggtgg agcatgtggt  540
ttaattcnaa gcaacncnaa naaccttacc nngtcttgac atcctctgaa aannntnnag  600
atagggcttc tccntc                                                 616

SEQ ID NO: 83          moltype = DNA  length = 703
FEATURE                Location/Qualifiers
source                 1..703
                       mol_type = genomic DNA
                       organism = Bacillus cereus
SEQUENCE: 83
cacgccgcgt gagtgatgaa ggctttcggg tcgtaaaact ctgttgttag ggaagaacaa  60
gtgctagttg aataagctgg caccttgacg gtacctaacc agaaagccac ggctaactac  120
gtgccagcag ccgcggtaat acgtaggtgg caagcgttat ccggaattat tgggcgtaaa  180
gcgcgcgcag gtggtttctt aagtctgatg tgaaagccca cggctcaacc gtggagggtc  240
attggaaact gggagacttg agtgcagaag aggaaagtgg aattccatgt gtagcggtga  300
```

```
aatgcgtaga gatatggagg aacaccagtg gcgaaggcga ctttctggtc tgtaactgac  360
actgaggcgc gaaagcgtgg ggagcaaaca ggattagata ccctggtagt ccacgccgta  420
aacgatgagt gctaagtgtt agagggtttc cgccctttag tgctgaagtt aacgcattaa  480
gcactccgcc tggggagtac ggccgcaagg ctgaaactca aaggaattga cgggggcccg  540
cacaagcggt ggagcatgtg gtttaattcg aagcaacgcg aagaacctta ccaggtcttg  600
acatcctctg aaaaccctag agatagggct tctccttcgg gagcagagtg acaggtggtg  660
catggttgtc gtcagctcgt gtcgtgagat gttgggttaa ntc                   703

SEQ ID NO: 84          moltype = DNA  length = 717
FEATURE                Location/Qualifiers
source                 1..717
                       mol_type = genomic DNA
                       organism = Bacillus thuringiensis
SEQUENCE: 84
ctganggnnc aacgccgcgt gagtgatgaa ggctttcggg tcgtaaaact ctgttgttag  60
ggaagaacaa gtgctagttg aataagctgg caccttgacg gtacctaacc agaaagccac  120
ggctaactac gtgccagcag ccgcggtaat acgtaggtgg caagcgttat ccggaattat  180
tgggcgtaaa gcgcgcgcag gtggtttctt aagtctgatg tgaaagccca cggctcaacc  240
gtggagggtc attggaaact gggagacttg agtgcagaag aggaaagtgg aattccatgt  300
gtagcggtga aatgcgtaga gatatggagg aacaccagtg gcgaaggcga ctttctggtc  360
tgtaactgac actgaggcgc gaaagcgtgg ggagcaaaca ggattagata ccctggtagt  420
ccacgccgta aacgatgagt gctaagtgtt agagggtttc cgccctttag tgctgaagtt  480
aacgcattaa gcactccgcc tggggagtac ggccgcaagg ctgaaactca aaggaattga  540
cgggggcccg cacaagcggt ggagcatgtg gtttaattcg aagcaacgcg aagaacctta  600
ccaggtcttg acatcctctg aaaaccctag agatagggct tctccttcgg gagcagagtg  660
acaggtggtg catggttgtc gtcagctcgt gtcgtgagat gttgggttaa gtcccgc     717

SEQ ID NO: 85          moltype = DNA  length = 712
FEATURE                Location/Qualifiers
source                 1..712
                       mol_type = genomic DNA
                       organism = Bacillus megaterium
SEQUENCE: 85
ggancacgcc gcgtgagtga tgaaggcttt cgggtcgtaa aactctgttg ttagggaaga  60
acaagtacna gagtaactgc tngtaccttg acggtaccta accagaaagc cacggctaac  120
tacgtgccag cagccgcggt aatacgtagg tggcaagcgt tatccggaat tattgggcgt  180
aaagcgcgcg caggcggttt cttaagtctg atgtgaaagc ccacggctca accgtggagg  240
gtcattggaa actggggaac ttgagtgcag aagagaaaag cggaattcca cgtgtagcgg  300
tgaaatgcgt agagatgtgg aggaacacca gtggcgaagg cggctttttg gtctgtaact  360
gacgctgagg cgcgaaagcg tggggagcaa acaggattag ataccctggt agtccacgcc  420
gtaaacgatg agtgctaagt gttagagggt ttccgccctt tagtgctgca gctaacgcat  480
taagcactcc gcctggggag tacggtcgca agactgaaac tcaaaggaat tgacgggggc  540
ccgcacaagc ggtggagcat gtggtttaat tcgaagcaac gcgaagaacc ttaccaggtc  600
ttgacatcct ctgacaactc tagagataga gcgttcccct tcgggggaca gagtgacagg  660
tggtgcatgg ttgtcgtcag ctcgtgtcgt gagatgttgg gttaagtccc gc          712

SEQ ID NO: 86          moltype = DNA  length = 714
FEATURE                Location/Qualifiers
source                 1..714
                       mol_type = genomic DNA
                       organism = Bacillus sp.
SEQUENCE: 86
ggancacgcc gcgtgnnnng nngaaggttt tcggatcgta aagctctgtt gttagggaag  60
aacaagtgca agagtaactg cttgcacctt gacggtacct aaccagaaag ccacggctaa  120
ctacgtgcca gcagccgcgg taatacgtag gtggcaagcg ttgtccggaa ttattgggcg  180
taaagggctc gcaggcggtt tcttaagtct gatgtgaaag cccccggctc aaccggggag  240
ggtcattgga aactgggaaa cttgagtgca gaagaggaga gtggaattcc acgtgtagcg  300
gtgaaatgcg tagagatgtg gaggaacacc agtggcgaag gcgactctct ggtctgtaac  360
tgacgctgag gagcgaaagc gtggggagcg aacaggatta gataccctgg tagtccacgc  420
cgtaaacgat gagtgctaag tgttaggggg tttccgcccc ttagtgctgc agctaacgca  480
ttaagcactc cgcctgggga gtacggtcgc aagactgaaa ctcaaaggaa ttgacggggg  540
cccgcacaag cggtggagca tgtggtttaa ttcgaagcaa cgcgaagaac cttaccaggt  600
cttgacatcc tctgacaacc ctagagatag ggctttccct tcggggacag agtgacaggt  660
ggtgcatggt tgtcgtcagc tcgtgtcgtg agatgttggg ttaagtcccg caac        714

SEQ ID NO: 87          moltype = DNA  length = 718
FEATURE                Location/Qualifiers
source                 1..718
                       mol_type = genomic DNA
                       organism = Bacillus circulans
SEQUENCE: 87
aagtctgang gancacgccg cgtgagtgat gaaggttttc ggatcgtaaa actctgttgt  60
tagggaagaa caagtacaag agtaactgct tgtaccttga cggtacctaa ccagaaagcc  120
acggctaact acgtgccagc agccgcggta atacgtaggt ggcaagcgtt gtccggaatt  180
attgggcgta aagcgcgcgc aggcggtcct ttaagtctga tgtgaaagcc cacggctcaa  240
ccgtggaggg tcattggaaa ctggggaact tgagtgcaga agagaagagt ggaattccac  300
gtgtagcggt gaaatgcgta gagatgtgga ggaacaccag tggcgaaggc gactctttgg  360
tctgtaactg acgctgaggc gcgaaagcgt ggggagcaaa caggattaga taccctggta  420
gtccacgccg taaacgatga gtgctaagtg ttagagggtt tccgcccttt agtgctgcag  480
```

```
caaacgcatt aagcactccg cctggggagt acggccgcaa ggctgaaact caaaggaatt  540
gacgggggcc cgcacaagcg gtggagcatg tggtttaatt cgaagcaacg cgaagaacct  600
taccaggtct tgacatcctc tgacactcct agagatagga cgttcccctt cgggggacag  660
agtgacaggt ggtgcatggt tgtcgtcagc tcgtgtcgtg agatgttggg ttaagtcc    718

SEQ ID NO: 88          moltype = DNA  length = 718
FEATURE                Location/Qualifiers
source                 1..718
                       mol_type = genomic DNA
                       organism = Bacillus subtilis
SEQUENCE: 88
gtctgnngga ncacgccgcg tgagtgatga aggttttcgg atcgtaaagc tctgttgtta  60
gggaagaaca agtaccgttc gaatagggcg gtaccttgac ggtacctaac cagaaagcca  120
cggctaacta cgtgccagca gccgcggtaa tacgtaggtg gcaagcgttg tccggaatta  180
ttgggcgtaa agggctcgca ggcggtttct taagtctgat gtgaaagccc ccggctcaac  240
cggggagggt cattggaaac tggggaactt gagtgcagaa gaggagagtg gaattccacg  300
tgtagcggtg aaatgcgtag agatgtggag gaacaccagt ggcgaaggcg actctctggt  360
ctgtaactga cgctgaggag cgaaagcgtg gggagcgaac aggattagat accctggtag  420
tccacgccgt aaacgatgag tgctaagtgt tagggggttt ccgcccctta gtgctgcagc  480
taacgcatta agcactccgc ctggggagta cggtcgcaag actgaaactc aaaggaattg  540
acgggggccc gcacaagcgg tggagcatgt ggtttaattc gaagcaacgc gaagaacctt  600
accaggtctt gacatcctct gacaatccta gagataggac gtccccttcg gggcagagt   660
gacaggtggt gcatggttgt cgtcagctcg tgtcgtgaga tgttgggtta agtcccgc    718

SEQ ID NO: 89          moltype = DNA  length = 713
FEATURE                Location/Qualifiers
source                 1..713
                       mol_type = genomic DNA
                       organism = Lysinibacillus fusiformis
SEQUENCE: 89
ctgatggagc acgccgcgtg agtgaagaag gatttcggtt cgtaaaactc tgttgtaagg  60
gaagaacaag tacagtagta actggctgta ccttgacggt accttattag aaagccacgg  120
ctaactacgt gccagcagcc gcggtaatac gtaggtggca agcgttgtcc ggaattattg  180
ggcgtaaagc gcgcgcaggt ggtttcttaa gtctgatgtg aaagcccacg gctcaaccgt  240
ggagggtcat tggaaactgg gagacttgag tgcagaagag gatagtggaa ttccaagtgt  300
agcggtgaaa tgcgtagaga tttggaggaa caccagtggc gaaggcgact atctggtctg  360
taactgacac tgaggcgcga aagcgtgggg agcaaacagg attagatacc ctggtagtcc  420
acgccgtaaa cgatgagtgc taagtgttag gggtttccg ccccttagtg ctgcagctaa   480
cgcattaagc actccgcctg gggagtacgg tcgcaagact gaaactcaaa ggaattgacg  540
ggggcccgca caagcggtgg agcatgtggt ttaattcgaa gcaacgcgaa gaaccttacc  600
aggtcttgac atcccgttga ccactgtaga gatatggttt ccccttcggg ggcaacggtg  660
acaggtggtg catggttgtc gtcagctcgt gtcgtgagat gntgggttaa ntc         713

SEQ ID NO: 90          moltype = DNA  length = 715
FEATURE                Location/Qualifiers
source                 1..715
                       mol_type = genomic DNA
                       organism = Lysinibacillus sphaericus
SEQUENCE: 90
ctgatggagc ancgccgcgt gagtgaagaa ggttttcgga tcgtaaaact ctgttgtaag  60
ggaagaacaa gtacagtagt aactggctgt accttgacgg taccttatta gaaagccacg  120
gctaactacg tgccagcagc cgcggtaata cgtaggtggc aagcgttgtc cggaattatt  180
gggcgtaaag cgcgcgcagg cggtccttta agtctgatgt gaaagcccac ggctcaaccg  240
tggagggtca ttggaaactg gggacttga gtgcagaaga ggaaagtgga attccaagtg   300
tagcggtgaa atgcgtagag atttggagga acaccagtgg cgaaggcgac tttctggtct  360
gtaactgacg ctgaggcgcg aaagcgtggg gagcaaacag gattagatac cctggtagtc  420
cacgccgtaa acgatgagtg ctaagtgtta gggggtttcc gccccttagt gctgcagcta  480
acgcattaag cactccgcct ggggagtacg gtcgcaagac tgaaactcaa aggaattgac  540
gggggcccgc acaagcggtg gagcatgtgg tttaattcga agcaacgcga agaaccttac  600
caggtcttga catcccgttg accactgtag agatatagtt tccccttcgg gggcaacggt  660
gacaggtggt gcatggttgt cgtcagctcg tgtcgtgaga tgtngggtta antcc       715

SEQ ID NO: 91          moltype = DNA  length = 717
FEATURE                Location/Qualifiers
source                 1..717
                       mol_type = genomic DNA
                       organism = Bacillus aryabhattai
SEQUENCE: 91
ggnncaacgc cgcgtgagtg atgaaggctt tcgggtcgta aaactctgtt gttagggaag  60
aacaagtacg agagtaactg ctcgtacctt gacggtacct aaccagaaag ccacggctaa  120
ctacgtgcca gcagccgcgg taatacgtag gtggcaagcg ttatccggaa ttattgggcg  180
taaagcgcgc gcaggcggtt tcttaagtct gatgtgaaag cccacggctc aaccgtggag  240
ggtcattgga aactggggaa cttgagtgca gaagagaaaa gcggaattcc acgtgtagcg  300
gtgaaatgcg tagagatgtg gaggaacacc agtggcgaag gcggcttttt ggtctgtaac  360
tgacgctgag gcgcgaaagc gtggggagca aacaggatta gataccctgg tagtccacgc  420
cgtaaacgat gagtgctaag tgttagaggg tttccgccct ttagtgctgc agctaacgca  480
ttaagcactc cgcctgggga gtacggtcgc aagactgaaa ctcaaaggaa ttgacggggg  540
cccgcacaag cggtggagca tgtggtttaa ttcgaagcaa cgcgaagaac cttaccaggt  600
cttgacatcc tctgacaact ctagagatag agcgttcccc ttcgggggac agagtgacag  660
```

```
gtggtgcatg gttgtcgtca gctcgtgtcg tgagatgttg ggttaagtcc cgcaacg     717

SEQ ID NO: 92          moltype = DNA  length = 718
FEATURE                Location/Qualifiers
source                 1..718
                       mol_type = genomic DNA
                       organism = Bacillus aryabhattai
SEQUENCE: 92
tctganggnn cacgccgcgt gagtgatgaa ggctttcggg tcgtaaaact ctgttgttag  60
ggaagaacaa gtacgagagt aactgctcgt accttgacgg tacctaacca gaaagccacg  120
gctaactacg tgccagcagc cgcggtaata cgtaggtggc aagcgttatc cggaattatt  180
gggcgtaaag cgcgcgcagg cggtttctta agtctgatgt gaaagcccac ggctcaaccg  240
tggagggtca ttggaaactg gggaacttga gtgcagaaga gaaaagcgga attccacgtg  300
tagcggtgaa atgcgtagag atgtggagga acaccagtgg cgaaggcggc tttttggtct  360
gtaactgacg ctgaggcgcg aaagcgtggg gagcaaacag gattagatac cctggtagtc  420
cacgccgtaa acgatgagtg ctaagtgtta gagggtttcc gccctttagt gctgcagcta  480
acgcattaag cactccgcct ggggagtacg gtcgcaagac tgaaactcaa aggaattgac  540
gggggcccgc acaagcggtg gagcatgtgg tttaattcga agcaacgcga agaaccttac  600
caggtcttga catcctctga caactctaga gatagagcgt tccccttcgg gggacagagt  660
gacaggtggt gcatggttgt cgtcagctcg tgtcgtgaga tgttgggtta agtcccgc    718

SEQ ID NO: 93          moltype = DNA  length = 716
FEATURE                Location/Qualifiers
source                 1..716
                       mol_type = genomic DNA
                       organism = Bacillus flexus
SEQUENCE: 93
gganaacgc cgcgtgagtg angaaggctt tcgggtcgta aaactctgtt gttagggaag  60
aacaagtaca agagtaactg cttgtacctt gacggtacct aaccagaaag ccacggctaa  120
ctacgtgcca gcagccgcgg taatacgtag gtggcaagcg ttatccggaa ttattgggcg  180
taaagcgcgc gcaggcggtt tcttaagtct gatgtgaaag cccacggctc aaccgtggag  240
ggtcattgga aactggggaa cttgagtgca gaagagaaaa gcggaattcc acgtgtagcg  300
gtgaaatgcg tagagatgtg gaggaacacc agtggcgaag gcggcttttt ggtctgtaac  360
tgacgctgag gcgcgaaagc gtggggagca aacaggatta gataccctgg tagtccacgc  420
cgtaaacgat gagtgctaag tgttagaggg tttccgccct ttagtgctgc agctaacgca  480
ttaagcactc cgcctgggga gtacggtcgc aagactgaaa ctcaaaggaa ttgacggggg  540
cccgcacaag cggtggagca tgtggtttaa ttcgaagcaa cgcgaagaac cttaccaggt  600
cttgacatcc tctgacaact ctagagatag agcgttcccc ttcgggggac agagtgacag  660
gtggtgcatg gttgtcgtca gctcgtgtcg tgagatgttg ggttaagtcc cgcaac      716

SEQ ID NO: 94          moltype = DNA  length = 676
FEATURE                Location/Qualifiers
source                 1..676
                       mol_type = genomic DNA
                       organism = Paracoccus kondratievae
SEQUENCE: 94
gccgcgtgag tgnnnaagnc cctagggttg taaagctctt tcanctggga agataatgac  60
tgtaccagca gaagaagccc cggctaactc cgtgccagca gccgcggtaa tacggagggg  120
gctagcgttg ttcggaatta ctgggcgtaa agcgcacgta ggcggaccgg aaagttgggg  180
gtgaaatccc ggggctcaac cccggaactg ccttcaaaac tatcggtctg gagttcgaga  240
gaggtgagtg gaattccgag tgtagaggtg aaattcgtag atattcggag gaacaccagt  300
ggcgaaggcg gctcactggc tcgatactga cgctgaggtg cgaaagcgtg gggagcaaac  360
aggattagat accctggtag tccacgccgt aaacgatgaa tgccagtcgt cgggcagcat  420
gctgttcggt gacacaccta acggattaag cattccgcct ggggagtacg gtcgcaagat  480
taaaactcaa aggaattgac gggggcccgc acaagcggtg gagcatgtgg tttaattcga  540
agcaacgcgc agaaccttac caacccttga catcccagga cagcccgaga gatcgggtct  600
ccacttcggt ggcctggaga caggtgctgc atggctgtcg tcagctcgtg tcgtgagatg  660
ttcggttaag tccggc                                                  676

SEQ ID NO: 95          moltype = DNA  length = 728
FEATURE                Location/Qualifiers
source                 1..728
                       mol_type = genomic DNA
                       organism = Enterobacter cloacae
SEQUENCE: 95
ctgnngcagc cntgccgcgt gtatgaagaa ggncttcggg ttgtaaagta ctttcagcgg  60
ggaggaaggt gttgtggtta ataaccacag caattgacgt tacccgcaga agaagcaccg  120
gctaactccg tgccagcagc cgcggtaata cggagggtgc aagcgttaat cggaattact  180
gggcgtaaag cgcacgcagg cggtctgtca agtcggatgt gaaatccccg ggctcaacct  240
gggaactgca ttcgaaactg gcaggctaga gtcttgtaga ggggggtaga attccaggtg  300
tagcggtgaa atgcgtagag atctggagga ataccggtgg cgaaggcggc ccctggaca  360
aagactgacg ctcaggtgcg aaagcgtggg gagcaaacag gattagatac cctggtagtc  420
cacgccgtaa acgatgtcga tttggaggtt gtgcccttga ggcgtggctt ccggagctaa  480
cgcgttaaat cgaccgcctg gggagtacgg ccgcaaggtt aaaactcaaa tgaattgacg  540
ggggcccgca caagcggtgg agcatgtggt ttaattcgat gcaacgcgaa gaaccttacc  600
tggtcttgac atccacagaa ctttccagag atggattggt gccttcggga actgtgagac  660
aggtgctgca tggctgtcgt cagctcgtgt tgtgaaatgt tgggttaagt cccgcaacna  720
nncgcaac                                                           728
```

```
SEQ ID NO: 96          moltype = DNA  length = 717
FEATURE                Location/Qualifiers
source                 1..717
                       mol_type = genomic DNA
                       organism = Bacillus nealsonii
SEQUENCE: 96
tgnngganca acgccgcgtg agtgatgaag gttttcggat cgtaaaactc tgttgttagg  60
gaagaacaag tacgagagta actgctcgta ccttgacggt acctaaccag aaagccacgg  120
ctaactacgt gccagcagcc gcggtaatac gtaggtggca agcgttgtcc ggaattattg  180
ggcgtaaagc gcgcgcaggc ggtcctttaa gtctgatgtg aaagcccacg gctcaaccgt  240
ggagggtcat tggaaactgg gggacttgag tgcagaagag aagagtggaa ttccacgtgt  300
agcggtgaaa tgcgtagaga tgtggaggaa caccagtggc gaaggcgact ctttggtctg  360
taactgacgc tgaggcgcga aagcgtgggg agcaaacagg attagatacc ctggtagtcc  420
acgccgtaaa cgatgagtgc taagtgttag agggtttccg ccctttagtg ctgcagcaaa  480
cgcattaagc actccgcctg gggagtacgg ccgcaaggct gaaactcaaa ggaattgacg  540
ggggcccgca caagcggtgg agcatgtggt ttaattcgaa gcaacgcgaa gaaccttacc  600
aggtcttgac atctcctgac aatcctagag ataggacgtt ccccttcggg ggacaggatg  660
acaggtggtg catggttgtc gtcagctcgt gtcgtgagat gttgggttaa gtcccgc     717

SEQ ID NO: 97          moltype = DNA  length = 702
FEATURE                Location/Qualifiers
source                 1..702
                       mol_type = genomic DNA
                       organism = Bacillus subtilis
SEQUENCE: 97
cgccgcgtga gtgatgaagg ttttcggatc gtaaagctct gttgttaggg aagaacaagt  60
gccgttcaaa tagggcggca ccttgacggt acctaaccag aaagccacgg ctaactacgt  120
gccagcagcc gcggtaatac gtaggtggca agcgttgtcc ggaattattg ggcgtaaagg  180
gctcgcaggc ggtttcttaa gtctgatgtg aaagcccccg gctcaaccgg ggagggtcat  240
tggaaactgg ggaacttgag tgcagaagag gagagtggaa ttccacgtgt agcggtgaaa  300
tgcgtagaga tgtggaggaa caccagtggc gaaggcgact ctctggtctg taactgacgc  360
tgaggagcga aagcgtgggg agcgaacagg attagatacc ctggtagtcc acgccgtaaa  420
cgatgagtgc taagtgttag ggggtttccg ccccttagtg ctgcagctaa cgcattaagc  480
actccgcctg gggagtacgg tcgcaagact gaaactcaaa ggaattgacg ggggcccgca  540
caagcggtgg agcatgtggt ttaattcgaa gcaacgcgaa gaaccttacc aggtcttgac  600
atcctctgac aatcctagag ataggacgtc cccttcgggg gcagagtgac aggtggtgca  660
tggttgtcgt cagctcgtgt cgtgagatgt tgggttaagt cc                     702

SEQ ID NO: 98          moltype = DNA  length = 680
FEATURE                Location/Qualifiers
source                 1..680
                       mol_type = genomic DNA
                       organism = Alcaligenes faecalis
SEQUENCE: 98
cttcgggttg taaagtactt ttggcagaga agaaaaggta tctcctaata cgagatactg  60
ctgacggtat ctgcagaata agcaccggct aactacgtgc cancagccgc ggtaatacgt  120
agggtgcaag cgttaatcgg aattactggg cgtaaagcgt gtgtaggcgg ttcggaaaga  180
aagatgtgaa atcccagggc tcaaccttgg aactgcattt ttaactgccg agctagagta  240
tgtcagaggg gggtagaatt cnnntgtagc anngaaatgc gtagatatgt ggaggaatac  300
cgatggcgaa ggcagccccc tgggataata ctgacgctca gacacgaaag cgtggggagc  360
aaacaggatt agataccctg gtagtccacg ccctaaacga tgtcaactag ctgttggggc  420
cgttaggcct tagtagcgca gctaacgcgt gaagttgacc gcctggggag tacggtcgca  480
agattaaaac tcaaaggaat tgacggggac ccgcacaagc ggtggatgat gtggattaat  540
tcgatgcaac gcgaaaaacc ttacctaccc ttgacatgtc tggaaagccg aagagatttg  600
gccgtgctcg caagagaacc ggaacacagg tgctgcatgg ctgtcgtcag ctcgtgtcgt  660
gagatgttgg gttaagtccc                                               680

SEQ ID NO: 99          moltype = DNA  length = 640
FEATURE                Location/Qualifiers
source                 1..640
                       mol_type = genomic DNA
                       organism = Paenibacillus massiliensis
SEQUENCE: 99
cttanngnnt gannnnnctt gnnaanaaag ccccggctaa ctacntgcca ncanccgcgg  60
taatacntan ggngcaagcg ttgtccggaa ttattgggcg taaagcgcgc gcaggcggtc  120
ntttaagtct ggtgtttaag cccggggctc aaccccggat cncncgggaa actggatgac  180
ttgantgcnn aanaagagag tggaattccn ngtgtancgg tgaaatgcnt ananatgtgn  240
angaacacca ntggcnaang cnactctctg ggctgtaact gacnctgang cncgaaagcg  300
tggggagcaa acangattan ataccctggt antccacgcc ntanacnatn antgctaggt  360
gttnngggtt tcnataccct tgntgccnaa nttaacacat taancactcc gcctggnnan  420
tacngtcnca anantgaaac tcnnangaan tgacngggac ccgcacaagc nntgnantat  480
gtggtttaan tnnnnncaac ncnaanaanc ttaccnngnc ttgacatctn aatgaccngn  540
gcananatgt ncctttcctt cngnacattc nngacaggtg gtgcatggnt gtcntcnnct  600
cntgtcnngn gatgttgggt taantccccg cancnannnn                         640

SEQ ID NO: 100         moltype = DNA  length = 678
FEATURE                Location/Qualifiers
source                 1..678
                       mol_type = genomic DNA
```

```
                        organism = Bacillus subtilis
SEQUENCE: 100
aagctctgtt gttagggaag aacaagtacc gttcgaatag ggcggtacct tgacggtacc  60
taaccagaaa gccacggcta actacgtgcc agcagccgcg gtaatacgta ggtggcaagc  120
gttgtccgga attattgggc gtaaagggct cgcaggcggt ttcttaagtc tgatgtgaaa  180
gcccccggct caaccgggga gggtcattgg aaactgggga acttgagtgc agaagaggag  240
agtggaattc cacgtgtagc ggtgaaatgc gtagagatgt ggaggaacac cagtggcgaa  300
ggcgactctc tggtctgtaa ctgacgctga ggagcgaaag cgtggggagc gaacaggatt  360
agataccctg gtagtccacg ccgtaaacga tgagtgctaa gtgttagggg gtttccgccc  420
cttantgctg cagctaacgc attaagcact ccgcctgggg agtacggtcg caagactgaa  480
actcaaagga attgacgggg gcccgcacaa gcggtggagc atgtggttta attcgaagca  540
acgcgaanaa ccttaccagg tcttgacatc ctctgacaat cctagagata ggacgtcccc  600
ttcgggggca gagtgacagg tggtgcatgg ttgtcgtcan ctcgtgtcgt gagatgttgg  660
nttaagtccc gcaacgag                                                678

SEQ ID NO: 101          moltype = DNA  length = 743
FEATURE                 Location/Qualifiers
source                  1..743
                        mol_type = genomic DNA
                        organism = Bacillus megaterium
SEQUENCE: 101
aagnctttcg gnncgtaaaa ctctgttgtt agggaagaac aagtacgaga gtaactgctc  60
gtaccttgac ggtacctaac cagaaagcca cggctaacta cgtgccagca gccgcggtaa  120
tacgtaggtg gcaagcgtta tccggaatta ttgggcgtaa agcgcgcgca ggcggtttct  180
taagtctgat gtgaaagccc acggctcaac cgtggagggt cattggaaac tggggaactt  240
gagtgcagaa gagaaaagcg gaattccacg tgtagcggtg aaatgcgtag agatgtggag  300
gaacaccagt ggcgaaggcg gctttttggt ctgtaactga cgctgaggcg cgaaagcgtg  360
gggagcaaac aggattagat accctggtag tccacgccgt aaacgatgag tgctaagtgt  420
tagagggttt ccgcccttta gtgctgcagc taacgcatta agcactccgc ctggggagta  480
cggtcgcaag actgaaactc aaaggaattg acgggggccc gcacaagcgg tggagcatgt  540
ggtttaattc gaagcaacgc gaagaacctt accaggtctt gacatcctct gacaactcta  600
gagatagagc gttccccttc gggggacaga gtgacaggtg gtgcatggtt gtcgtcagct  660
cgtgtcgtga gatgttgggt taagtcccnn ncnnnnnnnn nnnnnnnntc tnaganncgn  720
gctgacnann ccangcaccn ngg                                          743

SEQ ID NO: 102          moltype = DNA  length = 980
FEATURE                 Location/Qualifiers
source                  1..980
                        mol_type = genomic DNA
                        organism = Bacillus thuringiensis
SEQUENCE: 102
tggacgaagt ctgacgganc acgccgcgtg agtgatgaag gctttcgggt cgtaaaactc  60
tgttgttagg gaagaacaag tgctagttga ataagctggc accttgacgg tacctaacca  120
gaaagccacg gctaactacg tgccagcagc cgcggtaata cgtaggtggc aagcgttatc  180
cggaattatt gggcgtaaag cgcgcgcagg tggtttctta agtctgatgt gaaagcccac  240
ggctcaaccg tggagggtca ttggaaactg ggagacttga gtgcagaaga ggaaagtgga  300
attccatgtg tagcggtgaa atgcgtagag atatggagga acaccagtgg cgaaggcgac  360
tttctggtct gtaactgaca ctgaggcgcg aaagcgtggg gagcaaacag gattagatac  420
cctggtagtc cacgccgtaa acgatgagtg ctaagtgtta gagggtttcc gccctttagt  480
gctgaagtta acgcattaag cactccgcct ggggagtacg gccgcaaggc tgaaactcaa  540
aggaattgac gggggcccgc acaagcggtg gagcatgtgg tttaattcga agcaacgcga  600
agaaccttac caggtcttga catcctctga aaaccctaga gatagggctt ctccttcggg  660
agcagagtga caggtggtgc atggttgtcg tcagctcgtg tcgtgagatg ttgggttaag  720
tcccgcaann ggccgcaacc caacanncnn cgacacgagc tgacgacaac catgnnccac  780
cagtnnctct gctctcgaag gagaagcccc annnnnaggg tttttcgagg atgtnnngan  840
ctggtnnggg nnntcgcgtt gcttcgaatt aaaccacatg ctcnnnnnnn tgnggnnccc  900
cnagtcnatt nnttngagtc tannnctgga nccggannna annngnnnnn gnnnanttgc  960
gttaattggg gnaancccgg                                              980

SEQ ID NO: 103          moltype = DNA  length = 731
FEATURE                 Location/Qualifiers
source                  1..731
                        mol_type = genomic DNA
                        organism = Bacillus mycoides
SEQUENCE: 103
agtctgnngg ancacgccgc gtgagtgnng aaggctttcg ggtcgtaaaa ctctgttgtt  60
agggaagaac aagtgctagt tgaataagct ggcaccttga cggtacctaa ccagaaagcc  120
acggctaact acgtgccagc agccgcggta atacgtaggt ggcaagcgtt atccggaatt  180
attgggcgta aagcgcgcgc aggtggtttc ttaagtctga tgtgaaagcc cacggctcaa  240
ccgtggaggg tcattggaaa ctgggagact tgagtgcaga agaggaaagt ggaattccat  300
gtgtagcggt gaaatgcgta gagatatgga ggaacaccag tggcgaaggc gactttctgg  360
tctgtaactg acactgaggc gcgaaagcgt ggggagcaaa caggattaga taccctggta  420
gtccacgccg taaacgatga gtgctaagtg ttagagggtt tccgcccttt agtgctgaag  480
ttaacgcatt aagcactccg cctggggagt acggccgcaa ggctgaaact caaaggaatt  540
gacgggggcc cgcacaagcg gtggagcatg tggtttaatt cgaagcaacg cgaagaacct  600
taccaggtct tgacatcctc tgacaaccct agagataggg cttccccttc gggggcagag  660
tgacaggtgg tgcatggttg tcgtcagctc gtgtcgtgag atgttgggtt aagtcccgca  720
acnannngca a                                                       731
```

```
SEQ ID NO: 104          moltype = DNA  length = 714
FEATURE                 Location/Qualifiers
source                  1..714
                        mol_type = genomic DNA
                        organism = Bacillus pseudomycoides
SEQUENCE: 104
ctganggganc acgccgcgtg agtgatgaag gctttcgggt cgtaaaactc tgttgttagg  60
gaagaacaag tgctagttga ataagctggc accttgacgg tacctaacca gaaagccacg  120
gctaactacg tgccagcagc cgcggtaata cgtaggtggc aagcgttatc cggaattatt  180
gggcgtaaag cgcgcgcagg tggtttctta agtctgatgt gaaagcccac ggctcaaccg  240
tggagggtca ttggaaactg ggagacttga gtgcagaaga ggaaagtgga attccatgtg  300
tagcggtgaa atgcgtagag atatggagga acaccagtgg cgaaggcgac tttctggtct  360
gtaactgaca ctgaggcgcg aaagcgtggg gagcaaacag gattagatac cctggtagtc  420
cacgccgtaa acgatgagtg ctaagtgtta gagggtttcc gccctttagt gctgaagtta  480
acgcattaag cactccgcct ggggagtacg gccgcaaggc tgaaactcaa aggaattgac  540
gggggcccgc acaagcggtg gagcatgtgg tttaattcga agcaacgcga agaaccttac  600
caggtcttga catcctctga aaactctaga gatagagctt ctccttcggg agcagagtga  660
caggtggtgc atggttgtcg tcagctcgtg tcgtgagatg ntgggntaag tccc        714

SEQ ID NO: 105          moltype = DNA  length = 740
FEATURE                 Location/Qualifiers
source                  1..740
                        mol_type = genomic DNA
                        organism = Bacillus cereus
SEQUENCE: 105
tctgnnggan caacnccgcg tgagtgatga angctttcgg gtcgtaaaac tctgttgtta  60
gggaagaaca agtgctagtt gaataagctg gcaccttgac ggtacctaac cagaaagcca  120
cggctaacta cgtgccagca gccgcggtaa tacgtaggtg gcaagcgtta tccggaatta  180
ttgggcgtaa agcgcgcgca ggtggtttct taagtctgat gtgaaagccc acggctcaac  240
cgtggagggt cattggaaac tgggagactt gagtgcagaa gaggaaagtg gaattccatg  300
tgtagcggtg aaatgcgtag agatatggag gaacaccagt ggcgaaggcg actttctggt  360
ctgtaactga cactgaggcg cgaaagcgtg gggagcaaac aggattagat accctggtag  420
tccacgccgt aaacgatgag tgctaagtgt tagagggttt ccgcccttta gtgctgaagt  480
taacgcatta agcactccgc ctggggagta cggccgcaag gctgaaactc aaaggaattg  540
acgggggccc gcacaagcgg tggagcatgt ggtttaattc gaagcaacgc gaagaacctt  600
accaggtctt gacatcctct gaaaacccta gagatagggc ttctccttcg ggagcagagt  660
gacaggtggt gcatggttgt cgtcagctcg tgtcgtgaga tgntgggtta agtcccgcaa  720
cganccgcaa ccnnannnnn                                              740

SEQ ID NO: 106          moltype = DNA  length = 850
FEATURE                 Location/Qualifiers
source                  1..850
                        mol_type = genomic DNA
                        organism = Bacillus pumilus
SEQUENCE: 106
ctganggganc acgccgcgtg agtgatgaag gttttcggat cgtaaagctc tgttgttagg  60
gaagaacaag tgcgagagta actgctcgca ccttgacggt acctaaccag aaagccacgg  120
ctaactacgt gccagcagcc gcggtaatac gtaggtggca agcgttgtcc ggaattattg  180
ggcgtaaagg gctcgcaggc ggtttcttaa gtctgatgtg aaagcccccg gctcaaccgg  240
ggagggtcat tggaaactgg gaaacttgag tgcagaagag gagagtggaa ttccacgtgt  300
agcggtgaaa tgcgtagaga tgtggaggaa caccagtggc gaaggcgact ctctggtctg  360
taactgacgc tgaggagcga aagcgtgggg agcgaacagg attagatacc ctggtagtcc  420
acgccgtaaa cgatgagtgc taagtgttag ggggtttccg ccccttagtg ctgcagctaa  480
cgcattaagc actccgcctg gggagtacgg tcgcaagact gaaactcaaa ggaattgacg  540
ggggcccgca caagcggtgg agcatgtggt ttaattcgaa gcaacgcgaa gaaccttacc  600
aggtcttgac atcctctgac aaccctagag atagggcttt cccttcgggg acagagtgac  660
aggtggtgca tggttgtcgt cagctcgtgt cgtgagatgt tgggttaagt cccgnacnnn  720
nnnnnnnnnn nnncntctnn nanncgngct gannanncca tgcaccnncn gtcantctnn  780
nnnnggnnaa nncntattnn tngggtngnn cagangangt cagacnggnn nggtnctnnn  840
nttgcnnnat                                                         850

SEQ ID NO: 107          moltype = DNA  length = 711
FEATURE                 Location/Qualifiers
source                  1..711
                        mol_type = genomic DNA
                        organism = Bacillus mycoides
SEQUENCE: 107
ggagcacgcc gcgtgagtgn ngaaggcttt cgggtcgtaa aactctgttg ttagggaaga  60
acaagtgcta gttgaataag ctggcacctt gacggtacct aaccagaaag ccacggctaa  120
ctacgtgcca gcagccgcgg taatacgtag gtggcaagcg ttatccggaa ttattgggcg  180
taaagcgcgc gcaggtggtt tcttaagtct gatgtgaaag cccacggctc aaccgtggag  240
ggtcattgga aactgggaga cttgagtgca gaagaggaaa gtggaattcc atgtgtagcg  300
gtgaaatgcg tagagatatg gaggaacacc agtggcgaag gcgactttct ggtctgtaac  360
tgacactgag gcgcgaaagc gtggggagca aacaggatta gataccctgg tagtccacgc  420
cgtaaacgat gagtgctaag tgttagaggg tttccgccct ttagtgctga agttaacgca  480
ttaagcactc cgcctgggga gtacggccgc aaggctgaaa ctcaaaggaa ttgacggggg  540
cccgcacaag cggtggagca tgtggtttaa ttcgaagcaa cgcgaagaac cttaccaggt  600
cttgacatcc tctgaaaact ctagagatag agcttctcct tcgggagcag agtgacaggt  660
ggtgcatggt tgtcgtcagc tcgtgtcgtg agatgttggg ttaagtcccg c           711
```

```
SEQ ID NO: 108         moltype = DNA  length = 21
FEATURE                Location/Qualifiers
source                 1..21
                       mol_type = other DNA
                       note = Primer
                       organism = synthetic construct
SEQUENCE: 108
actcctacgg gaggcagcag t                                       21

SEQ ID NO: 109         moltype = DNA  length = 16
FEATURE                Location/Qualifiers
source                 1..16
                       mol_type = other DNA
                       note = Primer
                       organism = synthetic construct
SEQUENCE: 109
gggttgcgct cgttgc                                             16

SEQ ID NO: 110         moltype = DNA  length = 16
FEATURE                Location/Qualifiers
source                 1..16
                       mol_type = other DNA
                       note = Primer
                       organism = synthetic construct
SEQUENCE: 110
gggttgcgct cgttac                                             16

SEQ ID NO: 111         moltype = DNA  length = 996
FEATURE                Location/Qualifiers
source                 1..996
                       mol_type = genomic DNA
                       organism = Bacillus thuringiensis
SEQUENCE: 111
atgaatttag ctaaattccc gagaaaaaaa tatacagaat catatacacc aattgaaaag  60
ttaaacaatt tttctgaagc acttggtggc ccgactattt attttaaacg agatgattta  120
cttggtttaa cagccggtgg taataagacg agaaagttag aatttttagt tgcggatgca  180
caggaaaagg gtgcagatac gttaattaca gctggtggta ttcagtcaaa tcattgccgc  240
ctgacacttg ctgctgcggt aaaagaaaaa atgaaatgta ttcttgtatt agaggaaggg  300
cttgagccag aagagaagag agactttaac ggaaactatt tcttatatca cttattaggt  360
gctgaaaacg tcattgttgt accgaacgga gcagacctga tggaagagat gaataaagta  420
gcgaaagaag taagtgaaaa aggtagtaca ccatatgtaa ttccagttgg tggatcaaac  480
cctacgggcg caatgggata cgttgcttgt gcgcaagaaa ttatggcgca atcatttgag  540
caaggaattg atttcagttc agttgtttgt gtaagtggta gcggcggtat gcatgctggt  600
ttaattactg gtttttctgg aacacaaagc catattcctg taatcgggat taatgtaagt  660
agaggaaaag ctgagcaaga agagaaagta gcaaaacttg tagatgaaac ttcagcacac  720
gttggtattc caaactttat ctcgcgcgac gctgttacgt gctttgatga atatgtagga  780
ccaggctatg cgttaccaac gccggaaatg gtagaggcag ttcagttact tgcgaaaaca  840
gaaggtattt tacttgatcc agtgtataca ggtaaggcag tagcgggatt aatcgactta  900
attagaaaag gtaaatttaa taaggaagac aatattttat tcgtacattc aggtggttca  960
ccagctttat atgcgaatac ttctttattt gcgtaa                       996

SEQ ID NO: 112         moltype = DNA  length = 996
FEATURE                Location/Qualifiers
source                 1..996
                       mol_type = other DNA
                       organism = Bacillus thuringiensis
SEQUENCE: 112
atgaatttag ctaaattccc gagaaaaaaa tatacagaat catatacacc aattgaaaag  60
ttaaacaatt tttctgaagc acttggtggc ccgactattt attttaaacg agatgattta  120
cttggtttaa cagccggtgg taataagacg agaaagttag aatttttagt tgcggatgca  180
caggaaaagg gtgcagatac gttaattaca gctggtggta ttcagtcaaa tcattgccgc  240
ctgacacttg ctgctgcggt aaaagaaaaa atgaaatgta ttcttgtatt agaggaaggg  300
cttgagccag aagagaagag agactttaac ggaaactatt tcttatatca cttattaggt  360
gctgaaaacg tcattgttgt accgaacgga gcagacctga tggaagagat gaataaagta  420
gcgaaagaag taagtgaaaa aggtagtaca ccatatgtaa ttccagttgg tggatcaaac  480
cctacgggcg caatgggata cgttgcttgt gcgcaagaaa ttatggcgca atcatttgag  540
caaggaattg atttcagttc agttgtttgt gtaagtggta gcggcggtat gcatgctggt  600
ttaattactg gtttttctgg aacacaaagc catattcctg taatcgggat taatgtaagt  660
agaggaaaag ctgagcaaga agagaaagta gcaaaacttg tagatgaaac ttcagcacac  720
gttggtattc caaactttat ctcgcgcgac gctgttacgt gctttgatga atatgtagga  780
ccaggctatg cgttaccaac gccggaaatg gtagaggcag ttcagttact tgcgaaaaca  840
gaaggtattt tacttgatcc agtgtatgaa ggtaaggcag tagcgggatt aatcgactta  900
attagaaaag gtaaatttaa taaggaagac aatattttat tcgtacattt aggtggttca  960
ccagctttat atgcgaatac ttctttattt gcgtaa                       996

SEQ ID NO: 113         moltype = AA  length = 331
FEATURE                Location/Qualifiers
source                 1..331
```

```
                        mol_type = protein
                        organism = Bacillus thuringiensis
SEQUENCE: 113
MNLAKFPRKK YTESYTPIEK LNNFSEALGG PTIYFKRDDL LGLTAGGNKT RKLEFLVADA  60
QEKGADTLIT AGGIQSNHCR LTLAAAVKEK MKCILVLEEG LEPEEKRDFN GNYFLYHLLG  120
AENVIVVPNG ADLMEEMNKV AKEVSEKGST PYVIPVGGSN PTGAMGYVAC AQEIMAQSFE  180
QGIDFSSVVC VSGSGGMHAG LITGFSGTQS HIPVIGINVS RGKAEQEEKV AKLVDETSAH  240
VGIPNFISRD AVTCFDEYVG PGYALPTPEM VEAVQLLAKT EGILLDPVYT GKAVAGLIDL  300
IRKGKFNKED NILFVHSGGS PALYANTSLF A                                331

SEQ ID NO: 114          moltype = AA  length = 331
FEATURE                 Location/Qualifiers
source                  1..331
                        mol_type = protein
                        organism = Bacillus thuringiensis
SEQUENCE: 114
MNLAKFPRKK YTESYTPIEK LNNFSEALGG PTIYFKRDDL LGLTAGGNKT RKLEFLVADA  60
QEKGADTLIT AGGIQSNHCR LTLAAAVKEK MKCILVLEEG LEPEEKRDFN GNYFLYHLLG  120
AENVIVVPNG ADLMEEMNKV AKEVSEKGST PYVIPVGGSN PTGAMGYVAC AQEIMAQSFE  180
QGIDFSSVVC VSGSGGMHAG LITGFSGTQS HIPVIGINVS RGKAEQEEKV AKLVDETSAH  240
VGIPNFISRD AVTCFDEYVG PGYALPTPEM VEAVQLLAKT EGILLDPVYE GKAVAGLIDL  300
IRKGKFNKED NILFVHLGGS PALYANTSLF A                                331

SEQ ID NO: 115          moltype = AA  length = 259
FEATURE                 Location/Qualifiers
source                  1..259
                        mol_type = protein
                        organism = Bacillus cereus
SEQUENCE: 115
HENDGGSKIK IVHRWSAEDK HKEGVNSHLW IVNRAIDIMS RNKTLVKQDR VALLNEWRTE  60
LENGIYAADY ENPYYDNSTF ASHFYDPDNG KTYIPYAKQA KETGAKYFKL AGESYKNKDM  120
KQAFFYLGLS LHYLGDVNQP MHAANFTNLS YPQGFHSKYE NFVDTIKDNY KVTDGNGYWN  180
WKGTNPEDWI HGAAVVAKQD YAGIVNDNTK DWFVRAAVSQ EYADKWRAEV TPMTGKRLMD  240
AQRVTAGYIQ LWFDTYGDR                                              259

SEQ ID NO: 116          moltype = AA  length = 326
FEATURE                 Location/Qualifiers
source                  1..326
                        mol_type = protein
                        organism = Bacillus cereus
SEQUENCE: 116
MRNKKLILKL FICSTIFITF VFALHDKRVV AASSVNELEN WSKWMQPIPD NIPLARISIP  60
GTHDSGTFKL QNPIKQVWGM TQEYDFRYQM DHGARIFDIR GRLTDDNTIV LHHGPLYLYV  120
TLHEFINEAK QFLKDNPSET IIMSLKKEYE DMKGAENSFS STFEKNYFVD PIFLKTEGNI  180
KLGDARGKIV LLKRYSGSNE SGGYNNFYWP DNETFTTTVN KNVNVTVQDK YKVSYDEKVK  240
SIKDTINETM NNSEDLNHLY INFTSLSSGG TAWNSPYYYA SYINPEIAAY IKQENPKRVG  300
WVIQDYISDK WSPILYQEVI RTNKSL                                      326

SEQ ID NO: 117          moltype = AA  length = 407
FEATURE                 Location/Qualifiers
source                  1..407
                        mol_type = protein
                        organism = Acidovorax avenae
SEQUENCE: 117
MSGGHRVALL QGSAELFSAL VADMDAALSD IQFETYIFDC TGSGADIAEA LIRAARRGVR  60
VHLVVDGVGT GRLCSPWPER FEEAGVRMQV YSPLGPLGLL LPRRWRRLHR KLCVVDGCVL  120
YCGGINVLDD LHDPNHGALE SPRFDFAVRV EGRLVEEAGE AMEQVWWRLQ ATRDARQRRL  180
ADLMCDLRAA AQARQAERLA REAAPGGAAA AHGLRAGLLL RDNLRNRSRI ERAYRRAIGN  240
ARHEVIIANA YFLPGRKLRH ALVLAARRGV RVRLLLQGRY EYFMQYHAAR PVYGALLAAG  300
VEIHEYAPSF LHAKVAVIDA QGEHPWATVG SSNLDPLSML LAREANVVVE DAGFARALRA  360
RLVDAMEHAG RQLDPQAYGA RPWGQRLRDR VAFALMRLAL WVTGSRY                407

SEQ ID NO: 118          moltype = AA  length = 320
FEATURE                 Location/Qualifiers
source                  1..320
                        mol_type = protein
                        organism = Burkholderia cepacia
SEQUENCE: 118
AAGYAATRYP IILVHGLSGT DKYAGVLEYW YGIQEDLQQN GATVYVANLS GFQSDDGPNG  60
RGEQLLAYVK TVLAATGATK VNLVGHSQGG LSSRYVAAVA PDLVASVTTI GTPHRGSEFA  120
DFVQDVLAYD PTGLSSSVIA AFVNVFGILT SSSHNTNQDA LAALQTLTTA RAATYNQNYP  180
SAGLGAPGSC QTGAPTETVG GNTHLLYSWA GTAIQPTLSV FGVTGATDTS TLPLVDPANV  240
LDLSTLALFG TGTVMINRGS GQNDGLVSKC SALYGKVLST SYKWNHLDEI NQLLGVRGAY  300
AEDPVAVIRT HANRLKLAGV                                             320

SEQ ID NO: 119          moltype = AA  length = 453
FEATURE                 Location/Qualifiers
source                  1..453
                        mol_type = protein
```

```
                        organism = Pseudomonas fluorescens
SEQUENCE: 119
ITLYSYHNLD NGFAVGYQHN GLGLGLPATL VGALLGSTDS QGVIPGIPWN PDSEKAALEA  60
VQKAGWTPIS ASALGYAGKV DARGTFFGEK AGYTTAQVEV LGKYDDAGKL LEIGIGFRGT  120
SGPRETLISD SIGDLISDLL AALGPKDYAK NYAGEAFGGL LKNVADYAGA HGLTGKDVVV  180
SGHSLGGLAV NSMADLSNYK WAGFYKDANY VAYASPTQSA GDKVLNIGYE NDPVFRALDG  240
SSFNLSSLGV HDKPHESTTD NIVSFNDHYA STLWNVLPFS IVNLPTWVSH LPTAYGDGMT  300
RILESGFYDQ MTRDSTVIVA NLSDPARANT WVQDLNRNAE PHKGNTFIIG SDGNDLIQGG  360
NGADFIEGGK GNDTIRDNSG HNTFLFSGHF GNDRVIGYQP TDKLVFKDVQ GSTDLRDHAK  420
VVGADTVLTF GADSVTLVGV GHGGLWTEGV VIG                             453

SEQ ID NO: 120          moltype = AA  length = 355
FEATURE                 Location/Qualifiers
source                  1..355
                        mol_type = protein
                        organism = Burkholderia stearothermophilus
SEQUENCE: 120
MDKLIVDDLH LSYGANPILK GVSFELKAGE VVCLLGASGS GKTTLLRAVA GLEQPSDGRI  60
QLDDRVFFDG AKRVDLPVEQ RSLGLVFQSY ALWPHRTVAD NVGYGLKLRR VAPAEQKRRV  120
QSALDQLGLG HLAERFPHQL SGGQQQRVAI ARALVYNPPV ILLDEPLSNL DAKLREEARA  180
WLRELIVSLG LSALCVTHDQ TEAMAMSDRI LLLRNGRIEQ EGTPAELYGA PRSLYTAEFM  240
GSNNRIDARV AAIDGECVTL AGDGWEIRAM ARDTLAPGQD AQAVIRLERV QVTDGPGANR  300
LQADLVTSMY LGDRWEYLFH CGDMRLRAFG HVPRAAGKHW IEFPTNDCWA FAKAG       355

SEQ ID NO: 121          moltype = AA  length = 258
FEATURE                 Location/Qualifiers
source                  1..258
                        mol_type = protein
                        organism = Thermomyces lanuginosus
SEQUENCE: 121
MVGFTPVALA ALAATGALAF PAGNATELEK RQTTPNSEGW HDGYYYSWWS DGGAQATYTN  60
LEGGTYEISW GDGGNLVGGK GWNPGLNARA VRVPQDRNRI VIRPRSFESL KAFLTPTSLT  120
CTQIHFEGVY QPNGNSYLAV YGWTRNPLVE YYIVENFGTY DPSSGATDLG TVECDGSIYR  180
LGKTTRVNAP SIDGTQTFDQ YWSVRQDKRT SGTVQTGCHF DAWARAGLNV NGDHYYQIVA  240
TEGYFSSGYA RITVADVG                                              258

SEQ ID NO: 122          moltype = AA  length = 860
FEATURE                 Location/Qualifiers
source                  1..860
                        mol_type = protein
                        organism = Neocallimastix patriciarum
SEQUENCE: 122
MKFSSANKIL FSGLVASANA YDLLKDYAGD LKIGVAANAM RFSNSNYVNA MKAFNMMVAE  60
NDCKLSGIQQ QKGVYNFNGC DNHYNKAKEL GMEFRGHCLI WHSYQPSWFQ NADANTLKNA  120
IVDHITKTLQ HYEGKIKVWD VVNEAIDDNS NGNGWNMRRS FLYNKVPNFV DLAFQTARKV  180
SPNTKLFYND YNAEGVYAKA ESIYNFVSDL KKRNIPIDGV GLQYHVGAKE QPSYNKINDL  240
IGRYCKLGLE VHITELDVKL QGDQNGQSQA FSNALKACLA NSCCKAFLVW GVGDNDSWLG  300
ANEQALLFNG SYQPKPVYNT LLNILKTSAR PASSSAKTLP GNSKSKTLPG VNSKTLPGNK  360
SKTLPGASKT LPGNKSKTLP GGNSNTLPGN KSKTLPGGNS KTLPGNKSRT LPGGNSKTLP  420
GGKSRTLPGG NSKTLPGGKS KTLPGGNSKT LPGGKSKTLP GGNSKTLPGG SSKTLPGGKS  480
KTLPGGNSKT LPGGSSKTLP GGKSKTLPGG SSKTLPGGKS KTLPGGNSKT LPGGNSKTLP  540
GGSSKTLPGG KSKTLPGGNS KTLPGGSSKT LPGGKSKTLP GGNSKTLPGG NSKTLPGGKS  600
KTLPGGNSKT LPGGSSKTLP GGKSKTLPGG SSKTLPGGKS KTLPGGNSKT LPGGNSKTLP  660
GGSSKTLPGG KSKTLPGGSS KTLPGGKSKT LPGGNSKTLP GGKSKTLPGG NSKTLPGGKS  720
KTLPGGNSKT LPGGKSKTLP GGNSKTLPGG SSKTLPGGKS KTLPGGNSKT LPGGKSKTLP  780
GGNTKTLPGG ACKPTTVTVT QKVTVTVTVE SQPTQGGMNQ GGGNCAAKWG QCGGNGFNGP  840
TCCQNGSRCQ FVNEWYSQCL                                            860

SEQ ID NO: 123          moltype = AA  length = 535
FEATURE                 Location/Qualifiers
source                  1..535
                        mol_type = protein
                        organism = Bacillus pumilus
SEQUENCE: 123
MKITNPVLKG FNPDPSICRA GEDYYMAVST FEWFPGVQIY HSKDLIHWRL AARPLQKTSQ  60
LDMKGNPDSG GVWAPCLSYA DGQFWLIYSD IKVVDGPFKD GHNYLVTADA VDGEWSDPVR  120
LNSSGFDPSL FHDPSGKKYV LNMLWDHREK HHSFAGIALQ EYSVSEKKLV GERKVIFKGT  180
PIKLTEAPHL YYINDVYYLL TAEGGTRYEH AATIARSSRI DGPYEVHPDN PILTAFHAPS  240
HPLQKCGHAS IVQTHTNEWY LAHLTGRPIH SSKESIFQQR GWCPLGRETA IQKLEWKDGW  300
PYVVGGKEGL LEVEAPAMSV KEFSPTYHIV DEFKDSSLNR HFQTLRIPFT DQIGSVTENP  360
HHLRLYGQES LTSKFTQAFV ARRWQSFYFE AETAVSFFPK NFQQAAGLVN YYNTENWTAL  420
QVTYDDALGR ILELSVCENL AFSQPLIKKI IIPDEIPYVY LKVTVQRETY TYSYSFDQQE  480
WEKIDVPLES THLSDDFIRG GGFFTGAFVG MQCQDTSGER LPADFKYFRY EETTE       535

SEQ ID NO: 124          moltype = AA  length = 238
FEATURE                 Location/Qualifiers
source                  1..238
                        mol_type = protein
                        note = Streptomyces species N174
```

```
                         organism = Streptomyces sp.
SEQUENCE: 124
AGAGLDDPHK KEIAMELVSS AENSSLDWKA QYKYIEDIGD GRGYTGGIIG FCSGTGDMLE  60
LVQHYTDLEP GNILAKYLPA LKKVNGSASH SGLGTPFTKD WATAAKDTVF QQAQNDERDR  120
VYFDPAVSQA KADGLRALGQ FAYYDAIVMH GPGNDPTSFG GIRKTAMKKA RTPAQGGDET  180
TYLNAFLDAR KAAMLTEAAH DDTSRVDTEQ RVFLKAGNLD LNPPLKWKTY GDPYVINS    238

SEQ ID NO: 125           moltype = AA  length = 363
FEATURE                  Location/Qualifiers
source                   1..363
                         mol_type = protein
                         organism = Paenibacillus sp.
SEQUENCE: 125
ADASQIVSEM GAGWNLGNQL EAAVNGTPNE TAWGNPTVTP ELIKKVKAAG FKSIRIPVSY  60
LNNIGSAPNY TINAAWLNRI QQVVDYAYNE GLYVIINIHG DGYNSVQGGW LLVNGGNQTA  120
IKEKYKKVWQ QIATKFSNYN DRLIFESMNE VFDGNYGNPN SAYYTNLNAY NQIFVDTVRQ  180
TGGNNNARWL LVPGWNTNID YTVGNYGFTL PTDNYRSSAI PSSQKRIMIS AHYYSPWDFA  240
GEENGNITQW GATSTNPAKK STWGQEDYLE SQFKSMYDKF VTQGYPVVIG EFGSIDKTSY  300
DSSNNVYRAA YAKAVTAKAK KYKMVPVYWD NGHNGQHGFA LFNRSNNTVT QQNIINAIMQ  360
GMQ                                                                363

SEQ ID NO: 126           moltype = AA  length = 442
FEATURE                  Location/Qualifiers
source                   1..442
                         mol_type = protein
                         organism = Helix pomatia
SEQUENCE: 126
MLSLVIALCV VGSLSAHLPE VFVHYQDGAL HFKMQHVPGL KEVNFNYQLG SQAKNVIPKM  60
GTANKGGDGY WHLTDKKIDL QPGDSIQYNA VAWGTAGKLH APVASWVYAP EPTRGPRRLR  120
GAVMFRDDFN GGGLDTNNWN YEVSMYGGMN WEFQVYTNDK SNVYTNNGKL FLKPTKTVDD  180
PRWDENFLHS GVMDVAQIWG YCTQSAQYGC HREGKNGILP PVMSGKVKSK PVLKYGTVEV  240
RARIPKGDWL WPAIWMLPRD SHYGGWPRSG EIDIMESRGN VRASGHGVNE VSSTLHWGTS  300
AGDNHYGQTT HAKQAADWSN SFHTWRLEWT HDHIATFVDN QQILRVTPPS GGFSELGHTS  360
NIWAGNDKMA PFDKEFYAIF NVAVGGTNGF FPENWDYGYP KPWSNTSPHA AQDWWNGRSK  420
WESSWQGDKV AMEIDYIEMR YL                                           442

SEQ ID NO: 127           moltype = AA  length = 374
FEATURE                  Location/Qualifiers
source                   1..374
                         mol_type = protein
                         organism = Aspergillus saitoi
SEQUENCE: 127
APAPTRKGFT INQIARPANK TRTVNLPGLY ARSLAKFGGT VPQSVKEAAS KGSAVTTPQN  60
NDEEYLTPVT VGKSTLHLDF DTGSADLWVF SDELPSSEQT GHDLYTPSSS ATKLSGYSWD  120
ISYGDGSSAS GDVYRDTVTV GGVTTNKQAV EAASKISSEF VQDTANDGLL GLAFSSINTV  180
QPKAQTTFFD TVKSQLDSPL FAVQLKHDAP GVYDFGYIDD SKYTGSITYT DADSSQGYWG  240
FSTDGYSIGD GSSSSSGFSA IADTGTTLIL LDDEIVSAYY EQVSGAQESY EAGGYVFSCS  300
TDLPDFTVVI GDYKAVVPGK YINYAPVSTG SSTCYGGIQS NSGLGLSILG DVFLKSQYVV  360
FNSEGPKLGF AAQA                                                    374

SEQ ID NO: 128           moltype = AA  length = 298
FEATURE                  Location/Qualifiers
source                   1..298
                         mol_type = protein
                         organism = Bacillus sp.
SEQUENCE: 128
AAATGFYVNG GKLYDSTGKP FYMRGINHGH SWFKNDLNTA IPAIAKTGAN TVRIVLSNGT  60
QYTKDDLNSV KNIINVVNAN KMIAVLEVHD ATGKDDFNSL DAAVNYWISI KEALIGKEDR  120
VIVNIANEWY GTWNGSAWAD GYKKAIPKLR DAGIKNTLIV DAAGWGQYPQ SIVDYGQSVF  180
AADSQKNTAF SIHMYEYAGK DAATVKSNME NVLNKGLALI IGEFGGYHTN GDVDEYAIMK  240
YGLEKGVGWL AWSWYGNSSG LNYLDLATGP NGSLTSYGNT VVNDTYGIKN TSQKAGIF    298

SEQ ID NO: 129           moltype = AA  length = 349
FEATURE                  Location/Qualifiers
source                   1..349
                         mol_type = protein
                         organism = Aspergillus japonicus
SEQUENCE: 129
APSRVSDFTK RSTCTFTDAA TASESKTSCS DIVLKDITVP AGETLNLKDP NDGTTVTFEG  60
TTTWEYEEWD GPLLRISGKD ITVTQSSDAV LDGNGAKWWD GEGTNGGKTK PKFFYAHDLD  120
DSKISGLYIK NTPVQAISVE SDNLVIEDVT IDNSDGDSEG GHNTDGFDIS ESTYITITGA  180
TVKNQDDCVA INSGENIYFS GGTCSGGHGL SIGSVGGRDD NTVKNVTFID STVSDSENGV  240
RIKTVYDATG TVEDITYSNI QLSGISDYGI VIEQDYENGD PTGTPSNGVT ISDVTLEDIT  300
GSVDSDAVEI YILCGDGSCS DWTMSGIDIT GGETSSDCEN VPSGASCDQ              349

SEQ ID NO: 130           moltype = AA  length = 310
FEATURE                  Location/Qualifiers
source                   1..310
                         mol_type = protein
```

```
                         organism = Triticum aestivum
SEQUENCE: 130
ELPLVEHPAK NDGSLSLLVV GDWGRNGTYN QSRVAEQMGK VGERLDIDFV VSTGDNFYEN  60
GLTGVHDQQF EESFTNIYTA QSLQKPWYLV LGNHDYRGDA LAQLDPVMRK LDERFVCMRS  120
FLVNAEIVEF FFIDTTPFQL KYWTHPKDSH YDWRGVAPRK DYIANLLKDL DEAMKKSTAK  180
WKIAIGHHTM RSVSDHGDTE ELLQLLLPVL KVNGIDFYIN GHDHCLEHIS SRDSPIQYFT  240
SGGGSKAWRG VYQPNDDKIQ FFYDGQGFMS LQLNQDQADF IFYDVSGKVL YEFTSHKTNH  300
FQPSIYVTAE                                                   310

SEQ ID NO: 131           moltype = AA  length = 447
FEATURE                  Location/Qualifiers
source                   1..447
                         mol_type = protein
                         organism = Triticum aestivum
SEQUENCE: 131
RSEFPSTDMP LDSEWFATPK GYNAPQQVHI TQGDYDGKAV IVSWVTPSEP APSQVFYSKE  60
ENRYDQKAEG TMTNYTFYDY KSGYIHHCLV DGLEYNTKYY YKIGTGDSAR EFWFQTPPAI  120
DTDASYTFGI IGDLGQTFNS LSTLQHYLKS GGESVLFVGD LSYADRYQHN DGIRWDSWGR  180
FVERSTAYQP WIWNSGNHEI EYRPDLGETS TFKPYLHRYS TPYLASKSSS PMWYAVRRAS  240
AHIIVLSSYS PFVKYTPQWM WLKGELKRVD REKTPWLIVL MHAPMYNSNN AHYMEGESMR  300
AAFEKWFVKY KVDLVFAGHV HAYERSYRIS NINYNVTSGN RYPVPDKSAP VYITVGDGGN  360
QEGLAWRFND PQPDYSAFRE ASFGHSTLQL VNRTHAVYQW NRNDDGKHVP TDNVVFHNQY  420
WAGNTRRRRL KKKHLRYESL QSLMSML                                447

SEQ ID NO: 132           moltype = AA  length = 530
FEATURE                  Location/Qualifiers
source                   1..530
                         mol_type = protein
                         organism = Triticum aestivum
SEQUENCE: 132
AAEPASTLTG PSRPVTVALR KDRGHAVDLP DTDPRVQRRA TGWAPEQITV ALSAAPTSAW  60
VSWITGEFQM GGTVKPLNPG TVASVVRYGL AADSLVHEAT GDALVYSQLY PFEGLQNYTS  120
GIIHHVRLQG LEPATKYYYQ CGDPGIPGAM SAVHAFRTMP AVGPRSYPGR IAVVGDLGLT  180
YNTTSTVDHM VSNRPDLVLL VGDVCYANMY LTNGTGADCY SCAFGKSTPI HETYQPRWDY  240
WGRYMEAVTS GTPMMVVEGN HEIEEQIGNK TFAAYRSRFA FPSTESGSFS PFYYSFDAGG  300
IHFIMLAAYA DYSRSGEQYR WLVKDLAKVD RAVTPWLVAG WHAPWYTTYK AHYREVECMR  360
VAMEELLYSH GLDIAFTGHV HAYERSNRVF NYTLDPCGAV HISVGDGGNR EKMATTHADE  420
PGHCPDPRPK PNAFIGCFCA FNFTSGPAAG RFCWDRQPDY SAYRESSFGH GILEVKNETH  480
ALWRWHRNQD HYGSAGDEIY IVREPHRCLH KHNSTRPAHG RQNTTRESGG           530

SEQ ID NO: 133           moltype = AA  length = 521
FEATURE                  Location/Qualifiers
source                   1..521
                         mol_type = protein
                         organism = Triticum aestivum
SEQUENCE: 133
AAEPASTLTG PSRPVTVTLR EDRGHAVDLP DTDPRVQRRA TGWAPEQIAV ALSAAPTSAW  60
VSWITGEFQM GGTVKPLDPG TVASVVRYGL AADSLVRQAT GDALVYSQLY PFEGLQNYTS  120
GIIHHVRLQG LEPATKYYYQ CGDPALPGAM SAVHAFRTMP AVGPRSYPGR IAVVGDLGLT  180
YNTTSTVDHM ASNRPDLVLL LGDVSYANLY LTNGTGADCY SCAFGKSTPI HETYQPRWDY  240
WGRYMEAVTS GTPMVVVEGN HEIEEQIGNK TFAAYRSRFA FPSTESGSFS PFYYSFDAGG  300
IHFVMLGAYA DYGRSGEQYR WLEKDLAKVD RSVTPWLVAG WHAPWYTTYK AHYREVECMR  360
VAMEELLYSH GLDIAFTGHV HAYERSNRVF NYTLDPCGAV HISVGDGGNR EKMATTHADE  420
PGHCPEPRAK PNAFIGGFCA FNFTSGPAAG RFCWDRQPDY SAYRESSFGH GILEVKNETH  480
ALWRWHRNQD MYGSAGDEIY IVREPHRCLH KHNSTRPTHG R                    521

SEQ ID NO: 134           moltype = AA  length = 521
FEATURE                  Location/Qualifiers
source                   1..521
                         mol_type = protein
                         organism = Triticum aestivum
SEQUENCE: 134
AAAAEPASTL EGPSWPVTVP LREDRGHAVD LPDTDPRVQR RVTGWAPEQI AVALSAAPTS  60
AWVSWITGDF QMGGAVKPLD PGTVGSVVRY GLAADSLVRE ATGDALVYSQ LYPFEGLQNY  120
TSGIIHHVRL QGLEPGTKYY YQCGDPAIPG ATSAVHAFRT MPAVGPRSYP GRIAVVGDLG  180
LTYNTTSTVE HMASNQPDLV LLLGDVSYAN LYLTNGTGTD CYSCSFAKST PIHETYQPRW  240
DYWGRYMESV TSTTPMMVVE GNHEIEQQIG NKTFAAYSAR FAFPSKESDS FSPFYYSFDA  300
GGIHFIMLAA YAAYSKSGEQ YRWLEKDLAK VDRSVTPWLV AGWHAPWYST YKAHYREAEC  360
MRVAMEELLY SYGLDIVFTG HVHAYERSNR VFNYTLDPCG AVHISVGDGG NREKMATTHA  420
DDPGRCPEPL STPDDFMGGF CAFNFTSDPA AGSFCWDRQP DYSAYRESSF GHGILEVKNE  480
THALWKWHRN QDLYQGGVGD EIYIVREPER CLLKSSIAAY F                    521

SEQ ID NO: 135           moltype = AA  length = 24
FEATURE                  Location/Qualifiers
source                   1..24
                         mol_type = protein
                         organism = Bacillus cereus
SEQUENCE: 135
MKKKVLALAA AITLVAPLQN VAFA                                   24
```

```
SEQ ID NO: 136          moltype = DNA  length = 876
FEATURE                 Location/Qualifiers
source                  1..876
                        mol_type = genomic DNA
                        organism = Bacillus thuringiensis
SEQUENCE: 136
tctgacggag caacgccgcg tgagtgatga aggctttcgg gtcgtaaaac tctgttgtta  60
gggaagaaca agtgctagtt gaataagctg gcaccttgac ggtacctaac cagaaagcca  120
cggctaacta cgtgccagca gccgcggtaa tacgtaggtg gcaagcgtta tccggaatta  180
ttgggcgtaa agcgcgcgca ggtggtttct taagtctgat gtgaaagccc acggctcaac  240
cgtggagggt cattggaaac tgggagactt gagtgcagaa gaggaaagtg gaattccatg  300
tgtagcggtg aaatgcgtag agatatggag gaacaccagt ggcgaaggcg actttctggt  360
ctgtaactga cactgaggcg cgaaagcgtg gggagcaaac aggattagat accctggtag  420
tccacgccgt aaacgatgag tgctaagtgt tagagggttt ccgcccttta gtgctgaagt  480
taacgcatta agcactccgc ctggggagta cggccgcaag gctgaaactc aaaggaattg  540
acgggggccc gcacaagcgg tggagcatgt ggtttaattc gaagcaacgc gaagaacctt  600
accaggtctt gacatcctct gaaaacccta gagatagggc ttctccttcg ggagcagagt  660
gacaggtggt gcatggttgt cgtcagctcg tgtcgtgaga tgttgggtta agtcccgcaa  720
cgagcgcaac ccttgatctt agttgccatc attaagttgg gcactctaag gtgactgccg  780
gtgacaaacc ggaggaaggt ggggatgacg tcaaatcatc atgcccctta tgacctgggc  840
tacacacgtg ctacaatgga cggtacaaag agctgc                            876

SEQ ID NO: 137          moltype = AA  length = 44
FEATURE                 Location/Qualifiers
source                  1..44
                        mol_type = protein
                        organism = Burkholderia cepacia
SEQUENCE: 137
MARTMRSRVV AGAVACAMSI APFAGTTAVM TLATTHAAMA ATAP                   44

SEQ ID NO: 138          moltype = AA  length = 23
FEATURE                 Location/Qualifiers
source                  1..23
                        mol_type = protein
                        organism = Pseudomonas fluorescens
SEQUENCE: 138
MGIFDYKNLG TEGSKTLFAD AMA                                          23

SEQ ID NO: 139          moltype = AA  length = 40
FEATURE                 Location/Qualifiers
source                  1..40
                        mol_type = protein
                        note = Streptomyces species N174
                        organism = Streptomyces sp.
SEQUENCE: 139
MHSQHRTARI ALAVVLTAIP ASLATAGVGY ASTQASTAVK                        40

SEQ ID NO: 140          moltype = AA  length = 32
FEATURE                 Location/Qualifiers
source                  1..32
                        mol_type = protein
                        organism = Paenibacillus sp.
SEQUENCE: 140
MFKKWKKFGI SSLALVLVAA VAFTGWSAKA SA                                32

SEQ ID NO: 141          moltype = AA  length = 20
FEATURE                 Location/Qualifiers
source                  1..20
                        mol_type = protein
                        organism = Aspergillus saitoi
SEQUENCE: 141
MVVFSKTAAL VLGLSTAVSA                                              20

SEQ ID NO: 142          moltype = AA  length = 28
FEATURE                 Location/Qualifiers
source                  1..28
                        mol_type = protein
                        organism = Bacillus sp.
SEQUENCE: 142
MAKLQKGTIL TVIAALMFVI LGSAAPKA                                     28

SEQ ID NO: 143          moltype = AA  length = 21
FEATURE                 Location/Qualifiers
source                  1..21
                        mol_type = protein
                        organism = Aspergillus japonicus
SEQUENCE: 143
MPSAKPLFCL ATLAGAALAA P                                            21
```

-continued

```
SEQ ID NO: 144          moltype = AA  length = 25
FEATURE                 Location/Qualifiers
source                  1..25
                        mol_type = protein
                        organism = Triticum aestivum
SEQUENCE: 144
MARGSMAAVL AVLAVAALRC APAAA                                       25

SEQ ID NO: 145          moltype = AA  length = 30
FEATURE                 Location/Qualifiers
source                  1..30
                        mol_type = protein
                        organism = Triticum aestivum
SEQUENCE: 145
MRGLGFAALS LHVLLCLANG VSSRRTSSYV                                  30

SEQ ID NO: 146          moltype = AA  length = 18
FEATURE                 Location/Qualifiers
source                  1..18
                        mol_type = protein
                        organism = Triticum aestivum
SEQUENCE: 146
MWWGSLRLLL LLAAAVAA                                               18

SEQ ID NO: 147          moltype = AA  length = 15
FEATURE                 Location/Qualifiers
source                  1..15
                        mol_type = protein
                        organism = Triticum aestivum
SEQUENCE: 147
MGIWRGSLPL LLLAA                                                  15
```